US012337038B2

(12) United States Patent
Khan et al.

(10) Patent No.: US 12,337,038 B2
(45) Date of Patent: Jun. 24, 2025

(54) CONJUGATES COMPRISING CLEAVABLE BETA-GLUCURONIDE-CONTAINING LINKERS

(71) Applicant: AstraZeneca AB, Södertälje (SE)

(72) Inventors: Akbar Husain Khan, Waltham, MA (US); Andreas Lothar Severino Maderna, Waltham, MA (US); Maximillian Taro William Lee, London (GB); Mattia Cocco, London (GB); Boliang Deng, Waltham, MA (US); Jonathan David Beadle, London (GB); Albano Galan Coca, London (GB); Alla Pryyma, Waltham, MA (US); Nicole Danielle Bartolo, Waltham, MA (US); Luke Masterson, London (GB); William Robert Fraser Goundry, Macclesfield (GB)

( * ) Notice: Subject to any disclaimer, the term of this patent is extended or adjusted under 35 U.S.C. 154(b) by 0 days.

(21) Appl. No.: 18/630,179

(22) Filed: Apr. 9, 2024

(65) Prior Publication Data
US 2024/0366781 A1 Nov. 7, 2024

Related U.S. Application Data

(60) Provisional application No. 63/496,709, filed on Apr. 18, 2023.

(51) Int. Cl.
*A61K 47/68* (2017.01)
*A61K 47/54* (2017.01)
*A61K 47/60* (2017.01)
*A61P 35/00* (2006.01)

(52) U.S. Cl.
CPC ........ *A61K 47/6889* (2017.08); *A61K 47/545* (2017.08); *A61K 47/549* (2017.08); *A61K 47/60* (2017.08); *A61K 47/6849* (2017.08); *A61P 35/00* (2018.01)

(58) Field of Classification Search
CPC combination set(s) only.
See application file for complete search history.

(56) References Cited

U.S. PATENT DOCUMENTS

2024/0366768 A1   11/2024   Khan et al.

FOREIGN PATENT DOCUMENTS

| WO | 2007011968 A2 | 1/2007 |
| WO | 2009099741 A1 | 8/2009 |
| WO | 2013053873 A1 | 4/2013 |
| WO | 2013055990 A1 | 4/2013 |
| WO | 2014100762 A1 | 6/2014 |
| WO | 2015057699 A2 | 4/2015 |
| WO | 2015095301 A2 | 6/2015 |
| WO | 2015182984 A1 | 12/2015 |
| WO | 2015195904 A1 | 12/2015 |
| WO | 2015196089 A1 | 12/2015 |
| WO | 2015196167 A1 | 12/2015 |
| WO | 2016094505 A1 | 6/2016 |
| WO | 2016094509 A1 | 6/2016 |
| WO | 2016094517 A1 | 6/2016 |
| WO | 2016149535 A1 | 9/2016 |

(Continued)

OTHER PUBLICATIONS

Jeffrey SC, De Brabander J, Miyamoto J, Senter PD. Expanded Utility of the β-Glucuronide Linker: ADCs That Deliver Phenolic Cytotoxic Agents. ACS Med Chem Lett. Jun. 14, 2010;1(6):277-80. doi: 10.1021/ml100039h. PMID: 24900208; PMCID: PMC4007898. (Year: 2010).*

(Continued)

*Primary Examiner* — Adam Weidner
*Assistant Examiner* — Laura Ann Essex

(57) ABSTRACT

The specification relates to conjugates comprising a linker of Formula (IA):

and pharmaceutically acceptable salts thereof. The specification also relates the use of the conjugates for the treatment of diseases such as cancer, and intermediates useful for the synthesis of the conjugates.

26 Claims, 9 Drawing Sheets

(56) References Cited

FOREIGN PATENT DOCUMENTS

| | | | |
|---|---|---|---|
| WO | WO-2017089895 A1 * | 6/2017 | ............. A61K 31/45 |
| WO | 2017165851 A1 | 9/2017 | |
| WO | 2017214233 A1 | 12/2017 | |
| WO | 2017214282 A1 | 12/2017 | |
| WO | 2017214301 A1 | 12/2017 | |
| WO | 2017214322 A1 | 12/2017 | |
| WO | 2017214335 A1 | 12/2017 | |
| WO | 2017214339 A1 | 12/2017 | |
| WO | 2017214456 A1 | 12/2017 | |
| WO | 2017214458 A2 | 12/2017 | |
| WO | 2017214462 A2 | 12/2017 | |
| WO | 2018031690 A1 | 2/2018 | |
| WO | 2018075600 A1 | 4/2018 | |
| WO | 2018112253 A1 | 6/2018 | |
| WO | 2018175994 A1 | 9/2018 | |
| WO | 2019215510 A2 | 11/2019 | |
| WO | 2019232449 A1 | 12/2019 | |
| WO | 2019236954 A1 | 12/2019 | |
| WO | 2019243825 A1 | 12/2019 | |
| WO | 2020014541 A2 | 1/2020 | |
| WO | 2020089811 A1 | 5/2020 | |
| WO | 2020092617 A1 | 5/2020 | |
| WO | 2020132655 A1 | 6/2020 | |
| WO | 2020154437 A1 | 7/2020 | |
| WO | 2020252015 A1 | 12/2020 | |
| WO | 2020252043 A1 | 12/2020 | |
| WO | 2021046426 A1 | 3/2021 | |
| WO | 2021137646 A1 | 7/2021 | |
| WO | 2021198965 A1 | 10/2021 | |
| WO | 2021198966 A1 | 10/2021 | |
| WO | 2021207701 A1 | 10/2021 | |
| WO | 2022031652 A1 | 2/2022 | |
| WO | 2022048883 A1 | 3/2022 | |
| WO | 2022072538 A1 | 4/2022 | |
| WO | 2022097117 A1 | 5/2022 | |
| WO | 2022112942 A2 | 6/2022 | |
| WO | 2022155518 A1 | 7/2022 | |
| WO | 2022170002 A1 | 8/2022 | |
| WO | 2022211508 A1 | 10/2022 | |
| WO | 2024006272 A1 | 1/2024 | |
| WO | 2024006542 A1 | 1/2024 | |
| WO | 2024015229 A1 | 1/2024 | |

OTHER PUBLICATIONS

Jeffrey Scott, Andreyka JB, Bernhardt SX, Kissler KM, Kline T, Lenox JS, Moser RF, Nguyen MT, Okeley NM, Stone IJ, Zhang X, Senter PD. Development and properties of beta-glucuronide linkers for monoclonal antibody-drug conjugates. Bioconjug Chem. May-Jun. 2006;17(3):831-40. doi: 10.1021/bc0600214. (Year: 2006).*

Ralhan, Krittika; et al. RSC Adv., 2015, 5, 104417-104425. https://doi.org/10.1039/C5RA23441G (Year: 2015).*

Jasinska, Lidia; et al. Macromolecules 2011, 44, 9, 3458-3466. https://doi.org/10.1021/ma200256v (Year: 2011).*

Han S., et al., "The Potential of Topoisomerase Inhibitor-Based Antibody-Drug Conjugates", Pharmaceutics, vol. 14, No. 8, Aug. 16, 2022, pp. 1-15.

International Search Report and Written Opinion for International Application No. PCT/EP2024/059544, mailed Jul. 4, 2024, 13 Pages.

International Search Report and Written Opinion for International Application No. PCT/EP2024/059545, mailed Jul. 4, 2024, 15 Pages.

Weng W., et al., "Antibody-Exatecan Conjugates with a Novel Self-immolative Moiety Overcome Resistance in Colon and Lung Cancer", Cancer Discovery, vol. 13, No. 4, Apr. 3, 2023, pp. 951-973, doi: 10.1158/2159-8290.CD-22-1368.

* cited by examiner

CONJUGATES COMPRISING CLEAVABLE BETA-GLUCURONIDE-CONTAINING LINKERS

CROSS-REFERENCE TO RELATED APPLICATION

This application claims benefit under 35 U.S.C. § 119 (e) of the U.S. Provisional Application No. 63/496,709, filed Apr. 18, 2023. The above listed application is incorporated by reference herein in its entirety for all purposes.

This specification relates to certain conjugates comprising cleavable linkers, and to pharmaceutical compositions containing them. This specification also relates to the use of the conjugates in methods of treating diseases such as cancer. This specification further relates to processes and intermediate compounds involved in the preparation of the conjugates.

BACKGROUND

Antibody drug conjugates (ADCs) are an established method to deliver a drug to biological target. It is possible to use an enzymatically cleavable linker to release free drug at the target, so that the free drug can have a therapeutic effect. Through transcriptomic and proteomic profiling of various solid tumour cell lines, β-glucuronidase expression has been identified as being upregulated and typically localised to the lysosome. WO2007011968 and WO2015182984 disclose certain antibody drug conjugates comprising β-glucuronidase-cleavable linkers.

There remains a need for conjugates having β-glucuronidase-cleavable linkers that can selectively deliver a drug to a biological target and that have favourable physicochemical properties, including solubility and lipophilicity. The conjugates of the disclosure may be used for the treatment of diseases such as cancer.

General Description

The specification relates to conjugates comprising a linker of Formula (IA):

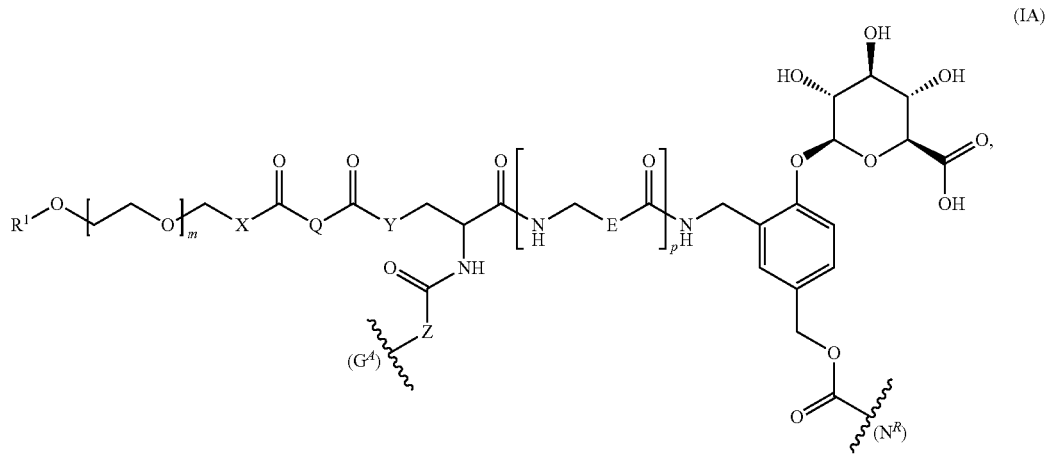

and pharmaceutically acceptable salts thereof, as defined herein.

In a first aspect there is provided a conjugate of Formula (I)

  (I)

or a pharmaceutically acceptable salt thereof, wherein
Ab is an antibody or antigen-binding fragment thereof,
k is an integer from 1 to 10,
each $G^A$ is independently a conjugation group conjugated to the antibody or antigen-binding fragment thereof,
each $D^R$ is independently a drug comprising a nitrogen atom $N^R$,
each $J^A$ is independently a group of Formula (IA)

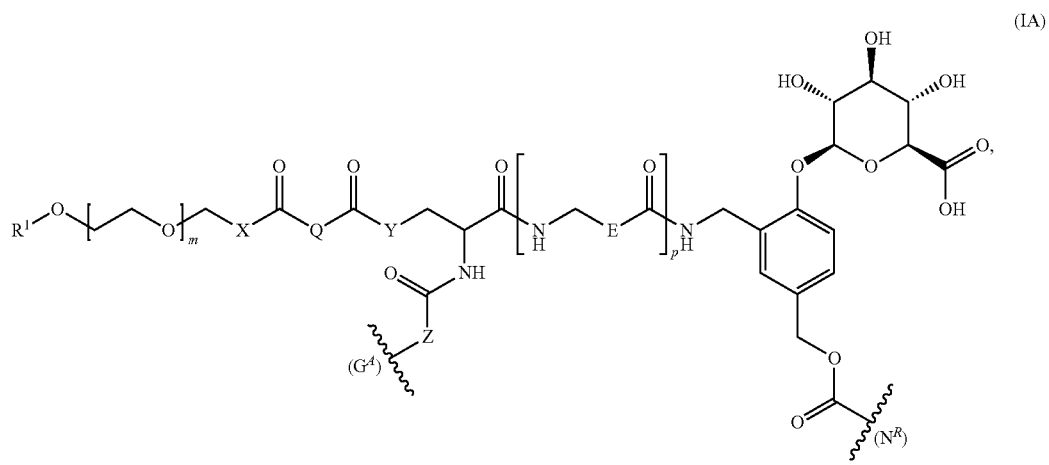

E is $(CH_2)_{n1}$, wherein n1 is 0, 1, 2 or 3,
Q is

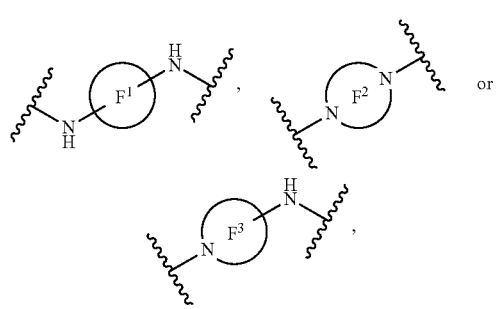

wherein Ring $F^1$ is a saturated bicyclic ring having 6, 7, or 8 carbon atoms and optionally 1 or 2 oxygen atoms, Ring $F^2$ is a saturated bicyclic ring having the 2 nitrogen atoms shown, 4, 5, 6, 7 or 8 carbon atoms and optionally 1 oxygen atom, and Ring $F^3$ is a saturated bicyclic ring having the 1 nitrogen atom shown, 5, 6, 7 or 8 carbon atoms and optionally 1 oxygen atom,
$R^1$ is $C_{1-4}$ alkyl,
X is $(CH_2)_{n2}$, wherein n2 is 0, 1, 2 or 3,
Y is $(CH_2)_{n3}$, wherein n3 is 0, 1, 2, 3 or 4,
Z is $(CH_2)_{n4}$, wherein n4 is 1, 2, 3, 4 or 5, m is an integer from 5 to 17,
p is 1 or 0,
$(G^A)$ indicates the point of attachment to $G^A$, and
$(N^R)$ indicates the point of attachment to the nitrogen atom $N^R$.

In a further aspect there is provided a conjugate of Formula (IC)

  (IC)

or a pharmaceutically acceptable salt thereof, wherein each $D^C$ is

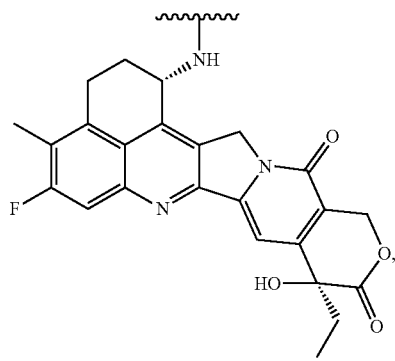 [SMILES: *N[C@H]1CCc2c(C)c(F)cc3nc4c(c1c23)Cn1c-4cc2c(c1=O)COC(=O)[C@]2(O)CC]

each $J^A$ is independently a group of Formula (ICA)

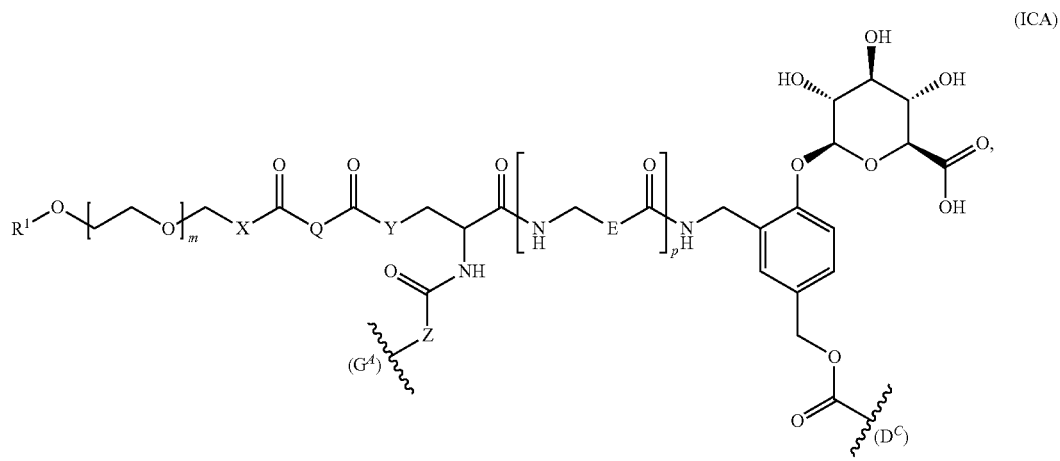

wherein Ab, $G^A$, k, E, Q, $R^1$, X, Y, Z, m and p are as defined above for a conjugate of Formula (I), ($G^A$) indicates the point of attachment to $G^A$, and ($D^C$) indicates the point of attachment to $D^C$.

In a further aspect there is provided a conjugate of Formula (IM)

$$Ab\text{-}(G^A\text{-}J^A\text{-}D^M)_k \quad (IM)$$

or a pharmaceutically acceptable salt thereof, wherein each $D^M$ is

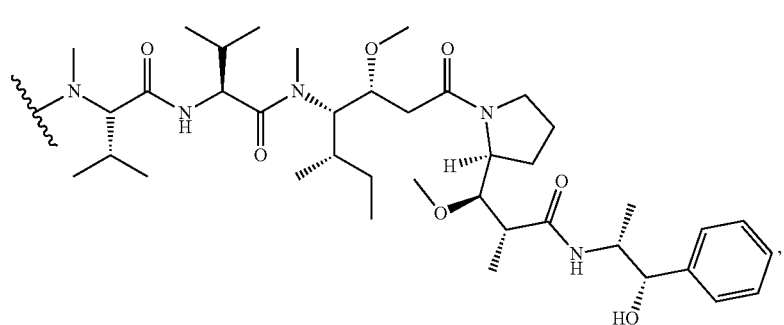

each $J^A$ is independently a group of Formula (IMA)

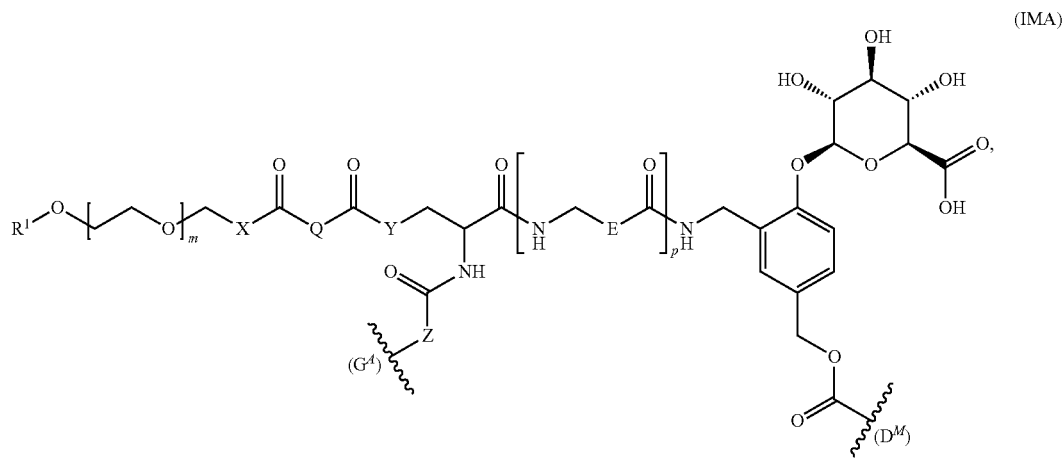

wherein Ab, $G^A$, k, E, Q, $R^1$, X, Y, Z, m and p are as defined above for a conjugate of Formula (I), ($G^A$) indicates the point of attachment to $G^A$, and ($D^M$) indicates the point of attachment to $D^M$.

In a further aspect there is provided a conjugate of Formula (IT)

$$Ab-(G^A-J^A-D^C)_k \qquad (IT)$$

or a pharmaceutically acceptable salt thereof, wherein each $D^T$ is

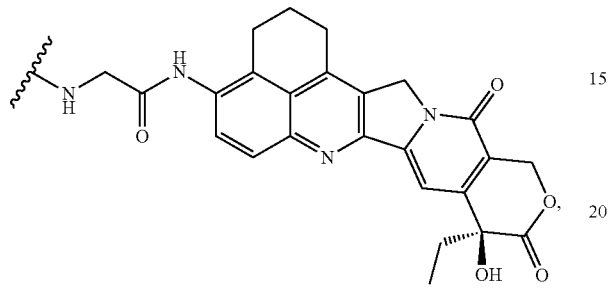

each $J^A$ is independently a group of Formula (ITA)

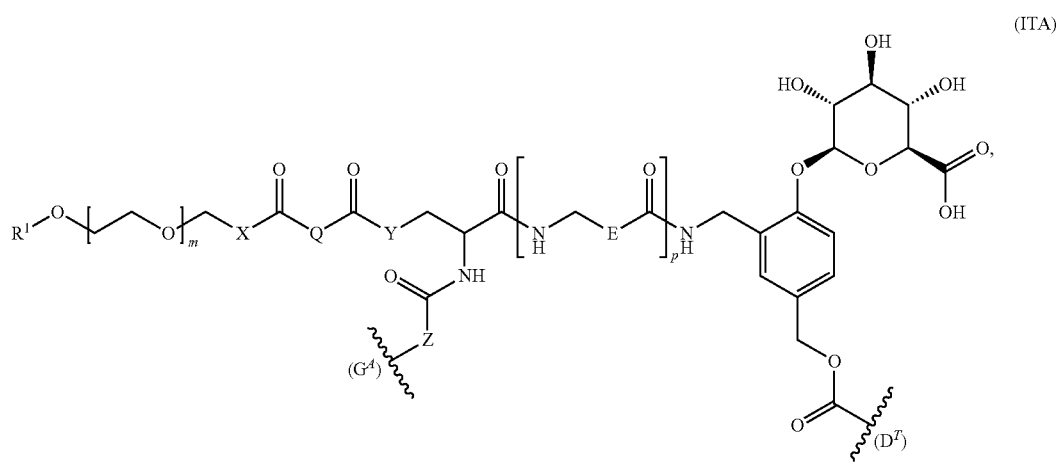

wherein Ab, $G^A$, k, E, Q, $R^1$, X, Y, Z, m and p are as defined above for a conjugate of Formula (I), ($G^A$) indicates the point of attachment to $G^A$, and ($D^T$) indicates the point of attachment to $D^T$.

In a further aspect there is provided a pharmaceutical composition comprising a conjugate of Formula (I), (IC), (IM) or (IT), or a pharmaceutically acceptable salt thereof and a pharmaceutically acceptable excipient.

In a further aspect there is provided a conjugate of Formula (I), (IC), (IM) or (IT), or a pharmaceutically acceptable salt thereof, for use in therapy.

In a further aspect there is provided a conjugate of Formula (I), (IC), (IM) or (IT), or a pharmaceutically acceptable salt thereof, for use in the treatment of cancer.

In a further aspect there is provided the use of a conjugate of Formula (I), (IC), (IM) or (IT), or a pharmaceutically acceptable salt thereof, in the manufacture of a medicament.

In a further aspect there is provided the use of a conjugate of Formula (I), (IC), (IM) or (IT), or a pharmaceutically acceptable salt thereof, in the manufacture of a medicament for the treatment of cancer.

In a further aspect there is provided a method of treating cancer in a patient comprising administering to the patient an effective amount of a conjugate of Formula (I), (IC), (IM) or (IT), or a pharmaceutically acceptable salt thereof.

In a further aspect there is provided a compound of Formula (II)

$$G^B-J^B-D^R \qquad (II)$$

or a salt thereof, wherein $G^B$ is a conjugation group for conjugation to an antibody or antigen-binding fragment thereof, $D^R$ is a drug comprising a nitrogen atom $N^R$,
$J^B$ is a group of Formula (IIA)

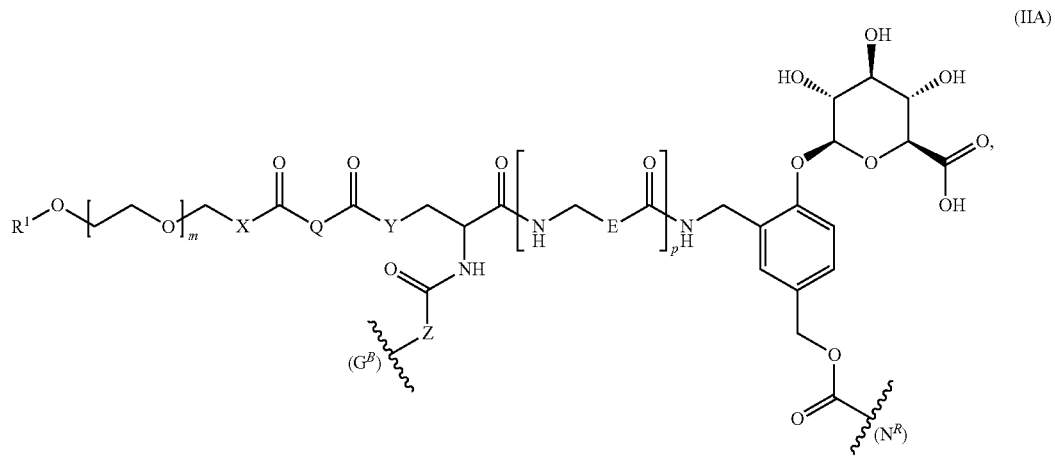

(IIA)

wherein E, Q, $R^1$, X, Y, Z, m and p are as defined above for a conjugate of Formula (I), ($G^B$) indicates the point of attachment to $G^B$, and ($N^R$) indicates the point of attachment to the nitrogen atom $N^R$.

In a further aspect there is provided a compound of Formula (IIC)

$$G^B\text{-}J^B\text{-}D^C \qquad \text{(IIC)}$$

or a salt thereof, wherein $G^B$ is a conjugation group for conjugation to an antibody or antigen-binding fragment thereof,
$J^B$ is a group of Formula (IICA)

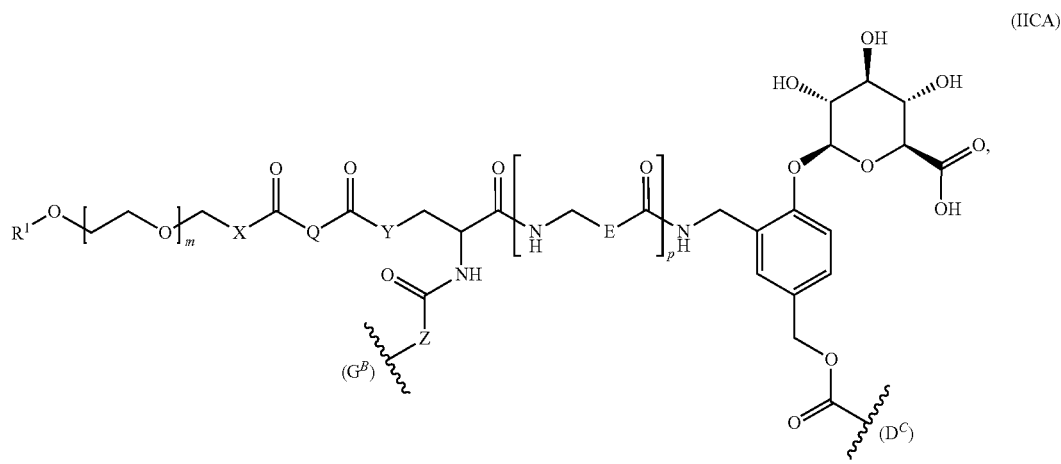

(IICA)

wherein $D^C$, E, Q, $R^1$, X, Y, Z, m and p are as defined above for a conjugate of Formula (IC), ($G^B$) indicates the point of attachment to $G^B$, and ($D^C$) indicates the point of attachment to $D^C$.

In a further aspect there is provided a compound of Formula (IIM)

$$G^B\text{-}J^B\text{-}D^M \qquad (IIM)$$

or a salt thereof, wherein $G^B$ is a conjugation group for conjugation to an antibody or antigen-binding fragment thereof, $J^B$ is a group of Formula (IIMA)

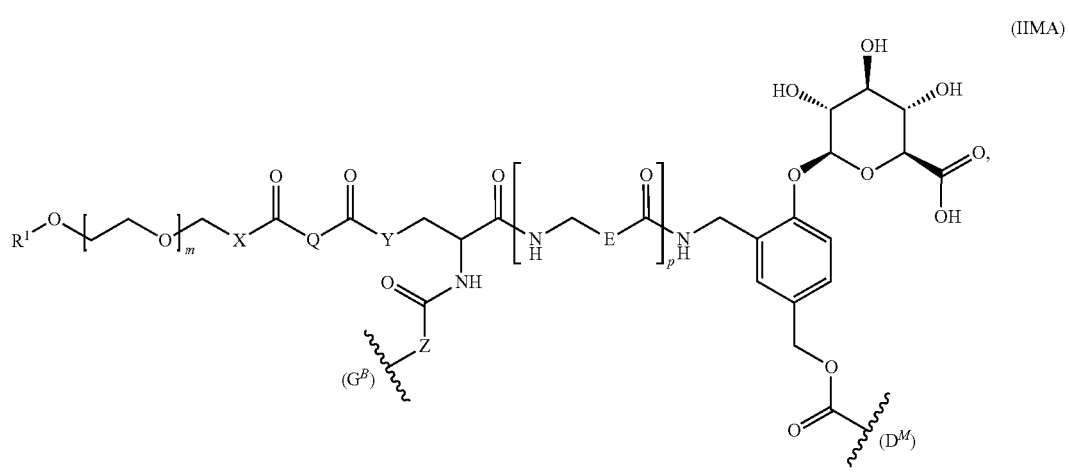

(IIMA)

wherein $D^M$, E, Q, $R^1$, X, Y, Z, m and p are as defined above for a conjugate of Formula (IM), ($G^B$) indicates the point of attachment to $G^B$, and ($D^M$) indicates the point of attachment to $D^M$.

In a further aspect there is provided a compound of Formula (IIT)

$$G^B\text{-}J^B\text{-}D^T \qquad (IIT)$$

or a salt thereof, wherein $G^B$ is a conjugation group for conjugation to an antibody or antigen-binding fragment thereof, $J^B$ is a group of Formula (IITA)

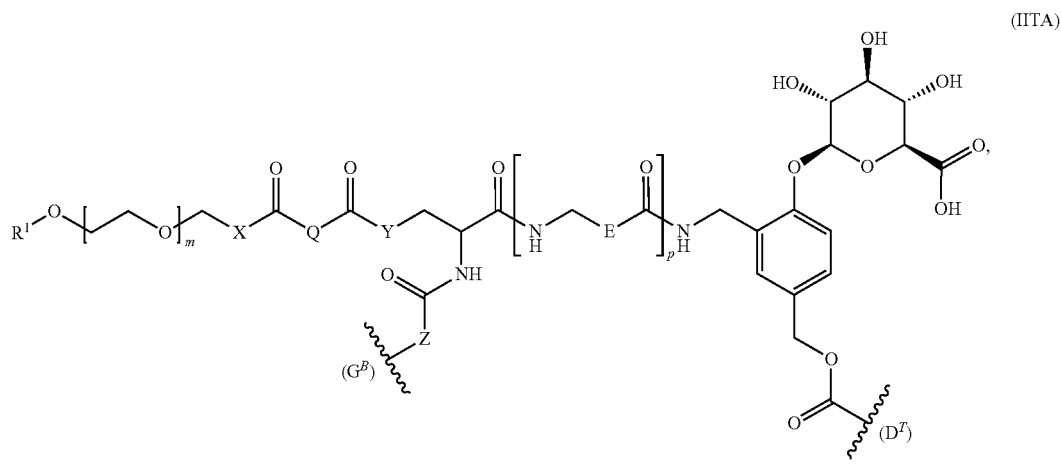

(IITA)

wherein $D^T$, E, Q, $R^1$, X, Y, Z, m and p are as defined above for a conjugate of Formula (IT), ($G^B$) indicates the point of attachment to $G^B$, and ($D^T$) indicates the point of attachment to $D^T$.

In a further aspect there is provided intermediates useful for the synthesis of a compound of Formula (II), (IIC), (IIM) or (IIT), or a salt thereof.

A conjugate of Formula (I), (IC), (IM) or (IT), or a pharmaceutically acceptable salt thereof, may undergo enzymatic cleavage to release a free drug. Conjugates of Formula (I), (IC), (IM) or (IT) may exhibit improved efficacy and/or advantageous physical properties (for example, higher stability, lower lipophilicity, higher aqueous solubility, higher permeability and/or lower plasma protein binding), and/or favourable toxicity profiles (for example reduced off target toxicity), and/or favourable metabolic or pharmacokinetic profiles, in comparison with other conjugates. In embodiments, Conjugates of Formula (I), (IC), (IM) or (IT) exhibit improved colloidal stability in comparison with other conjugates. As such, conjugates of Formula (I), (IC), (IM) or (IT) may be especially suitable for use in therapy, such as the treatment of cancer.

Definitions

So that the present specification may be more readily understood, certain terms are explicitly defined below. In addition, definitions are set forth as appropriate throughout the detailed description. Where examples are provided for a definition, they are not limiting.

The prefix $C_{x-y}$, where x and y are integers, indicates the numerical range of carbon atoms that are present in a group.

As used herein the term "alkyl" refers to a saturated, linear or branched hydrocarbon radical having the specified number of carbon atoms. Examples of $C_{1-4}$alkyl groups include methyl (Me), ethyl (Et), n-propyl ($^n$Pr), i-propyl ($^i$Pr), n-butyl ($^n$Bu), i-butyl ($^i$Bu), s-butyl ($^s$Bu), and t-butyl ($^t$Bu). Examples of $C_{1-6}$ alkyl groups include methyl, ethyl, n-propyl, i-propyl, n-butyl, i-butyl, s-butyl, t-butyl, n-pentyl and n-hexyl.

As used herein the term "bicyclic ring" refers to a fused, bridged or spirocyclic bicyclic ring.

As used herein the term "conjugation group for conjugation to an antibody, or antigen-binding fragment thereof" refers to an atom or group of atoms capable of forming a covalent bond to an antibody, or antigen-binding fragment thereof, through a chemical reaction.

The use of "—*" in formulas of this specification indicates the point of attachment to the antibody or antigen-binding fragment thereof. By way of illustration

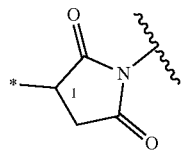 [SMILES: *C1CC(=O)N(*)C1=O]

indicates that there is a covalent bond connecting the antibody, or antigen-binding fragment thereof, to the carbon atom marked 1.

For the avoidance of doubt, the use of "⊥" in formulas of this specification denotes the point of covalent attachment to a group, where the group is other than the antibody or antigen-binding fragment thereof.

Certain embodiments of this specification include a group which is said to be "optionally substituted". In further embodiments said group is unsubstituted.

As used herein

is ring $F^1$,

is ring $F^2$, and

is ring $F^3$.

Units, prefixes, and symbols are denoted in their International System of Units (SI) accepted form. Numeric ranges are inclusive of the numbers defining the range.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary of Biochemistry and Molecular Biology, Revised, 2000, Oxford University Press, provide one of skill with a general dictionary of many of the terms used in this disclosure.

DESCRIPTION OF FIGURES

Embodiments and experiments illustrating the principles of the disclosure will now be discussed with reference to the accompanying figures in which.

DETAILED DESCRIPTION

Figure 1A:
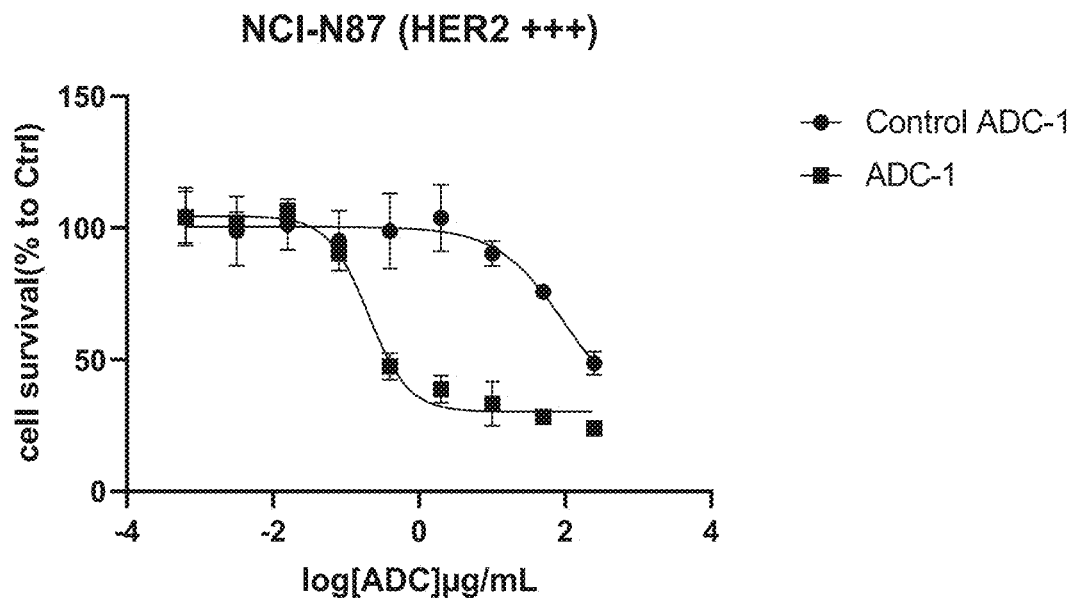
FIG. 1A illustrates cytotoxicity data for ADC-1 and Control ADC-1 in a Her2+++ NCI-N87 cell line.
Figure 1B:
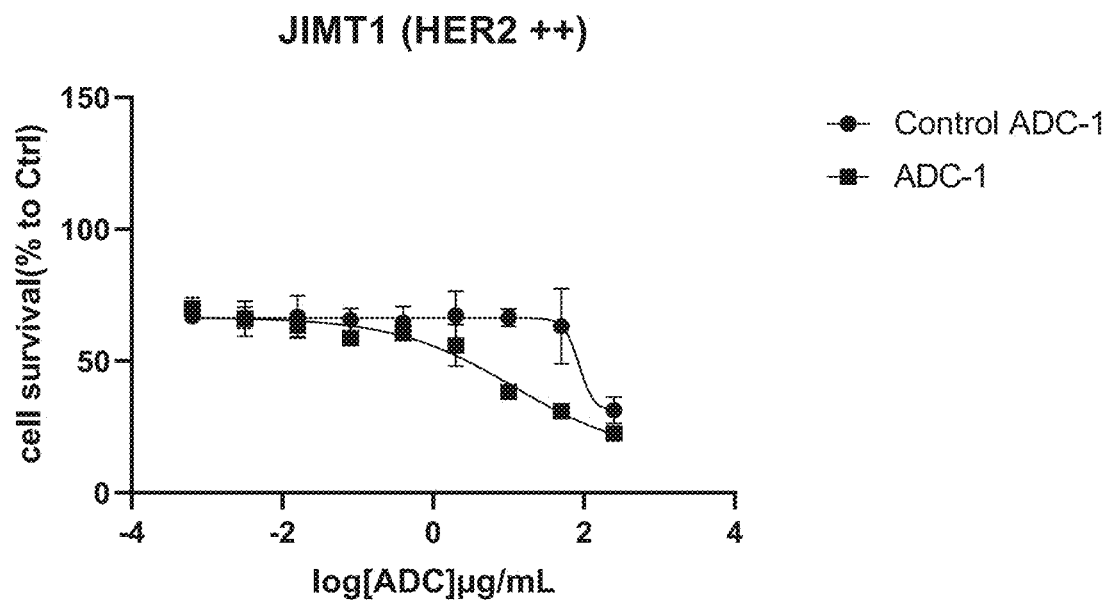
FIG. 1B illustrates cytotoxicity data for ADC-1 and Control ADC-1 in a HER2++ JIMT1 cell line.
Figure 2A:
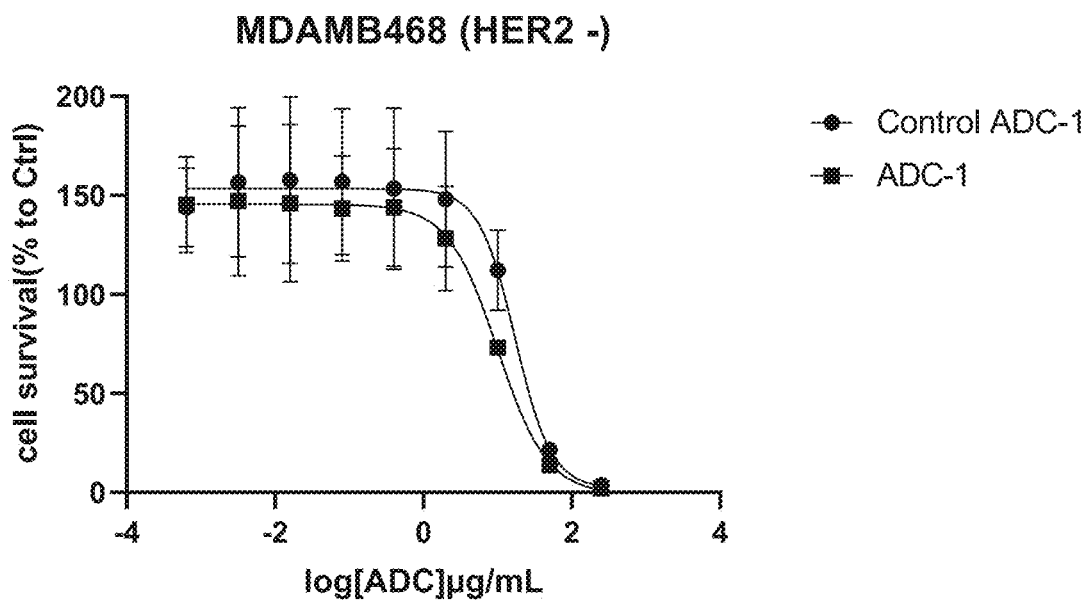
FIG. 2A illustrates cytotoxicity data for ADC-1 and Control ADC-1 in a HER2− MDAMB468 cell line.
Figure 2B:
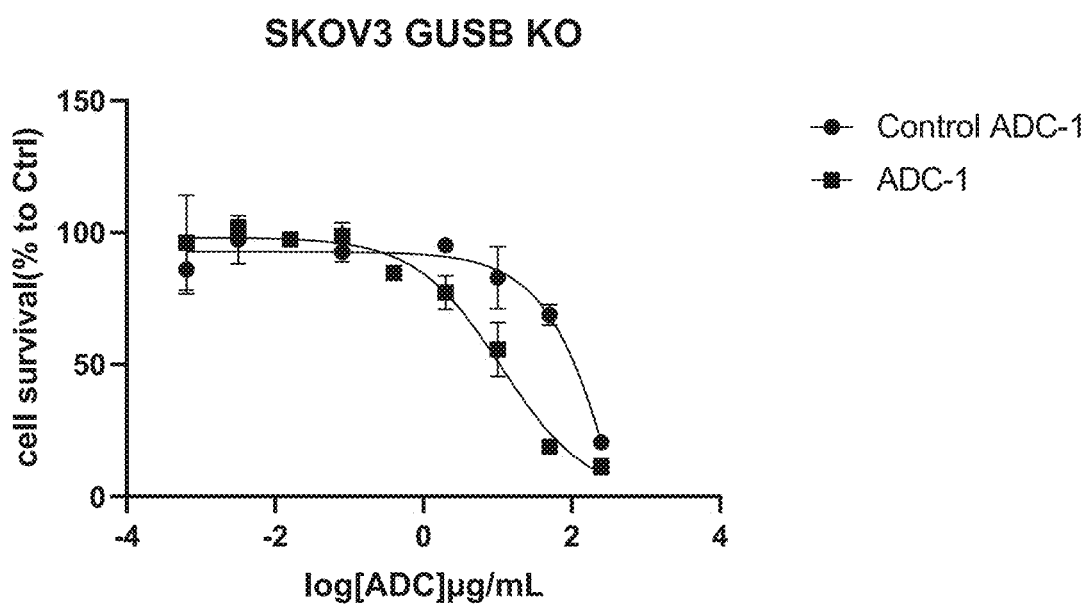
FIG. 2B illustrates cytotoxicity data for ADC-1 and Control ADC-1 in a Her2+++ SKOV3 cell line.
Figure 3:
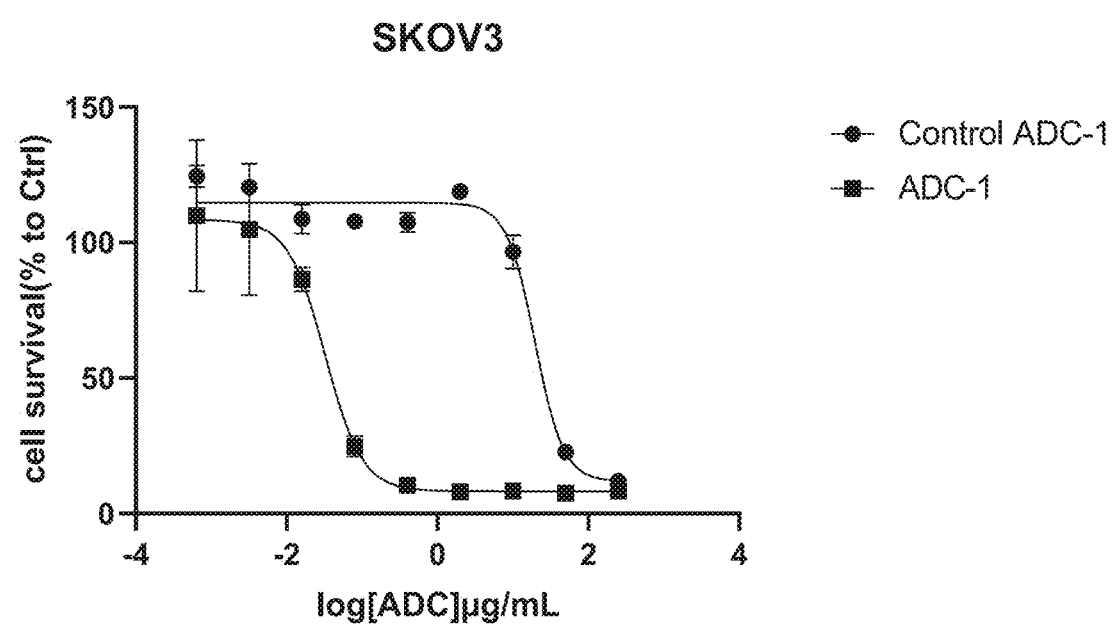
FIG. 3 illustrates cytotoxicity data for ADC-1 and Control ADC-1 in a SKOV3 GUSB KO cell line.
Figure 4A:
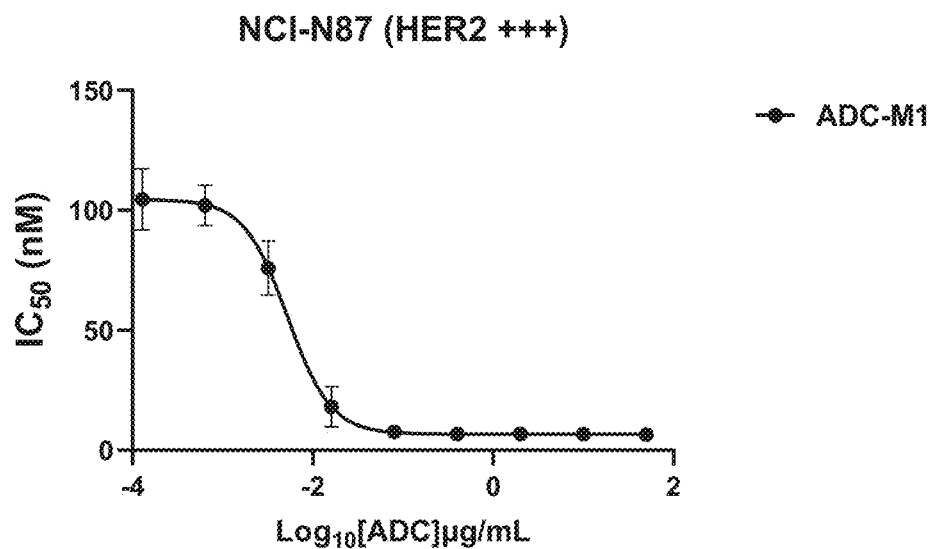
FIG. 4A illustrates cytotoxicity data for ADC-M1 in a Her2+++ NCI-N87 cell line.
Figure 4B:
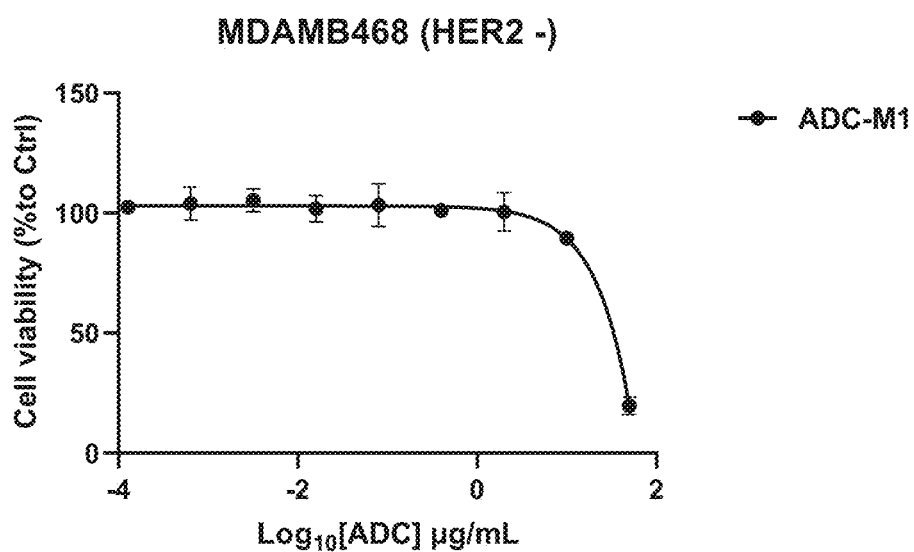
FIG. 4B illustrates cytotoxicity data for ADC-M1 in a HER2− MDAMB468 cell line.
Figure 5A:
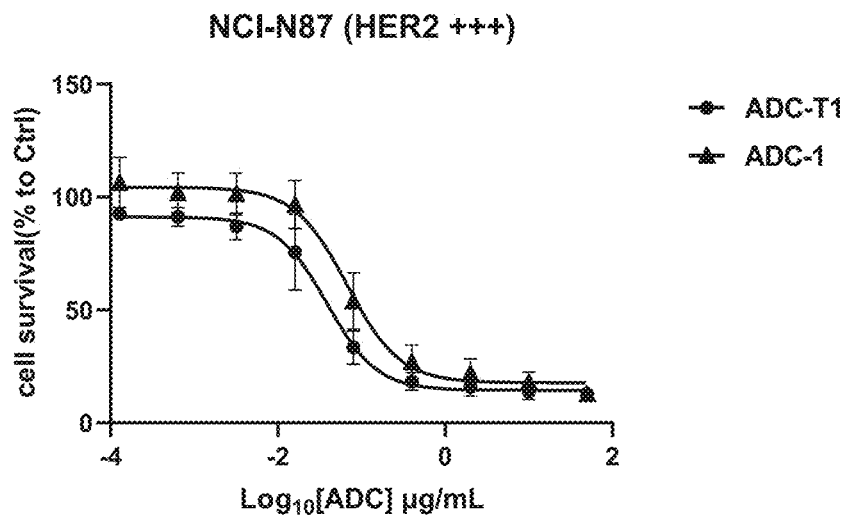
FIG. 5A illustrates cytotoxicity data for ADC-T1 and ADC-1 in a Her2+++ NCI-N87 cell line.
Figure 5B:
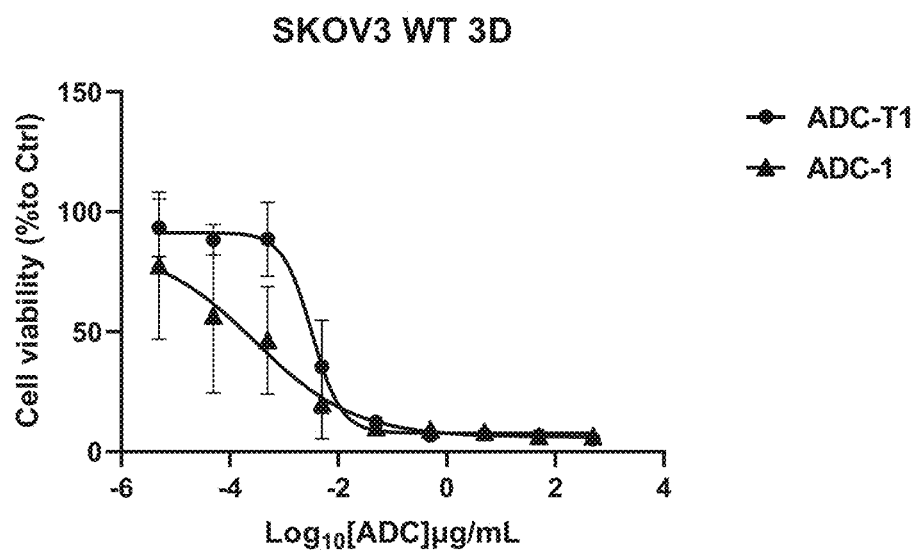
FIG. 5B illustrates cytotoxicity data for ADC-T1 and ADC-1 in a HER2+++/GUSB+++ SKOV3 WT cell line.
Figure 5C:
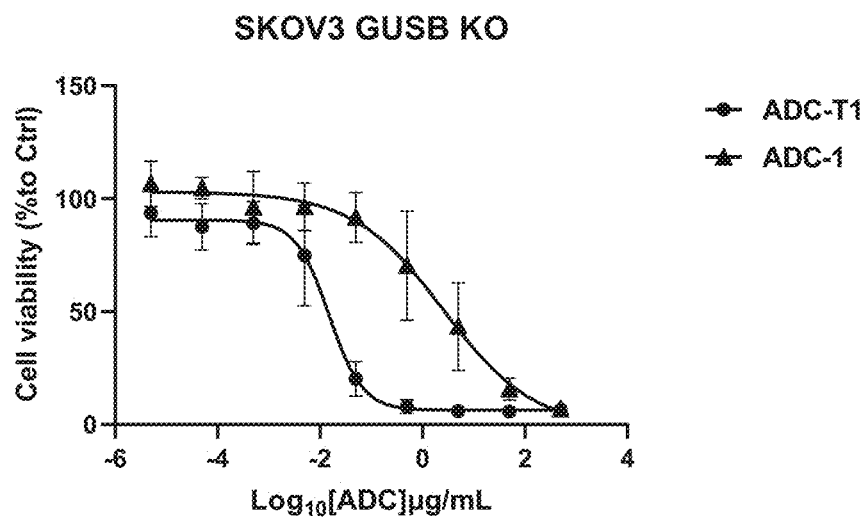
FIG. 5C illustrates cytotoxicity data for ADC-T1 and ADC-1 in a HER2+++/GUSB-SKOV3 GUSB KO cell line.
Figure 5D:
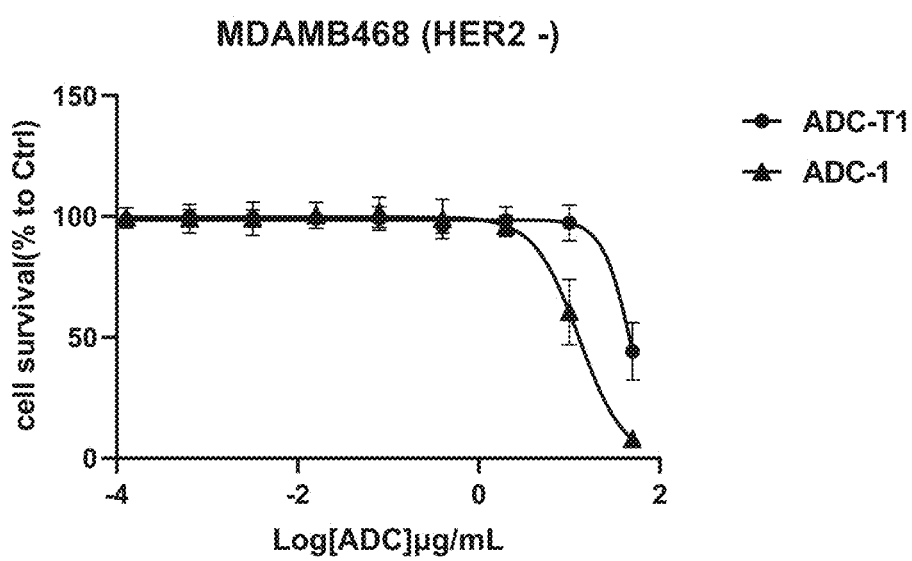
FIG. 5D illustrates cytotoxicity data for ADC-T1 and ADC-1 in a HER2− MDAMB468 cell line.
Figure 6A:
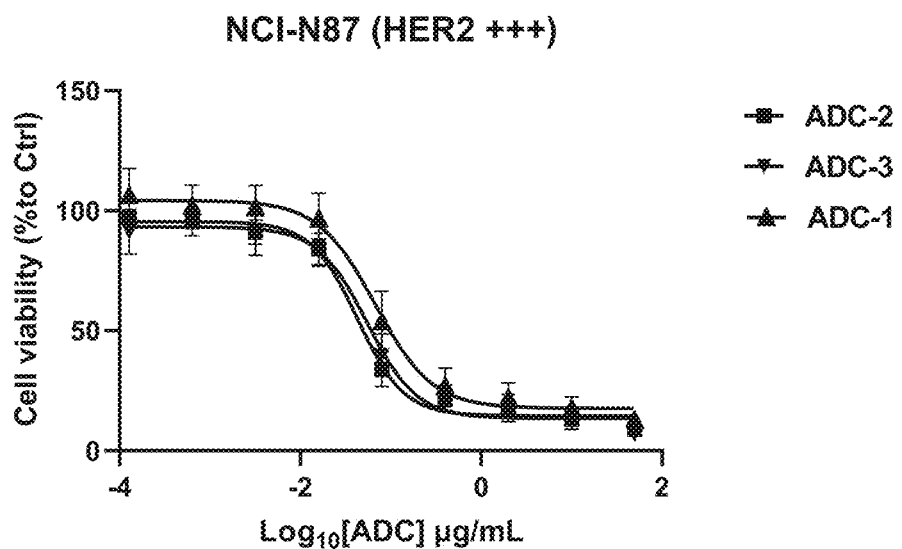
FIG. 6A illustrates cytotoxicity data for ADC-3, ADC-2 and ADC-1 in a Her2+++ NCI-N87 cell line.
Figure 6B:
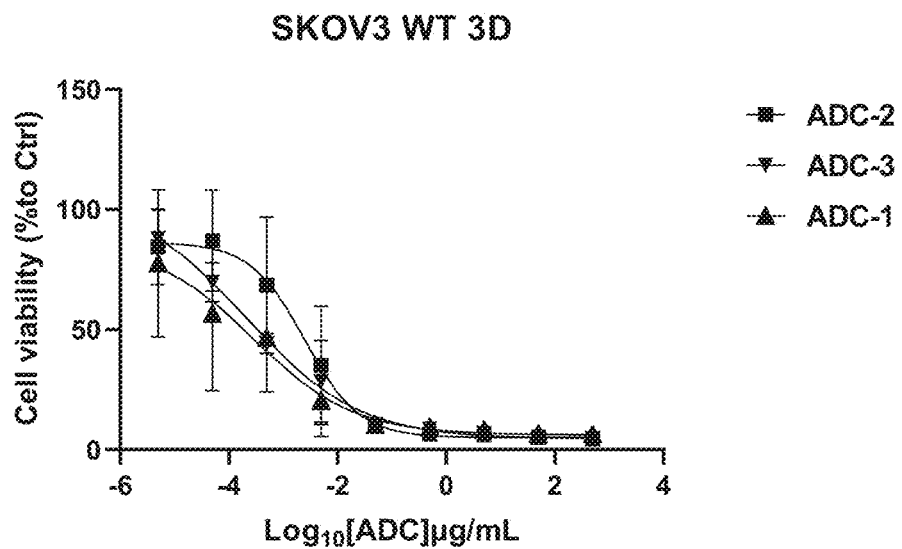
FIG. 6B illustrates cytotoxicity data for ADC-3, ADC-2 and ADC-1 in a HER2+++/GUSB+++ SKOV3 WT cell line.
Figure 6C:
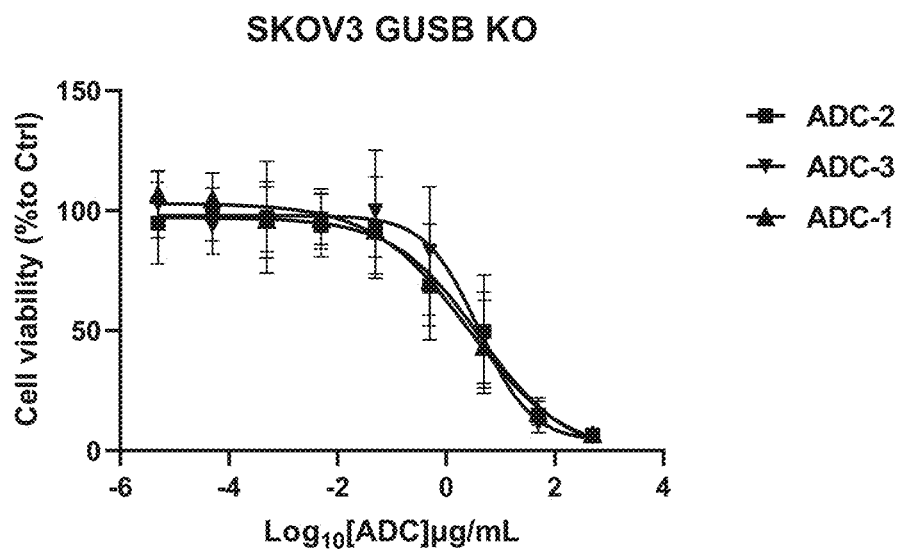
FIG. 6C illustrates cytotoxicity data for ADC-3, ADC-2 and ADC-1 in a HER2+++/GUSB-SKOV3 GUSB KO cell line.
Figure 6D:
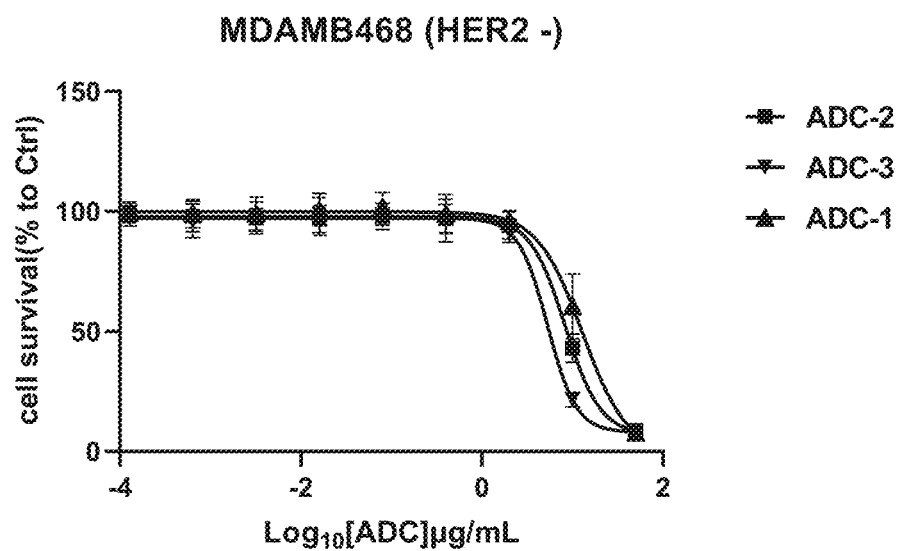
FIG. 6D illustrates cytotoxicity data for ADC-3, ADC-2 and ADC-1 in a HER2– MDAMB468 cell line.

In one aspect, this specification provides a conjugate of Formula (I), (IC), (IM) or (IT), or a pharmaceutically acceptable salt thereof, as defined above.

In embodiments there is provided a conjugate of Formula (I), (IC), (IM) or (IT), or a pharmaceutically acceptable salt thereof, wherein k is 1, 2, 3, 4, 5, 6, 7, 8, 9 or 10. In further embodiments k is an integer from 2 to 10. In further embodiments k is an integer from 2 to 8. In further embodiments k is 4. In further embodiments k is 8.

In embodiments there is provided a conjugate of Formula (I), (IC), (IM) or (IT), or a pharmaceutically acceptable salt thereof, wherein $G^A$ is selected from

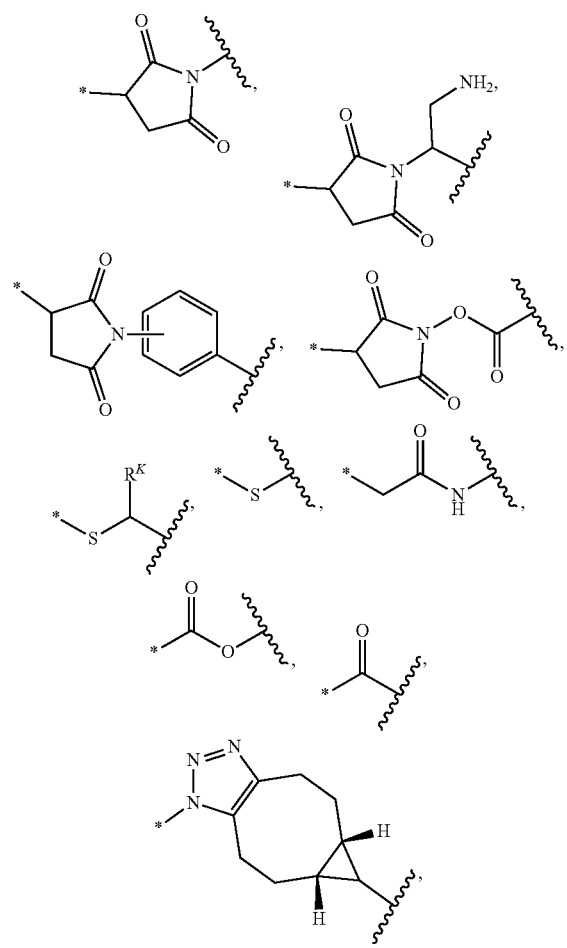

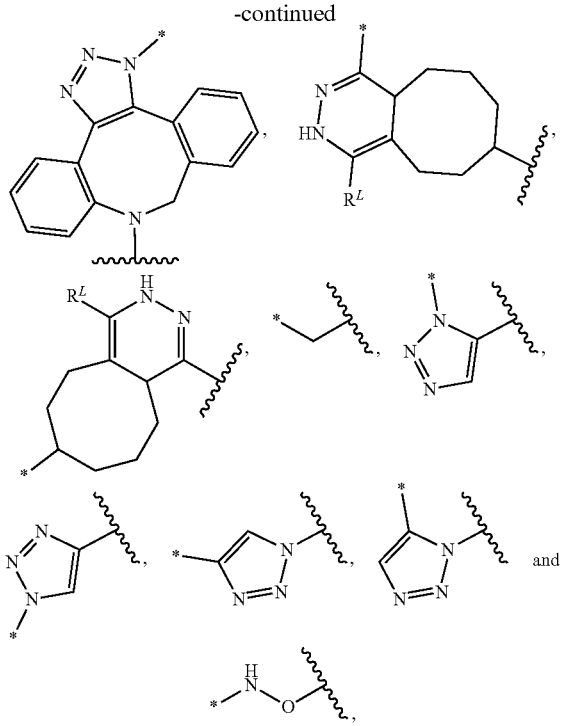

wherein $R^K$ is H or $CH_3$, $R^L$ is $C_{1-6}$ alkyl, and ⟋* indicates the point of attachment to the antibody, or antigen-binding fragment thereof.

In embodiments there is provided a conjugate of Formula (I), (IC), (IM) or (IT), or a pharmaceutically acceptable salt thereof, wherein $G^A$ is selected from

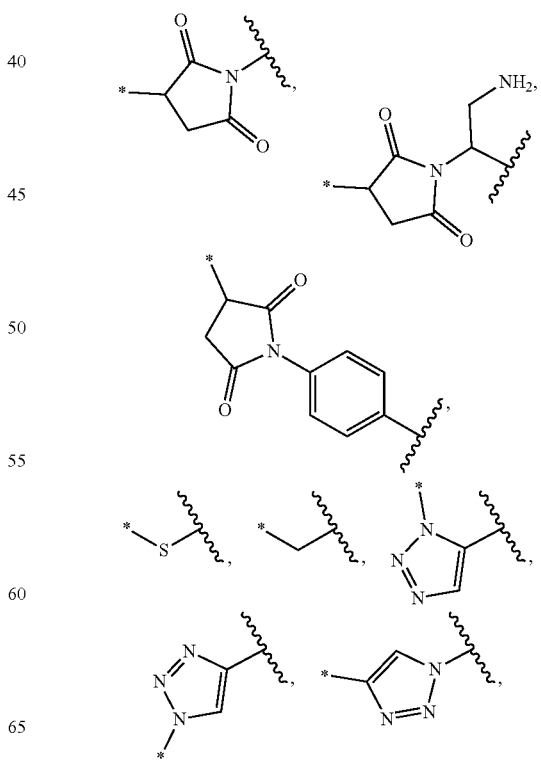

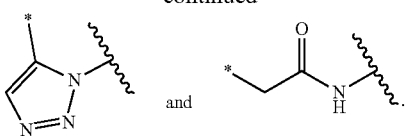 and 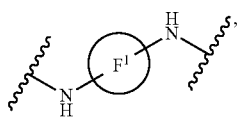

In embodiments there is provided a conjugate of Formula (I), (IC), (IM) or (IT), or a pharmaceutically acceptable salt thereof, wherein $G^A$ is

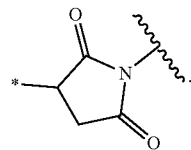 [SMILES: *C1CC(=O)N(*)C1=O]

In embodiments there is provided a conjugate of Formula (I), (IC), (IM) or (IT), or a pharmaceutically acceptable salt thereof, wherein $G^A$ is

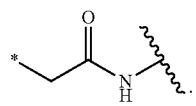

In embodiments there is provided a conjugate of Formula (I), (IC), (IM) or (IT), or a pharmaceutically acceptable salt thereof, wherein $G^A$ is

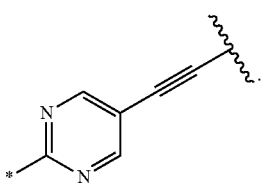 [SMILES: *C#Cc1cnc(*)nc1]

In embodiments there is provided a conjugate of Formula (I), (IC), (IM) or (IT), or a pharmaceutically acceptable salt thereof, wherein Q is

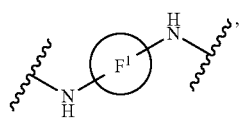

and wherein ring $F^1$ is a saturated bicyclic ring having 6, 7 or 8 carbon atoms and optionally 1 or 2 oxygen atoms. In further embodiments the bicyclic ring is a fused bicyclic ring.

In embodiments there is provided a conjugate of Formula (I), (IC), (IM) or (IT), or a pharmaceutically acceptable salt thereof, wherein Q is and ring F is a saturated bicyclic ring having 6, 7 or 8 carbon atoms and 1 or 2 oxygen atoms. In further embodiments the bicyclic ring is a fused bicyclic ring.

In embodiments there is provided a conjugate of Formula (I), (IC), (IM) or (IT), or a pharmaceutically acceptable salt thereof, wherein Q is

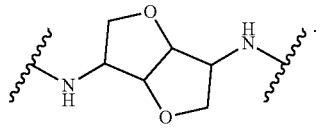 [SMILES: *NC1COC2C(N*)COC12]

In embodiments there is provided a conjugate of Formula (I), (IC), (IM) or (IT), or a pharmaceutically acceptable salt thereof, wherein Q is

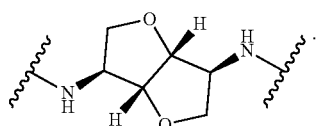

In embodiments there is provided a conjugate of Formula (I), (IC), (IM) or (IT), or a pharmaceutically acceptable salt thereof, wherein Q is

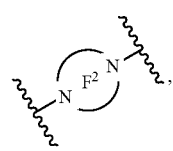

and wherein Ring $F^2$ is a saturated bicyclic ring having the 2 nitrogen atoms shown, 4, 5, 6, 7 or 8 carbon atoms and optionally 1 oxygen atom. In further embodiments the bicyclic ring is a spirocyclic bicyclic ring. In further embodiments the bicyclic ring is a bridged bicyclic ring.

In embodiments there is provided a conjugate of Formula (I), (IC), (IM) or (IT), or a pharmaceutically acceptable salt thereof, wherein Q is

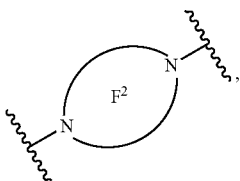

and wherein Ring $F^2$ is a saturated bicyclic ring having the 2 nitrogen atoms shown and 4, 5, 6, 7 or 8 carbon atoms. In further embodiments the bicyclic ring is a spirocyclic bicyclic ring. In further embodiments the bicyclic ring is a bridged bicyclic ring.

In embodiments there is provided a conjugate of Formula (I), (IC), (IM) or (IT), or a pharmaceutically acceptable salt thereof, wherein Q is

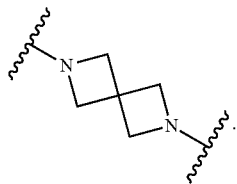 [SMILES: *N1CC2(C1)CN(*)C2]

In embodiments there is provided a conjugate of Formula (I), (IC), (IM) or (IT), or a pharmaceutically acceptable salt thereof, wherein Q is

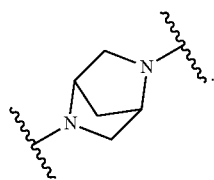 [SMILES: *N1CC2CC1CN2*]

In embodiments there is provided a conjugate of Formula (I), (IC), (IM) or (IT), or a pharmaceutically acceptable salt thereof, wherein Q is

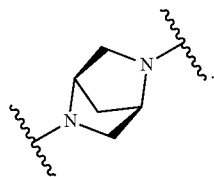 [SMILES: *N1C[C@H]2C[C@@H]1CN2*]

In embodiments there is provided a conjugate of Formula (I), (IC), (IM) or (IT), or a pharmaceutically acceptable salt thereof, wherein Q is

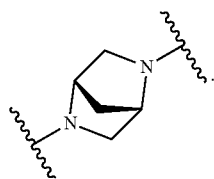 [SMILES: *N1C[C@@H]2C[C@H]1CN2*]

In embodiments there is provided a conjugate of Formula (I), (IC), (IM) or (IT), or a pharmaceutically acceptable salt thereof, wherein Q is

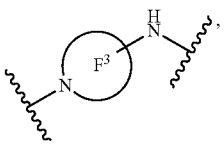

wherein Ring $F^3$ is a saturated bicyclic ring having the 1 nitrogen atom shown, 5, 6, 7 or 8 carbon atoms and optionally 1 oxygen atom. In further embodiments the bicyclic ring is a spirocyclic bicyclic ring. In further embodiments the bicyclic ring is a bridged bicyclic ring.

In embodiments there is provided a conjugate of Formula (I), (IC), (IM) or (IT), or a pharmaceutically acceptable salt thereof, wherein Q is

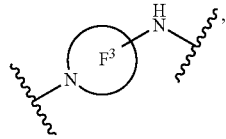

wherein Ring $F^3$ is a saturated bicyclic ring having the 1 nitrogen atom shown and 5, 6, 7 or 8 carbon atoms. In further embodiments the bicyclic ring is a spirocyclic bicyclic ring. In further embodiments the bicyclic ring is a bridged bicyclic ring.

In embodiments there is provided a conjugate of Formula (I), (IC), (IM) or (IT), or a pharmaceutically acceptable salt thereof, wherein E is $(CH_2)_{n1}$, wherein n1 is 0, 1, 2 or 3. In further embodiments E is a covalent bond. In further embodiments E is $CH_2$. In further embodiments E is $(CH_2)_2$. In further embodiments E is $(CH_2)_3$.

In embodiments there is provided a conjugate of Formula (I), (IC), (IM) or (IT), or a pharmaceutically acceptable salt thereof, wherein X is $(CH_2)_{n2}$, wherein n2 is 0, 1, 2 or 3. In further embodiments X is a covalent bond. In further embodiments X is $CH_2$. In further embodiments X is $(CH_2)_2$. In further embodiments X is $(CH_2)_3$.

In embodiments there is provided a conjugate of Formula (I), (IC), (IM) or (IT), or a pharmaceutically acceptable salt thereof, wherein Y is $(CH_2)_{n3}$, wherein n3 is 0, 1, 2, 3 or 4. In further embodiments Y is a covalent bond. In further embodiments Y is $CH_2$. In further embodiments Y is $(CH_2)_2$. In further embodiments Y is $(CH_2)_3$. In further embodiments Y is $(CH_2)_4$.

In embodiments there is provided a conjugate of Formula (I), (IC), (IM) or (IT), or a pharmaceutically acceptable salt thereof, wherein Z is $(CH_2)_{n4}$, wherein n4 is 1, 2, 3, 4 or 5. In further embodiments Z is $CH_2$. In further embodiments Z is $(CH_2)_2$. In further embodiments Z is $(CH_2)_3$. In further embodiments Z is $(CH_2)_4$. In further embodiments Z is $(CH_2)_5$.

In embodiments there is provided a conjugate of Formula (I), (IC), (IM) or (IT), or a pharmaceutically acceptable salt thereof, wherein m is 5, 6, 7, 8, 9, 10, 11, 12, 13, 14, 15, 16 or 17. In further embodiments m is an integer from 6 to 16. In further embodiments m is an integer from 7 to 15. In further embodiments m is an integer from 8 to 14. In further embodiments m is an integer from 9 to 13. In further embodiments m is an integer from 10 to 12. In further embodiments m is 11.

In embodiments there is provided a conjugate of Formula (I), (IC), (IM) or (IT), or a pharmaceutically acceptable salt thereof, wherein $R^1$ is $C_{1-4}$ alkyl. In further embodiments $R^1$ is $CH_3$.

In embodiments there is provided a conjugate of Formula (I), (IC), (IM) or (IT), or a pharmaceutically acceptable salt thereof, wherein p is 1.

In embodiments there is provided a conjugate of Formula (I), or a pharmaceutically acceptable salt thereof, wherein each $J^4$ is a group of Formula (IB)

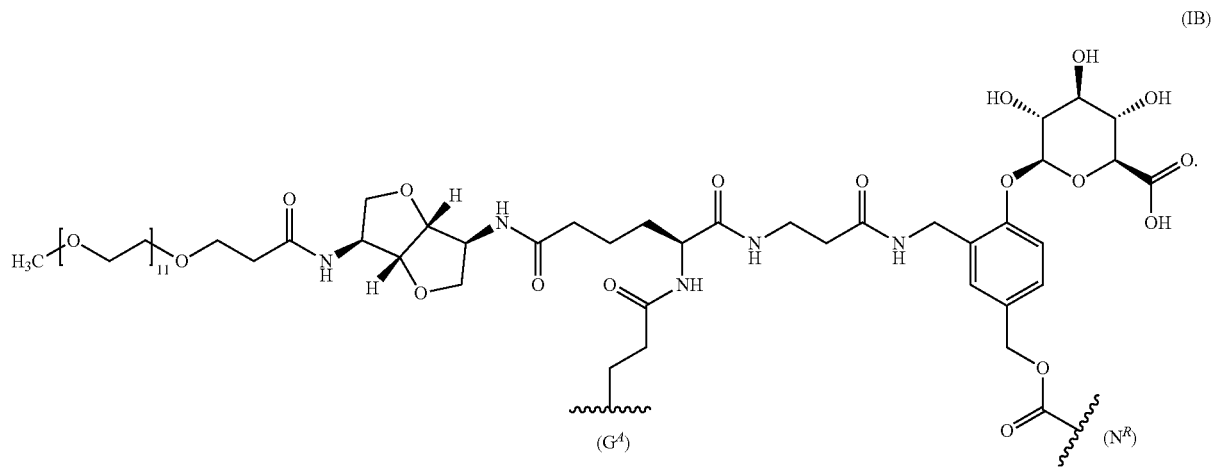
(IB)
In embodiments there is provided a conjugate of Formula (I), or a pharmaceutically acceptable salt thereof, wherein each $J^A$ is a group of Formula (IB')
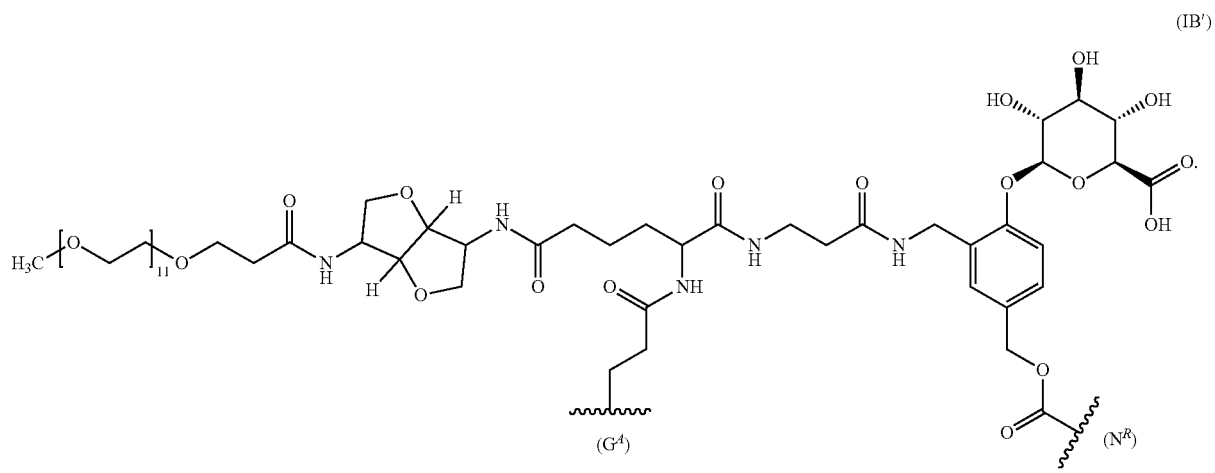
(IB')
In embodiments there is provided a conjugate of Formula (I), or a pharmaceutically acceptable salt thereof, wherein each $J^A$ is a group of Formula (IB2)
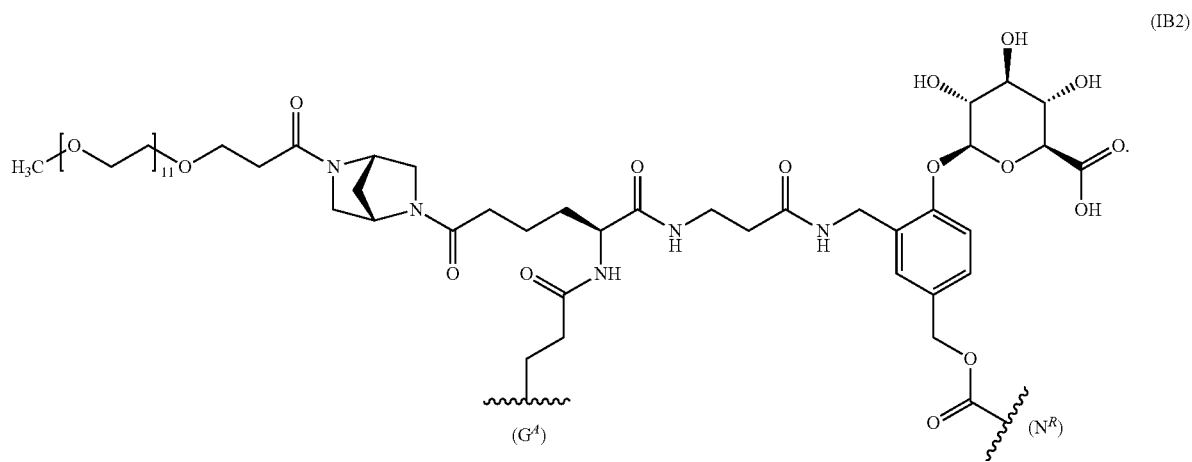
(IB2)

In embodiments there is provided a conjugate of Formula (IC), or a pharmaceutically acceptable salt thereof, wherein each $J^A$ is a group of Formula (ICB)
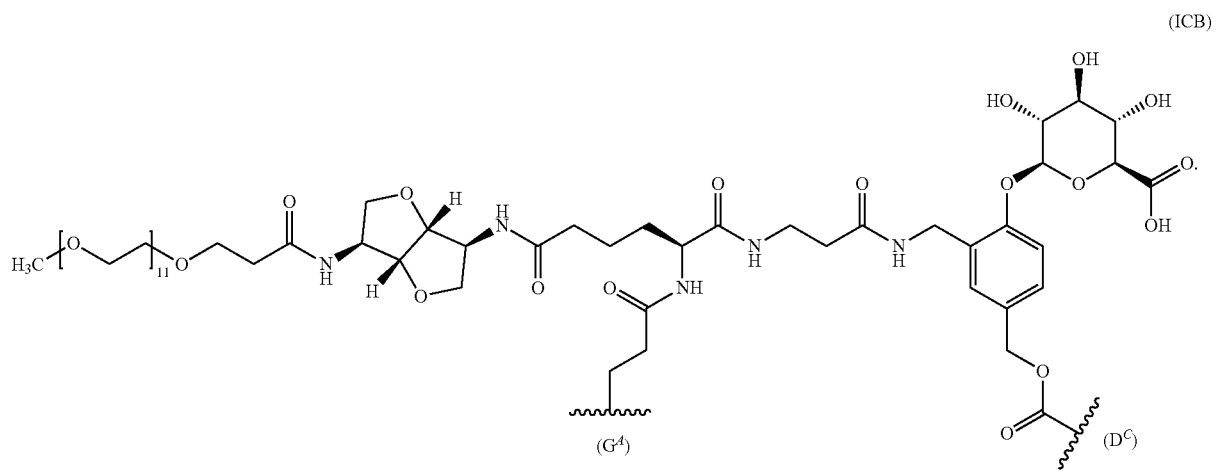
In embodiments there is provided a conjugate of Formula (IC), or a pharmaceutically acceptable salt thereof, wherein each $J^A$ is a group of Formula (ICB')
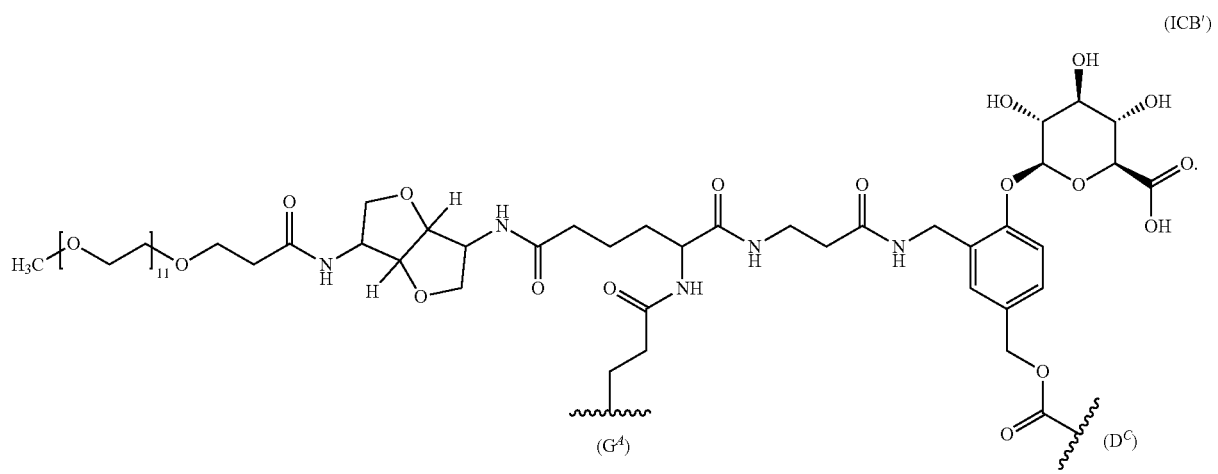

In embodiments there is provided a conjugate of Formula (IC), or a pharmaceutically acceptable salt thereof, wherein each $J^A$ is a group of Formula (ICB2)
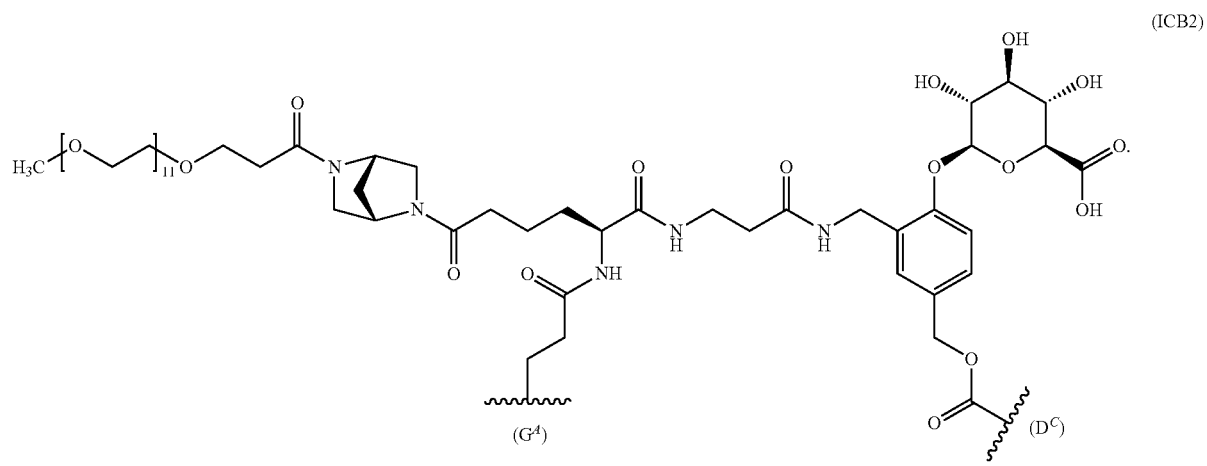
(ICB2)
In embodiments there is provided a conjugate of Formula (IM), or a pharmaceutically acceptable salt thereof, wherein each $J^A$ is a group of Formula (IMB)
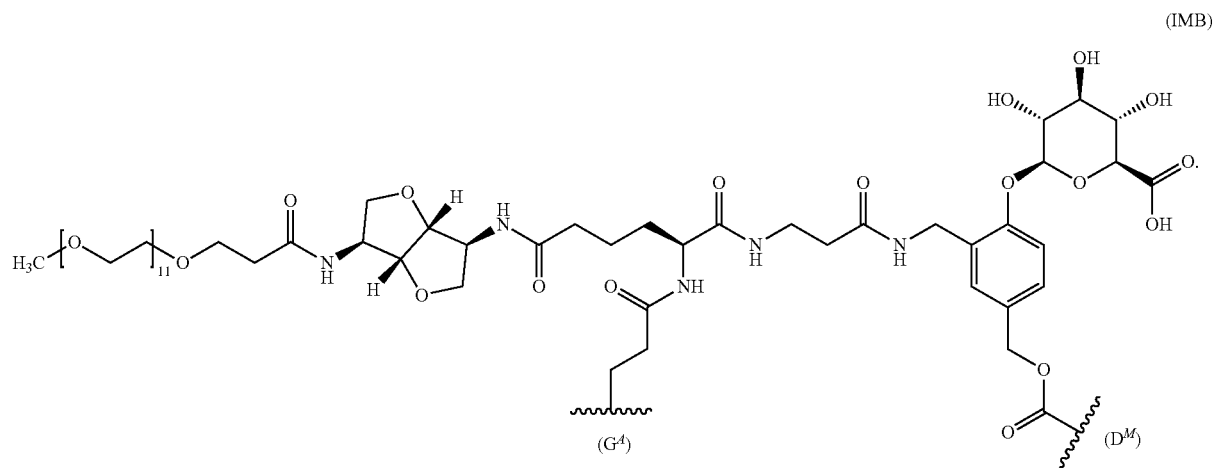
(IMB)

In embodiments there is provided a conjugate of Formula (IM), or a pharmaceutically acceptable salt thereof, wherein each $J^A$ is a group of Formula (IMB')
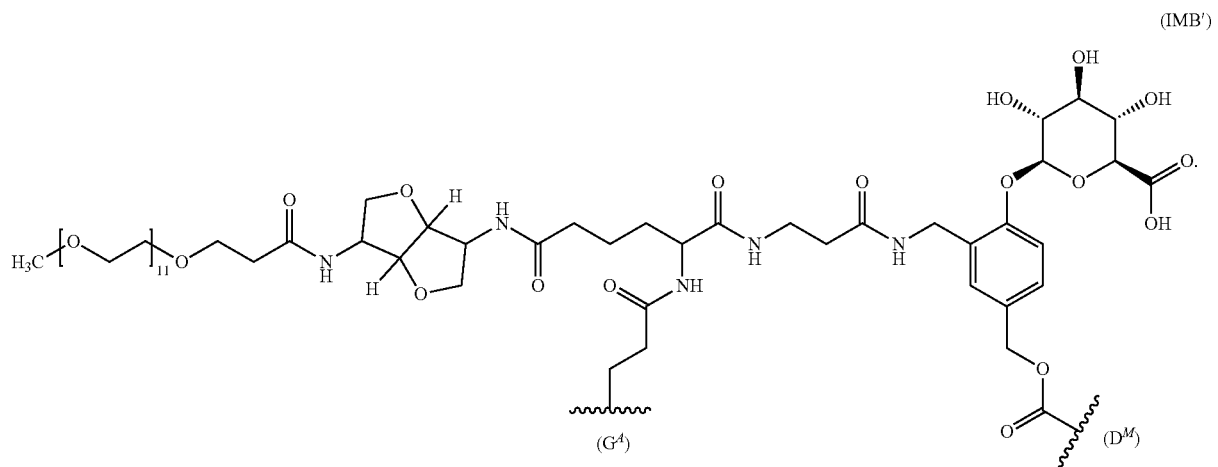
In embodiments there is provided a conjugate of Formula (IM), or a pharmaceutically acceptable salt thereof, wherein each $J^A$ is a group of Formula (IMB2)
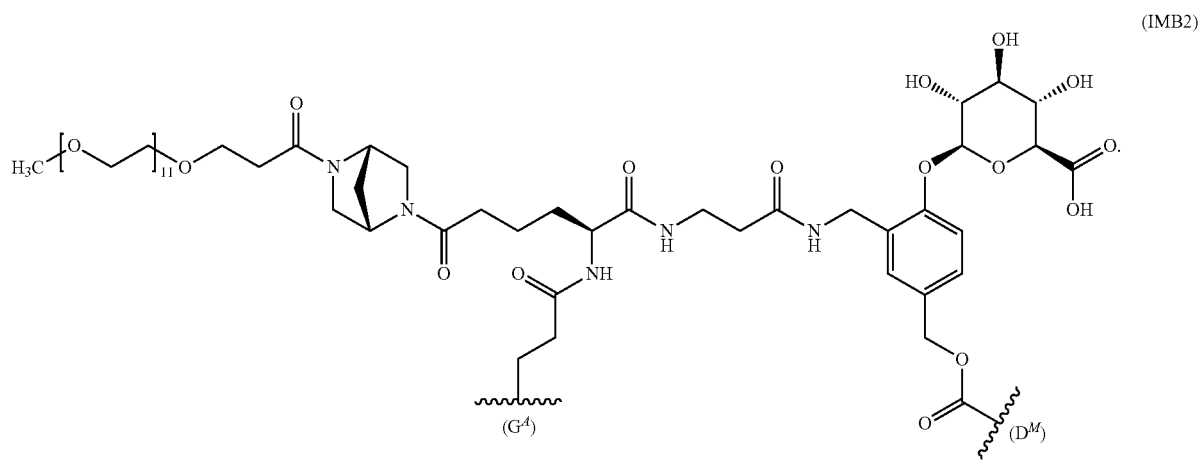

In embodiments there is provided a conjugate of Formula (IT), or a pharmaceutically acceptable salt thereof, wherein each $J^A$ is a group of Formula (ITB)
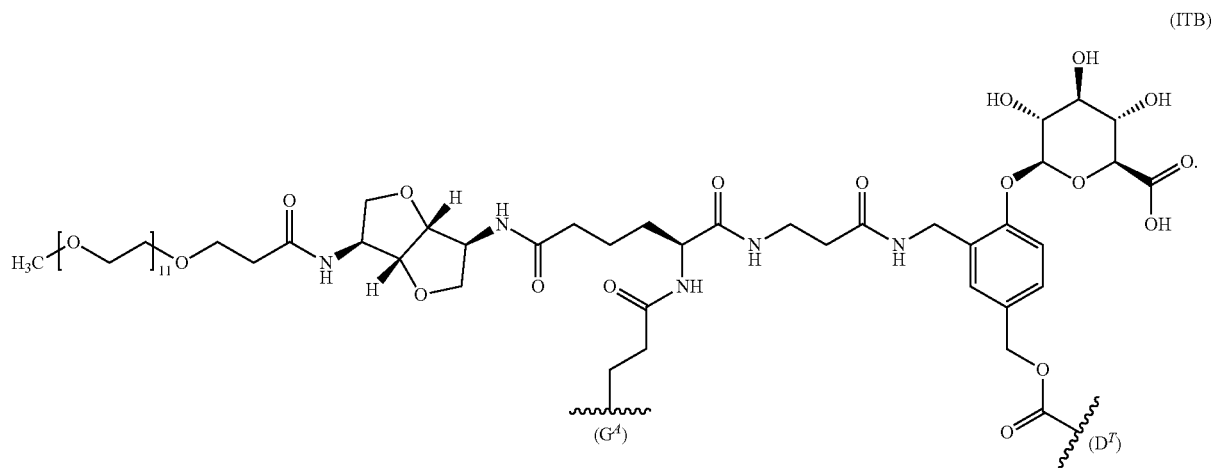
In embodiments there is provided a conjugate of Formula (IT), or a pharmaceutically acceptable salt thereof, wherein each $J^A$ is a group of Formula (ITB')
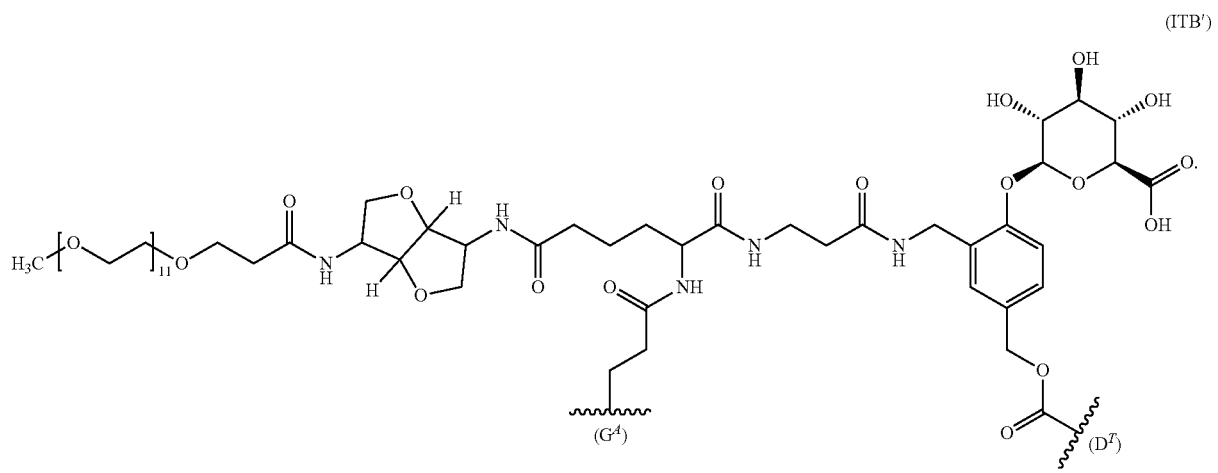

In embodiments there is provided a conjugate of Formula (IT), or a pharmaceutically acceptable salt thereof, wherein each $J^A$ is a group of Formula (ITB2)

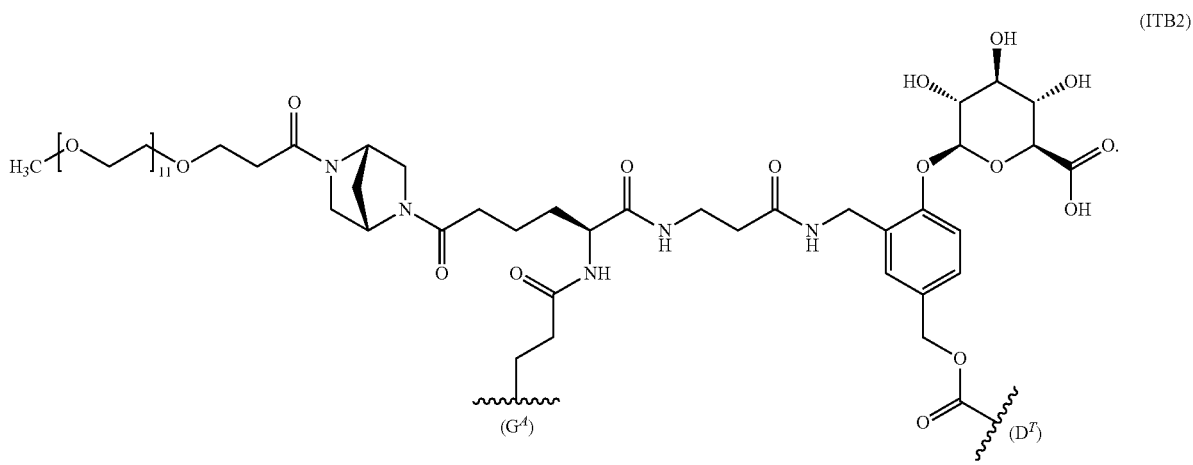

In a further aspect there is provided a compound of Formula (II)

$$G^B\text{-}J^B\text{-}D^R \qquad (II)$$

or a salt thereof, wherein $G^B$ is a conjugation group for conjugation to an antibody or antigen-binding fragment thereof,
$D^R$ is a drug comprising a nitrogen atom $N^R$,
$J^B$ is a group of Formula (IIA)

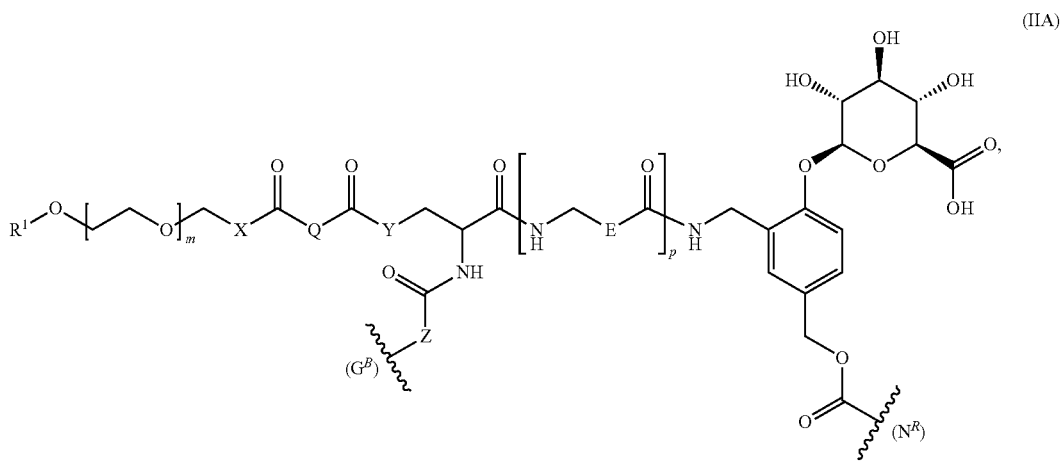

wherein E, Q, $R^1$, X, Y, Z, m and p are as defined in any of the embodiments of a conjugate of Formula (I) disclosed herein, ($G^B$) indicates the point of attachment to $G^B$, and ($N^R$) indicates the point of attachment to the nitrogen atom $N^R$.

In a further aspect there is provided a compound of Formula (IIC)

$$G^B\text{-}J^B\text{-}D^C \qquad (IIC)$$

or a salt thereof, wherein $G^B$ is a conjugation group for conjugation to an antibody or antigen-binding fragment thereof, $J^B$ is a group of Formula (IICA)

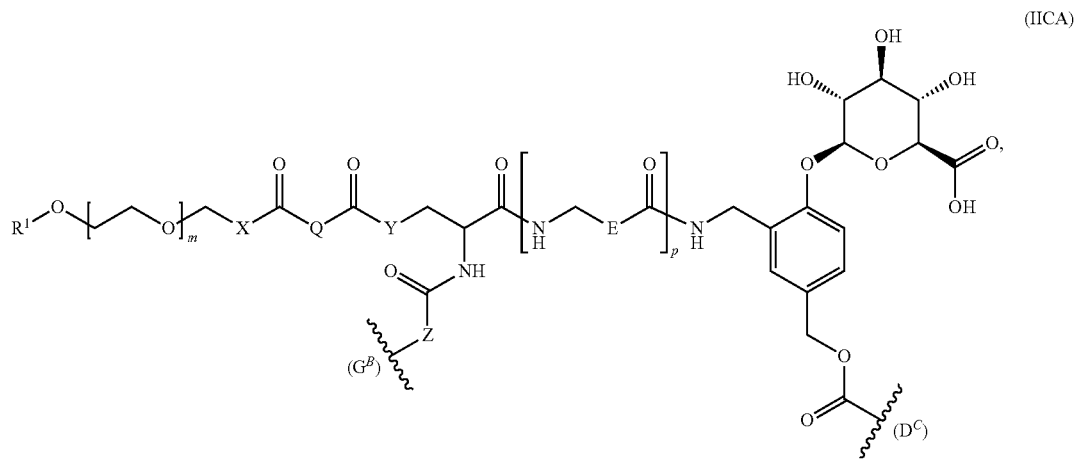

wherein $D^C$, E, Q, $R^1$, X, Y, Z, m and p are as defined in any embodiment of a conjugate of Formula (IC) disclosed herein, ($G^B$) indicates the point of attachment to $G^B$, and ($D^C$) indicates the point of attachment to $D^C$.

In a further aspect there is provided a compound of Formula (IIM)

$$G^B\text{-}J^B\text{-}D^M \qquad (IIM)$$

or a salt thereof, wherein $G^B$ is a conjugation group for conjugation to an antibody or antigen-binding fragment thereof, $J^B$ is a group of Formula (IIMA)

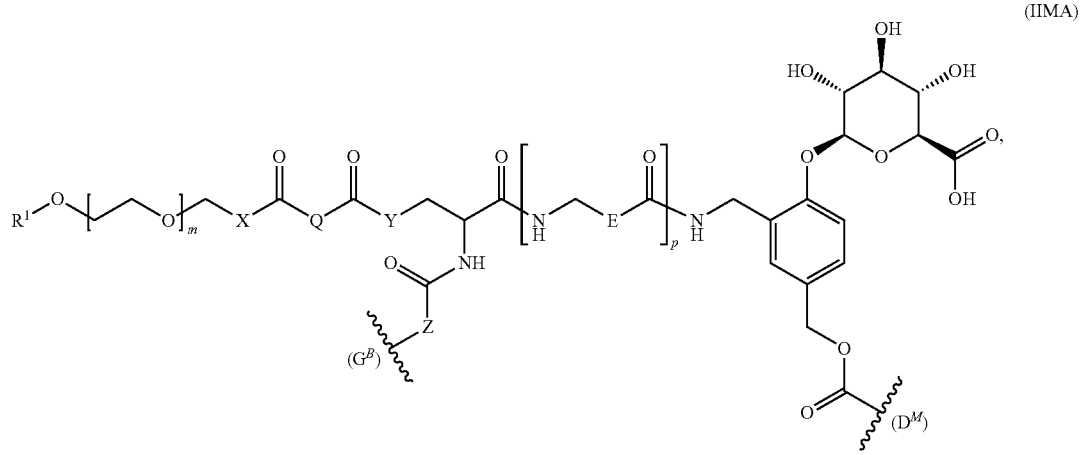

wherein $D^M$, E, Q, $R^1$, X, Y, Z, m and p are as defined in any embodiment of a conjugate of Formula (IM) disclosed herein, ($G^B$) indicates the point of attachment to $G^B$, and ($D^M$) indicates the point of attachment to $D^M$.

In a further aspect there is provided a compound of Formula (IIT)

$$G^B\text{-}J^B\text{-}D^M \qquad \text{(IT)}$$

or a salt thereof, wherein $G^B$ is a conjugation group for conjugation to an antibody or antigen-binding fragment thereof, $J^B$ is a group of Formula (IITA)

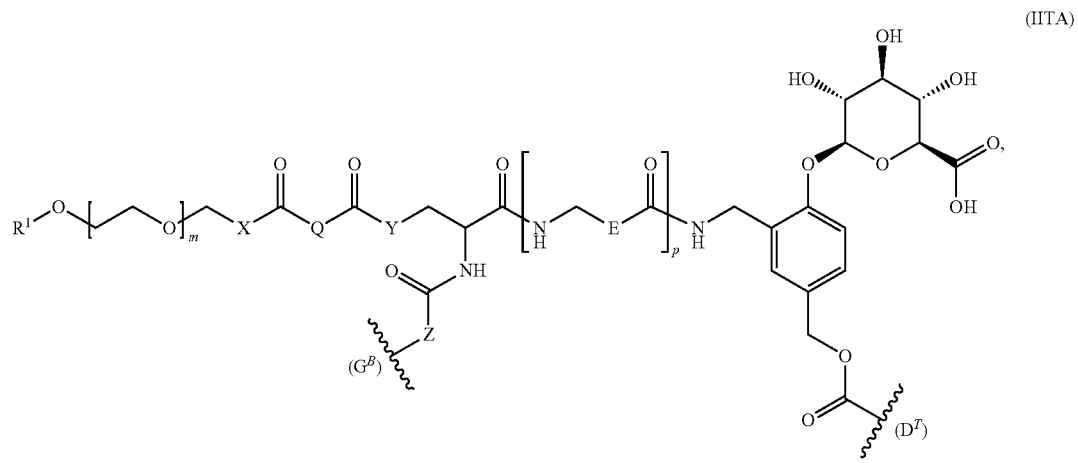

(IITA)

wherein $D^M$, E, Q, $R^1$, X, Y, Z, m and p are as defined in any embodiment of a conjugate of Formula (IT) disclosed herein, ($G^B$) indicates the point of attachment to $G^B$, and ($D^T$) indicates the point of attachment to $D^T$.

In embodiments there is provided a compound of Formula (II), (IIC), (IIM) or (IIT), or a salt thereof, wherein $G^B$ is selected from

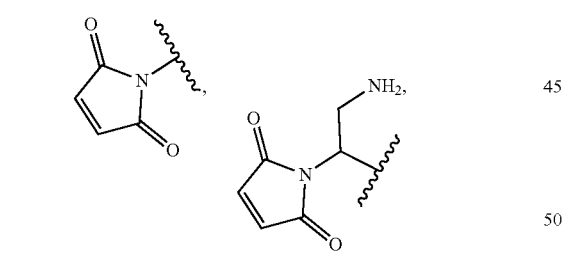

-continued

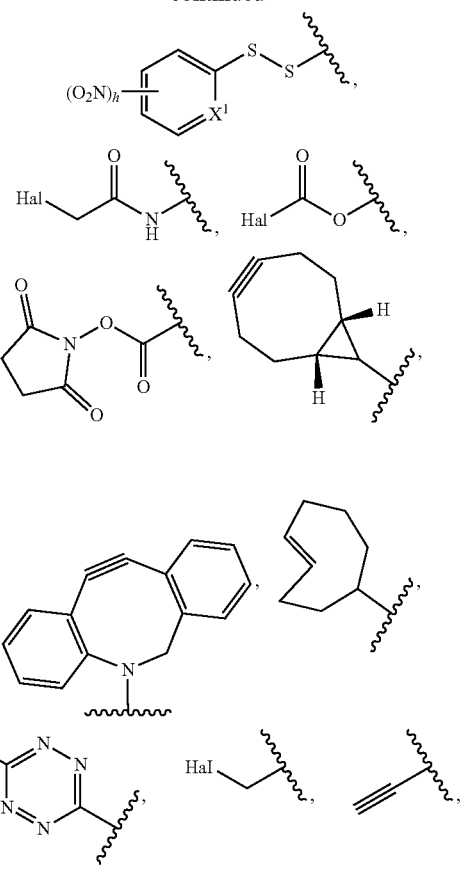

-continued

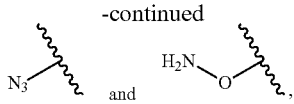
and wherein $X^1$ is CH or N, h is 0 or 1, Hal is Cl, Br or I, $R^K$ is H or $CH_3$, and $R^1$ is $C_{1-6}$ alkyl.

In embodiments there is provided a compound of Formula (II), (IIC), (IIM) or (IIT), or a salt thereof, wherein $G^B$ is selected from

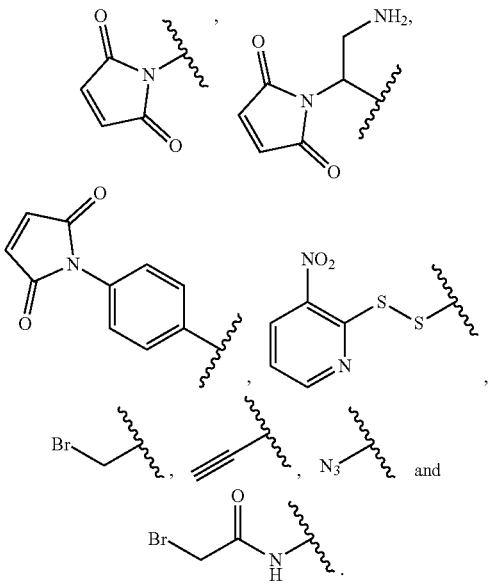

In embodiments there is provided a compound of Formula (II), (IIC), (IIM) or (IIT), or a salt thereof, wherein $G^B$ is

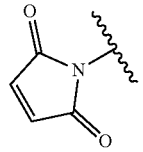

In embodiments there is provided a compound of Formula (II), (II), (IIM) or (IIT), or a salt thereof, wherein $G^B$ is

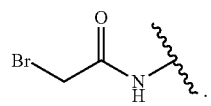

In embodiments there is provided a compound of Formula (II), (IIC), (IIM) or (IIT), or a salt thereof, wherein $G^B$ is

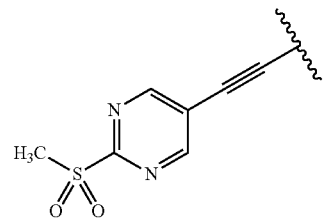

In embodiments there is provided a compound of Formula (II) or a salt thereof, wherein $J^B$ is a group of Formula (IIB)

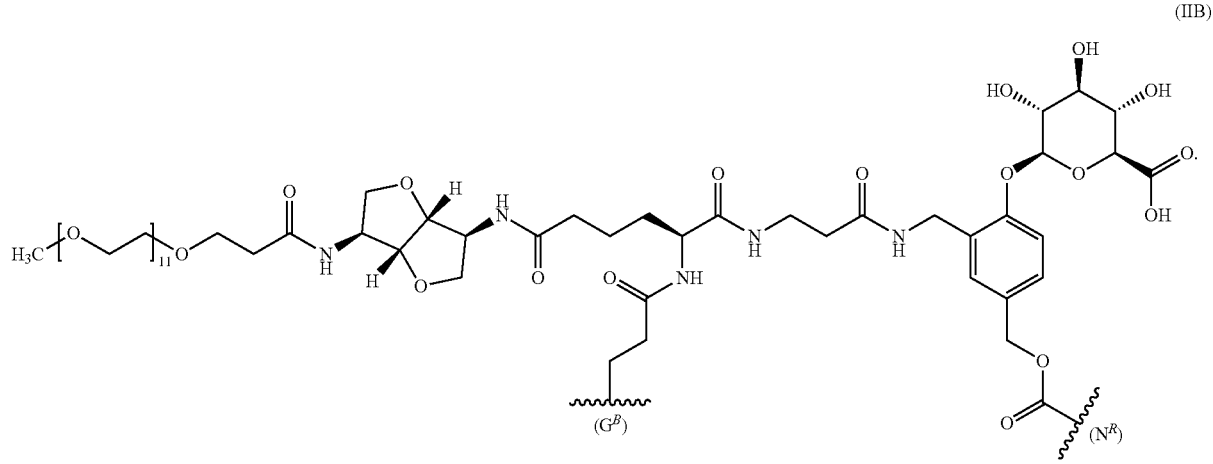

In embodiments there is provided a compound of Formula (II) or a salt thereof, wherein $J^B$ is a group of Formula (IIB2)
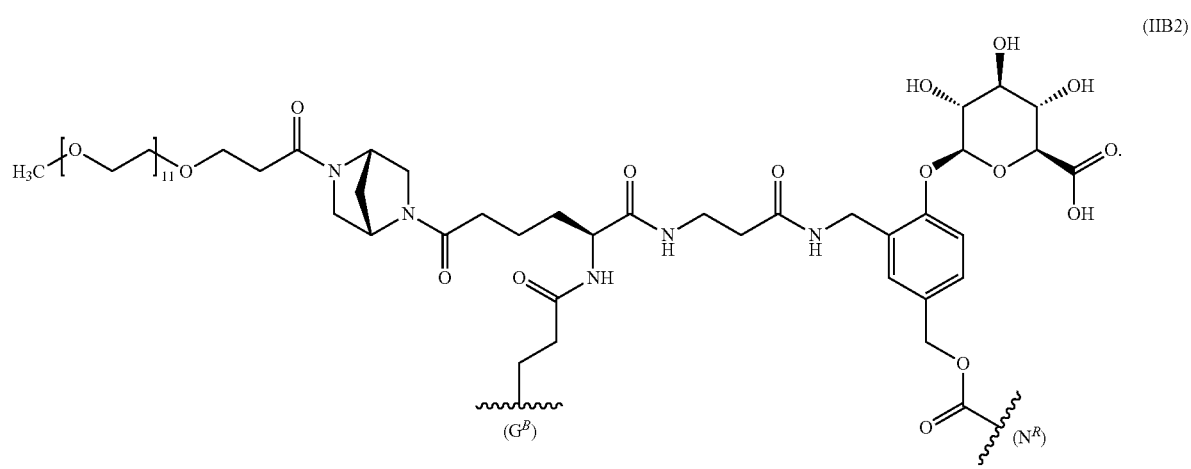
In embodiments there is provided a compound of Formula (IIC) or a salt thereof, wherein $J^B$ is a group of Formula (IICB)
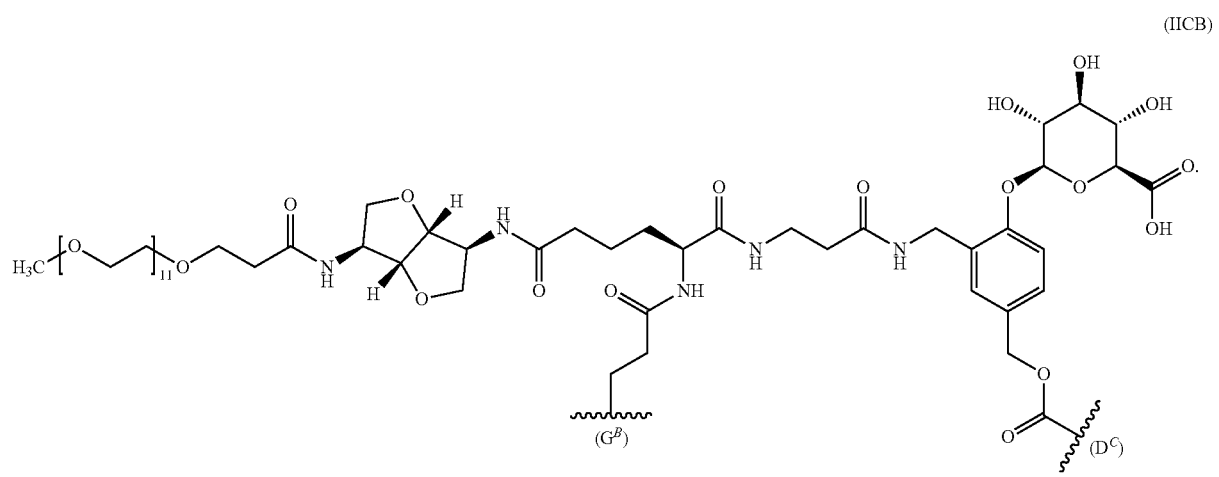

In embodiments there is provided a compound of Formula (II) or a salt thereof, wherein $J^B$ is a group of Formula (IICB2)

In embodiments there is provided a compound of Formula (IIM) or a salt thereof, wherein $J^B$ is a group of Formula (IIMB)

In embodiments there is provided a compound of Formula (IIM) or a salt thereof, wherein $J^B$ is a group of Formula (IIMB2)
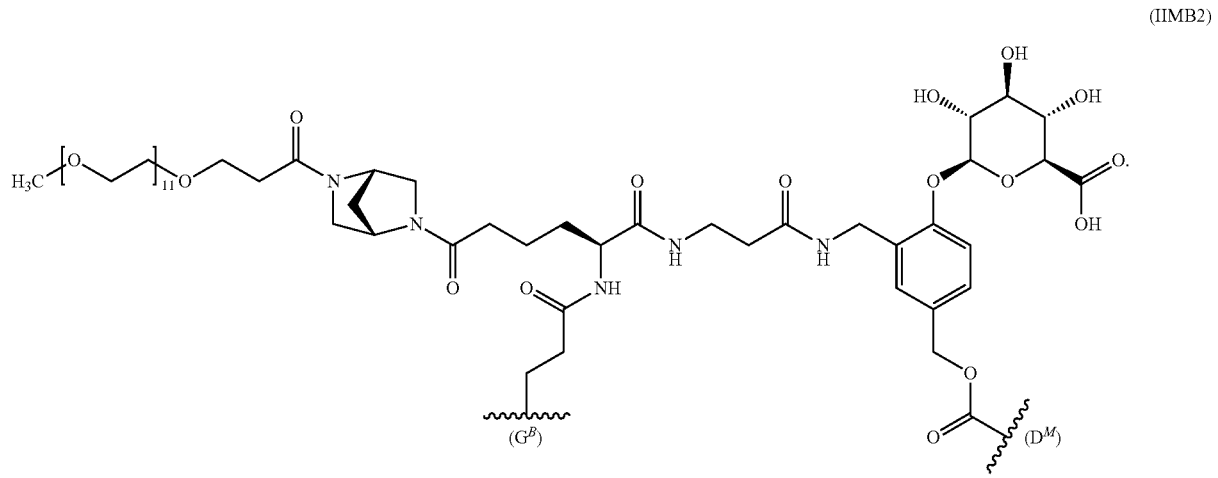
(IIMB2)
In embodiments there is provided a compound of Formula (IIT) or a salt thereof, wherein $J^B$ is a group of Formula (IITB)
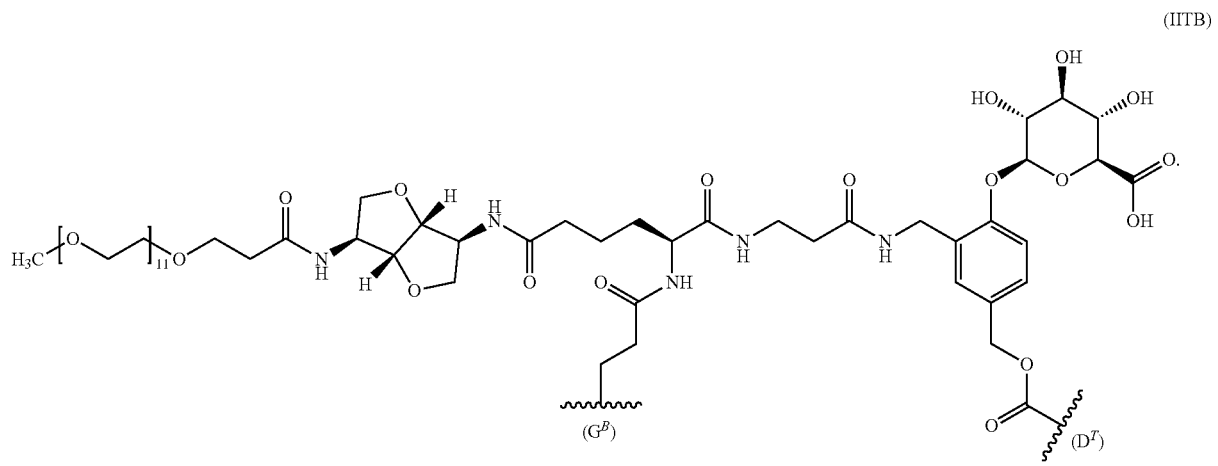
(IITB)

In embodiments there is provided a compound of Formula (IIT) or a salt thereof, wherein $J^B$ is a group of Formula (IITB2)
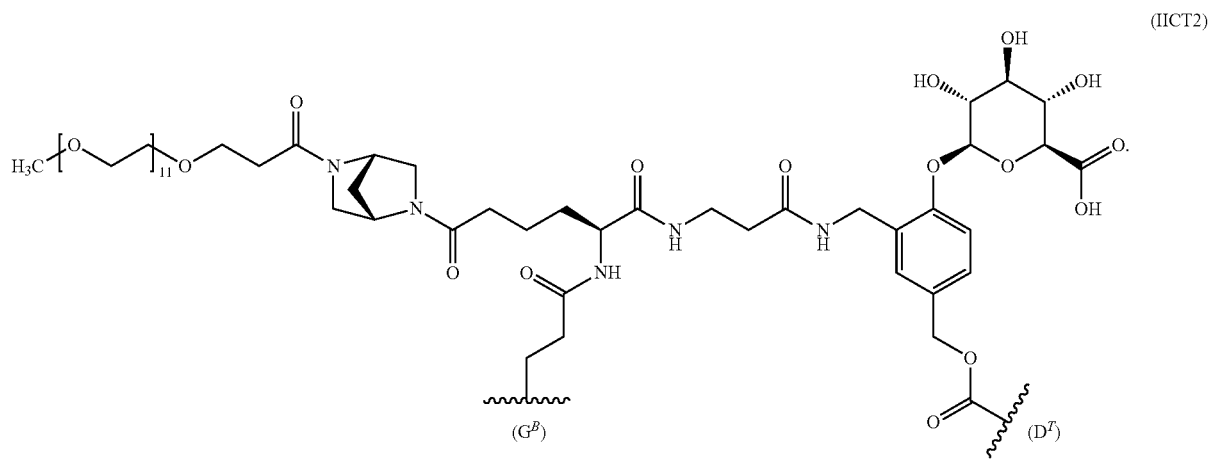
In embodiments there is provided a compound of Formula (IIC) selected from;
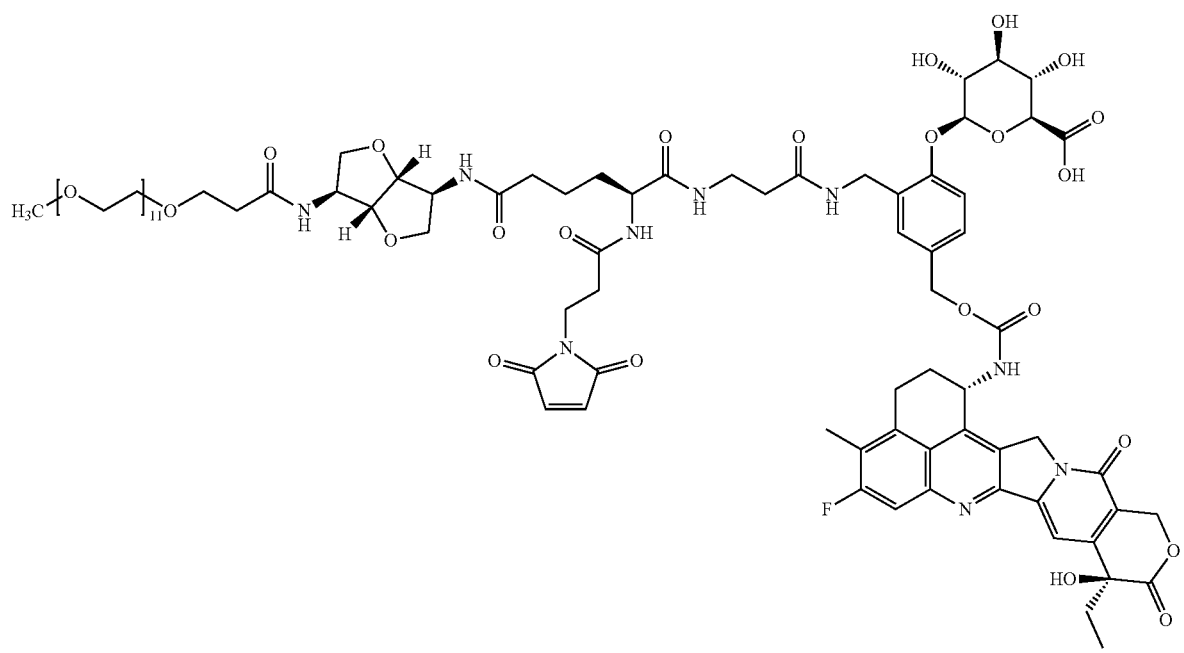

(2S,3S,4S,5R,6S)-6-(2-((3-((S)-6-(((3S,3aR,6S,6aR)-6-(2,5,8,11,14,17,20,23,26,29,32,35-dodecaoxaoctatriacontan-38-amido)hexahydrofuro[3,2-b]furan-3-yl)amino)-2-(3-(2,5-dioxo-2,5-dihydro-1H-pyrrol-1-yl)propanamido)-6-oxohexanamido)propanamido)methyl)-4-(((((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)carbamoyl)oxy)methyl)phenoxy)-3,4,5-trihydroxytetrahydro-2H-pyran-2-carboxylic acid, and

5

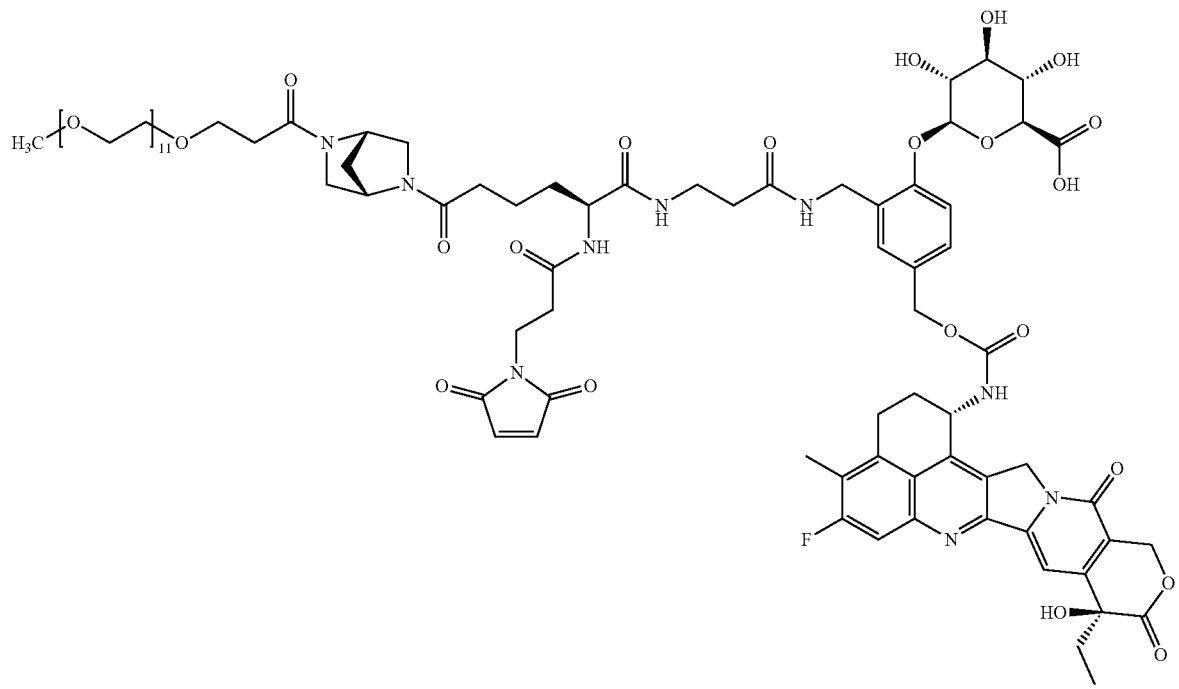

(2S,3S,4S,5R,6S)-6-(2-((3-((S)-6-((1S,4S)-5-(2,5,8,11,14,17,20,23,26,29,32,35-dodecaoxaoctatriacontan-38-oyl)-2,5-diazabicyclo[2.2.1]heptan-2-yl)-2-(3-(2,5-dioxo-2,5-dihydro-1H-pyrrol-1-yl)propanamido)-6-oxohexanamido)propanamido)methyl)-4-(((((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)carbamoyl)oxy)methyl)phenoxy)-3,4,5-trihydroxytetrahydro-2H-pyran-2-carboxylic acid, or a salt thereof.

In embodiments there is provided a compound of Formula (IIC), that is
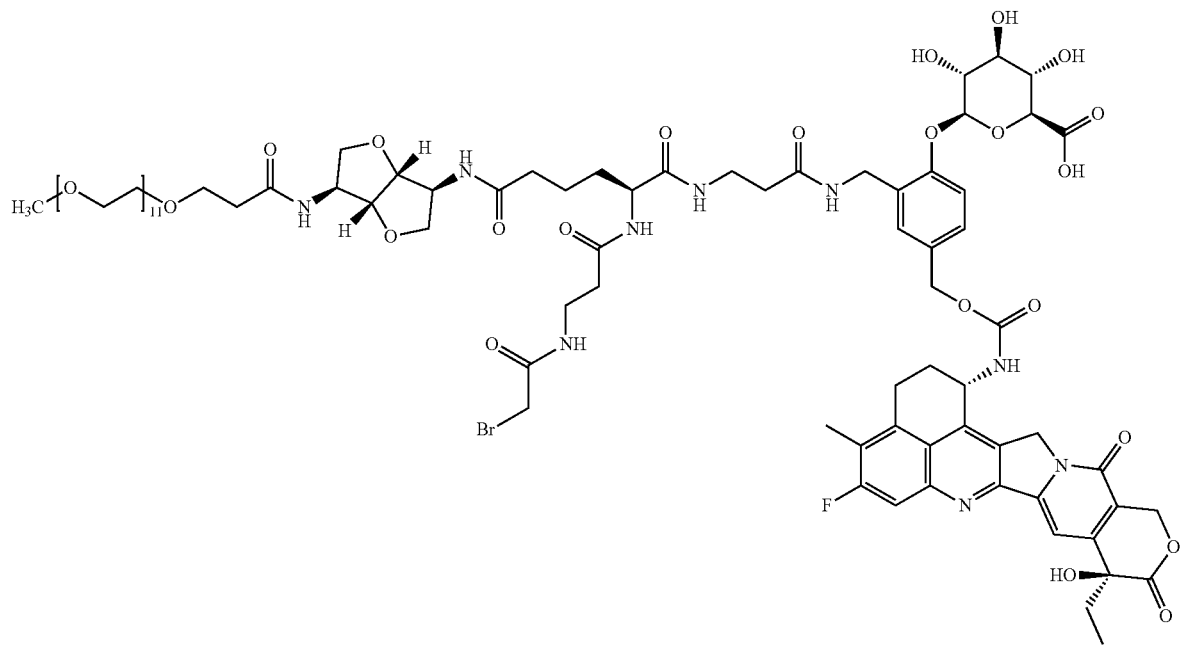

(2S,3S,4S,5R,6S)-6-(2-((S)-8-(4-(((3S,3aR,6S,6aR)-6-(2,5,8,11,14,17,20,23,26,29,32,35-dodecaoxaoctatriacontan-38-amido)hexahydrofuro[3,2-b]furan-3-yl)amino)-4-oxobutyl)-15-bromo-3,7,10,14-tetraoxo-2,6,9,13-tetraazapentadecyl)-4-(((((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino-[1,2-b]quinolin-1-yl)carbamoyl)oxy)methyl)phenoxy)-3,4,5-trihydroxytetrahydro-2H-pyran-2-carboxylic acid, or a salt thereof.

In embodiments there is provided a compound of Formula (IIM) that is;

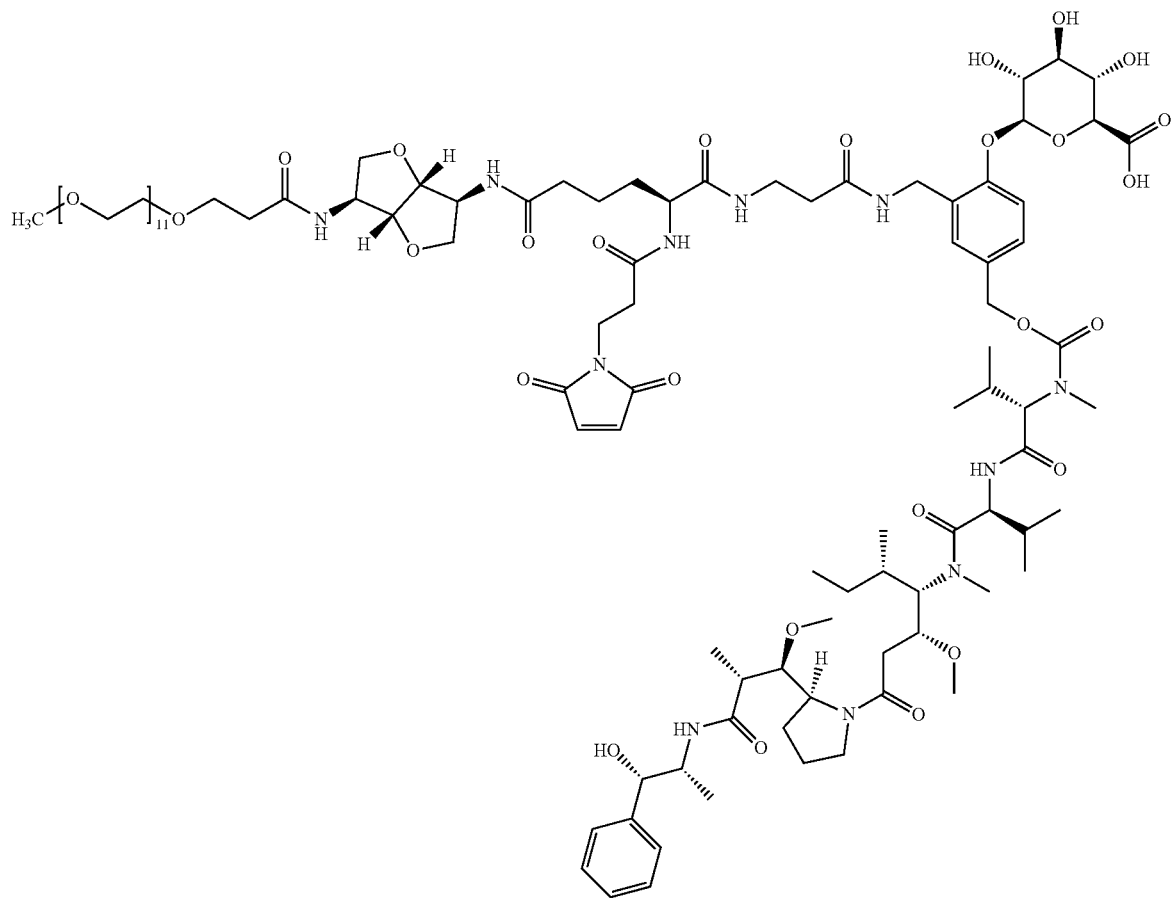

(2S,3S,4S,5R,6S)-6-(2-((3-((S)-6-(((3S,3aR,6S,6aR)-6-(2,5,8,11,14,17,20,23,26,29,32,35-dodecaoxaoctatriacontan-38-amido)hexahydrofuro[3,2-b]furan-3-yl)amino)-2-(3-(2,5-dioxo-2,5-dihydro-1H-pyrrol-1-yl)propanamido)-6-oxohexanamido)propanamido)methyl)-4-((5S,8S,11S,12R)-11-((S)-sec-butyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenoxy)-3,4,5-trihydroxytetrahydro-2H-pyran-2-carboxylic acid, or a salt thereof.

In embodiments there is provided a compound of Formula (IIT) that is;

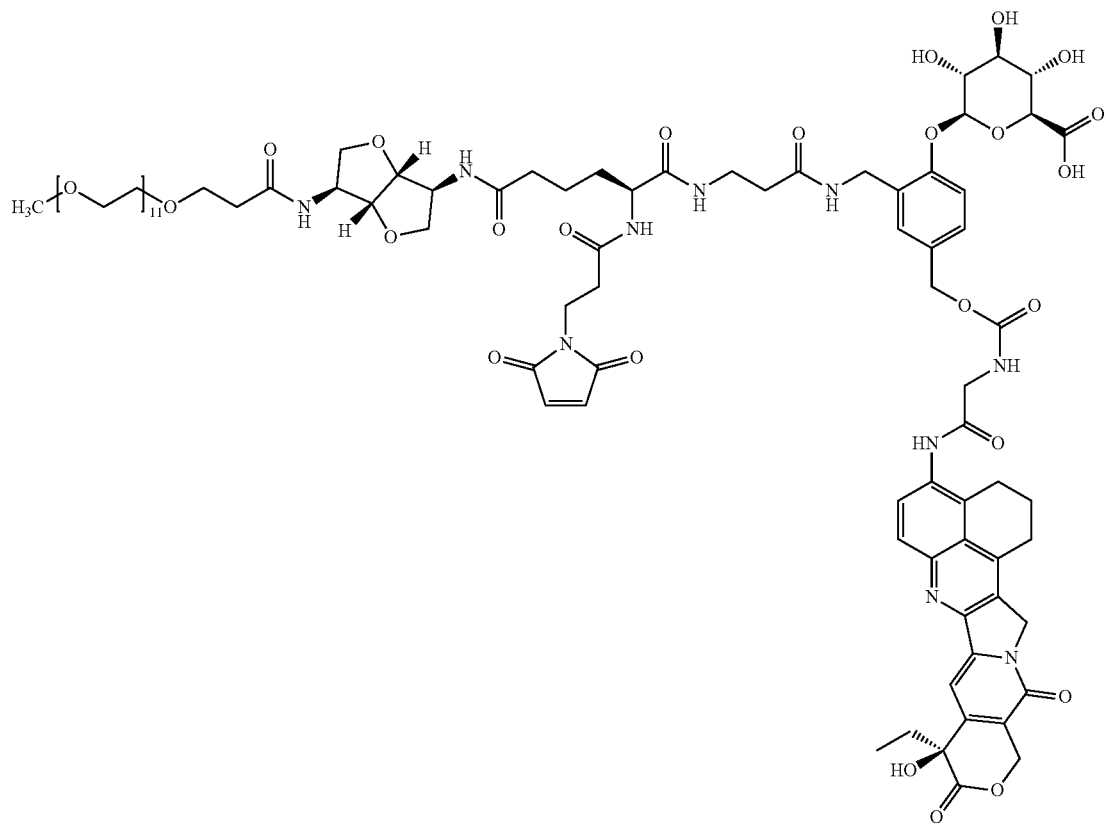

(2S,3S,4S,5R,6S)-6-(2-((3-((S)-6-(((3S,3aR,6S,6aR)-6-(2,5,8,11,14,17,20,23,26,29,32,35-dodecaoxaoctatriacontan-38-amido)hexahydrofuro[3,2-b]furan-3-yl)amino)-2-(3-(2,5-dioxo-2,5-dihydro-1H-pyrrol-1-yl)propanamido)-6-oxohexanamido)propanamido)methyl)-4-(((((2-(((S)-9-ethyl-9-hydroxy-10,13-dioxo-2,3,9,10,13,15-hexahydro-1H,12H-benzo[de]pyrano[3',4':6,7]indolizino[1,2-b]quinolin-4-yl)amino)-2-oxoethyl)carbamoyl)oxy)methyl)phenoxy)-3,4,5-trihydroxytetrahydro-2H-pyran-2-carboxylic acid, or a salt thereof.

In a further aspect there is provided a compound of Formula (III)

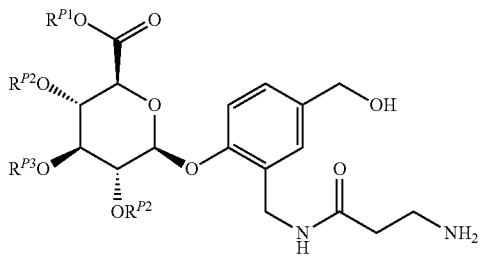

(III)

or a salt thereof, wherein $R^{P1}$ is a carboxylic acid protecting group, and each $R^{P2}$ is independently an alcohol protecting group.

In embodiments there is provided a compound of Formula (III) or a salt thereof, that is (2S,3S,4S,5R,6S)-2-((allyloxy)carbonyl)-6-(2-((3-aminopropanamido)methyl)-4-(hydroxymethyl)phenoxy)tetrahydro-2H-pyran-3,4,5-triyl triacetate or a salt thereof.

In a further aspect there is provided a compound of Formula (IV)

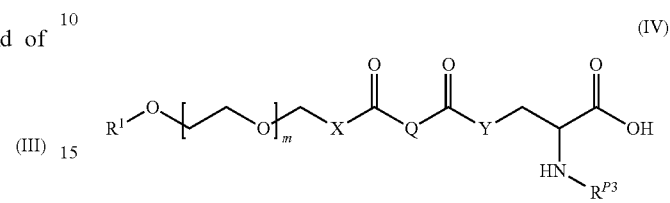

(IV)

or a salt thereof, wherein Q, $R^1$, X, Y and m are as defined in any embodiment of a conjugate of Formula (I), and $R^{P3}$ is an amine protecting group.

In embodiments there is provided a compound of Formula (IV) or a salt thereof, that is (S)-6-(((3S,3aR,6S,6aR)-6-(2,5,8,11,14,17,20,23,26,29,32,35-dodecaoxaoctatriacontan-38-amido)hexahydrofuro[3,2-b]furan-3-yl)amino)-2-((((9H-fluoren-9-yl)methoxy)carbonyl)amino)-6-oxohexanoic acid or a salt thereof.

In a further aspect there is provided a compound of Formula (V)

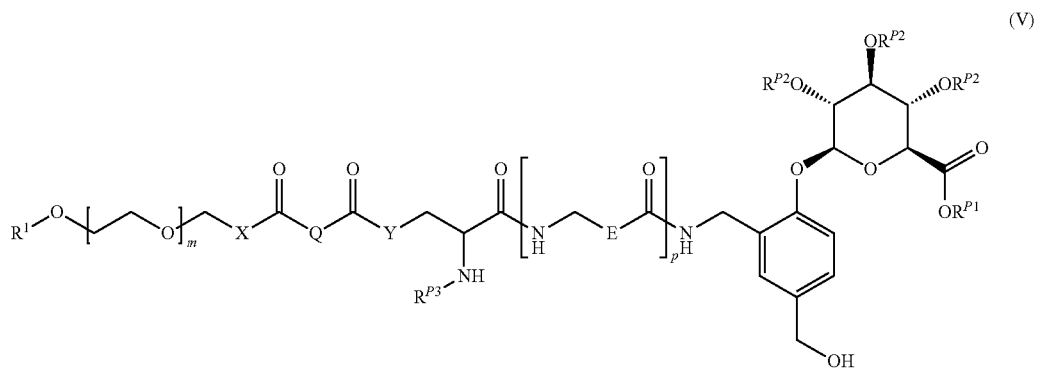

(V)

or a salt thereof, wherein E, Q, $R^1$, X, Y, m and p are as defined in any embodiment of a conjugate of Formula (I), $R^{P1}$ is a carboxylic acid protecting group, each $R^{P2}$ is independently an alcohol protecting group and $R^{P3}$ is an amine protecting group.

In embodiments there is provided a compound of Formula (V) or a salt thereof, that is (2S,3R,4S,5S,6S)-2-(2-((S)-5-(4-(((3S,3aR,6S,6aR)-6-(2,5,8,11,14,17,20,23,26,29,32,35-dodecaoxaoctatriacontan-38-amido)hexahydrofuro[3,2-b]furan-3-yl)amino)-4-oxobutyl)-1-(9H-fluoren-9-yl)-3,6,10-trioxo-2-oxa-4,7,11-triazadodecan-12-yl)-4-(hydroxymethyl)phenoxy)-6-((allyloxy)carbonyl)tetrahydro-2H-pyran-3,4,5-triyl triacetate or a salt thereof.

In a further aspect there is provided a compound of Formula (VI)

$$J^{VI}\text{-}D^R \quad (VI)$$

or a salt thereof, wherein $D^R$ is a drug comprising a nitrogen atom $N^R$, $J^{VI}$ is a group of Formula (VIA)

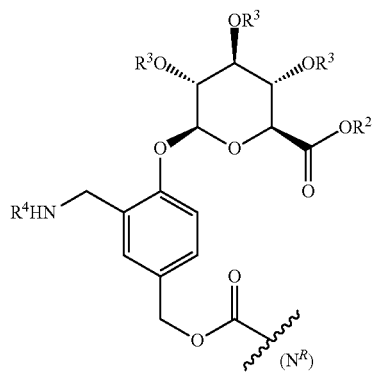

(VIA)

wherein $R^2$ is H or $R^{P1}$, each $R^3$ is independently H or $R^{P2}$, $R^4$ is H or $R^{P3}$, and ($N^R$) indicates the point of attachment to the nitrogen atom $N^R$, wherein $R^{P1}$ is a carboxylic acid protecting group, each $R^{P2}$ is independently an alcohol protecting group and $R^{P3}$ is an amine protecting group.

In a further aspect there is provided a compound of Formula (VIC)

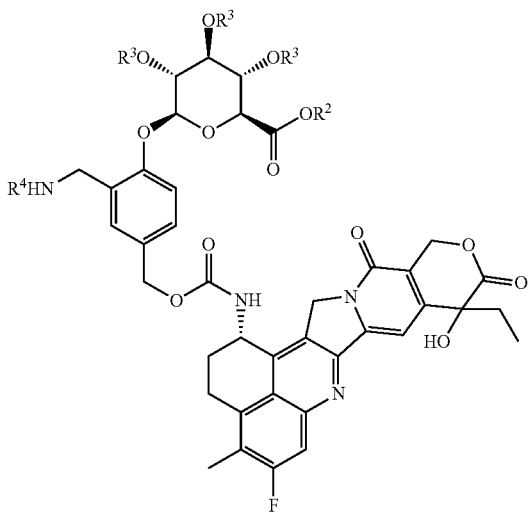

(VIC)

or a salt thereof, wherein $R^2$ is H or $R^{P1}$, each $R^3$ is independently H or $R^{P2}$, and $R^4$ is H or $R^{P3}$, $R^{P1}$ is a carboxylic acid protecting group, each $R^{P2}$ is independently an alcohol protecting group and $R^{P3}$ is an amine protecting group.

In a further aspect there is provided a compound of Formula (VIM)

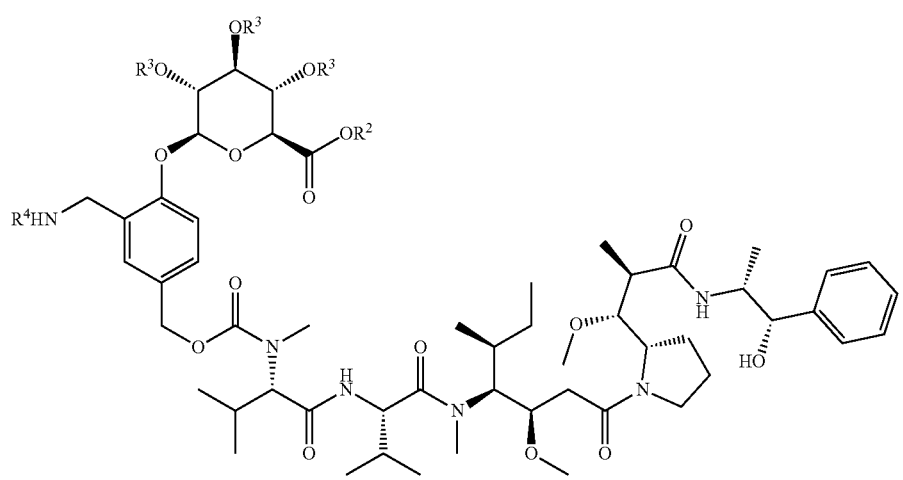

(VIM)

or a salt thereof, wherein $R^2$ is H or $R^{P1}$, each $R^3$ is independently H or $R^{P2}$, and $R^4$ is H or $R^{P3}$, $R^{P1}$ is a carboxylic acid protecting group, each $R^{P2}$ is independently an alcohol protecting group and $R^{P3}$ is an amine protecting group.

In embodiments there is provided a compound of Formula (VI) or a salt thereof, that is (2S,3S,4S,5R,6S)-6-(2-(aminomethyl)-4-((5S,8S,11S,12R)-11-((S)-sec-butyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenoxy)-3,4,5-trihydroxytetrahydro-2H-pyran-2-carboxylic acid or a salt thereof.

In a further aspect there is provided a compound of Formula (VII)

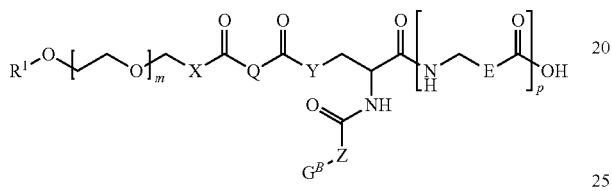

(VII)

or a salt thereof, wherein $G^B$ is a conjugation group for conjugation to an antibody or antigen-binding fragment thereof, and E, Q, $R^1$, X, Y, Z, m and p are as defined in any embodiment of a conjugate of Formula (I).

In embodiments there is provided a compound of Formula (VII) or a salt thereof, that is 3-((S)-6-(((3S,3aR,6S,6aR)-6-(2,5,8,11,14,17,20,23,26,29,32,35-dodecaoxaoctatriacontan-38-amido)hexahydrofuro[3,2-b]furan-3-yl)amino)-2-(3-(2,5-dioxo-2,5-dihydro-1H-pyrrol-1-yl)propanamido)-6-oxohexanamido)propanoic acid or a salt thereof.

In a further aspect there is provided a compound of Formula (VIII)

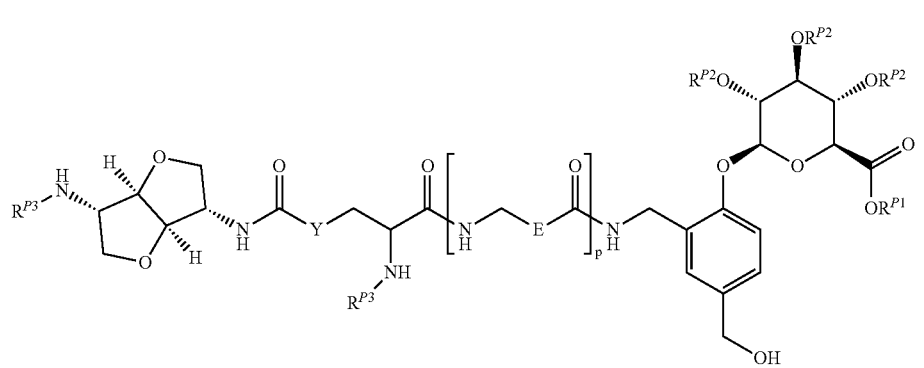

(VIII)

or a salt thereof, wherein E, Y and p are as defined in any embodiment of a conjugate of Formula (I), $R^{P1}$ is a carboxylic acid protecting group, each $R^{P2}$ is independently an alcohol protecting group and $R^{P3}$ is an amine protecting group.

In embodiments there is provided a compound of Formula (VIII) or a salt thereof, that is allyl (2S,3S,4S,5R,6S)-6-[2-[[3-[[(2S)-6-[[(3S,3aR,6S,6aR)-6-(tert-butoxycarbonylamino)-2,3,3a,5,6,6a-hexahydrofuro[3,2-b]furan-3-yl]amino]-2-(9H-fluoren-9-ylmethoxycarbonylamino)-6-oxohexanoyl]amino]propanoylamino]methyl]-4-(hydroxymethyl)phenoxy]-3,4,5-triacetoxytetrahydropyran-2-carboxylate, or a salt thereof.

In a further aspect there is provided a compound of Formula (IX)

$$G^B\text{-}J^{IX}\text{-}D^R \qquad (IX)$$

or a salt thereof, wherein $G^B$ is a conjugation group for conjugation to an antibody or antigen-binding fragment thereof,
$D^R$ is a drug comprising a nitrogen atom $N^R$,
$J^{IX}$ is a group of Formula (IXA)

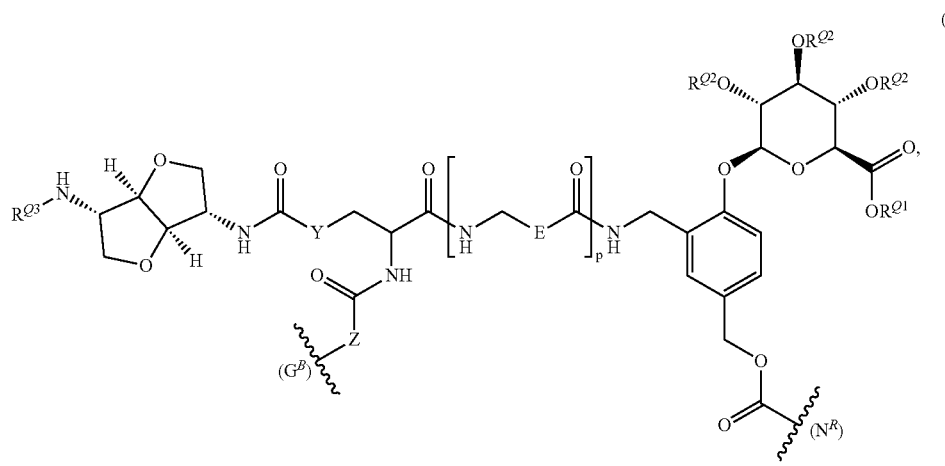

(IXA)

wherein E, Y, Z and p are as defined in any embodiment of a conjugate of Formula (I), ($G^B$) indicates the point of attachment to $G^B$, and ($N^R$) indicates the point of attachment to the nitrogen atom $N^R$, $R^{Q1}$ is H or $R^{P1}$, each $R^{Q2}$ is independently H or $R^{P2}$ and $R^{Q3}$ is H or $R^{P3}$, wherein $R^{P1}$ is a carboxylic acid protecting group, each $R^{P2}$ is independently an alcohol protecting group and $R^{P3}$ is an amine protecting group.

In embodiments there is provided a compound of Formula (IX), or a salt thereof, wherein $R^{Q1}$ is H, each $R^{Q2}$ is H and $R^{Q3}$ is H. In further embodiments, $G^B$ is

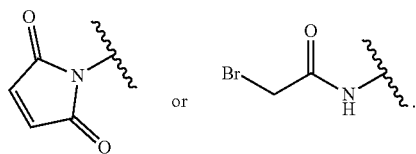 [SMILES: *N1C(=O)C=CC1=O ; *NC(=O)CBr]

In embodiments there is provided a compound of Formula (IX), or a salt thereof, wherein, $R^{Q1}$ is H, each $R^{Q2}$ is H and $R^{Q3}$ is $R^{P3}$. In further embodiments, $R^{Q1}$ is H, each $R^{Q2}$ is H and $R^{Q3}$ is tert-butyloxycarbonyl (Boc). In further embodiments, $G^B$ is

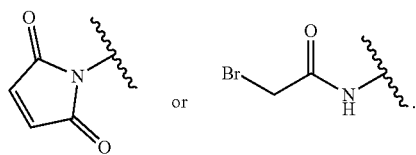 [SMILES: *N1C(=O)C=CC1=O ; *NC(=O)CBr]

In embodiments there is provided a compound of Formula (III), (V), (VI), (VIC), (VIM), (VIII) or (IX), or a salt thereof, wherein $R^{P1}$ is selected from benzyl, allyl and $C_{1-4}$ alkyl. In further embodiments $R^{P1}$ is allyl. In further embodiments $R^{P1}$ is methyl.

In embodiments there is provided a compound of Formula (III), (V), (VI), (VIC), (VIM), (VIII) or (IX), or a salt thereof, wherein each $R^{P2}$ is independently selected from benzyl, C(O)OCH$_2$CH=CH$_2$ and acetyl. In further embodiments each $R^{P2}$ is acetyl.

In embodiments there is provided a compound of Formula (IV), (V), (VI), (VIC), (VIM), (VIII) or (IX), or a salt thereof, wherein $R^{P3}$ is selected from trifluoroacetyl, tert-butyloxycarbonyl (Boc), benzyloxycarbonyl (Cbz) and fluorenylmethoxycarbonyl (Fmoc). In further embodiments $R^{P3}$ is fluorenylmethoxycarbonyl.

The present specification is intended to include all isotopes of atoms occurring in the present compounds and conjugates. Isotopes will be understood to include those atoms having the same atomic number but different mass numbers. For example, isotopes of hydrogen include tritium and deuterium. Isotopes of carbon include $^{13}$C and $^{14}$C. Isotopes of nitrogen include $^{15}$N.

The compounds disclosed herein may contain one or more chiral centers. Accordingly, if desired, such compounds can be prepared or isolated as pure stereoisomers, i.e. as individual enantiomers, diastereoisomers, or as a stereoisomerically enriched mixture. All such stereoisomer (and enriched) mixtures are included within the scope of the embodiments, unless otherwise stated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

Unless stereochemistry is explicitly indicated in a chemical structure or chemical name, the chemical structure or chemical name is intended to embrace all possible stereoisomers, diastereoisomers, conformers, rotamers and tautomers of the compound depicted. For example, a compound containing a chiral carbon atom is intended to embrace both the (R) enantiomer and the (S) enantiomer, as well as mixtures of the enantiomers, including racemic mixtures; and a compound containing two chiral carbons is intended to embrace all enantiomers and diastereoisomers including (R,R), (S,S), (R,S) and (S,R).

A suitable pharmaceutically acceptable salt of a conjugate of Formula (I), (IC), (IM) or (IT) is, for example, an acid addition salt. An acid addition salt of a conjugate of Formula (I), (IC), (IM) or (IT), may be formed by bringing the compound into contact with a suitable inorganic or organic acid under conditions known to the skilled person. An acid addition salt may for example be formed using an inorganic acid selected from hydrochloric acid, hydrobromic acid, sulphuric acid and phosphoric acid. An acid addition salt may also be formed using an organic acid selected from trifluoroacetic acid, citric acid, maleic acid, oxalic acid, acetic acid, formic acid, benzoic acid, fumaric acid, succinic acid, tartaric acid, lactic acid, pyruvic acid, methanesulfonic acid, benzenesulfonic acid and para-toluenesulfonic acid.

A suitable pharmaceutically acceptable salt of a conjugate of Formula (I), (IC), (IM) or (IT) is, for example, a base addition salt. A base addition salt of a conjugate of Formula (I), (IC), (IM) or (IT) may be formed by bringing the compound into contact with a suitable inorganic or organic base under conditions known to the skilled person. A base addition salt may for example be an alkali metal salt (such as a sodium, potassium, or lithium salt) or an alkaline earth metal salt (such as a calcium salt), which may be formed using an alkali metal or alkaline earth metal hydroxide or alkoxide (e.g., an ethoxide or methoxide). A base addition salt may also be formed using a suitably basic organic amine (e.g., a choline or meglumine salt).

A further suitable pharmaceutically acceptable salt of a conjugate of Formula (I), (IC), (IM) or (IT) is, for example, a salt formed within a patient's body after administration of a conjugate of Formula (I), (IC), (IM) or (IT) to the patient.

In a further aspect there is provided a pharmaceutical composition comprising a conjugate of Formula (I), (IC), (IM) or (IT), or a pharmaceutically acceptable salt thereof and a pharmaceutically acceptable excipient.

The term "pharmaceutical composition" refers to a preparation which is in such form as to permit the biological activity of the active ingredient, and which contains no additional components which are unacceptably toxic to a patient to which the composition would be administered. Such compositions can be sterile. A pharmaceutical composition according to the present specification will comprise a conjugate of Formula (I), (IC), (IM) or (IT) or a pharmaceutically acceptable salt thereof, or a pharmaceutically acceptable salt thereof, and a pharmaceutically acceptable excipient.

In embodiments there is provided a pharmaceutical composition comprising a conjugate of Formula (I), (IC), (IM) or (IT), or a pharmaceutically acceptable salt thereof, and a pharmaceutically acceptable excipient, carrier, buffer or stabiliser. Such materials should be non-toxic and should not interfere with the efficacy of the active ingredient. The precise nature of the carrier or other material will depend on the route of administration, which may be oral, or by injection, e.g. cutaneous, subcutaneous, or intravenous.

In embodiments there is provided a pharmaceutical composition comprising a conjugate of Formula (I), (IC), (IM) or (IT), or a pharmaceutically acceptable salt thereof, and a pharmaceutically acceptable, non-toxic, sterile carrier. In further embodiments the carrier is a physiological saline, non-toxic buffer, or preservative. Suitable formulations for use in the therapeutic methods disclosed herein are described in Remington's Pharmaceutical Sciences, 22nd ed., Ed. Lloyd V. Allen, Jr. (2012), the contents of which are incorporated by reference.

Examples of suitable excipients include one or more of water, saline, phosphate buffered saline, dextrose, glycerol and ethanol, as well as any combination thereof. In embodiments there is provided a pharmaceutical composition comprising a conjugate of Formula (I), (IC), (IM) or (IT), or a pharmaceutically acceptable salt thereof, and one or more isotonic agents. In further embodiments the one or more isotonic agents are selected from a sugar, a polyalcohol and sodium chloride.

In embodiments there is provided a pharmaceutical composition comprising a conjugate of Formula (I), (IC), (IM) or (IT), or a pharmaceutically acceptable salt thereof, contained within one or more formulations selected from a capsule, a tablet, an aqueous suspension, a solution, a nasal aerosol, and a lyophilised powder which can be reconstituted to make a suspension or solution before use.

In embodiments there is provided a pharmaceutical composition comprising a conjugate of Formula (I), (IC), (IM) or (IT), or a pharmaceutically acceptable salt thereof, a buffer, a surfactant and/or a stabiliser agent. In further embodiments the buffer is an acetate, phosphate or citrate buffer. In further embodiments the surfactant is polysorbate. In further embodiments the stabiliser agent is human albumin.

The pharmaceutical composition comprising a conjugate of Formula (I), (IC), (IM) or (IT), or a pharmaceutically acceptable salt thereof, can be administered to a patient by any appropriate systemic or local route of administration. For example, administration may be oral, buccal, sublingual, ophthalmic, intranasal, intratracheal, pulmonary, topical, transdermal, urogenital, rectal, subcutaneous, intravenous, intra-arterial, intraperitoneal, intramuscular, intracranial, intrathecal, epidural, intraventricular or intratumoural.

The pharmaceutical composition comprising a conjugate of Formula (I), (IC), (IM) or (IT), or a pharmaceutically acceptable salt thereof, can be formulated for administration by any appropriate means, for example by epidermal or transdermal patches, ointments, lotions, creams, or gels; by nebulisers, vaporisers, or inhalers; by injection or infusion; or in the form of capsules, tablets, liquid solutions or suspensions in water or non-aqueous media, drops, suppositories, enemas, sprays, or powders. The most suitable route for administration in any given case will depend on the physical and mental condition of the subject, the nature and severity of the disease, and the desired properties of the formulation.

Pharmaceutical compositions comprising a conjugate of Formula (I), (IC), (IM) or (IT), or a pharmaceutically acceptable salt thereof, for oral administration may be in tablet, capsule, powder or liquid form. A tablet may comprise a solid carrier or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. A capsule may comprise a solid carrier such a gelatin.

For intravenous, cutaneous or subcutaneous injection, or injection at the site of affliction, the conjugate of Formula (I), (IC), (IM) or (IT), or a pharmaceutically acceptable salt thereof, will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

In one aspect there is provided a conjugate of Formula (I), (IC), (IM) or (IT), or a pharmaceutically acceptable salt thereof, for use in therapy.

In one aspect there is provided a conjugate of Formula (I), (IC), (IM) or (IT), or a pharmaceutically acceptable salt thereof, for use in the treatment of cancer.

Where "cancer" is mentioned, this includes both non-metastatic cancer and also metastatic cancer, such that treating cancer involves treatment of both primary tumours and also tumour metastases.

The term "therapy" is intended to have its normal meaning of dealing with a disease in order to entirely or partially relieve one, some or all of its symptoms, or to correct or compensate for the underlying pathology. The term "therapy" also includes "prophylaxis" unless there are specific indications to the contrary. The terms "therapeutic" and "therapeutically" should be interpreted in a corresponding manner.

The term "prophylaxis" is intended to have its normal meaning and includes primary prophylaxis to prevent the development of the disease and secondary prophylaxis whereby the disease has already developed and the patient is temporarily or permanently protected against exacerbation or worsening of the disease or the development of new symptoms associated with the disease.

The term "treatment" is used synonymously with "therapy". Similarly the term "treat" can be regarded as "applying therapy" where "therapy" is as defined herein.

In embodiments there is provided a conjugate of Formula (I), (IC), (IM) or (IT), or a pharmaceutically acceptable salt thereof, for use in the treatment of HER2 positive cancer.

In one aspect there is provided the use of a conjugate of Formula (I), (IC), (IM) or (IT), or a pharmaceutically acceptable salt thereof, as described herein, in the manufacture of a medicament, such as a medicament for the treatment of cancer.

In one aspect there is provided a method of treating cancer in a patient comprising administering to the patient an effective amount of a conjugate of Formula (I), (IC), (IM) or (IT), or a pharmaceutically acceptable salt thereof.

Terms such as "treating" or "treatment" refer to both (1) therapeutic measures that cure, slow down, lessen symptoms of, and/or halt progression of a diagnosed pathologic condition or disorder and (2) prophylactic or preventative measures that prevent and/or slow the development of a targeted pathologic condition or disorder. Thus, those in need of treatment include those already with the disorder; those prone to have the disorder; and those in whom the disorder is to be prevented. In certain aspects, a patient is successfully "treated" for cancer according to the methods of the present disclosure if the patient shows, e.g., total, partial, or transient remission of a certain type of cancer.

The term "effective amount" means an amount of an active ingredient which is sufficient enough to significantly and positively modify the symptoms and/or conditions to be treated (e.g., provide a positive clinical response). The effective amount of an active ingredient for use in a pharmaceutical composition will vary with the particular condition being treated, the severity of the condition, the duration of the treatment, the nature of concurrent therapy, the particular active ingredient(s) being employed, the particular pharmaceutically-acceptable excipient(s)/carrier(s) utilized, and like factors within the knowledge and expertise of the attending physician.

The term "patient" refers to any animal (e.g., a mammal), including, but not limited to humans, non-human primates, rodents, and the like, which is to be the recipient of a particular treatment. In embodiments the term "patient" refers to a human subject.

In embodiments there is provided a method of treating cancer in a patient comprising administering to the patient an effective amount of a conjugate of Formula (I), (IC), (IM) or (IT), or a pharmaceutically acceptable salt thereof, wherein the cancer is a HER2 positive cancer.

In embodiments there is provided a conjugate of Formula (I), (IC), (IM) or (IT), or a pharmaceutically acceptable salt thereof, and an additional anti-tumour substance for the conjoint treatment of cancer.

In embodiments there is provided a combination for use in the treatment of cancer comprising a conjugate of the Formula (II), or a pharmaceutically acceptable salt thereof and an additional anti-tumour agent.

In embodiments there is provided a conjugate of the Formula (II), or a pharmaceutically acceptable salt thereof, in combination with an additional anti-tumour agent.

Herein, where the term "conjoint treatment" is used in reference to a combination treatment, it is to be understood that this may refer to simultaneous, separate or sequential administration. In one aspect, "conjoint treatment" refers to simultaneous administration. In another aspect, "conjoint treatment" refers to separate administration. In a further aspect, "conjoint treatment" refers to sequential administration.

In embodiments there is provided a method of treating cancer in a patient comprising administering to the patient an effective amount of a conjugate of Formula (I), (IC), (IM) or (IT), or a pharmaceutically acceptable salt thereof, and simultaneously, separately or sequentially administering at least one additional anti-tumour substance to said patient, where the amounts of the conjugate of Formula (I), (IC) or (IM) or a pharmaceutically acceptable salt thereof, and the additional anti-tumour substance are jointly effective in producing an anti-cancer effect.

Conjugation

Examples of $G^A$ and $G^B$ include, but are not limited to, the following, wherein $X^1$ is CH or N, h is 0 or 1, $R^K$ is H or $CH_3$, Hal is Cl, Br or I, $R^L$ is $C_{1-6}$ alkyl, and $\overset{*}{\frown}$ indicates the point of attachment to the antibody, or antigen-binding fragment thereof.

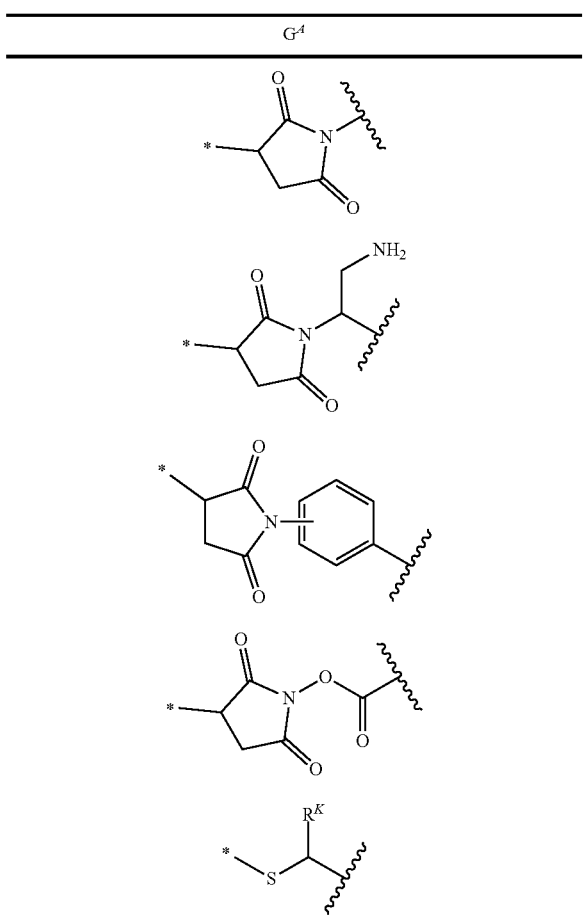

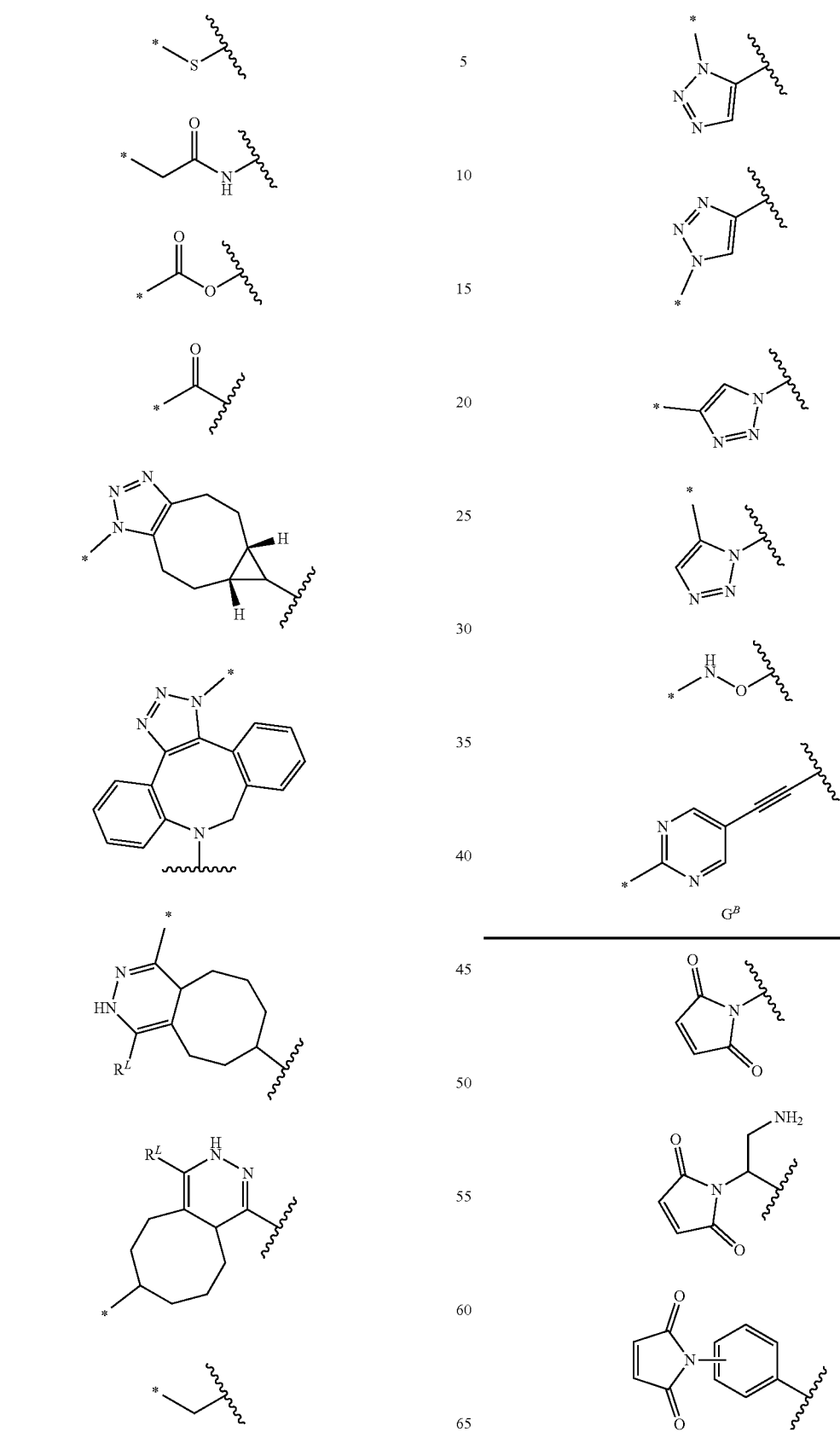

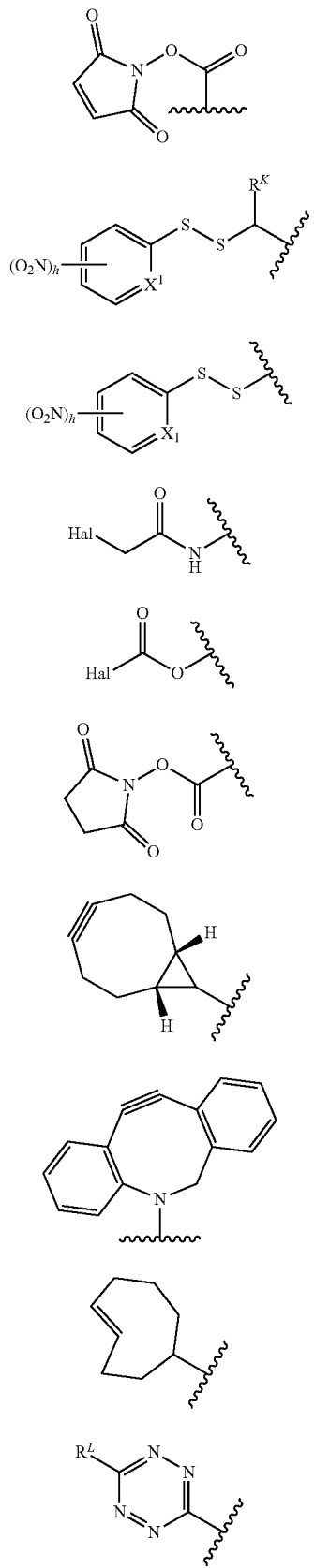

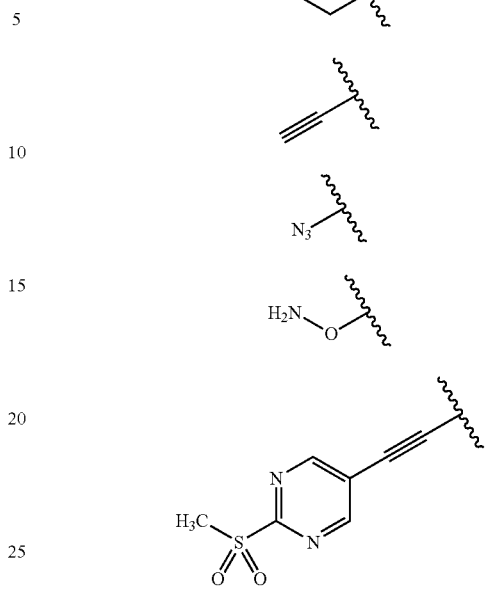

Antibody or Antigen-Binding Fragment Thereof

As used herein, the term "antibody" refers to an immunoglobulin molecule that specifically binds to, or is immunologically reactive with, a particular antigen.

In embodiments the antibody is isolated or recombinant. "Isolated", when used herein refers to a polypeptide, e.g., an antibody, that has been identified and separated and/or recovered from a cell or cell culture from which it was expressed. Ordinarily, an isolated antibody will be prepared by at least one purification step. Thus, an "isolated antibody" refers to an antibody which is substantially free of other antibodies having different antigenic specificities.

In embodiments the antibody comprises at least two "light chains" (LC) and two "heavy chains" (HC). The light chains and heavy chains of such antibodies are polypeptides consisting of several domains. Each heavy chain comprises a heavy chain variable region (abbreviated herein as "VH") and a heavy chain constant region (abbreviated herein as "CH"). The heavy chain constant region comprises the heavy chain constant domains CH1, CH2 and CH3 (antibody classes IgA, IgD, and IgG) and optionally the heavy chain constant domain CH4 (antibody classes IgE and IgM). Each light chain comprises a light chain variable domain (abbreviated herein as "VL") and a light chain constant domain (abbreviated herein as "CL").

In embodiments the antibody is a full-length antibody. An "intact" or "full-length" antibody, as used herein, refers to an antibody having two heavy (H) chain polypeptides and two light (L) chain polypeptides interconnected by disulfide bonds.

A "variable region" of an antibody refers to the variable region of the antibody light chain or the variable region of the antibody heavy chain, either alone or in combination. The variable regions VH and VL can be further subdivided into regions of hypervariability, termed complementarity determining regions (CDRs) (also known as hypervariable regions), interspersed with regions that are more conserved, termed framework regions (FRs). In embodiments each VH and VL is composed of three CDRs and four FRs, arranged from amino-terminus to carboxy-terminus in the following order: FR1, CDR1, FR2, CDR2, FR3, CDR3, FR4. The VH or VL chain of the antibody can further include all or part of a heavy or light chain constant region.

Binding between an antibody and its target antigen or epitope is mediated by the CDRs. The term "epitope" refers to a target protein region (e.g. polypeptide) capable of binding to (e.g. being bound by) an antibody or antigen-binding fragment of the disclosure. The CDRs are the main determinants of antigen specificity. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-lazikani et al. (1997) J. Molec. Biol. 273:927-948)). In addition, combinations of these two approaches are sometimes used in the art to determine CDRs.

The "constant domains" (or "constant regions") of the heavy chain and of the light chain are not involved directly in binding of an antibody to a target, but exhibit various effector functions. The constant regions of the antibodies can mediate the binding of the immunoglobulin to host tissues or factors, including various cells of the immune system (e.g., effector cells) and the first component (Clq) of the classical complement system.

There are five major classes of heavy chain constant region, classified as IgA, IgG, IgD, IgE and IgM, each with characteristic effector functions designated by isotype. Ig molecules interact with multiple classes of cellular receptors. For example, IgG molecules interact with three classes of Fcγ receptors (FcγR) specific for the IgG class of antibody, namely FcγRI, FcγRII, and FcγRIII. Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production. The important sequences for the binding of IgG to the FcγR receptors have been reported to be located in the CH2 and CH3 domains.

In embodiments the antibody or antigen-binding fragment thereof is an IgG isotype. The antibody or antigen-binding fragment thereof can be any IgG subclass, for example IgG1, IgG2, IgG3, or IgG4 isotype. In embodiments the antibody or antigen-binding fragment thereof is based on an IgG1 isotype.

The terms "Fc region", "Fc part" and "Fc" are used interchangeably herein and refer to the portion of a native immunoglobulin that is formed by two Fc chains. Each "Fc chain" comprises a constant domain CH2 and a constant domain CH3. Each Fc chain may also comprise a hinge region. A native Fc region is homodimeric. In embodiments the Fc region may be heterodimeric because it may contain modifications to enforce Fc heterodimerisation. The Fc region contains the carbohydrate moiety and binding sites for complement and Fc receptors (including the FcRn receptor), and has no antigen binding activity. Fc can refer to this region in isolation, or this region in the context of an antibody, antibody fragment, or Fc fusion protein. Polymorphisms have been found in a number of Fc domain sites, including but not limited to EU positions 270, 272, 312, 315, 356, and 358, resulting in minor variations between the sequences described in the instant application and sequences known in the art. As a result, every naturally occurring IgG Fc region is referred to as a "wild type IgG Fc domain" or "WT IgG Fc domain" (i.e., any allele). Human IgG1, IgG2, IgG3, and IgG4 heavy chain sequences can be obtained in a variety of sequence databases, including the UniProt database under accession numbers P01857 (IGHG1_HUMAN), P01859 (IGHG2_HUMAN), P01860 (IGHG3_HUMAN), and P01861 (IGHG4_HUMAN) respectively.

In embodiments the antibody of the disclosure is a monoclonal antibody. A "monoclonal antibody" (mAb) refers to a homogeneous antibody population involved in the highly specific recognition and binding of a single antigenic determinant, or epitope. This is in contrast to polyclonal antibodies that typically include different antibodies directed against different antigenic determinants. The term "monoclonal antibody" can encompass both full-length monoclonal antibodies as well as antibody fragments (such as Fab, Fab', F(ab')2, Fv), single chain (scFv) mutants, fusion proteins comprising an antibody portion, and any other modified immunoglobulin molecule comprising an antigen recognition site. Furthermore, "monoclonal antibody" refers to such antibodies made in any number of ways including, but not limited to, hybridoma, phage selection, recombinant expression, and transgenic animals. In embodiments the antibody of the disclosure is an isolated monoclonal antibody. In further embodiments the antibody is a fully human monoclonal antibody.

In embodiments the antibody of the disclosure is a full-length antibody described above. Alternatively, the antibody can be an antigen-binding fragment. The term "antigen-binding fragment" as used herein incudes any naturally-occurring or artificially-constructed configuration of an antigen-binding polypeptide comprising one, two or three light chain CDRs, and/or one, two or three heavy chain CDRs, wherein the polypeptide is capable of binding to the antigen.

In embodiments the antigen-binding fragment of the disclosure is a Fab fragment. The antibody according to the disclosure can also be a Fab', an Fv, an scFv, an Fd, a V NAR domain, an IgNAR, an intrabody, an IgG CH2, a minibody, a single-domain antibody, an Fcab, an scFv-Fc, F(ab')2, a di-scFv, a bi-specific T-cell engager (BITE), a F(ab')3, a tetrabody, a triabody, a diabody, a DVD-Ig, an (scFv)2, a mAb2 or a DARPin.

The terms "Fab fragment" and "Fab" are used interchangeably herein and contain a single light chain (e.g. a constant domain CL and a VL) and a single heavy chain (e.g. a constant domain CH1 and a VH).

The heavy chain of a Fab fragment is not capable of forming a disulfide bond with another heavy chain.

A "Fab' fragment" contains a single light chain and a single heavy chain but in addition to the CH1 and the VH, a "Fab' fragment" contains the region of the heavy chain between the CH1 and CH2 domains that is required for the formation of an inter-chain disulfide bond. Thus, two "Fab' fragments" can associate via the formation of a disulfide bond to form a F(ab')2 molecule.

A "F(ab')2 fragment" contains two light chains and two heavy chains. Each chain includes a portion of the constant region necessary for the formation of an inter-chain disulfide bond between two heavy chains.

An "Fv fragment" contains only the variable regions of the heavy and light chain. It contains no constant regions.

A "single-domain antibody" is an antibody fragment containing a single antibody domain unit (e.g., VH or VL).

A "single-chain Fv" ("scFv") is antibody fragment containing the VH and VL domain of an antibody, linked together to form a single chain. A polypeptide linker is commonly used to connect the VH and VL domains of the scFv.

A "tandem scFv", also known as a TandAb, is a single-chain Fv molecule formed by covalent bonding of two scFvs in a tandem orientation with a flexible peptide linker.

A "bi-specific T cell engager" (BiTE) is a fusion protein consisting of two single-chain variable fragments (scFvs) on a single peptide chain. One of the scFvs binds to T cells via the CD3 receptor, and the other to a tumour cell antigen.

A "diabody" is a small bivalent and bispecific antibody fragment comprising a heavy chain variable domain (VH) connected to a light chain variable domain (VL) on the same polypeptide chain (VH-VL) connected by a peptide linker that is too short to allow pairing between the two domains on the same chain (Kipriyanov, Int. J. Cancer 77 (1998), 763-772). This forces pairing with the complementary domains of another chain and promotes the assembly of a dimeric molecule with two functional antigen binding sites.

A "DARPin" is a bispecific ankyrin repeat molecule. DARPins are derived from natural ankyrin proteins, which can be found in the human genome and are one of the most abundant types of binding proteins. A DARPin library module is defined by natural ankyrin repeat protein sequences, using 229 ankyrin repeats for the initial design and another 2200 for subsequent refinement. The modules serve as building blocks for the DARPin libraries. The library modules resemble human genome sequences. A DARPin is composed of 4 to 6 modules. Because each module is approx. 3.5 kDa, the size of an average DARPin is 16-21 kDa. Selection of binders is done by ribosome display, which is completely cell-free and is described in He M. and Taussig MJ., Biochem Soc Trans. 2007, November; 35(Pt 5):962-5.

In embodiments the antibody or antigen-binding fragment thereof can be further modified to contain additional chemical moieties not normally part of the protein. Those derivatised moieties can improve the solubility, the biological half-life or absorption of the protein. The moieties can also reduce or eliminate any desirable side effects of the proteins and the like. An overview for those moieties can be found in Remington's Pharmaceutical Sciences, 22nd ed., Ed. Lloyd V. Allen, Jr. (2012).

Drug ($D^R$)

As used herein, $D^R$ is independently a drug comprising a nitrogen atom $N^R$. For a conjugate of Formula (I) or a pharmaceutically acceptable salt thereof, nitrogen atom $N^R$ is covalently attached to $J^A$. For a compound of Formula (II) or a salt thereof, nitrogen atom $N^R$ is covalently attached to $J^B$. For a compound of Formula (VI) or a salt thereof, nitrogen atom $N^R$ is covalently attached to $J^{VI}$. For a compound of Formula (IX) or a salt thereof, nitrogen atom $N^R$ is covalently attached to $J^{IX}$.

A conjugate of Formula (I) or a pharmaceutically acceptable salt thereof, may undergo cleavage to release the drug in its free drug form. $D^R$ may be represented as $N(R'')(R''')$, wherein $N(R'')(R''')$ is collectively the drug and the nitrogen atom shown is $N^R$. In this representation, the free drug form is $HN(R'')(R''')$.

For a conjugate of Formula (I) or a pharmaceutically acceptable salt thereof, or a compound of Formula (II) or a salt thereof, the nitrogen atom $N^R$ may be the nitrogen atom of a secondary of tertiary carbamate. In other words, the nitrogen atom $N^R$ may, in the free drug form, be the nitrogen atom of a primary or secondary amine.

In embodiments there is provided a conjugate of Formula (I) or a pharmaceutically acceptable salt thereof, or a compound of Formula (II), (VI) or (IX), or a salt thereof, wherein the nitrogen atom $N^R$ in the nitrogen atom of an aliphatic secondary of tertiary carbamate. In other words, the nitrogen atom $N^R$, in the free drug form, is the nitrogen atom of an aliphatic primary or secondary amine.

In embodiments the drug is a therapeutic agent. In further embodiments the drug is a cytotoxic drug. In further embodiments the drug is a DNA damage response inhibitor, antineoplastic agent and tubulin disrupting agent. In further embodiments the drug is a topoisomerase I inhibitor or microtubule inhibitor (MTI). In further embodiments the drug is a camptothecin drug.

In embodiments the drug is a diagnostic agent or an imaging agent.

In embodiments $D^R$ is

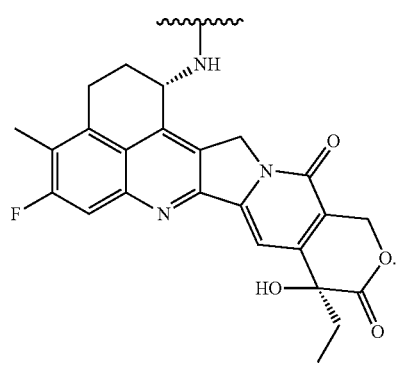 [SMILES: *N[C@H]1CCc2c(C)c(F)cc3nc4c(c1c23)Cn1c-4cc2c(c1=O)COC(=O)[C@]2(O)CC]

In embodiments $D^R$ is

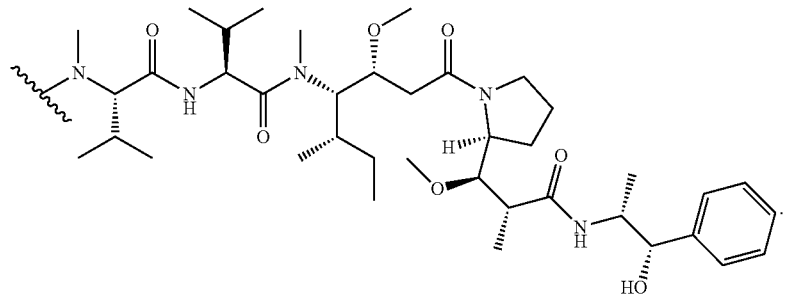 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@H](C)[C@@H](O)c1ccccc1)OC)C(C)C)C(C)C]

In embodiments $D^R$ is

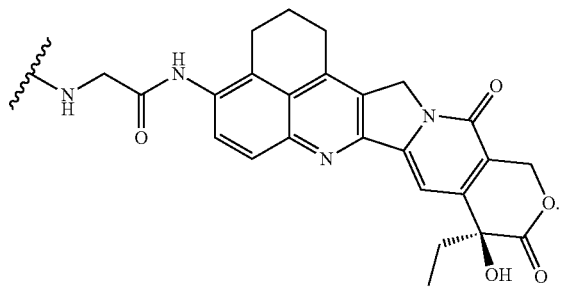 [SMILES: *NCC(=O)Nc1ccc2nc3c(c4c2c1CCC4)Cn1c-3cc2c(c1=O)COC(=O)[C@]2(O)CC]

In embodiments the free drug form of the drug is exatecan ((1S,9S)-1-amino-9-ethyl-5-fluoro-9-hydroxy-4-methyl-1,2,3,9,12,15-hexahydro-10H,13H-benzo[de]pyrano[3',4':6,7]indolizino[1,2-b]quinoline-10,13-dione).

In embodiments the free drug form of the drug is MMAE ((S)—N-((3R,4S,5S)-1-((S)-2-(((1R,2R)-3-(((1S,2R)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)-N,3-dimethyl-2-((S)-3-methyl-2-(methylamino)butanamido)butanamide).

In embodiments the free drug form of the drug is (S)-2-amino-N-(9-ethyl-9-hydroxy-10,13-dioxo-2,3,9,10,13,15-hexahydro-1H,12H-benzo[de]pyrano[3',4':6,7]indolizino[1,2-b]quinolin-4-yl)acetamide.

The released drug may, following release from the conjugate in the biological system, undergo a chemical modification, such as an enzyme-mediated chemical reaction and/or metabolism. As such, in embodiments the drug may be a pro-drug.

EXAMPLES

The specification will now be illustrated by the following non-limiting Examples.

General Information

Flash chromatography was performed using a BIOTAGE ISOLERA and fractions checked for purity using thin-layer chromatography (TLC). TLC was performed using MERCK KIESELGEL 60 F254 silica gel, with fluorescent indicator on aluminium plates. Visualisation of TLC was achieved with UV light.

Extraction and chromatography solvents were bought and used without further purification from VWR U.K.

All fine chemicals were purchased from SIGMA-ALDRICH unless otherwise stated.

Pegylated reagents were obtained from QUANTA BIODESIGN US via STRATECH UK.

LC/MS Conditions

Positive mode electrospray mass spectrometry was performed using a WATERS ACQUITY H-CLASS SQD2 using one of the following methods.

(a) The HPLC (WATERS ALLIANCE 2695) was run using a mobile phase of water (A) (formic acid 0.1%) and acetonitrile (B) (formic acid 0.1%).

LCMS 3 min: Initial composition 5% B held over 25 seconds, then increased from 5% B to 100% B over a 1 minute 35 seconds' period. The composition was held for 50 seconds at 100% B, then returned to 5% B in 5 seconds and held there for 5 seconds. The total duration of the gradient run was 3.0 minutes. Flow rate was 0.8 mL/minute. Wavelength detection range: 190 to 800 nm. Columns: WATERS ACQUITY UPLC BEH SHIELD RP18 1.7 μm 2.1×50 mm at 50° C. fitted with WATERS ACQUITY UPLC BEH SHIELD RP18 VANGUARD Pre-column, 130 A, 1.7 μm, 2.1 mm×5 mm.

LCMS 15 min: initial composition 5% B held over 1 min, then increase from 5% B to 100% B over a 9 min period. The composition was held for 2 min at 100% B, then returned to 5% B in 0.10 minutes and hold there for 3 min. Total gradient run time equals 15 min. Flow rate 0.6 mL/min. Wavelength detection range: 190 to 800 nm. Oven temperature: 50° C. Column: WATERS ACQUITY UPLC CSH C18 1.7 μm 2.1×100 mm fitted with WATERS ACQUITY UPLC CSH C18 VANGUARD Pre-column, 1.7 μm, 2.1 mm×5 mm.

(b) The HPLC (Agilent 1290) was run using a mobile phase of water (A) (TFA 0.03%) and acetonitrile (B) (0.03% TFA), or water (A) (TFA 0.05%) and acetonitrile (B) (0.05% TFA). Initial composition was (a) 100% A held for 2-4 minutes then increased to 90% B over 2-5 minutes, or (b) 5%-20% B increased to 90%-98% B over 3-17 minutes. Flow rate was 0.3-1.5 mL/minute. Column was (1) ATLANTIS T3 3 μm 4.6*150 mm at 40° C. (Detector ELSD or Wavelength detection range: 210 nm), (2) ACQUITY UPLC BEH C18 2.1*100 mm 1.7 m at 40° C. (Wavelength detection range: 210 nm or 220 nm), (3) UPLC BEH C18 1.7 m, 2.1*100 mm at 40° C. (Wavelength detection range: 223 nm), (4) XBRIDGE C18 (4.6*150,3.5 m) at 40° C., (5) ACQUITY UPLC HSS PFP 2.1*150 mm 1.8 m at 40° C. (Wavelength detection range: 220 nm), (6) UPLC BEH Phenyl 1.7 m, 2.1*150 mm at 40° C. (Wavelength detection range: 210 nm), (7) EC-C18 2.7 m, 3.0*50 mm at 40° C. (Wavelength detection range: 210 nm), or (8) YMC-Triart C18 50*3.0 mm S-3 um, 12 nm at 45° C. (Detector ELSD). Injection volume 2 μL.

HPLC Conditions

Reverse-phase ultra-fast high-performance liquid chromatography (UFLC) was carried out on a SHIMADZU PROMINENCE machine using a PHENOMENEX GEMINI NX 5μ C18 column (at 50° C.) dimensions: 150×21.2 mm. Eluents used were solvent A ($H_2O$ with 0.1% formic acid) and solvent B ($CH_3CN$ with 0.1% formic acid). All UFLC experiments were performed with gradient conditions: Initial composition 13% B increased to 30% B over a 3 minutes period, then increased to 45% B over 8 minutes and again to 100% over 6 minutes before returning to 13% over 2 min and hold for 1 min. The total duration of the gradient run was 20.0 minutes. Flow rate was 20.0 mL/minute and detection was at 254 and 223 nm.

NMR Method

Proton NMR chemical shift values were measured on the delta scale at 400 MHz using a BRUKER AV400. The following abbreviations have been used: s, singlet; d, doublet; t, triplet; q, quartet; quin, quintet; m, multiplet; br, broad. Coupling constants are reported in Hz.

Abbreviations

TLC Thin layer chromatography
UV Ultra violet
LCMS Liquid chromatography mass spectrometry
CSH Charged surface hybrid
UPLC Ultra-performance liquid chromatography
RP Reverse phase
NMR Nuclear magnetic resonance
DBU 1,8-Diazabicyclo[5.4.0]undec-7-ene
DMF Dimethyl formamide
DCM Dichloromethane
TBS Tert-butyl dimethyl silane MS Molecular sieves
TFA Trifluoro acetic acid
DMSO Dimethyl sulfoxide
ESI Electrospray ionisation
DIPEA Di isopropyl ethylamine
THF Tetra hydro furan
HATU Hexafluorophosphate azabenzotriazole tetramethyl uronium
TEA Triethylamine
HOPO 1-Hydroxy-2-pyridone
RT Retention time
ADC Antibody-drug conjugate
UHPLC Ultra-high performance liquid chromatography
mAb Monoclonal antibody
SEC Size exclusion chromatography
DAR Drug to antibody ratio
RPMI Roswell Park Memorial Institute
ND Not detectable
$IC_{50}$ Inhibitory concentration 50%
Fmoc fluorenylmethoxycarbonyl Intermediate 1

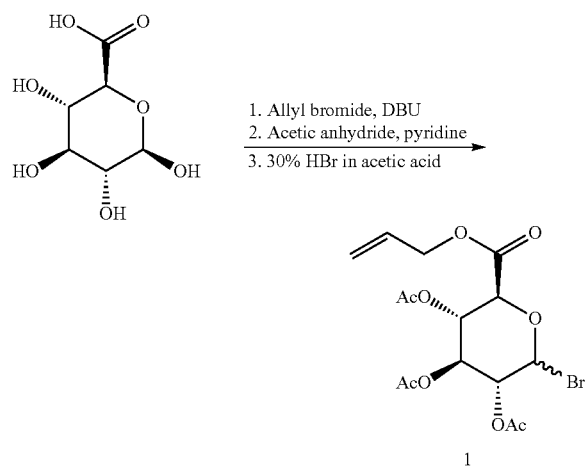

2,3,4,6,7,8,9,10-octahydropyrimido[1,2-a]azepine (26.5 ml, 177.35 mmol) was added dropwise to a 1-L round bottom flask containing (2S,3S,4S,5R,6R)-3,4,5,6-tetrahydroxytetrahydro-2H-pyran-2-carboxylic acid (31.3 g, 161.22 mmol) in DMF (100 ml) at 21° C. Next, 3-bromoprop-1-ene (16.72 ml, 193.47 mmol) was added to the reaction mixture dropwise over 10 minutes and the reaction was stirred at 21° C. for 24 hours. Reaction mixture was cooled to 0° C. and treated with pyridine (104 mL, 1289.60 mmol). Acetic anhydride (244 mL, 2579.20 mmol) was next added to the reaction mixture. The reaction was warmed up to room temperature and run for 2 hours at 21° C. Reaction mixture concentrated under reduced vacuum and the remaining pyridine was azeotropically removed with toluene (1×100 mL). Crude material was diluted with DCM (65 mL) and cooled to 0° C. 30% Hydrobromic acid in acetic acid (175 mL, 3226.03 mmol) was next added to the reaction mixture at 0° C. The reaction was warmed up to room temperature and run for 2 hours 30 minutes at 21° C. Solvent was evaporated then the compound was purified by normal phase flash column chromatography to afford (2S,3S,4S,5R, 6R)-2-((allyloxy)carbonyl)-6-bromotetrahydro-2H-pyran-3, 4,5-triyl triacetate Intermediate 1 (33 g, 48% yield) as a beige translucent material. $^1$H NMR (500 MHz, CDCl$_3$) δ 6.67 (d, J=4.0 Hz, 1H), 5.92 (ddt, J=16.6, 10.3, 6.0 Hz, 1H), 5.64 (t, J=9.7 Hz, 1H), 5.42-5.23 (m, 3H), 4.88 (dd, J=10.0, 4.0 Hz, 1H), 4.71-4.58 (m, 3H), 2.12 (s, 3H), 2.07 (s, 3H), 2.05 (s, 3H); LCMS (ESI) m/z 445.0 (M+Na)+.

Alternative Synthesis of Intermediate 1

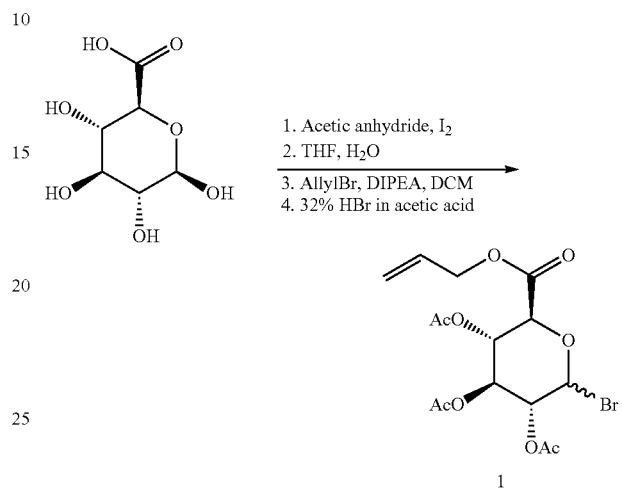

Iodine (1.19 kg, 4.69 mol) was added to acetic anhydride (3500 mL) stirred at 0-10° C. under nitrogen. The resulting mixture was adjusted to 20-30° C. and Glucuronic acid (7 kg, 36.06 mol) was added portion wise, maintaining the temperature at 25-30° C. The reaction was stirred at this temperature for 1 hour under nitrogen and then cooled to 0° C. A solution of sodium thiosulfate pentahydrate (2.33 kg) in water (35.2 L) was added to the stirred mixture at 0-10° C., and then stirred to 2 hours at 20-30° C. Water (35.2 L) was added to the stirred mixture, extracted with isopropyl acetate (3×35.2 L), and the organic layer was concentrated to dryness to give crude 1,2,3,4-tetra-O-acetyl-β-D-glucuronic acid (16.08 kg, 61% w/w assay, 75%). LCMS m/z (ES+), [M+Na]$^+$=384.6 Crude 1,2,3,4-tetra-O-acetyl-β-D-glucuronic acid, 61% w/w (16 kg; 27.05 mol) was dissolved in isopropyl acetate (42.83 kg) and stirred at 20-30° C. N,N-diisopropylethylamine (12.25 kg, 94.68 mol) was added to the reaction at 20-30° C. over 11 minutes followed by 3-bromopropene (9.8 kg, 81.15 mol) added dropwise at 20-30° C. over 5 minutes. The resulting mixture was stirred for 48 hours at 20-30° C. Isopropyl acetate (42.83 kg) and water (49 kg) were added to the stirred mixture. The organic layer separated and adjusted to pH 4-5 at 20-30° C. by addition of aqueous hydrochloric acid (0.6N, 43.71 kg). The separated organic layer was washed with brine (25% aqueous solution, 49 L), and concentrated to dryness to give crude 1,2,3,4-tetra-O-acetyl-β-D-glucuronic acid allyl ester as a brown solid (12.0 kg, 87.5% w/w assay, 86.6%). LCMS m/z (ES+), [M+Na]$^+$=424.833% hydrobromic acid in acetic acid (534 mL, 2.982 mol) was added dropwise to a stirred mixture of crude 1,2,3,4-tetra-O-acetyl-β-D-glucuronic acid allyl ester (200 g, 0.497 mol) in isopropyl acetate (500 mL) at 0° C. The reaction was adjusted to 20-30° C. and stirred for 8 hours. The reaction mixture was extracted with isopropyl acetate (2400 mL), and the extract washed with brine (25% aqueous, 3×2000 mL) and concentrated to dryness to give crude product as a black oil (231.3 g, 80.5%). LCMS (ES+), [M+Na]$^+$=445.2 & 447, $^1$H NMR (300 MHz, CDCl$_3$)

δ 6.65 (d, J=4.2 Hz, 1H), 5.59-5.84 (m, 1H), 5.62 (t, J=9.6 Hz, 1H), 5.40-5.23 (m, 3H), 4.87 (dd, J=9.9, 3.9 Hz, 1H), 4.66-4.59 (m, 3H), 2.21-2.03 (m, 9H)

Intermediate 2

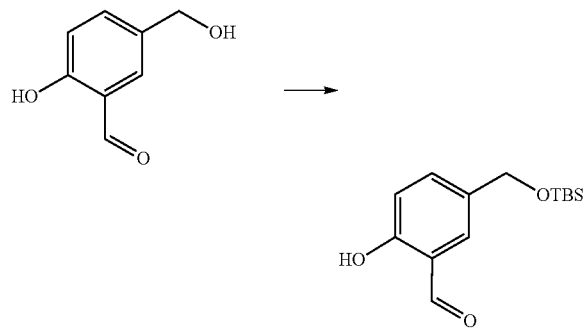

TBS-Cl (20.80 g, 138.02 mmol) in DCM (25 mL) was added dropwise to 1H-imidazole (17.90 g, 262.90 mmol) and 2-hydroxy-5-(hydroxymethyl)benzaldehyde (20 g, 131.45 mmol) in DCM (500 mL) at 0° C. over a period of 2 hours under nitrogen. The resulting mixture was stirred at 0° C. for 2 hours. The reaction mixture was quenched with water (500 mL), extracted with DCM (2×300 mL), the organic layer was dried over Na2SO4, filtered and evaporated to afford 5-(((tert-butyldimethylsilyl)oxy)methyl)-2-hydroxybenzaldehyde Intermediate 2 (35.0 g, 100%) as a colourless material. m/z (ES+), [M+Na]$^+$=289; NH$_4$HCO$_3$, HPLC tR=1.505 min Intermediate 3

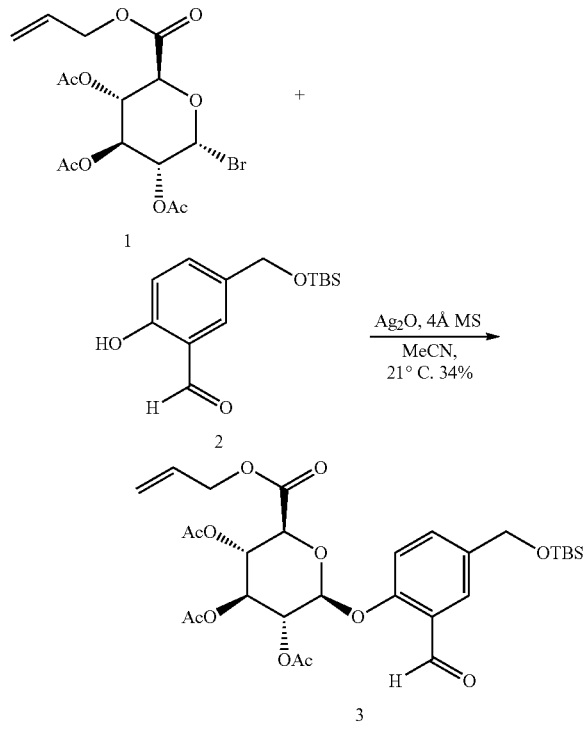

To a vacuum-dried 500 mL round-bottom flask was added molecular sieves (4 Å beads, 5.0 g), silver oxide (29.2 g, 125.8 mmol) and acetonitrile (150 mL), producing a black slurry. To this slurry was added a solution of Intermediate 1 (10.7 g, 25.2 mmol) in acetonitrile (50 mL) over 20 min followed by the addition of 5-(((tert-butyldimethylsilyl)oxy)methyl)-2-hydroxybenzaldehyde (Intermediate 2, 13.6 g, 51.1 mmol) in acetonitrile (50 mL) in one portion. The resulting mixture was stirred vigorously at 20° C. for 16 h. After 16 h, the reaction mixture was filtered through a 5-cm pad of Celite and rinsed with dichloromethane (3×25 mL). Solvent was evaporated then the compound was purified by normal phase flash column chromatography to afford (2S,3S,4S,5R,6S)-2-((allyloxy)carbonyl)-6-(4-(((tert-butyldimethylsilyl)oxy)methyl)-2-formylphenoxy)tetrahydro-2H-pyran-3,4,5-triyl triacetate as a white material Intermediate 3 (5.2 g, 34% yield). 1H NMR (400 MHz, CDCl$_3$) δ 10.34 (s, 1H), 7.77 (d, J=1.8 Hz, 1H), 7.58 (dd, J=8.6, 2.1 Hz, 1H), 7.14 (d, J=8.6 Hz, 1H), 5.81-5.92 (m, 1H), 5.39-5.35 (m, 4H), 5.28-5.22 (m, 2H), 4.71 (s, 2H), 4.58-4.67 (m, 2H), 4.20-4.28 (m, 1H), 2.073 (s, 3H), 2.069 (s, 3H), 2.04 (s, 3H), 0.94 (s, 9H), 0.11 (s, 6H); LCMS (ESI) m/z 626.3 (M+NH$_4$)+.

Intermediate 4

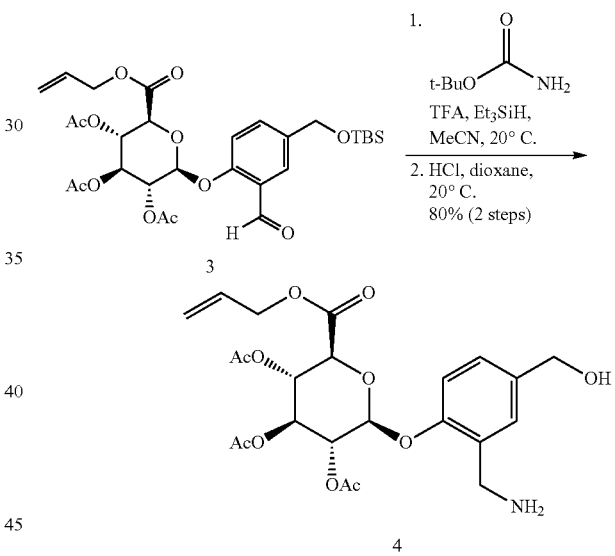

To a solution of Intermediate 3 (5.2 g, 8.6 mmol) in acetonitrile (40 mL) was added tert-butyl carbamate (3.8 g, 32.3 mmol), trifluoroacetic acid (2.0 mL, 25.9 mmol), and triethylsilane (4.1 mL, 25.8 mmol). Stirred for 2 h at 20° C. then solvent was evaporated. To the resulting colorless oil was added 1,4-dioxane (8 mL) and HCl (4.0 M in 1,4-dioxane, 50 mL, 200 mmol). The mixture was stirred at 20° C. for 30 min the solvent was evaporated. The resulting white powder was dissolved in DMSO (3 mL) then passed through cation-exchange resin pre-treated with methanol (WATERS PORAPAK CX). The desired compound was eluted off the resin with methanol to afford (2S,3S,4S,5R,6S)-2-((allyloxy)carbonyl)-6-(2-(aminomethyl)-4-(hydroxymethyl)phenoxy)tetrahydro-2H-pyran-3,4,5-triyl triacetate as a white material Intermediate 4 (2.5 g, 80% over 2 steps). 1H NMR (500 MHz, CDCl$_3$) δ 7.26 (d, J=2.2 Hz, 1H), 7.21 (dd, J=8.3, 2.2 Hz, 1H), 7.01 (d, J=8.3 Hz, 1H), 5.90-5.82 (m, 1H), 5.42-5.24 (m, 6H), 5.16 (d, J=7.1 Hz, 1H), 4.64-4.55 (m, 4H), 4.19 (d, J=9.3 Hz, 1H), 3.84 (d, J=14.0 Hz, 1H), 3.67 (d, J=14.0 Hz, 1H), 2.32 (s, 3H), 2.09 (s, 3H), 2.07 (s, 3H), 2.03 (s, 3H). LCMS (ESI) m/z 496.5 (M+H)+.

Intermediate 5

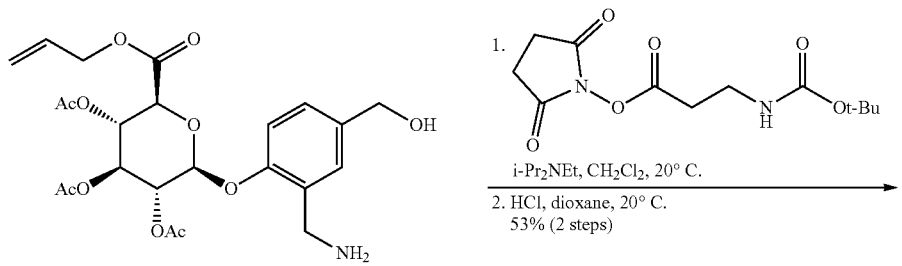

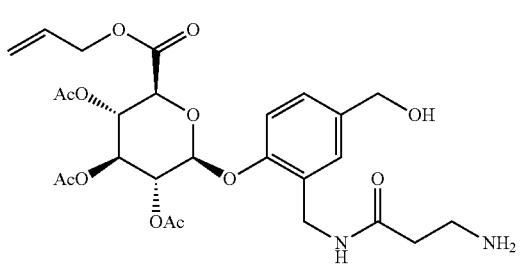

To a suspension of Intermediate 4 (2.5 g, 5.0 mmol) in dichloromethane (20 mL) was added N-ethyl-N-isopropyl-propan-2-amine (1.8 mL, 10.1 mmol) and 2,5-dioxopyrrolidin-1-yl 3-((tert-butoxycarbonyl)amino)propanoate (1.3 g, 4.4 mmol). Stirred at 20° C. for 10 minutes then water (50 mL) was added. Organic layer was separated then the aqueous layer was extracted with dichloromethane (3×30 mL). Combined organic layers were dried over $Na_2SO_4$ the solvent was evaporated. To a solution of (2S,3S,4S,5R,6S)-2-((allyloxy)carbonyl)-6-(2-((3-((tert-butoxycarbonyl)amino)propanamido)methyl)-4-(hydroxymethyl)phenoxy)tetrahydro-2H-pyran-3,4,5-triyl triacetate (2.8 g, 4.2 mmol) in dichloromethane (20 mL) was added hydrochloric acid (4.0 M in 1,4-dioxane, 2.6 mL, 83.9 mmol). Stirred at 20° C. for 2 h then solvent was evaporated. The compound was purified by reverse phase flash column chromatography to afford (2S,3S,4S,5R,6S)-2-((allyloxy)carbonyl)-6-(2-((3-aminopropanamido)methyl)-4-(hydroxymethyl)phenoxy)tetrahydro-2H-pyran-3,4,5-triyl triacetate as a colorless material Intermediate 5 (1.3 g, 53% over 2 steps). 1H NMR (500 MHz, $D_2O$) δ 7.22 (d, J=2.2 Hz, 1H), 7.16 (d, J=8.2 Hz, 1H), 7.09 (d, J=8.4 Hz, 1H), 5.84 (ddt, J=16.6, 10.5, 6.0 Hz, 1H), 5.44 (t, J=9.2 Hz, 1H), 5.38 (dd, J=7.6, 3.3 Hz, 1H), 5.35-5.23 (m, 4H), 4.62 (d, J=9.8 Hz, 1H), 4.56 (d, J=6.0 Hz, 2H), 4.51 (s, 2H), 4.26 (q, J=15.3 Hz, 2H), 3.23 (t, J=6.8 Hz, 2H), 2.68 (td, J=6.8, 1.9 Hz, 2H), 2.06 (d, J=10.4 Hz, 9H). LCMS (ESI) m/z 567.2 (M+H)+.

Alternative Synthesis of Intermediate 5

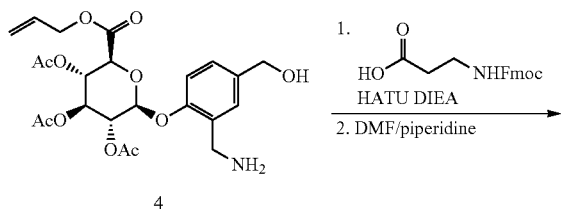

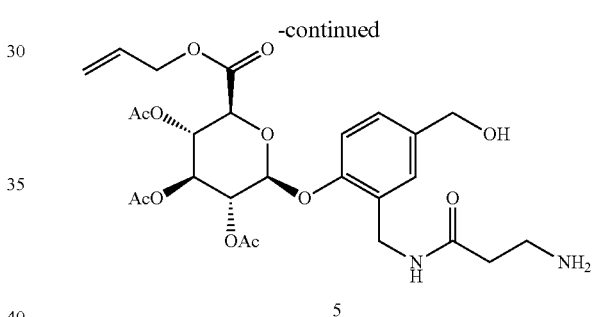

To a stirred reactor containing Intermediate 4 (2.1 kg, 90.5% w/w, 3.57 mol) and acetonitrile (19 L) was added Fmoc-β-alanine (1.11 kg, 3.57 mol). The stirred mixture was cooled to 0° C. To this was added hexafluorophosphate azabenzotriazole tetramethyl uronium (1.36 kg, 3.57 mol) and N,N-diisopropylethylamine (0.92 kg, 7.14 mol), and stirred for 4 hours, maintaining the temperature at 0° C. Water (19 L) and ethyl acetate (19 L) was added to the stirred mixture. The organic phase was separated and concentrated to ~19 L under vacuum. Ethyl acetate (28.5 L) was added to the concentrated solution and stirred at 20-25° C. for 18 hours. The resulting suspension was filtered, the cake washed with ethyl acetate (3.87 L), and dried under vacuum to (2S,3R,4S,5S,6S)-2-(2-((3-((((9H-fluoren-9-yl)methoxy)carbonyl)amino)propanamido)methyl)-4-(hydroxymethyl)phenoxy)-6-((allyloxy)carbonyl)tetrahydro-2H-pyran-3,4,5-triyl triacetate (1.6 kg, 99% w/w, 56%). LCMS m/z 789 [M+H]$^+$ To a stirred reactor containing (2S,3R,4S,5S,6S)-2-(2-((3-((((9H-fluoren-9-yl)methoxy)carbonyl)amino)propanamido)methyl)-4-(hydroxymethyl)phenoxy)-6-((allyloxy)carbonyl)tetrahydro-2H-pyran-3,4,5-triyl triacetate (1 kg, 1.27 mol) and tetrahydrofuran (10 L) at −45° C. under nitrogen was added 2,3,4,6,7,8,9,10-octahydropyrimido[1,2-a]azepine (385.98 g, 2.54 mol). The mixture was stirred at -45° C. for four hours then diluted with acetonitrile (5 L) and quenched by the addition of hydrogen chloride in tert-butyl methyl ether solution (2.54 L, 2.0 M, 5.07 mol). The mixture was concentrated to ~5 L under vacuum, and diluted with n-heptane (5 L). The acetonitrile layer was collected containing Intermediate 8 (3.88 kg of MeCN solution, 89.97% area, assumed 100%). LCMS m/z 566.6 [M+H]⁺

Intermediate 7

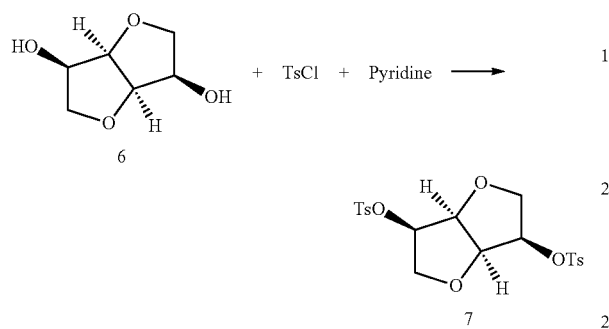

To a 250 mL round bottom flask was added Intermediate 6 (5.0 g, 34.21 mmol)) in dry DCM (100 mL) under nitrogen gas. To the solution was added pyridine (13.84 mL, 171.07 mmol) followed by tosyl-Cl (16.31 g, 85.53 mmol). The reaction mixture was stirred at 20° C. for 16 h. LC-MS analysis showed formation of desired product and completion of reaction. The reaction mixture was diluted with dichloromethane (200). Organic layer was separated, and compound was extracted in 200 mL dichloromethane. Combined organic layer was washed with HCl solution (1M-300 mL), brine (200 mL) and dried over magnesium sulfate. Solvent was removed under reduced pressure to get crude products. The compound was purified via silica gel column to give (3R,3aS,6R,6aS)-hexahydrofuro[3,2-b]furan-3,6-diyl bis(4-methylbenzenesulfonate) Intermediate 7 (14.90 g, 96%). 1H NMR (500 MHz, CDCl3) δ 7.90-7.76 (m, 4H), 7.45-7.33 (m, 4H), 4.94-4.80 (m, 2H), 4.55-4.44 (m, 2H), 3.94 (dd, J=9.6, 6.7 Hz, 2H), 3.75 (dd, J=9.6, 7.6 Hz, 2H), 2.48 (s, 6H). LCMS (ESI) m/z 455.21 (M+H)⁺.

Intermediate 8

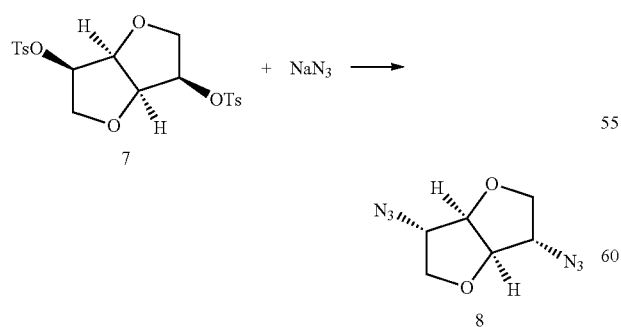

To a 50 mL round bottom flask was added Intermediate 7 (6.0 g, 13.20 mmol) in dry DMF (15 mL) under nitrogen gas. To the solution was added sodium azide (2.146 g, 33.00 mmol). The reaction mixture was at 140° C. for 3 hrs. LC-MS analysis showed formation of desired product and completion of reaction. The reaction mixture was diluted with dichloromethane (200×2 mL), and organic layer was separated, washed with water (200 mL), brine (200 mL) and dried over magnesium sulfate. Solvent was removed under reduced pressure to get (3S,3aR,6S,6aR)-3,6-diazidohexahydrofuro[3,2-b]furan Intermediate 8 (2.050 g, 79%). ¹H NMR (500 MHz, CDCl₃) δ 4.61 (d, J=1.9 Hz, 2H), 4.05 (d, J=4.0 Hz, 2H), 3.97-3.82 (m, 4H). LCMS (ESI) m/z 197.1 (M+H)⁺.

Intermediate 9

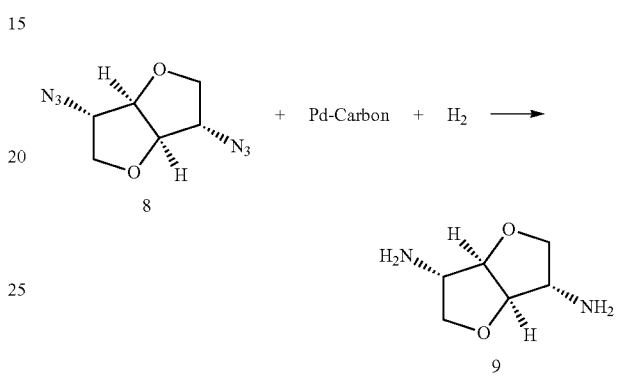

To a 250 mL round bottom flask was added Intermediate 8 (1 g, 5.10 mmol) in dry THF (20 mL) under nitrogen gas. To the solution was added barium palladium(II) carbonate (0.618 g, 0.51 mmol). The reaction mixture was flushed with hydrogen (1.028 g, 509.76 mmol) gas and stirred at 23° C. for 3 hrs. under H₂ gas. LC-MS analysis showed formation of desired product and completion of reaction. The reaction mixture was diluted with methanol (20 mL) filtered through celite pad. Celite pad was washed with methanol (50 mL). Filtrate was dried over magnesium sulfate. Solvent was removed under reduced pressure to get (3S,3aR,6S,6aR)-hexahydrofuro[3,2-b]furan-3,6-diamine Intermediate 9 (0.590 g, 80%). 1H NMR (500 MHz, DMSO) δ 4.23 (s, 2H), 3.68 (dd, J=8.7, 4.5 Hz, 2H), 3.41 (dd, J=8.7, 1.9 Hz, 2H), 3.23 (dd, J=4.5, 1.9 Hz, 2H), 1.54 (s, 4H). LCMS (ESI) m/z 145.2 (M+H)*.

Alternative Synthesis of Intermediate 9

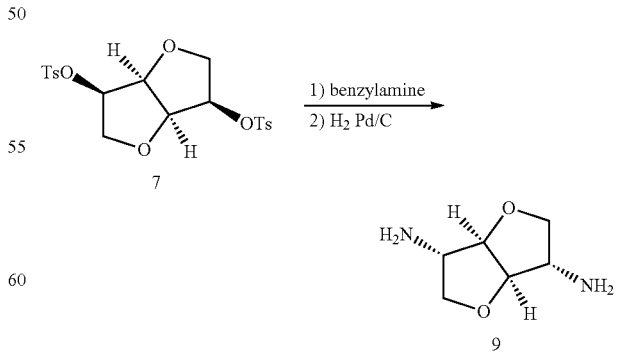

To reactor was added intermediate 6 (4 kg, 8.8 mol) and benzylamine (12 L) under nitrogen. The stirred mixture was heated to 160° C. for 24 hours then cooled to 20-25° C., diluted with tert-butyl methyl ether (80 L) and cooled further to 10° C. To this was added para-toluene sulfonic acid (12.11 kg, 70.44 mol), the mixture stirred for 2.5 hours at 20-25° C. and then filtered. The cake was washed with tert-butyl methyl ether (8 L) and the combined filtrates washed with saturated aqueous sodium hydrogen carbonate solution (20 L). The organic phase was evaporated to dryness, dissolved in ethanol (20 L) and evaporated to dryness to give crude intermediate 7 (3.05 kg, 80.5% w/w, 85.9%) LCMS m/z (ES+), [M+H]$^+$=325.1 To a reactor was added Intermediate 7 (1.5 kg, 3.08 mol) and ethanol (12.12 L) under a dry under nitrogen atmosphere. To the solution was added 10% wt palladium on carbon (120.8, 10% w/w).

The reaction mixture was flushed with hydrogen gas and stirred at 80° C. for 16 hours under hydrogen. Mixture cooled to 20-25° C. and filtered through cellulose (2.42 kg). The cake was washed with ethanol (2.44 L) and combined filtrates were concentrated to dryness. The residue was dissolved in acetonitrile (6.04 L) and concentrated to dryness to give Intermediate 9 (509 g, 84% w/w, 80.2%). LCMS m/z (ES+), [M+H]$^+$=145

Intermediate 11

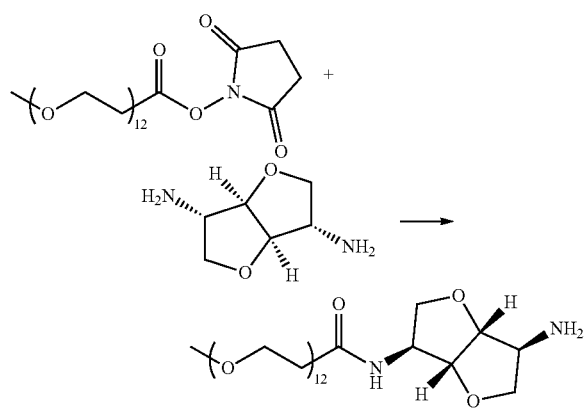

To a 250 mL round bottom flask was added Intermediate 9 (1.50 g, 10.40 mmol) in dry THF (25 mL) under nitrogen gas. To the solution was added sodium hydrogen carbonate (1.748 g, 20.81 mmol) and 2,5-dioxopyrrolidin-1-yl 2,5,8,11,14,17,20,23,26,29,32,35-dodecaoxaoctatriacontan-38-oate Intermediate 10 (7.13 g, 10.40 mmol) in portions under nitrogen gas and stirred at 20° C. for 6 hrs. LC-MS analysis showed formation of desired product and completion of reaction. The reaction mixture was quenched by addition of methanol (10 mL). The reaction mixture was diluted with methanol (20 mL) filtered through celite pad. Celite pad was washed with methanol (50 mL). Filtrate was dried over magnesium sulfate. Solvent was removed under reduced pressure to get crude product. the crud product was purified via silica gel column to give N-((3S,3aR,6S,6aR)-6-aminohexahydrofuro[3,2-b]furan-3-yl)-2,5,8,11,14,17,20,23,26, 29,32,35-dodecaoxaoctatriacontan-38-amide Intermediate 11 (4.00 g, 53.8%). 1H NMR (500 MHz, MeOD) δ 4.64-4.59 (m, 1H), 4.45 (dd, J=4.1, 1.3 Hz, 1H), 4.29 (dt, J=4.1, 1.9 Hz, 1H), 3.96 (ddd, J=10.2, 9.3, 4.9 Hz, 2H), 3.81-3.74 (m, 3H), 3.73-3.62 (m, 45H), 3.61-3.56 (m, 2H), 3.45 (dt, J=3.8, 1.8 Hz, 1H), 3.40 (s, 3H), 2.52-2.47 (m, 2H). LCMS (ESI) m/z 715.6 (M+H)$^+$.

Intermediate 13

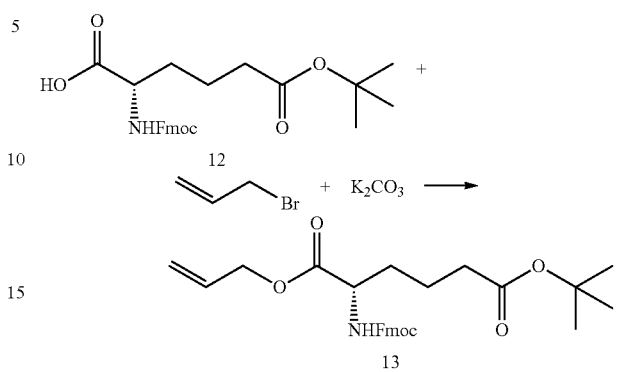

To a 250 mL round bottom flask was added (S)-2-((((9H-fluoren-9-yl)methoxy)carbonyl)amino)-6-(tert-butoxy)-6-oxohexanoic acid Intermediate 12 (5 g, 11.38 mmol) in dry DMF (20 mL) under nitrogen gas. To the solution was added potassium carbonate (3.14 g, 22.75 mmol) and 3-bromoprop-1-ene (1.485 mL, 17.06 mmol) in portions under nitrogen gas and stirred at 20° C. for 16 hrs. LC-MS analysis showed formation of desired product and completion of reaction. The reaction mixture was diluted with water (500 mL) and organic layer was extracted with ethyl acetate (2×300 mL), washed with water (300 mL), brine (200 mL) and dried over sodium sulfate (20 g). The solvent was removed to get crude product. The crude product was purified via silica gel column to give 1-allyl 6-(tert-butyl) (S)-2-((((9H-fluoren-9-yl)methoxy)carbonyl)amino) hexanedioate Intermediate 13 (5.10 g, 93%). $^1$H NMR (500 MHz, CDCl$_3$) δ 7.79-7.73 (m, 2H), 7.61 (q, J=3.9 Hz, 2H), 7.40 (t, J=7.5 Hz, 2H), 7.32 (tt, J=7.4, 1.2 Hz, 2H), 5.91 (ddt, J=16.5, 10.9, 5.8 Hz, 1H), 5.42-5.23 (m, 3H), 4.66 (d, J=5.8 Hz, 2H), 4.40 (q, J=4.8 Hz, 3H), 4.23 (t, J=7.1 Hz, 1H), 2.26 (t, J=7.2 Hz, 2H), 1.96-1.82 (m, 1H), 1.72 (dq, J=13.5, 6.1 Hz, 3H), 1.60-1.47 (m, 1H), 1.45 (s, 9H). LCMS (ESI) m/z 480.2 (M+H)$^+$.

Intermediate 14

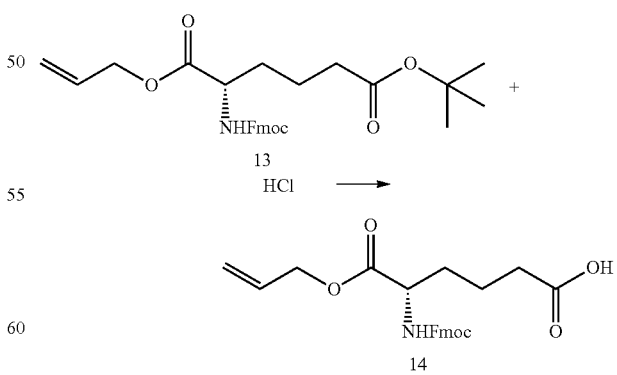

To a 100 mL round bottom flask was added Intermediate 13 (5 g, 10.43 mmol) in dry THF (20 mL) under nitrogen gas. To the solution was added HCl (13.03 mL, 52.13 mmol), 4 molar in dioxane under nitrogen gas and stirred at 20° C. for 6 hrs. LC-MS analysis showed formation of desired product and completion of reaction. The reaction mixture was diluted with water (200 mL) and organic layer was extracted with dichloromethane (2×300 mL), washed with brine (200 mL) and dried over sodium sulfate (20 g). The solvent was removed to get (S)-5-((((9H-fluoren-9-yl)methoxy)carbonyl)amino)-6-(allyloxy)-6-oxohexanoic acid Intermediate 14 (4.20 g, 95%). 1H NMR (500 MHz, CDCl$_3$) δ 7.75 (dq, J=7.6, 1.0 Hz, 2H), 7.62-7.52 (m, 2H), 7.42-7.35 (m, 2H), 7.30 (tt, J=7.4, 1.2 Hz, 2H), 5.90 (ddt, J=16.4, 10.8, 5.8 Hz, 1H), 5.48 (d, J=8.4 Hz, 1H), 5.37-5.20 (m, 2H), 4.64 (d, J=5.8 Hz, 2H), 4.40 (d, J=7.2 Hz, 3H), 4.22 (t, J=7.0 Hz, 1H), 2.45-2.24 (m, 2H), 1.93 (p, J=5.6 Hz, 1H), 1.72 (td, J=13.9, 6.8 Hz, 3H). (ESI) m/z 424.5 (M−H)⁻.

Intermediate 15

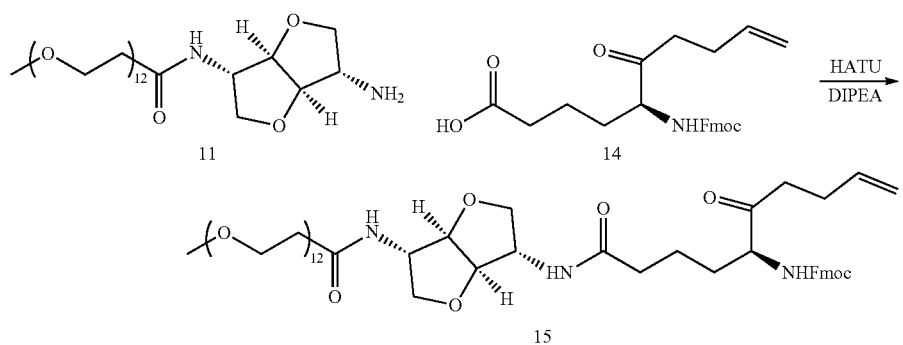

To a 100 mL round bottom flask was added Intermediate 14 (1.925 g, 4.55 mmol) under nitrogen gas. To the solution was added HATU (1.862 g, 4.90 mmol) followed by DIPEA (1.222 mL, 6.99 mmol). The reaction mixture was stirred at room temperature for 15 min then Intermediate 11 (2.5 g, 3.50 mmol). was added and reaction mixture was stirred at 23° C. for 3 hrs. LC-MS analysis showed formation of desired product and completion of reaction. The reaction mixture was diluted with DCM (300 mL), washed with water (200 mL), organic layer was extracted (2×100 mL), washed with Brine (50 mL), dried over sodium sulfate (5 g). Solvent was removed under reduced pressure to get crude product. The crude product was purified via silica gel column to give allyl (S)-6-((((3S,3aR,6S,6aR)-6-(2,5,8,11,14,17,20,23,26,29,32,35-dodecaoxaoctatriacontan-38-amido)hexahydrofuro[3,2-b]furan-3-yl)amino)-2-((((9H-fluoren-9-yl)methoxy)carbonyl)amino)-6-oxohexanoate Intermediate 15 (3.40 g, 87%) 1H NMR (500 MHz, MeOD) δ 7.86 (dd, J=7.6, 1.2 Hz, 2H), 7.74 (t, J=7.8 Hz, 2H), 7.46 (td, J=7.5, 1.4 Hz, 2H), 7.38 (tt, J=7.5, 1.3 Hz, 2H), 6.05-5.93 (m, 1H), 5.39 (dq, J=17.2, 1.6 Hz, 1H), 5.28 (dq, J=10.5, 1.4 Hz, 1H), 4.73-4.65 (m, 2H), 4.58 (qd, J=4.1, 1.0 Hz, 2H), 4.46 (dd, J=10.6, 7.0 Hz, 1H), 4.40 (dd, J=10.6, 7.0 Hz, 1H), 4.36-4.31 (m, 2H), 4.31-4.24 (m, 2H), 4.01 (ddd, J=9.6, 5.0, 1.1 Hz, 2H), 3.84-3.73 (m, 5H), 3.72-3.60 (m, 44H), 3.60-3.56 (m, 2H), 3.41 (s, 3H), 2.49 (td, J=6.0, 1.9 Hz, 2H), 2.31 (hept, J=7.2 Hz, 2H), 1.96-1.85 (m, 1H), 1.85-1.68 (m, 3H). LCMS (ESI) m/z 1121.3 (M+H)⁺.

Intermediate 16

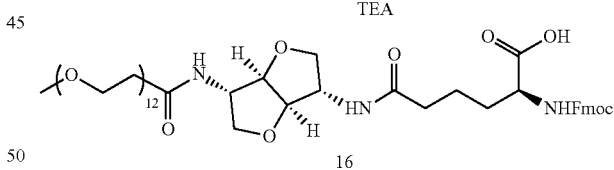

To a 50 mL round bottom flask was added Intermediate 15 (4.3 g, 3.84 mmol) in dry DCM (10 mL) under nitrogen gas. To the solution was added triethylamine (0.535 mL, 3.84 mmol) followed by triphenylphosphine (0.101 g, 0.38 mmol). To the reaction mixture was added Pd(PPh$_3$)$_4$ (0.444 g, 0.38 mmol) then formic acid (0.147 mL, 3.84 mmol) was added and reaction mixture was stirred at 23° C. for 6 hrs. LC-MS analysis showed formation of desired product and completion of reaction. Solvent was removed under reduced pressure to get crude products. The crude product was purified via silica gel column to give (S)-6-(((3S,3aR,6S,6aR)-6-(2,5,8,11,14,17,20,23,26,29,32,35-dodecaoxaocta-triacontan-38-amido)hexahydrofuro[3,2-b]furan-3-yl)amino)-2-((((9H-fluoren-9-yl)methoxy)carbonyl)amino)-6-oxohexanoic acid Intermediate 16 (3.50 g, 84%). ¹H NMR (500 MHz, DMSO) δ 8.12 (dd, J=10.2, 7.0 Hz, 2H), 7.90 (d, J=7.6 Hz, 2H), 7.74 (d, J=7.5 Hz, 2H), 7.63 (d, J=8.1 Hz, 1H), 7.46-7.38 (m, 2H), 7.34 (td, J=7.4, 1.2 Hz, 2H), 4.38 (s, 2H), 4.32-4.20 (m, 3H), 4.11 (ddt, J=7.2, 4.8, 2.1 Hz, 2H), 3.93 (td, J=8.4, 4.6 Hz, 1H), 3.85 (dd, J=9.3, 5.1 Hz, 2H), 3.63-3.57 (m, 4H), 3.54-3.45 (m, 42H), 3.45-3.40 (m, 2H), 3.24 (s, 3H), 2.33 (t, J=6.5 Hz, 2H), 2.09 (s, 3H), 1.68 (d, J=9.1 Hz, 1H), 1.64-1.48 (m, 3H). LCMS (ESI) m/z 1080.6 (M+H)$^+$.
Intermediate 17
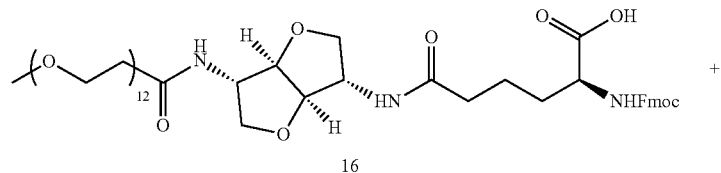
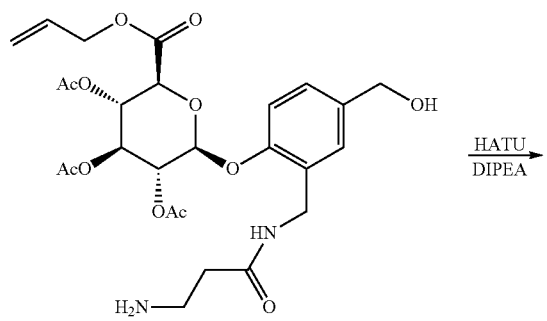
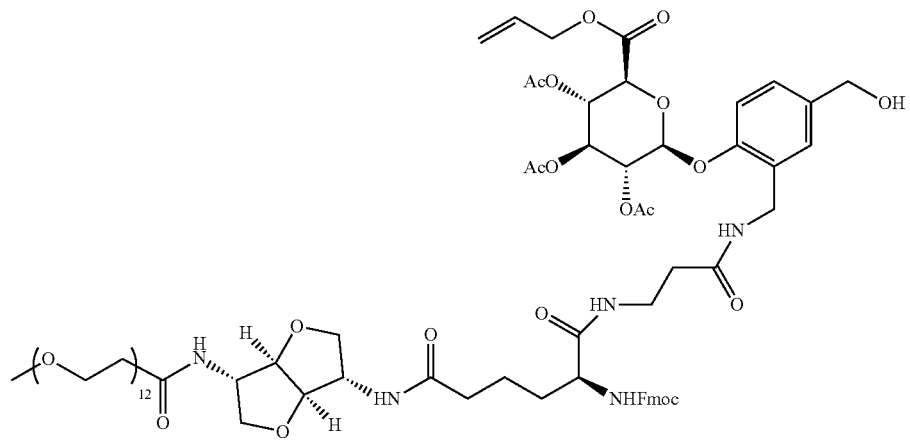

To a 100 mL round bottom flask was added Intermediate 16 (0.8 g, 0.74 mmol) under nitrogen gas. To the solution was added HATU (0.366 g, 0.96 mmol) followed by DIPEA (0.388 mL, 2.22 mmol). The reaction mixture was stirred at room temperature for 15 min then Intermediate 5 (0.670 g, 1.11 mmol). was added and reaction mixture was stirred at 23° C. for 3 hrs. LC-MS analysis showed formation of desired product and completion of reaction. The reaction mixture was diluted with DCM (100 mL), washed with water (100 mL), organic layer was extracted (2×100 mL), washed with Brine (100 mL), dried over sodium sulfate (15 g). Solvent was removed under reduced pressure and purified via silica gel column to give (2S,3R,4S,5S,6S)-2-(2-((S)-5-(4-(((3S,3aR,6S,6aR)-6-(2,5,8,11,14,17,20,23,26,29,32,35-dodecaoxaoctatriacontan-38-amido)hexahydrofuro[3,2-b]furan-3-yl)amino)-4-oxobutyl)-1-(9H-fluoren-9-yl)-3,6,10-trioxo-2-oxa-4,7,11-triazadodecan-12-yl)-4-(hydroxymethyl)phenoxy)-6-((allyloxy)carbonyl)tetrahydro-2H-pyran-3,4,5-triyl triacetate Intermediate 17 (0.640 g, 53.1%). 1H NMR (500 MHz, DMSO) δ 8.21 (t, J=6.0 Hz, 1H), 8.11 (dd, J=19.5, 6.9 Hz, 2H), 7.94 (t, J=5.8 Hz, 1H), 7.89 (d, J=7.5 Hz, 2H), 7.73 (t, J=7.0 Hz, 2H), 7.49-7.39 (m, 3H), 7.33 (td, J=7.5, 1.2 Hz, 2H), 7.17 (dd, J=8.4, 2.2 Hz, 1H), 7.13 (s, 1H), 7.01 (d, J=8.4 Hz, 1H), 5.89 (ddt, J=17.3, 10.5, 5.7 Hz, 1H), 5.56 (d, J=7.9 Hz, 1H), 5.48 (t, J=9.6 Hz, 1H), 5.33 (dq, J=17.2, 1.6 Hz, 1H), 5.26 (dq, J=10.5, 1.4 Hz, 1H), 5.19-5.07 (m, 3H), 4.76 (d, J=10.0 Hz, 1H), 4.62 (ddt, J=13.3, 5.6, 1.4 Hz, 1H), 4.54 (ddt, J=13.3, 5.8, 1.4 Hz, 1H), 4.44-4.36 (m, 4H), 4.31-4.18 (m, 4H), 4.11 (d, J=5.9 Hz, 3H), 3.93 (d, J=5.9 Hz, 1H), 3.88-3.81 (m, 2H), 3.66-3.56 (m, 5H), 3.56-3.45 (m, 42H), 3.45-3.39 (m, 3H), 3.29-3.27 (m, 1H), 3.24 (s, 3H), 3.18 (d, J=5.0 Hz, 1H), 2.33 (ddt, J=14.6, 10.0, 7.6 Hz, 4H), 2.10-2.05 (m, 2H), 2.04 (s, 3H), 1.99 (d, J=4.6 Hz, 6H), 1.54 (dt, J=43.7, 8.9 Hz, 4H). LCMS (ESI) m/z 1629.8 (M+H)+.

Intermediate 18

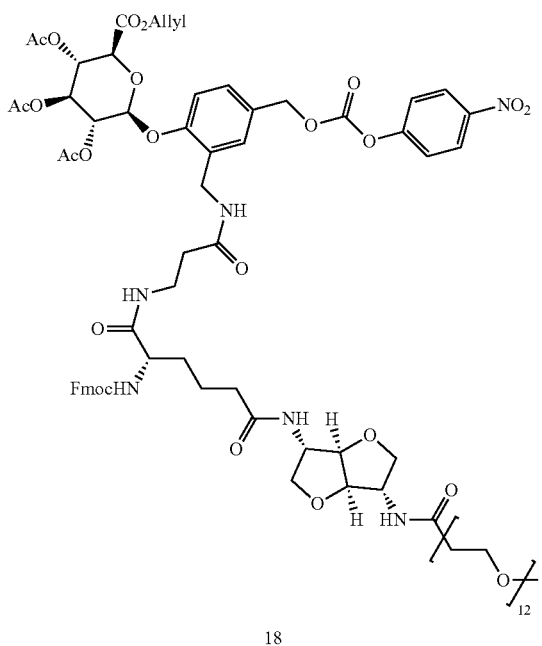

18

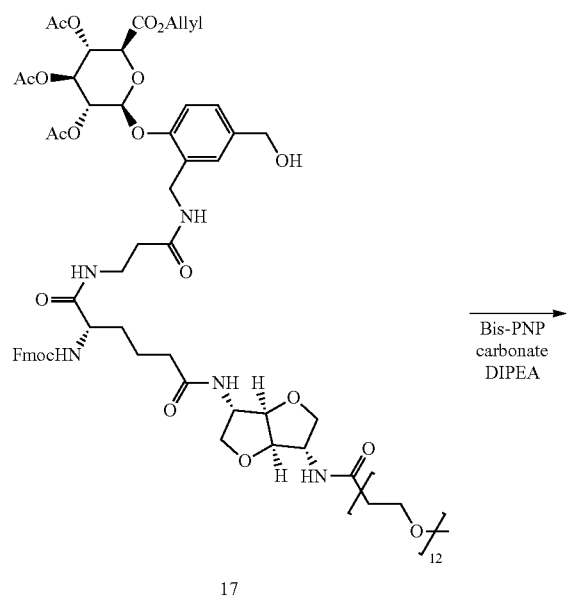

17

To a solution of Intermediate 17 (25.00 mg, 0.02 mmol, 1.0 eq) in DMF was added bis(4-nitrophenyl) carbonate (28.0 mg, 0.09 mmol, 4.5 eq) and DIPEA (0.013 mL, 0.08 mmol, 4.0 eq). The mixture was stirred at 23° C. for 2 hours. Following this time the mixture was concentrated in vacuo and the residue was sonicated in DCM (200 μL) and diethyl ether (2 mL). The resulting suspension was dried on vacuum filter and the process repeated. The residue was dried to give (2S,3R,4S,5S,6S)-2-(2-((S)-5-(4-(((3S,3aR,6S,6aR)-6-(2,5,8,11,14,17,20,23,26,29,32,35-dodecaoxaoctatriacontan-38-amido)hexahydrofuro[3,2-b]furan-3-yl)amino)-4-oxobutyl)-1-(9H-fluoren-9-yl)-3,6,10-trioxo-2-oxa-4,7,11-triazadodecan-12-yl)-4-((((4-nitrophenoxy)carbonyl)oxy)methyl)phenoxy)-6-((allyloxy)carbonyl)tetrahydro-2H-pyran-3,4,5-triyl triacetate Intermediate 18 (32 mg, 0.02 mmol, 91%) as a yellow material. RT 7.74 min. LCMS (ESI) m/z 1794.7 [M+H]+.

Intermediate 19

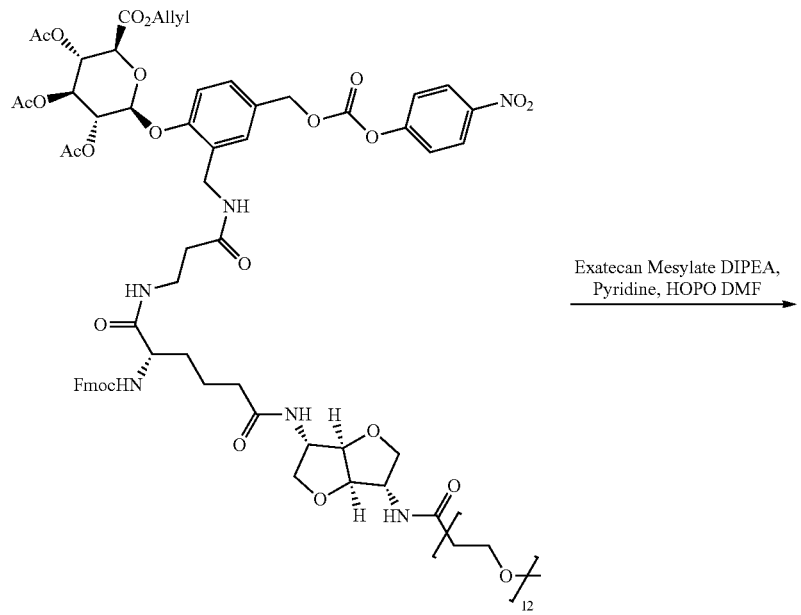

18

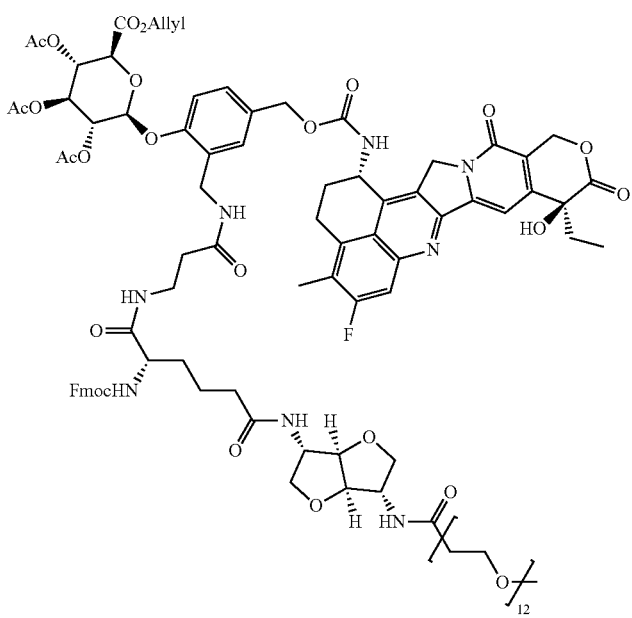

19

To a solution of exatecan mesylate (7.41 mg, 0.01 mmol, 1.0 eq) in DCM (1 mL) and DMF (1.000 mL) was added DIPEA (7.28 µl, 0.04 mmol, 4.0 eq), Intermediate 18 (25.00 mg, 0.01 mmol, 1.0 eq), and HOPO (1.703 mg, 0.02 mmol, 2.0 eq) and the resultant mixture was stirred at 23° C. for 18 hours. Following this time the mixture was concentrated in vacuo and the residue was purified by reverse phase flash column chromatography (C18 BIOTAGE prepacked column, 40-60% MeCN [0.1% formic acid]/water [0.1% formic acid]) to give (2S,3R,4S,5S,6S)-2-(2-((S)-5-(4-(((3S,3aR,6S,6aR)-6-(2,5,8,11,14,17,20,23,26,29,32,35-dodecaoxaoctatriacontan-38-amido)hexahydrofuro[3,2-b]furan-3-yl)amino)-4-oxobutyl)-1-(9H-fluoren-9-yl)-3,6,10-trioxo-2-oxa-4,7,11-triazadodecan-12-yl)-4-(((((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)carbamoyl)oxy)methyl)phenoxy)-6-((allyloxy)carbonyl)tetrahydro-2H-pyran-3,4,5-triyl triacetate Intermediate 19 (13 mg, 0.01 mmol, 63%) as a yellow material. RT 7.66 min. LCMS (ESI) 2090.3 [M+H]+.

Intermediate 20

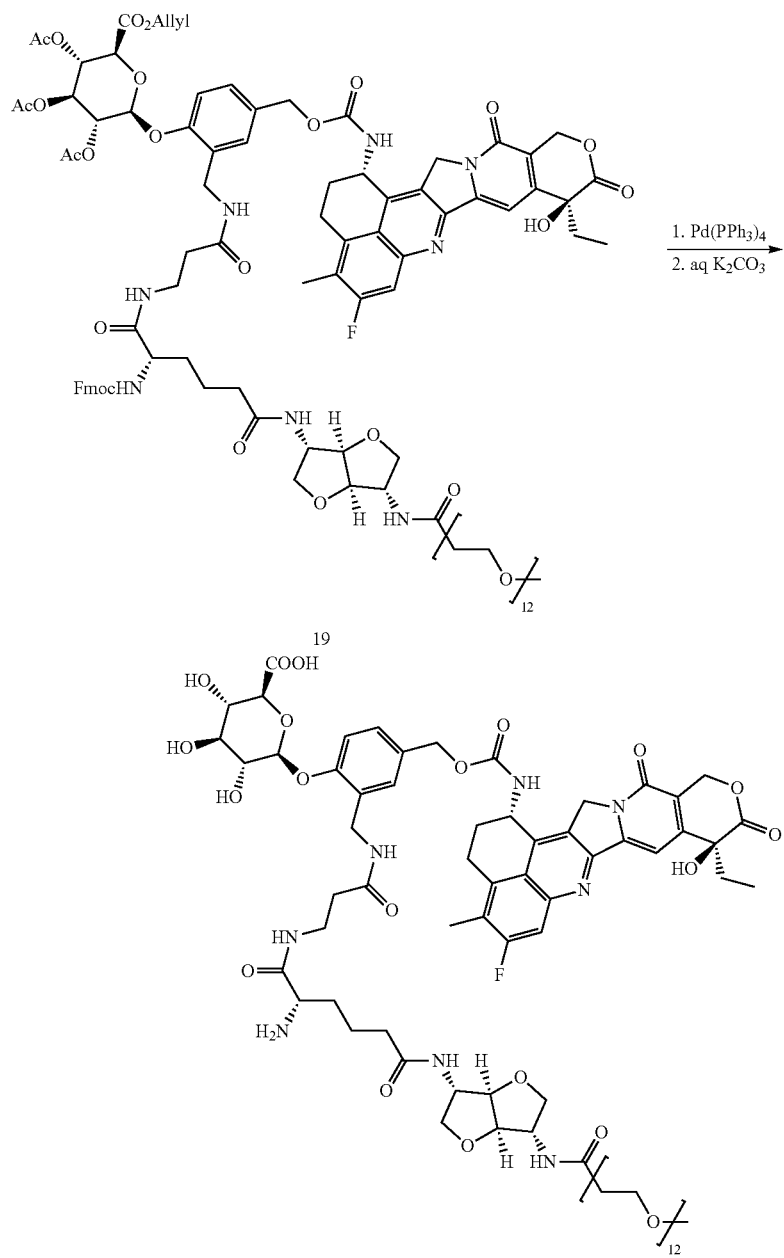

To a solution of Intermediate 19 (15.00 mg, 7.18 μmol, 1.0 eq) in DCM (1 mL) was added triethylamine (2.00 μl, 0.01 mmol, 1.4 eq), Pd(PPh$_3$)$_4$ (1.00 mg, 0.87 μmol, 12 mol %) and formic acid (0.541 μl, 0.01 mmol, 1.4 eq) and the mixture stirred at 23° C. for 18 hours the mixture. Following this time the reaction mixture was concentrated and the crude residue was dissolved in methanol (0.25 mL) and THF (0.25 mL). To this solution was added potassium carbonate (9.44 mg, 0.07 mmol, 10 eq) in water (0.5 mL) and the mixture was stirred at 23° C. for 3 hours. Following this time the mixture was concentrated in vacuo to remove organics. The remaining aqueous solution was acidified with citric acid (1 N) until pH 4 was reached and the mixture was stirred for 1 hour at 23° C. Following this time the mixture was filtered and the residue was purified by reverse phase flash column chromatography (C18 BIOTAGE prepacked column, 20-40% MeCN [0.1% formic acid]/water [0.1% formic acid]) to give (2S,3S,4S,5R,6S)-6-(2-((3-((S)-6-(((3S,3aR,6S,6aR)-6-(2,5,8,11,14,17,20,23,26,29,32,35-do-decaoxaoctatriacontan-38-amido)hexahydrofuro[3,2-b]furan-3-yl)amino)-2-amino-6-oxohexanamido)propanamido)methyl)-4-(((((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)carbamoyl)oxy)methyl)phenoxy)-3,4,5-trihydroxytetrahydro-2H-pyran-2-carboxylic acid Intermediate 20 (8.6 mg, 5.03 μmol, 70%) as a yellow material. RT 5.08 min. LCMS (ESI) 1702.6 [M+H]+.

Intermediate 21

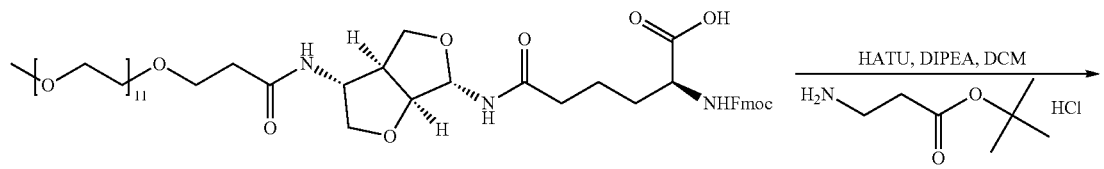

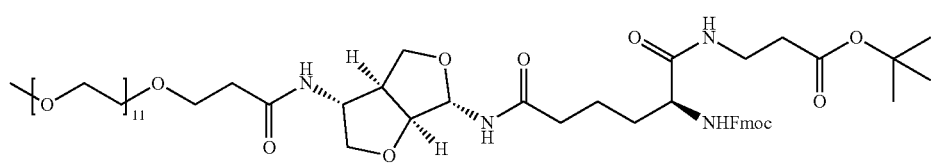

To Intermediate 16 (0.410 g, 0.38 mmol) in DCM (8 mL) was added tert-butyl 3-aminopropanoate hydrochloride (0.138 g, 0.76 mmol), HATU (0.289 g, 0.76 mmol) and DIPEA (0.265 mL, 1.52 mmol). DMF (2 mL) was added and the reaction mixture stirred at room temperature for 2 h. The reaction mixture was diluted with EtOAc. The organics were washed with sat. NaHCO$_3$, 1 M citric acid, and brine. The organics were dried and concentrated under reduced pressure to give 600 mg of crude tert-butyl 3-((S)-6-(((3S,3aR,6S,6aR)-6-(2,5,8,11,14,17,20,23,26,29,32,35-dodecaoxaoctatriacontan-38-amido)hexahydrofuro[3,2-b]furan-3-yl)amino)-2-((((9H-fluoren-9-yl)methoxy)carbonyl)amino)-6-oxohexanamido)propanoate Intermediate 21 which was used without further purification. LCMS (3 min): 1.78 min; 1208.6 [M+H]+.

Intermediate 22

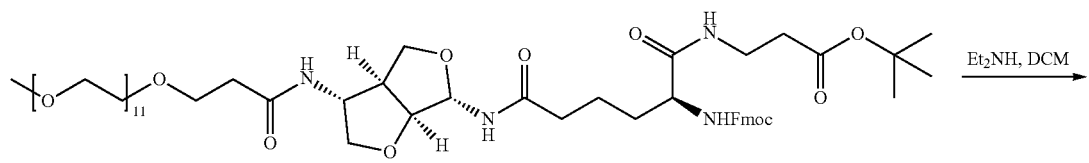

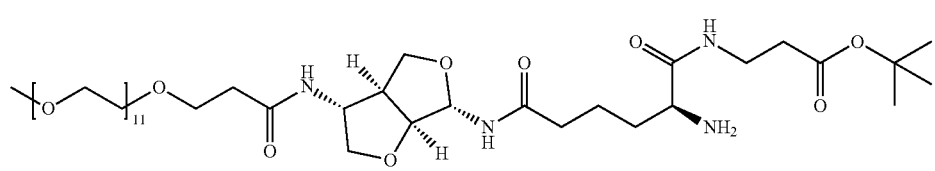

To crude Intermediate 21 (0.459 g, 0.38 mmol) in DCM (2 mL) was added diethylamine (2 mL). The reaction mixture was stirred at room temperature for 2 h. The reaction mixture was concentrated under reduced pressure to give a crude tert-butyl 3-((S)-6-(((3S,3aR,6S,6aR)-6-(2,5,8,11,14,17,20,23,26,29,32,35-dodecaoxaoctatriacontan-38-amido)hexahydrofuro[3,2-b]furan-3-yl)amino)-2-amino-6-oxohexanamido)propanoate Intermediate 22 which was used without purification. LCMS (3 min): 1.21 min; 986.5 [M+H]+.

Intermediate 23

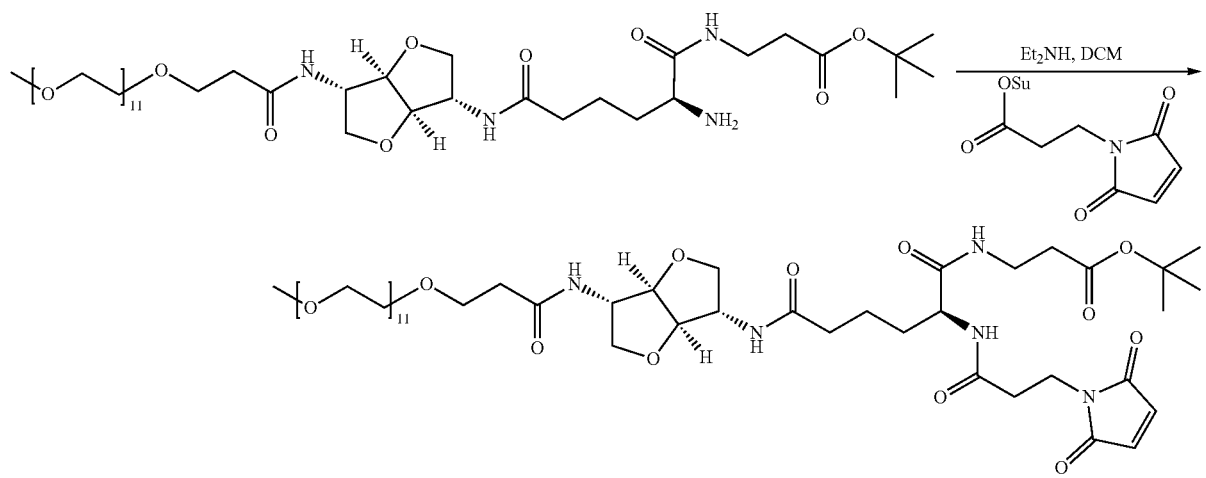

To crude Intermediate 22 (0.374 g, 0.38 mmol) in DMF (4 mL) was added 2,5-dioxopyrrolidin-1-yl 3-(2,5-dioxo-2,5-dihydro-1H-pyrrol-1-yl)propanoate (0.250 g, 0.94 mmol) and DIPEA (0.265 mL, 1.52 mmol). The reaction mixture was stirred at room temperature for 20 min. The reaction mixture was purified by column chromatography (5-40% MeCN in water+0.1% FA) to give tert-butyl 3-((S)-6-(((3S,3aR,6S,6aR)-6-(2,5,8,11,14,17,20,23,26,29,32,35-dodecaoxaoctatriacontan-38-amido)hexahydrofuro[3,2-b]furan-3-yl)amino)-2-(3-(2,5-dioxo-2,5-dihydro-1H-pyrrol-1-yl)propanamido)-6-oxohexanamido)propanoate Intermediate 23 (0.213 g, 49.3%) as a colourless material. LCMS (15 min): 5.41 min; 1137.5 [M+H]+, 1164.0 [M+Na]+.

Intermediate 24

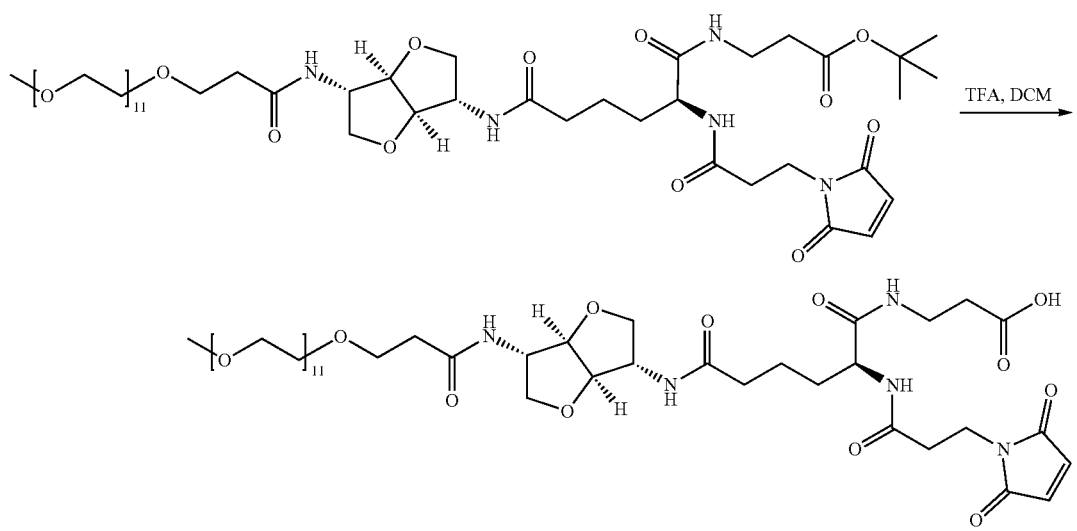

To Intermediate 23 (46 mg, 0.04 mmol) in DCM (2 mL) was added TFA (2 mL). The reaction mixture was stirred at room temperature for 2 h. The reaction mixture was concentrated under reduced pressure to give 3-((S)-6-(((3S,3aR,6S,6aR)-6-(2,5,8,11,14,17,20,23,26,29,32,35-dodecaoxaoctatriacontan-38-amido)hexahydrofuro[3,2-b]furan-3-yl)amino)-2-(3-(2,5-dioxo-2,5-dihydro-1H-pyrrol-1-yl)propanamido)-6-oxohexanamido)propanoic acid Intermediate 24 (50.0 mg, 114%) as a colourless material. LCMS (15 min): 4.58 min; 1081.3 [M+H]+.

Intermediate 25

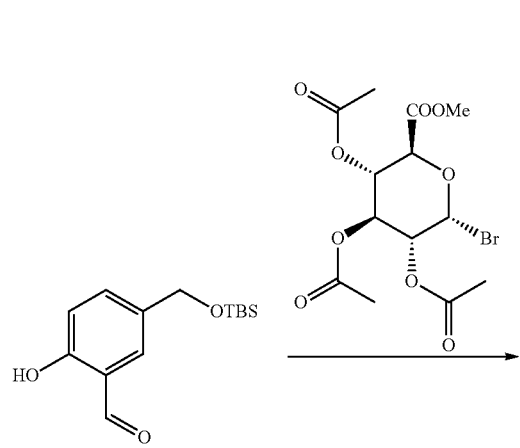

Silver(I) oxide p.a. (52.2 g, 225.22 mmol) was added to 4 A MS (30 g, 0.00 mmol), (2R,3R,4S,5S,6S)-2-bromo-6-(methoxycarbonyl)tetrahydro-2H-pyran-3,4,5-triyl triacetate (44.7 g, 112.61 mmol), Intermediate 2 (15 g, 56.30 mmol) in MeCN (500 mL) at 0° C. over a period of 2 hours under nitrogen. The resulting mixture was stirred at 25° C. for 16 hours. The mixture was filtered through a Celite pad. The crude product was purified by flash silica chromatography, elution gradient 0 to 30% EtOAc in petroleum ether. Pure fractions were evaporated to dryness to afford (2S,3R,4S,5S,6S)-2-(4-(((tert-butyldimethylsilyl)oxy)methyl)-2-formylphenoxy)-6-(methoxycarbonyl)tetrahydro-2H-pyran-3,4,5-triyl triacetate Intermediate 25 as a pale yellow material. m/z (ES+), [M+Na]+=605; TFA, HPLC tR=1.071 min.

Intermediate 26

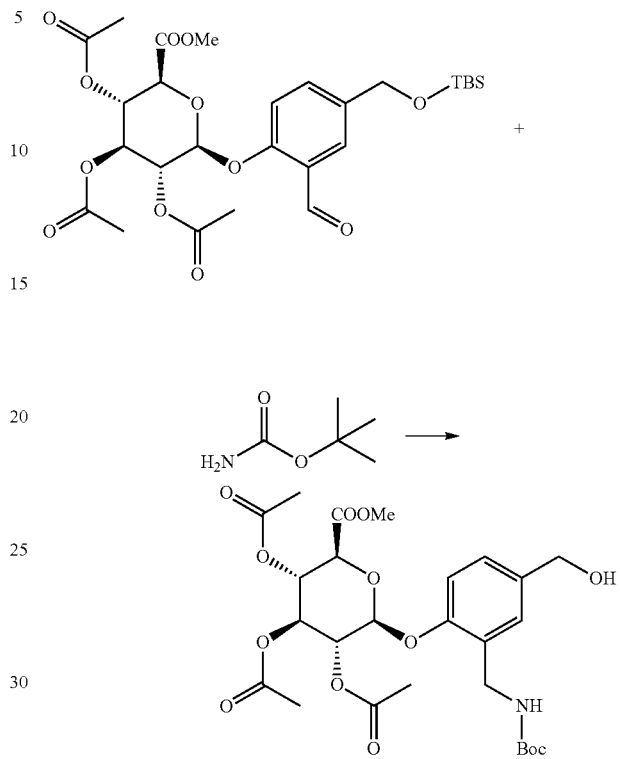

TFA (8 mL) was added to Et₃SiH (32 mL), tert-butyl carbamate (15.28 g, 130.43 mmol) and Intermediate 25 (20 g, 34.32 mmol) in MeCN (200 mL) at 0° C. under nitrogen. The resulting mixture was stirred at 0° C. for 16 hours. The reaction mixture was quenched with saturated NaHCO₃ (200 mL), extracted with EtOAc (2×300 mL), the organic layer was dried over Na2SO4, filtered and evaporated to afford colourless residue. The crude product was purified by flash silica chromatography, elution gradient 0 to 50% THF in petroleum ether. Pure fractions were evaporated to dryness to afford (2S,3R,4S,5S,6S)-2-(2-(((tert-butoxycarbonyl)amino)methyl)-4-(hydroxymethyl)phenoxy)-6-(methoxycarbonyl)tetrahydro-2H-pyran-3,4,5-triyl triacetate Intermediate 26 (18.80 g, 96%) as a pale yellow material. m/z (ES+), [M+Na]+=592; TFA, HPLC tR=1.088 min.

Intermediate 27

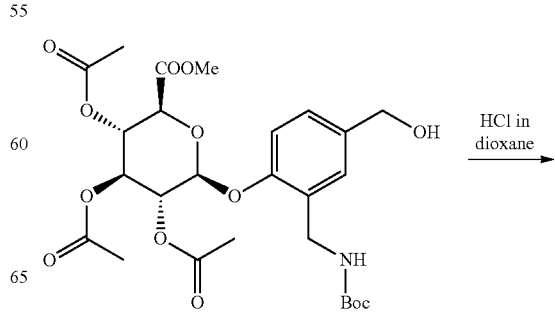

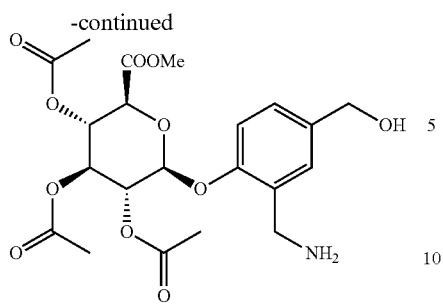

Intermediate 26 (10 g, 17.56 mmol) in HCl/1,4-dioxane (40 mL)/1,4-dioxane (40 mL) at 25° C. under nitrogen. The resulting mixture was stirred at 25° C. for 1 hour. The solvent was removed under reduced pressure afforded (2S, 3R,4S,5S,6S)-2-(2-(aminomethyl)-4-(hydroxymethyl)phenoxy)-6-(methoxycarbonyl)tetrahydro-2H-pyran-3,4,5-triyl triacetate hydrochloride Intermediate 27 as a white material. m/z (ES+), [M+H]+=470; TFA, HPLC tR=0.587 min.

Intermediate 28

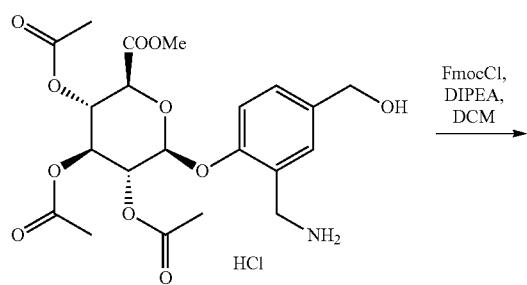

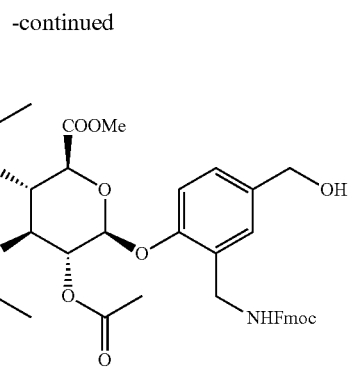

Intermediate 27 (1 g, 1.98 mmol), (9H-fluoren-9-yl) methyl carbonochloridate (0.767 g, 2.97 mmol) and DIPEA (1.036 mL, 5.93 mmol) in DCM (10 mL) stirred at RT for 3 hours. The reaction mixture was quenched with water (50 mL), extracted with DCM (2×50 mL), the combined organic layer was dried over Na2SO4, filtered and evaporated to afford residue. The crude product was purified by flash silica chromatography, elution gradient 0 to 80% petroleum ether in EtOAc. Pure fractions were evaporated to dryness to afford (2S,3R,4S,5S,6S)-2-(2-(((((9H-fluoren-9-yl) methoxy)carbonyl)amino)methyl)-4-(hydroxymethyl)phenoxy)-6-(methoxycarbonyl)tetrahydro-2H-pyran-3,4,5-triyl triacetate Intermediate 28 (0.952 g, 69.6%) as a white material. m/z (ES+), [M+H]+=692; TFA, HPLC tR=0.880 min.

Intermediate 29

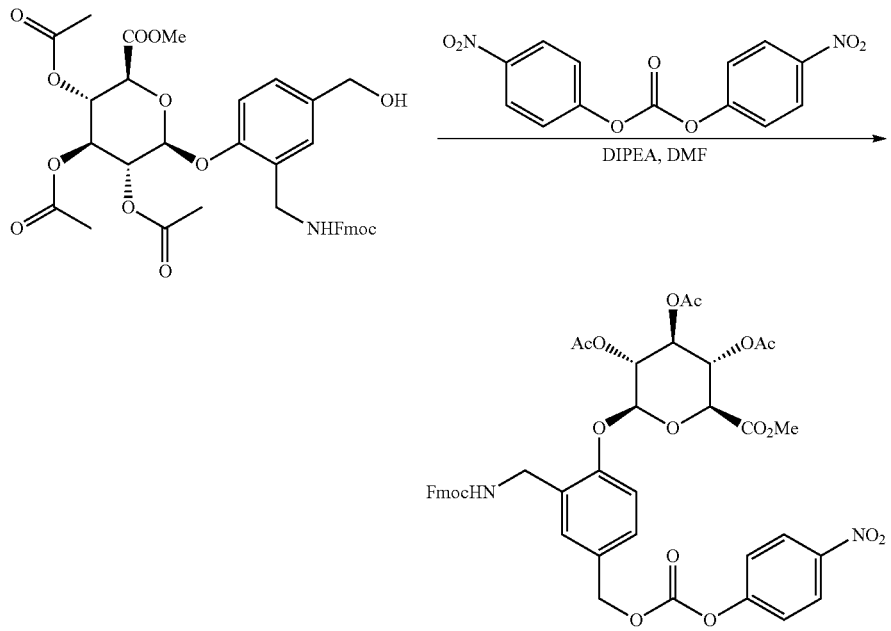

Intermediate 28 (3.5 g, 5.06 mmol), bis(4-nitrophenyl)carbonate (1.693 g, 5.57 mmol) and DIEA (1.326 mL, 7.59 mmol) in DMF (35 mL) stirred at RT for 3 hours. The reaction mixture was quenched with water (50 mL), extracted with EtOAc (2×50 mL), the combined organic layer was dried over Na2SO4, filtered and evaporated to afford residue. The crude product was purified by flash silica chromatography, elution gradient 0 to 100% EtOAc in petroleum ether. Pure fractions were evaporated to dryness to afford (2S,3R,4S,5S,6S)-2-(2-(((((9H-fluoren-9-yl)methoxy)carbonyl)amino)methyl)-4-((((4-nitrophenoxy)carbonyl)oxy)methyl)phenoxy)-6-(methoxycarbonyl)tetrahydro-2H-pyran-3,4,5-triyl triacetate Intermediate 29 (3.68 g, 85%) as a white material. m/z (ES+), [M+H]+=857; fa, HPLC tR=1.007 min Intermediate 30

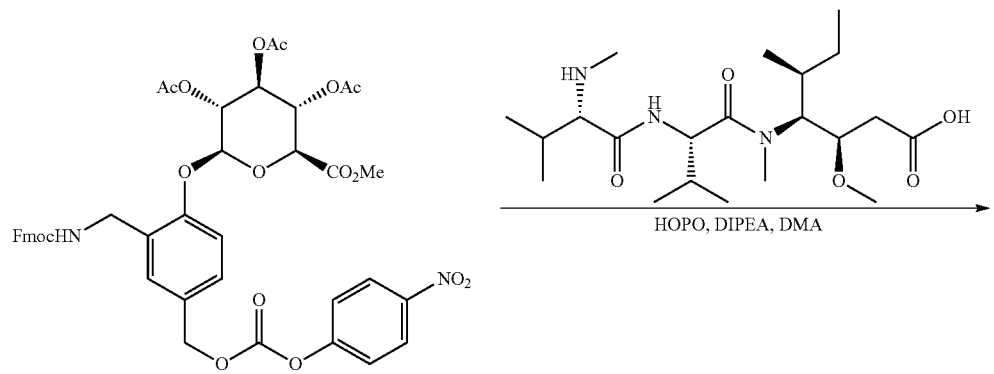

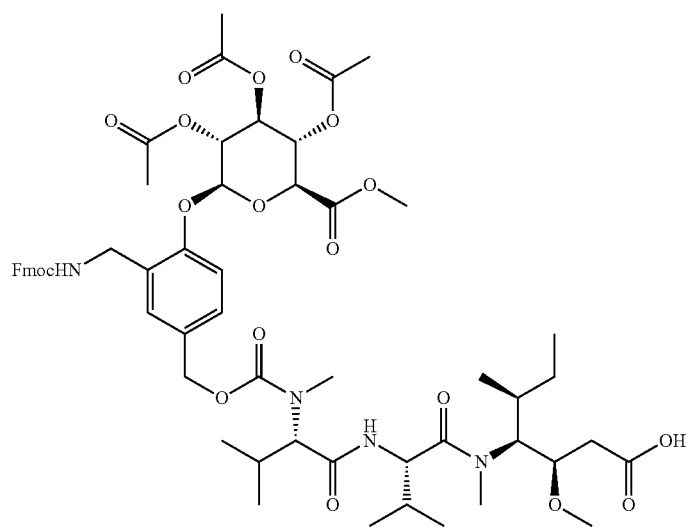

Intermediate 29 (1.5 g, 1.75 mmol), (3R,4S,5S)-4-((S)—N,3-dimethyl-2-((S)-3-methyl-2-(methylamino)butanamido)butanamido)-3-methoxy-5-methylheptanoic acid (0.728 g, 1.75 mmol), DIPEA (0.917 mL, 5.25 mmol) and 2-Hydroxypyridine-N-oxide (0.195 g, 1.75 mmol) in DMA (200 mL) stirred at RT for 18 hours. The reaction mixture was extracted with EA(3×50 mL), the organic layer was dried over Na2SO4, filtered and evaporated to afford yellow material. The crude product was purified by preparative HPLC (Column: XBRIDGE Prep1 phenyl OBD Colum, 30*150 nm 5 um; Mobile Phase A: Water (10 mmol/L NH4HCO3), Mobile Phase B: ACN; Flow rate: 60 mL/min; Gradient: isocratic 54-59; Wave Length: 220/254 nm; RT1 (min): 15. Fractions containing the desired compound were evaporated to dryness to afford (5S,8S,11S,12R)-1-(3-(((((9H-fluoren-9-yl)methoxy)carbonyl)amino)methyl)-4-(((2S,3R,4S,5S,6S)-3,4,5-triacetoxy-6-(methoxycarbonyl)tetrahydro-2H-pyran-2-yl)oxy)phenyl)-11-((S)-sec-butyl)-5,8-diisopropyl-12-methoxy-4,10-dimethyl-3,6,9-trioxo-2-oxa-4,7,10-triazatetradecan-14-oic acid Intermediate 30 (1.400 g, 70.6%) as a material. m/z (ES+), [M+H]+=1134; FA, HPLC tR=1.197 min Intermediate 31

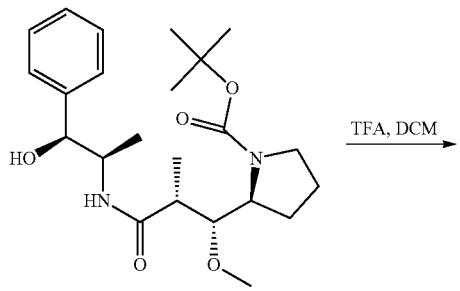

TFA, DCM

-continued

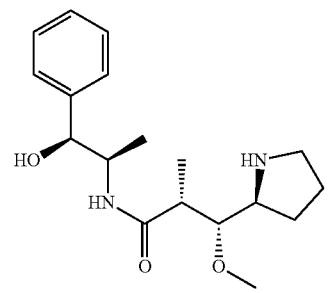

To tert-butyl (S)-2-((1R,2R)-3-(((1S,2R)-1-hydroxy-1-phenylpropan-2-yl)amino)-1-methoxy-2-methyl-3-oxopropyl)pyrrolidine-1-carboxylate (256 mg, 0.61 mmol) in DCM (2 mL) was added TFA (2 mL). The reaction mixture was stirred at room temperature for 2 h. The reaction mixture was concentrated under reduced pressure to give a crude (2R,3R)—N-((1S,2R)-1-hydroxy-1-phenylpropan-2-yl)-3-methoxy-2-methyl-3-((S)-pyrrolidin-2-yl)propanamide Intermediate 31 which was used without purification. LCMS (3 min): 0.55 min; 322.0 [M+H]+

Intermediate 32

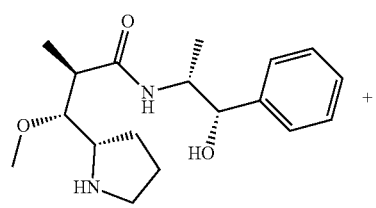

+

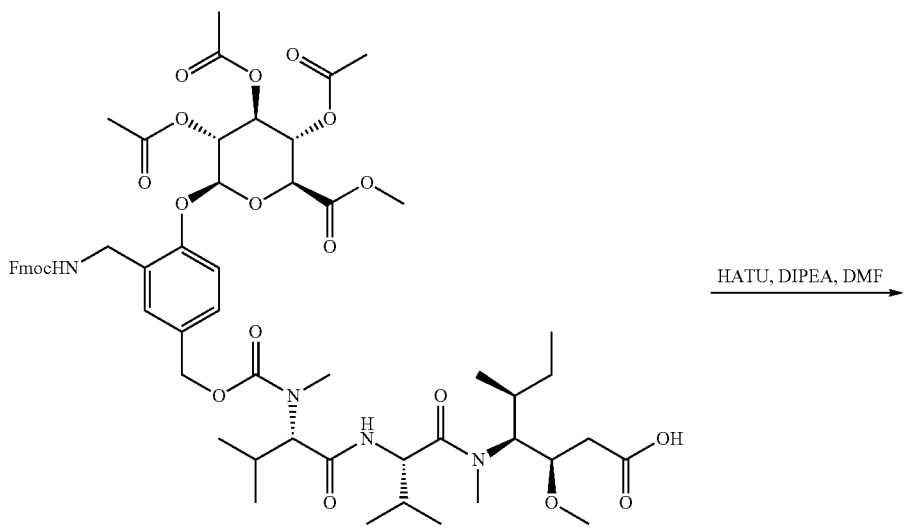

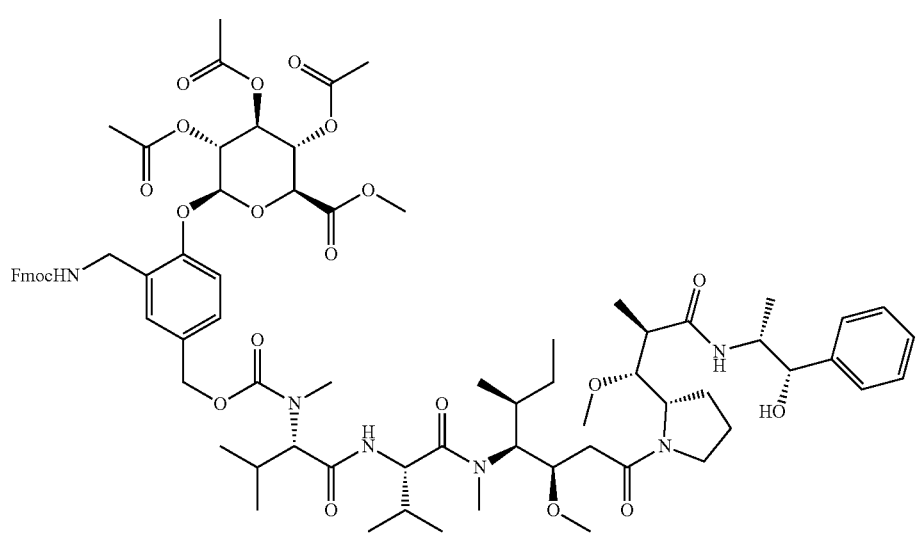

To crude Intermediate 31 (234 mg, 0.73 mmol) in DMF (5 mL) was added Intermediate 30 (486 mg, 0.429 mmol), HATU (269 mg, 0.71 mmol) and DIPEA (0.360 mL, 2.07 mmol). The reaction mixture was stirred at room temperature for 30 mins. The reaction mixture was concentrated under reduced pressure to give a crude. Purification by column chromatography (0-6% MeOH in DCM) gave (2S, 3R,4S,5S,6S)-2-(2-(((((9H-fluoren-9-yl)methoxy)carbonyl) amino)methyl)-4-((5S,8S,11S,12R)-11-((S)-sec-butyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenoxy)-6-(methoxycarbonyl)tetrahydro-2H-pyran-3,4,5-triyl triacetate Intermediate 32 (552 mg, 90%) as a colourless material. LCMS (15 min): 8.99 min; 1436.9 [M+H]+

111
Intermediate 33
112
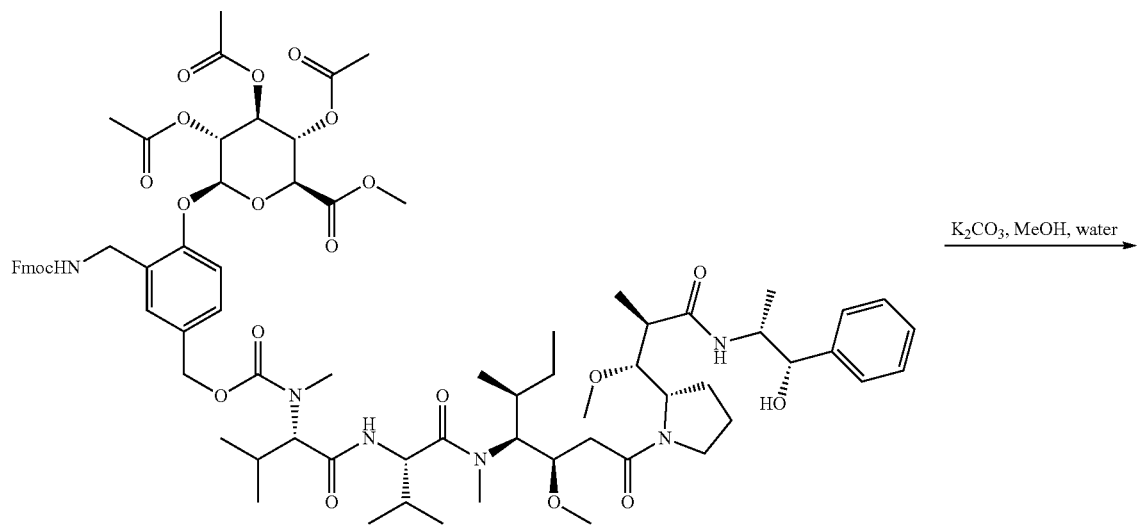
K₂CO₃, MeOH, water →
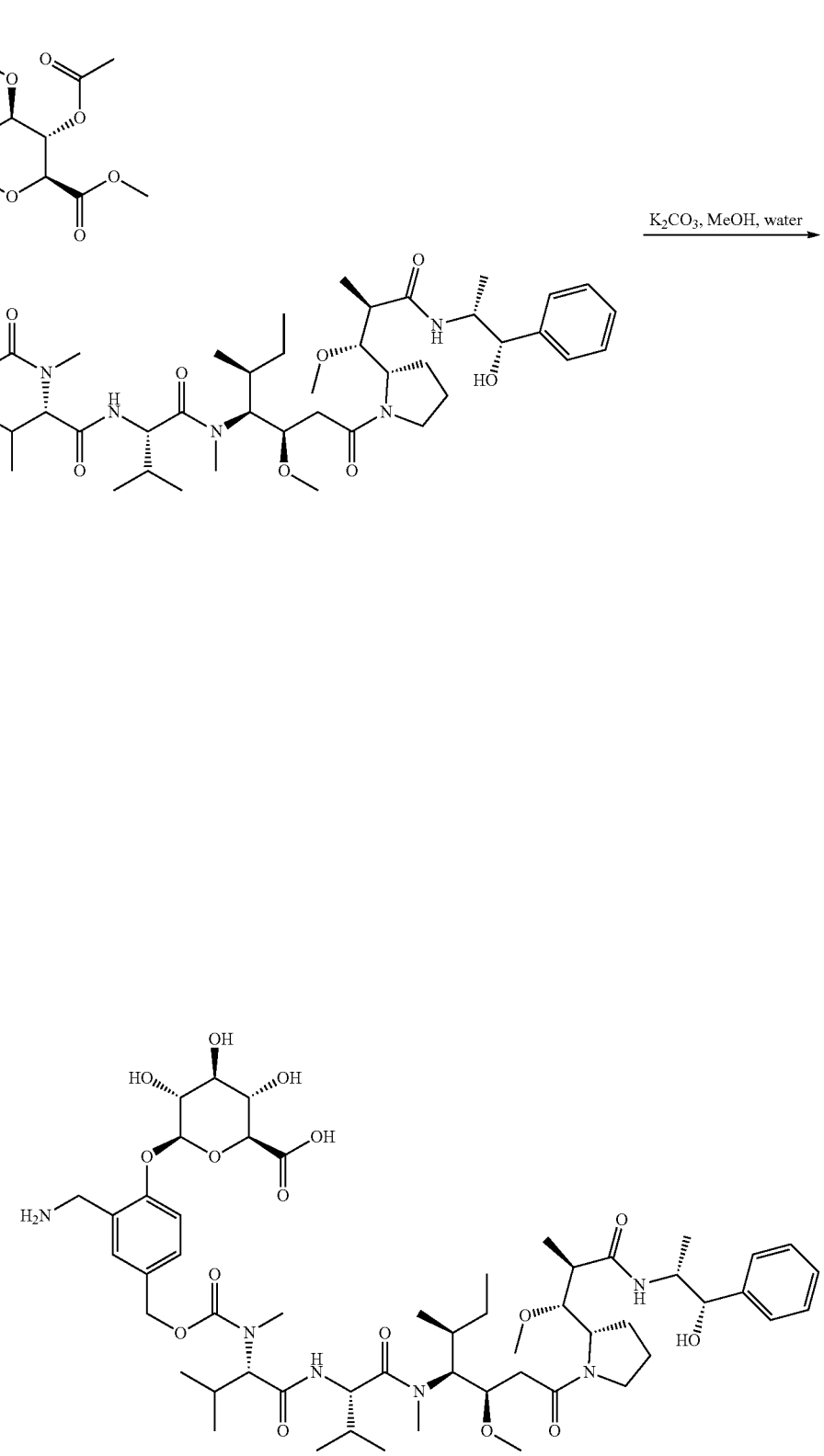

To Intermediate 32 (552 mg, 0.38 mmol) in MeOH (8 mL) and water (2 mL) was added potassium carbonate (531 mg, 3.84 mmol). The reaction mixture was stirred at room temperature for 3 h. Acetic acid (1.1 mL) was added and the reaction mixture purified by reverse phase chromatography (C18, 120 g, 5-40% MeCN in water+0.1% FA, 25 CV) to give (2S,3S,4S,5R,6S)-6-(2-(aminomethyl)-4-((5S,8S,11S,12R)-11-((S)-sec-butyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenoxy)-3,4,5-trihydroxytetrahydro-2H-pyran-2-carboxylic acid Intermediate 33 (259 mg, 62.8%) as a white material. LCMS (15 min): 5.57 min; 1074.9 [M+H]⁺.

Linker-Payload LP-1

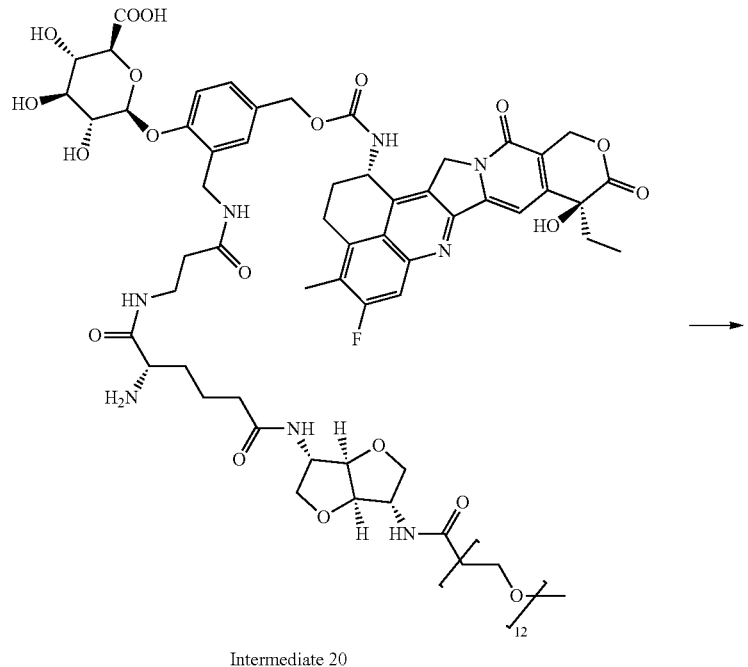

Intermediate 20

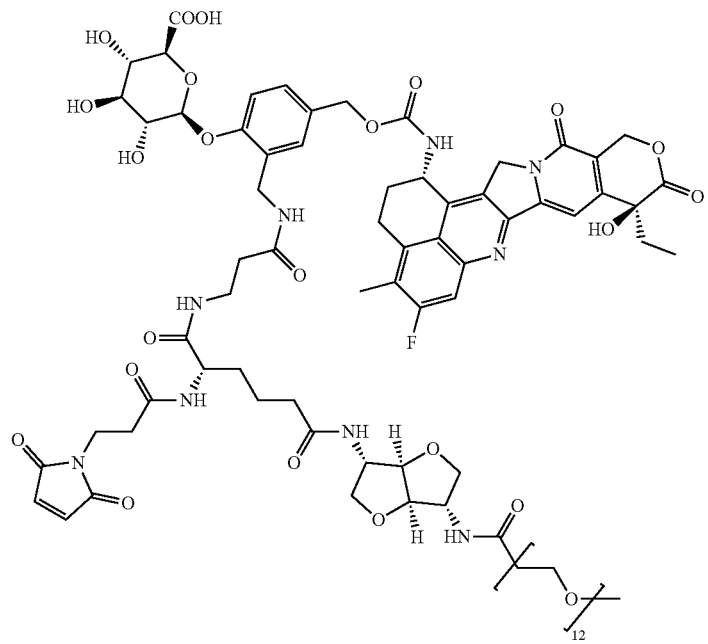

LP1

To a solution of Intermediate 20 (6.20 mg, 3.64 μmol, 1.0 eq) in DMF (0.5 mL) was added pyridine (0.7 μl, 5.5 μmol, 1.5 eq) and 2,5-dioxopyrrolidin-1-yl 3-(2,5-dioxo-2,5-dihydro-1H-pyrrol-1-yl)propanoate (0.970 mg, 3.64 μmol, 1.0 eq). The mixture was stirred at 23° C. for 3 hours. Following this time the reaction mixture was concentrated in vacuo and the residue purified by reverse phase HPLC (CSH 35% MeCN [0.1% formic acid]/water [0.1% formic acid] over 7 min) to give (2S,3S,4S,5R,6S)-6-(2-((S)-6-(((3S,3aR,6S,6aR)-6-(2,5,8,11,14,17,20,23,26,29,32,35-dodecaoxaoctatriacontan-38-amido)hexahydrofuro[3,2-b]furan-3-yl)amino)-2-(3-(2,5-dioxo-2,5-dihydro-1H-pyrrol-1-yl)propanamido)-6-oxohexanamido)propanamido)methyl)-4-(((((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)carbamoyl)oxy)methyl)phenoxy)-3,4,5-trihydroxytetrahydro-2H-pyran-2-carboxylic acid LP-1 (2.7 mg, 1.46 μmol, 40%) as a white material. RT 5.87 min. LCMS (ESI) 1853.5 [M+H]+. Linker-Payload LP-M1

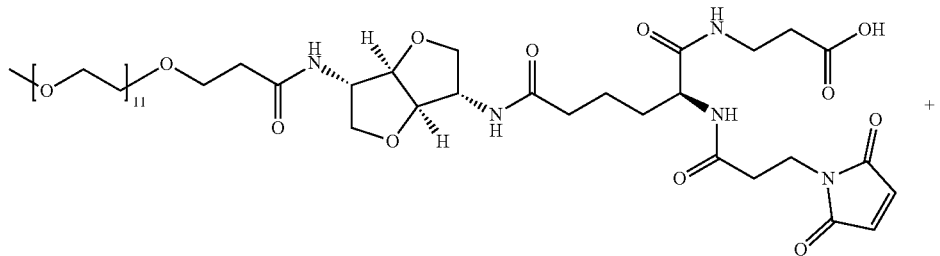

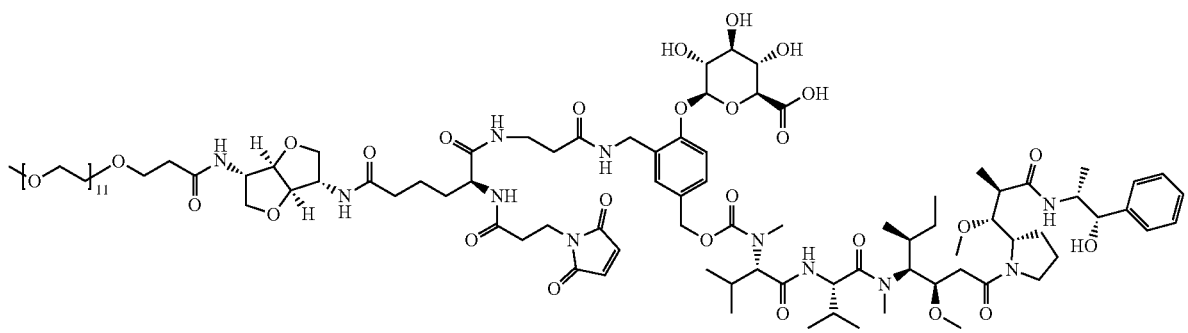

To Intermediate 24 (50 mg, 0.05 mmol) in DMF (3 mL) was added HATU (17.49 mg, 0.046 mmol) and DIPEA (0.039 mL, 0.22 mmol). The reaction mixture was stirred at room temperature for 10 min. Intermediate 33 (40 mg, 0.04 mmol) was added and the reaction mixture was stirred at room temperature for 2 h. The reaction mixture was purified by reverse phase chromatography (C18, 25 g, 5-50% MeCN in water+0.1% FA over 25 CV) and prep HPLC (15-50% MeCN in water+0.1% over 15 mins) to give (2S,3S,4S,5R,6S)-6-(2-((3-((S)-6-(((3S,3aR,6S,6aR)-6-(2,5,8,11,14,17,20,23,26,29,32,35-dodecaoxaoctatriacontan-38-amido)hexahydrofuro[3,2-b]furan-3-yl)amino)-2-(3-(2,5-dioxo-2,5-dihydro-1H-pyrrol-1-yl)propanamido)-6-oxohexanamido)propanamido)methyl)-4-((5S,8S,11S,12R)-11-((S)-sec-butyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenoxy)-3,4,5-trihydroxytetrahydro-2H-pyran-2-carboxylic acid LP-M1 (14.50 mg, 18.22%). LCMS (15 min): 2135.4 [M+H]+

Alternative Synthesis of LP-1

Intermediate A

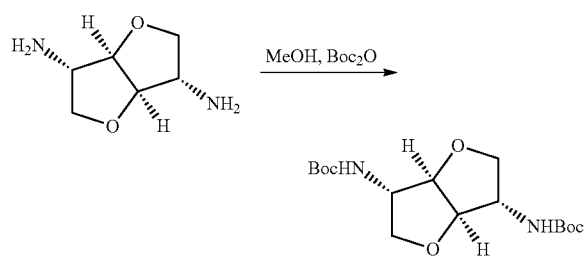

To intermediate 9 (22.0 g, 152.6 mmol) in methanol (440 mL) was added boc anhydride (83.3 g, 381.5 mmol, 2.5 eq) and the reaction was stirred for 2 hours at 20° C. ELSD analysis showed formation of the desired product and completion of the reaction. Solvent was removed under reduced pressure to get crude product. The crude product was slurried with MTBE (200 mL), filtered, washed with MTBE (40 mL) and dried to give tert-butyl N-[(3S,3aR,6S,6aR)-6-(tert-butoxycarbonylamino)-2,3,3a,5,6,6a-hexahydrofuro[3,2-b]furan-3-yl]carbamate Intermediate A (44.0 g, 84.3%). LCMS m/z 366.8 [M+Na]+

Intermediate B

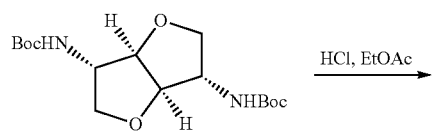

Intermediate C

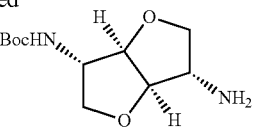

To intermediate A (2.0 g, 5.81 mmol, 1.0 eq) in Ethyl acetate (40 mL) was added HCl in ethyl acetate (4M, 8.0 mL) and the reaction was stirred for 6 hours at 20° C. ELSD analysis showed formation of the desired product and completion of the reaction. The reaction was quenched with potassium phosphate solution (2M, 20 mL), the layers were separated and the organic layer retained. The aqueous layer was extracted with ethyl acetate (10 mL) and the organic layers combined. Solvent was removed under reduced pressure to give tert-butyl N-[(3S,3aR,6S,6aR)-3-amino-2,3,3a,5,6,6a-hexahydrofuro[3,2-b]furan-6-yl]carbamate Intermediate B (800 mg, 57.1%). $^1$H NMR (400 MHz, DMSO-d6) δ 4.32 (m, 1H), 3.93 (m, 1H), 3.85 (m, 2H), 3.6 (m, 2H), 3.28 (m, 1H), 1.47 (s, 9H). LCMS m/z 145 [M+H-Boc]+

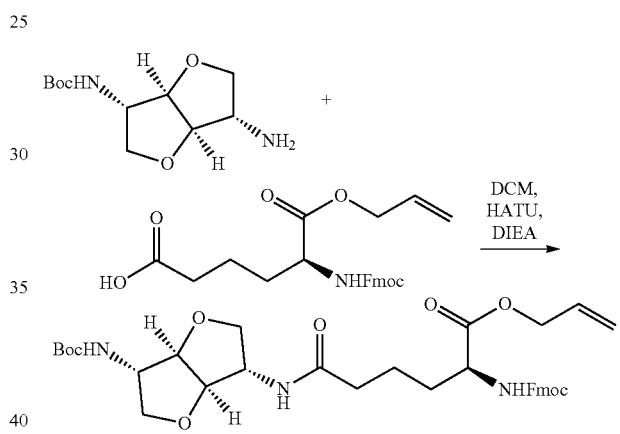

To a solution of Intermediate 14 (17.16 g, 40.5 mmol, 1.1 eq) in DCM (180 mL) at 25° C., was added HATU (16.8 g, 44.2 mmol, 1.2 eq) and DIPEA (10.9 ml, 62.6 mmol, 1.7 eq). The reaction mixture was stirred for 15 mins. To the reaction solution was added Intermediate B (9.0 g, 36.8 mmol, 1.0 eq) in DCM 90 mL)). The reaction mixture was stirred for 2 hours. LC-MS analysis showed formation of the desired product and completion of the reaction. The reaction mixture was washed twice with NaCl (15% aq, 90 mL) and the aqueous layers were discarded. Solvent was removed under reduced pressure to to give allyl (2S)-6-[[(3S,3aR,6S,6aR)-6-(tert-butoxycarbonylamino)-2,3,3a,5,6,6a-hexahydrofuro[3,2-b]furan-3-yl]amino]-2-(9H-fluoren-9-ylmethoxycarbonylamino)-6-oxo-hexanoate Intermediate C (9.0 g, 65.2%). LCMS m/z 671.6 [M+Na]+

Intermediate D

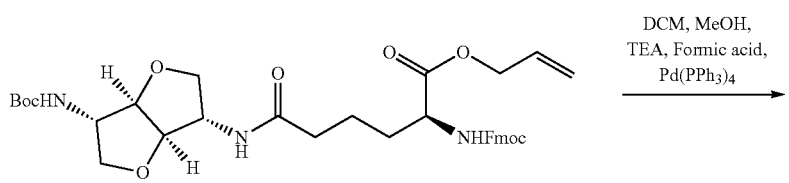

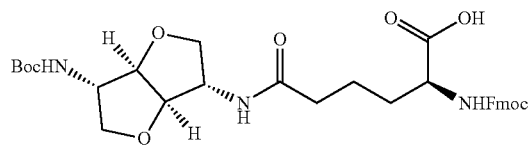

To a solution of Intermediate C (9.0 g, 13.9 mmol, 1.0 eq) in DCM/MeOH (20:1, 128.6 ml:6.4 mL) was added formic acid (1.05 mL, 27.7 mmol, 2.0 eq), triethylamine (5.79 mL, 41.6 mmol, 3.0 eq) and Pd(PPh$_3$)$_4$ (1.6 g, 1.39 mmol, 0.1 eq). The reaction mixture was stirred for 3 hours at 20-25° C. LC-MS analysis showed formation of the desired product and completion of the reaction. Solvent was removed under reduced pressure to get crude product. The crude product was purified via silica gel column (DCM to DCM:MeOH 4:1) to give (2S)-6-[[(3S,3aR,6S,6aR)-6-(tert-butoxycarbonylamino)-2,3,3a,5,6,6a-hexahydrofuro[3,2-b]furan-3-yl]amino]-2-(9H-fluoren-9-ylmethoxycarbonylamino)-6-oxo-hexanoic acid Intermediate D (7.0 g, 82.9%). LCMS m/z 610.1 [M+H]$^+$ Intermediate E

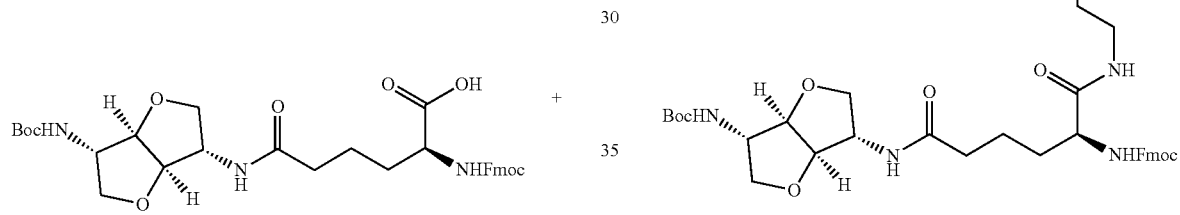

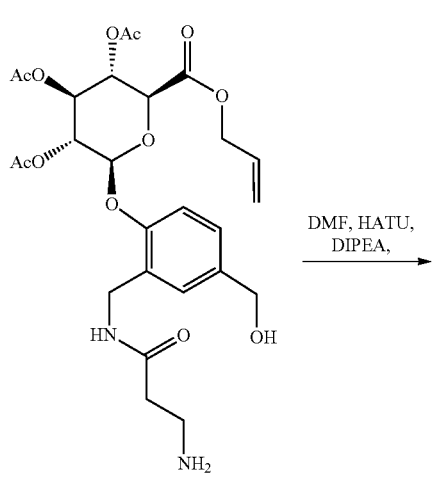

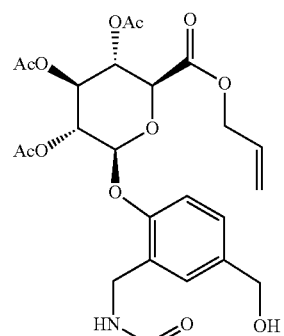

To a solution of Intermediate D (4.0 g, 6.56 mmol, 1.0 eq) in DMF (80 mL) at 0-5° C. was added Intermediate 5 (11.2 g, 19.7 mmol, 3.0 eq), HATU (3.74 g, 9.84 mmol, 1.5 eq), and DIPEA (3.43 mL, 19.7 mmol, 3.0 eq). The reaction mixture was stirred for 1 hours at 0-5° C. LC-MS analysis showed formation of the desired product and completion of the reaction. The reaction mixture was diluted with ethyl acetate (80 mL) and washed twice with NaCl (15% aq, 40 mL). The aqueous layers were discarded and the solvent was removed from the organic layer under reduced pressure to get crude product. The crude product was purified via silica gel column (EtOAC to 20% MeOH) to give allyl (2S,3S,4S,5R,6S)-6-[2-[[3-[[(2S)-6-[[(3S,3aR,6S,6aR)-6-(tert-butoxycarbonylamino)-2,3,3a,5,6,6a-hexahydrofuro[3,2-b]furan-3-yl]amino]-2-(9H-fluoren-9-ylmethoxycarbonylamino)-6-oxo-hexanoyl]amino]propanoylamino]methyl]-4-(hydroxymethyl)phenoxy]-3,4,5-triacetoxy-tetrahydropyran-2-carboxylate Intermediate E (3.6 g, 47.4%) LCMS m/z 1158.2 [M+H]$^+$ Intermediate F

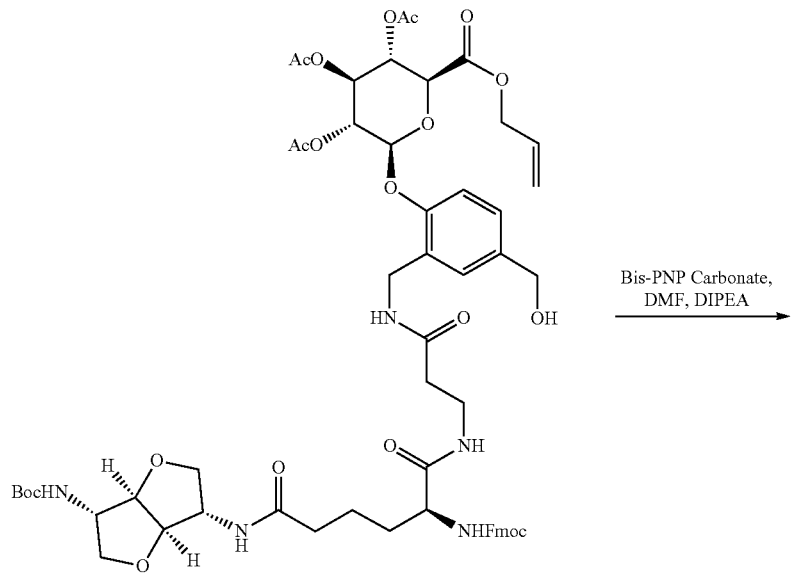

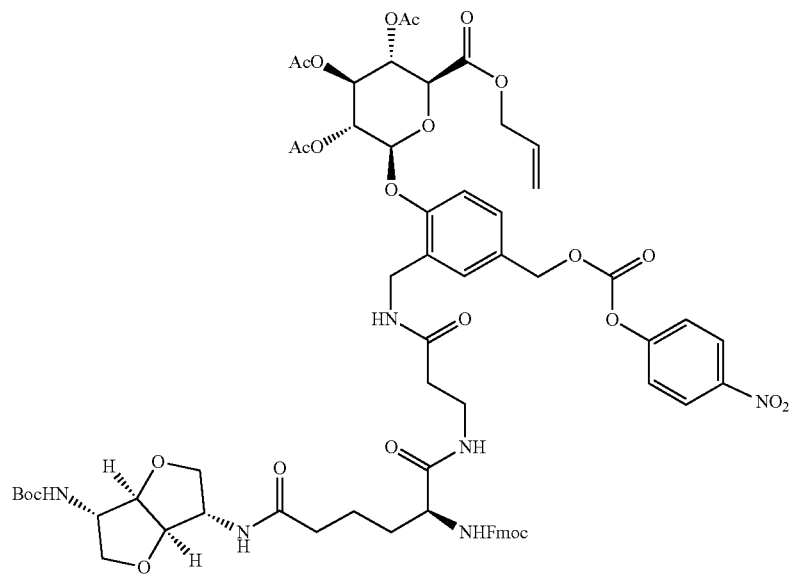

To a solution of Intermediate E (800 mg, 691 μmol, 1.0 eq) in DMF (8 mL) was added bis(4-nitrophenyl) carbonate (840 mg, 2.76 mmol, 4.0 eq) and DIPEA (481 μL, 2.76 mmol, 4.0 eq). The mixture was stirred at 20-25° C. for 2 hours. LC-MS analysis showed formation of the desired product and completion of the reaction. Solvent was removed under reduced pressure to get crude product. The crude product was purified via silica gel column (5%-50% MeCN in water, 0.1% formic acid) to give allyl (2S,3S,4S,5R,6S)-6-[2-[[3-[[(2S)-6-[[(3S,3aR,6S,6aR)-6-(tert-butoxycarbonylamino)-2,3,3a,5,6,6a-hexahydrofuro[3,2-b]furan-3-yl]amino]-2-(9H-fluoren-9-ylmethoxycarbonylamino)-6-oxo-hexanoyl]amino]propanoylamino]methyl]-4-[(4-nitrophenoxy)carbonyloxymethyl]phenoxy]-3,4,5-triacetoxy-tetrahydropyran-2-carboxylate Intermediate F (400 mg, 43.8%) 1H NMR (300 MHz, DMSO-d6) δ ppm 1.14-1.29 (m, 3H) 1.38 (s, 9H) 1.53 (br dd, J=18.52, 8.25 Hz, 4H) 1.98-2.09 (m, 12H) 2.13 (d, J=2.93 Hz, 1H) 2.32-2.45 (m, 2H) 3.35 (s, 11H) 3.58 (br d, J=6.42 Hz, 2H) 3.71 (s, 12H) 3.78-3.88 (m, 3H) 3.90-4.17 (m, 4H) 4.18-4.42 (m, 6H) 4.50-4.67 (m, 2H) 4.80 (d, J=10.09 Hz, 1H) 5.09-5.38 (m, 6H) 5.47-5.55 (m, 1H) 5.65 (d, J=7.89 Hz, 1H) 5.82-5.96 (m, 1H) 6.10 (s, 4H) 7.11 (d, J=8.44 Hz, 1H) 7.21 (br d, J=5.50 Hz, 1H) 7.28-7.37 (m, 4H) 7.37-7.44 (m, 3H) 7.46-7.61 (m, 3H) 7.65-7.76 (m, 2H) 7.89 (d, J=7.34 Hz, 2H) 7.99 (br t, J=5.50 Hz, 1H) 8.09 (d, J=6.97 Hz, 1H) 8.27-8.34 (m, 3H) LCMS m/z 1323.1 [M+H]$^+$ Intermediate G

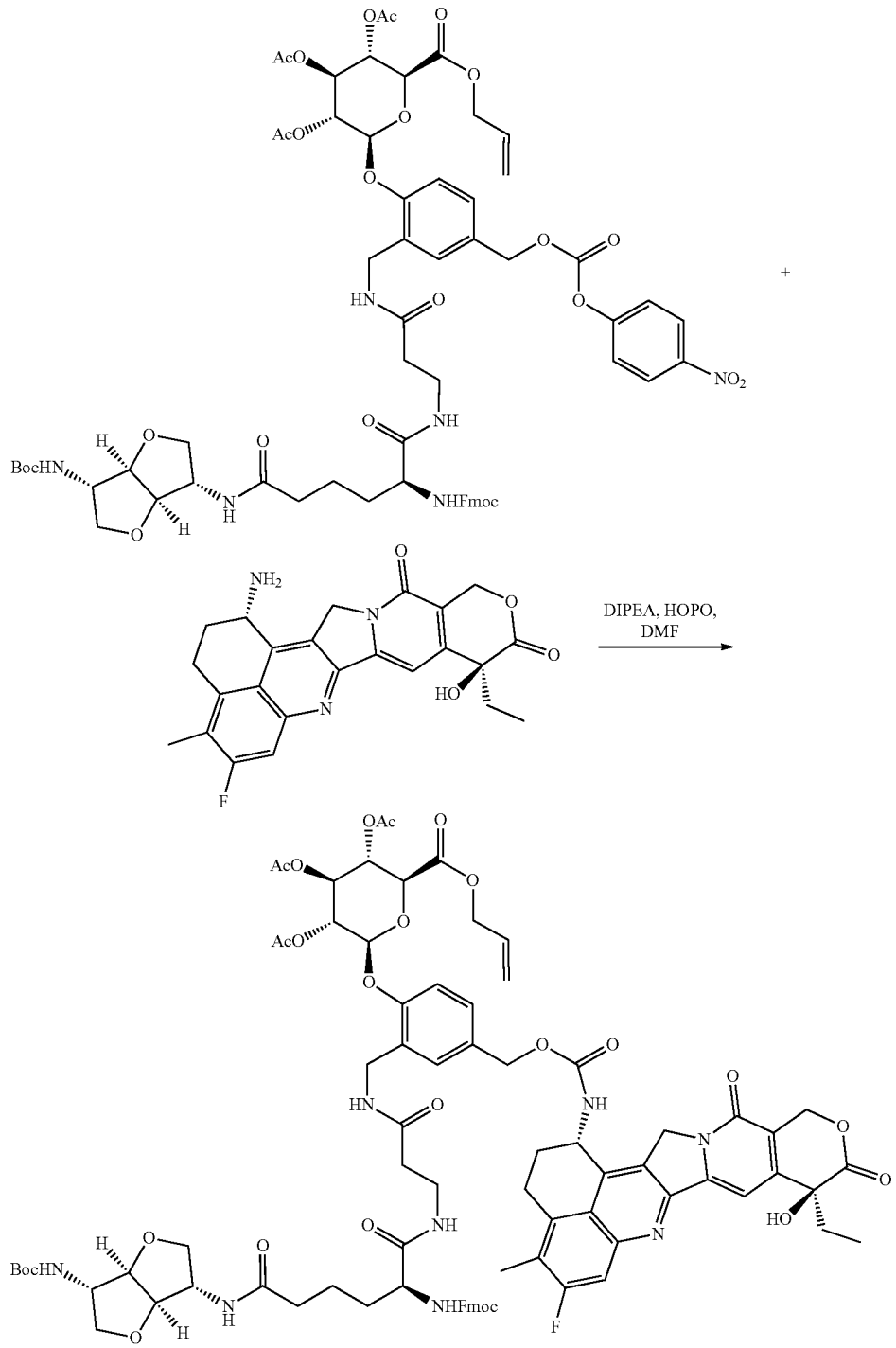

To a solution of exatecan mesylate (1.12 g, 2.12 mmol, 4.0 eq) in DMF (7 mL) was added DIPEA (369 μl, 2.12 mmol, 4.0 eq), Intermediate F (700 mg, 529 μmol, 1.0 eq), and HOPO (117.5 mg, 1.06 mmol, 2.0 eq) and the resultant mixture was stirred at 20-25° C. for 1 hour. LC-MS analysis showed formation of the desired product and completion of the reaction. The reaction mixture was diluted with ethyl acetate (9 mL) and washed with NaCl (15% aq, 12 mL). The solvent was removed under reduced pressure to get crude product. The crude product was slurried with ethyl acetate/MTBE (1:1, 5 mL), filtered and dried to give allyl (2S,3S,4S,5R,6S)-6-[2-[[3-[[(2S)-6-[[(3S,3aR,6S,6aR)-6-(tert-butoxycarbonylamino)-2,3,3a,5,6,6a-hexahydrofuro[3,2-b]furan-3-yl]amino]-2-(9H-fluoren-9-ylmethoxycarbonylamino)-6-oxo-hexanoyl]amino]propanoylamino]methyl]-4-[[(10S,23S)-10-ethyl-18-fluoro-10-hydroxy-19- methyl-5,9-dioxo-8-oxa-4,15-diazahexacyclo[14.7.1.0²,¹⁴.0⁴,¹³.0⁶,¹¹.0²⁰,²⁴]tetracosa-1,6 (11),12,14,16 (24),17,19-heptaen-23-yl]carbamoyloxymethyl]phenoxy]-3,4,5-triacetoxy-tetrahydropyran-2-carboxylate Intermediate G (360 mg, 73.5%). 1H NMR (400 MHz, DMSO-d6) δ ppm 0.81-0.94 (m, 2H) 1.11-1.26 (m, 3H) 1.37 (s, 6H) 1.42-1.59 (m, 3H) 1.81-1.92 (m, 1H) 1.95-2.15 (m, 9H) 2.29-2.44 (m, 3H) 2.73 (s, 1H) 2.89 (s, 1H) 3.49-3.61 (m, 2H) 3.71 (s, 16H) 3.81 (br d, J=6.36 Hz, 2H) 3.85-3.95 (m, 1H) 3.99-4.12 (m, 2H) 4.12-4.28 (m, 2H) 4.33 (br d, J=3.91 Hz, 1H) 4.39 (br d, J=4.16 Hz, 1H) 4.48-4.64 (m, 1H) 4.78 (br d, J=10.27 Hz, 1H) 5.06-5.34 (m, 5H) 5.41-5.53 (m, 2H) 5.60 (br d, J=7.58 Hz, 1H) 5.81-5.93 (m, 1H) 6.09 (s, 5H) 6.92 (d, J=8.26 Hz, 2H) 7.09 (br d, J=8.56 Hz, 1H) 7.17-7.42 (m, 5H) 7.64-7.79 (m, 2H) 7.80-7.90 (m, 1H) 7.93-7.99 (m, 1H) 8.00-8.14 (m, 3H) LCMS m/z 810.3 [M+2H]²⁺
Intermediate H
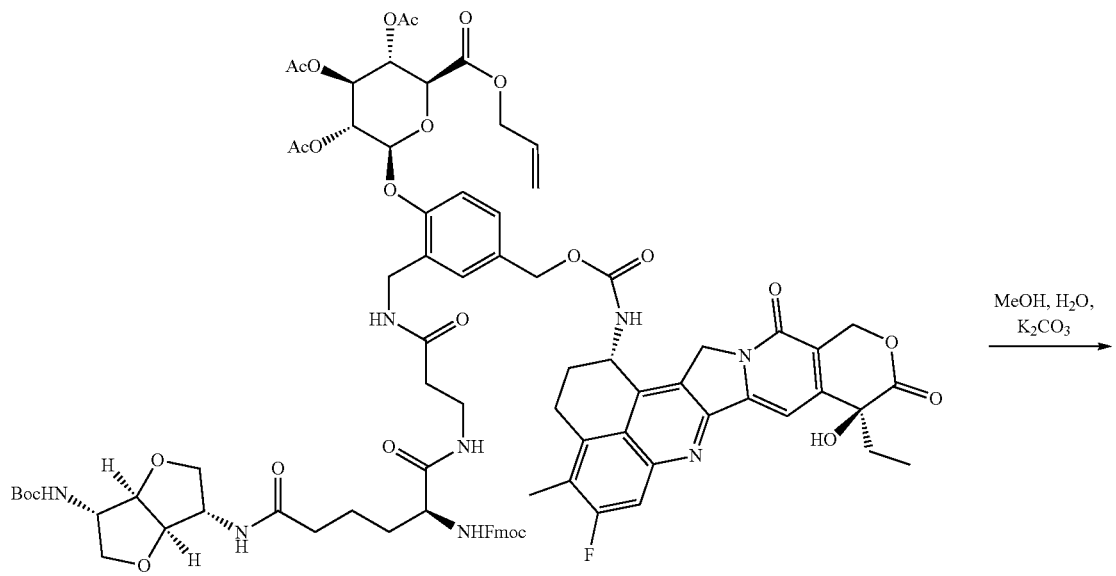
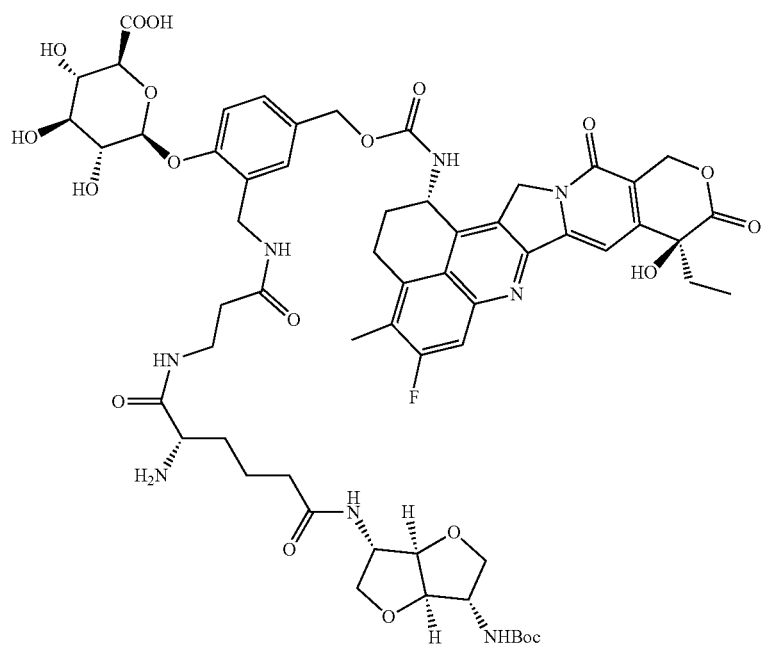

To a solution of Intermediate G (1.5 g 80%, 741 μmol, 1.0 eq) in MeOH (2.6 mL) was added $K_2CO_3$ (1.02 g, 7.41 mmol, 10.0 eq) and water (260 μL). The resultant mixture was stirred at 20-25° C. for 1 hour. LC-MS analysis showed formation of the desired product and completion of the reaction. Solvent was removed under reduced pressure to get crude product. The crude product was purified via silica gel column (5%-50% MeCN in water, 0.1% formic acid) to give (2S,3S,4S,5R,6S)-6-[2-[[3-[[(2S)-6-[[(3S,3aR,6S,6aR)-6-(tert-butoxycarbonylamino)-2,3,3a,5,6,6a-hexahydrofuro[3,2-b]furan-3-yl]amino]-2-amino-6-oxo-hexanoyl]amino]propanoylamino]methyl]-4-[[(10S,23S)-10-ethyl-18-fluoro-10-hydroxy-19-methyl-5,9-dioxo-8-oxa-4,15-diazahexacyclo[14.7.1.02,14.04,13.06,11.020,24]tetracosa-1,6 (11),12,14,16 (24),17,19-heptaen-23-yl]carbamoyloxymethyl]phenoxy]-3,4,5-trihydroxy-tetrahydropyran-2-carboxylic acid Intermediate H (450 mg, 67%) 1H NMR (500 MHz, DMSO-d6) δ ppm 0.84-0.92 (m, 3H) 1.24 (br s, 4H) 1.29 (br d, J=7.32 Hz, 1H) 1.38 (s, 8H) 1.43-1.53 (m, 2H) 1.60 (br s, 2H) 1.81-2.11 (m, 5H) 2.14-2.24 (m, 2H) 2.29-2.36 (m, 1H) 2.39 (s, 3H) 2.40-2.44 (m, 1H) 3.13-3.23 (m, 7H) 3.23-3.32 (m, 14H) 3.35 (br s, 12H) 3.50-3.60 (m, 8H) 3.77-3.85 (m, 3H) 4.05 (br s, 1H) 4.17 (br dd, J=13.43, 3.97 Hz, 1H) 4.34 (br d, J=3.36 Hz, 1H) 4.39 (d, J=3.97 Hz, 1H) 4.49 (br dd, J=13.28, 7.78 Hz, 1H) 4.60 (br d, J=6.71 Hz, 1H) 5.03 (br d, J=12.21 Hz, 1H) 5.10 (br d, J=12.21 Hz, 1H) 5.28 (br s, 3H) 5.45 (s, 2H) 6.52 (br s, 1H) 7.12 (d, J=8.24 Hz, 1H) 7.20 (br s, 1H) 7.32 (s, 1H) 7.32-7.34 (m, 1H) 7.40 (s, 1H) 7.78 (d, J=10.68 Hz, 1H) 8.03-8.15 (m, 1H) 8.17 (s, 2H) 8.24 (br d, J=6.10 Hz, 1H) 8.47 (br s, 1H) 9.30 (br s, 1H). LCMS m/z 616.2 $[M+2H]^{2+}$ Intermediate I

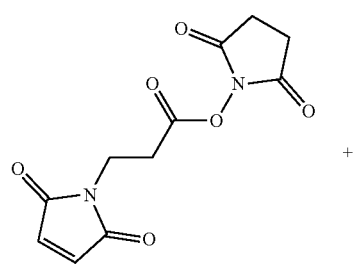 +

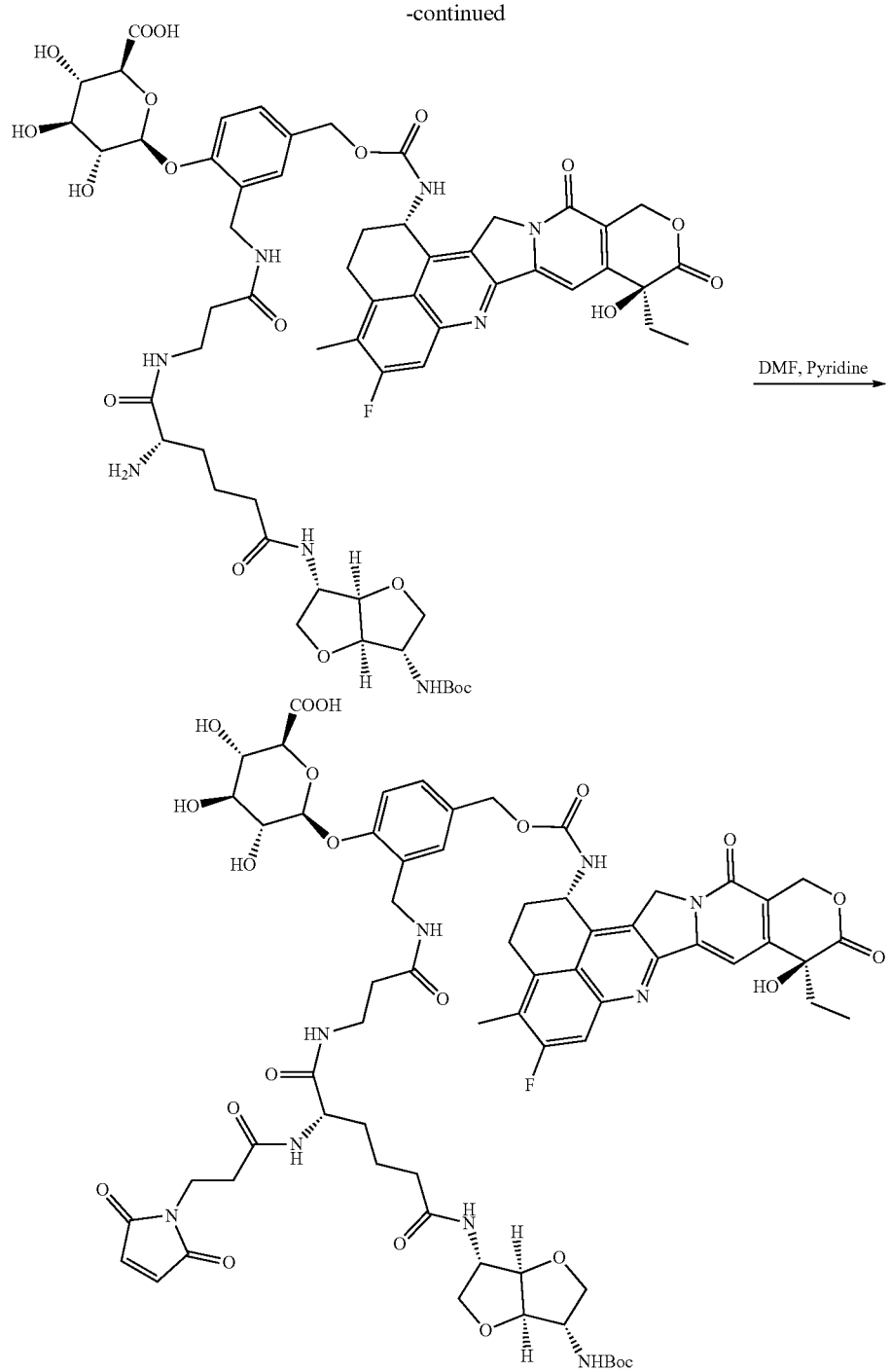

To a solution of Intermediate H (450 mg, 365 μmol, 1.0 eq) in DMF (4.5 mL) at 20-25° C. was added pyridine (225 μL) and N-succinimidyl 3-maleimidiopropionate (195 mg, 731 μmol, 2.0 eq) and the reaction mixture was stirred for 1 hour. LC-MS analysis showed formation of the desired product and completion of the reaction. Solvent was removed under reduced pressure to get crude product. The crude product was purified via silica gel column (5%-50% MeCN in water, 0.1% formic acid) to give (2S,3S,4S,5R,6S)-6-(2-((3-((S)-6-(((3S,3aR,6S,6aR)-6-((tert-butoxycarbonyl)amino)hexahydrofuro[3,2-b]furan-3-yl)amino)-2-(3-(2,5-dioxo-2,5-dihydro-1H-pyrrol-1-yl)propanamido)-6-oxohexanamido)propanamido)methyl)-4-(((((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)carbamoyl)oxy)methyl)phenoxy)-3,4,5-trihydroxytetrahydro-2H-pyran-2-carboxylic acid Intermediate 1 (230 mg, 52.4%) 1H NMR (500 MHz, DMSO-d6) δ ppm 0.84-0.91 (m, 2H) 1.23 (br d, J=9.77 Hz, 5H) 1.38 (s, 6H) 1.81-1.94 (m, 1H) 1.96-2.07 (m, 2H) 2.13-2.24 (m, 1H) 2.25-2.36 (m, 1H) 2.50-2.52 (m, 7H) 3.05-3.18 (m, 1H) 3.24 (br d, J=6.10 Hz, 2H) 3.29 (br s, 3H) 3.34 (br s, 24H) 3.51-3.63 (m, 4H) 3.71 (s, 9H) 3.75-3.88 (m, 3H) 4.01-4.15 (m, 2H) 4.21 (br d, J=9.46 Hz, 1H) 4.34

(d, J=3.66 Hz, 1H) 4.36-4.46 (m, 1H) 4.72 (br s, 1H) 5.06-5.15 (m, 1H) 5.27 (br s, 2H) 5.45 (s, 2H) 6.09 (s, 3H) 6.51 (s, 1H) 6.97 (s, 1H) 7.10 (d, J=8.24 Hz, 1H) 7.19 (br d, J=5.80 Hz, 1H) 7.31 (s, 1H) 7.33 (s, 1H) 7.77 (d, J=10.99 Hz, 1H) 7.94 (br t, J=5.34 Hz, 1H) 8.06 (br d, J=8.55 Hz, 1H) 8.12 (br d, J=6.71 Hz, 1H) 8.20 (br d, J=8.24 Hz, 1H) LCMS m/z 1382.1 [M+H]$^+$
Intermediate I
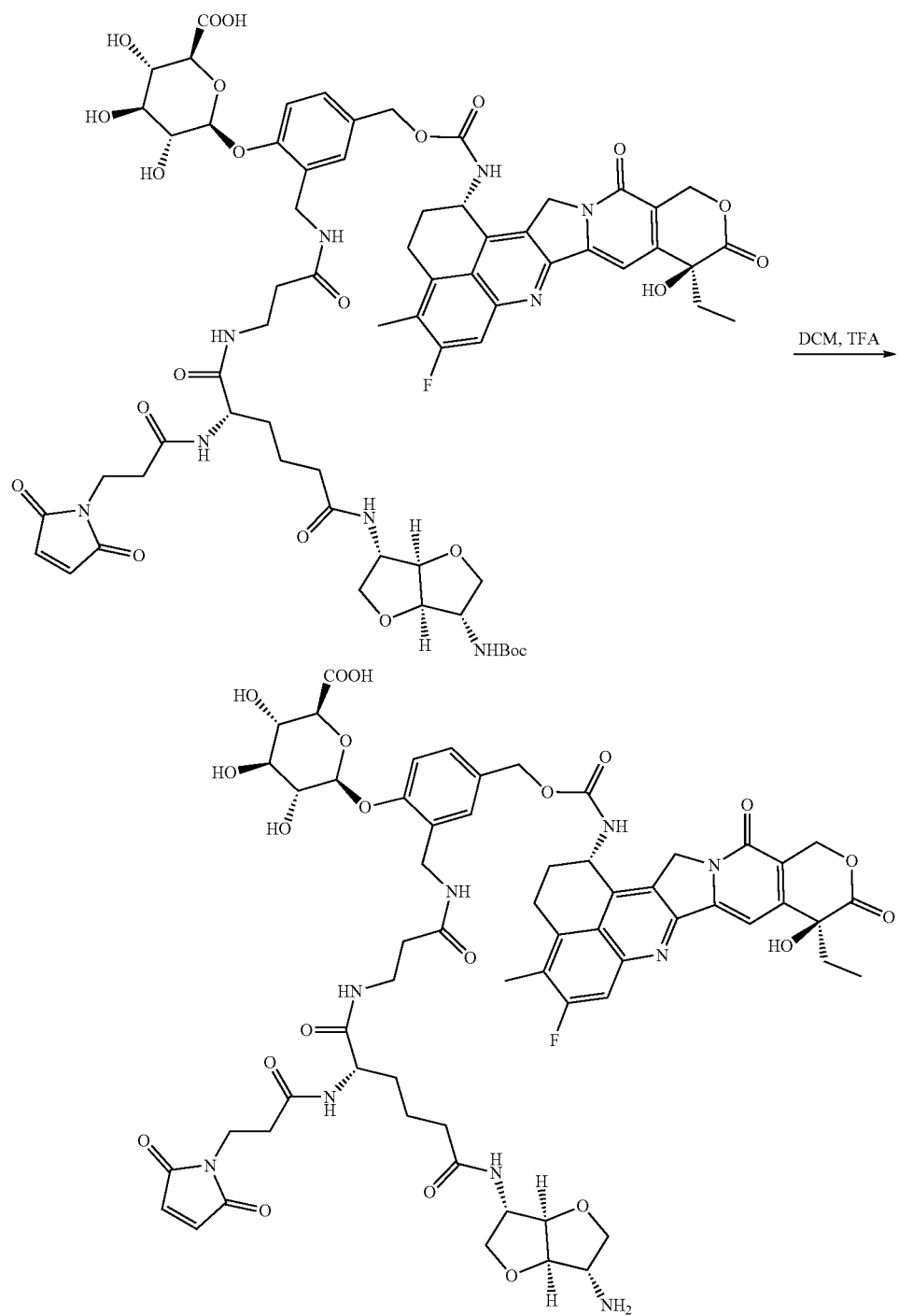

To a solution of Intermediate 1 (230 mg, 166 μmol, 1.0 eq) in DCM (2.6 mL) was added TFA (1.3 mL), and the reaction mixture was stirred for 1 hour at 25° C. LC-MS analysis showed formation of the desired product and completion of the reaction. Solvent was removed under reduced pressure to get crude product. The crude product was purified via silica gel column (5%-50% MeCN in water, 0.1% formic acid) to give (2S,3S,4S,5R,6S)-6-[2-[[3-[[(2S)-6-[[(3S,3aR,6S,6aR)-3-amino-2,3,3a,5,6,6a- hexahydrofuro[3,2-b]furan-6-yl]amino]-2-[3-(2,5-dioxopyrrol-1-yl)propanoylamino]-6-oxo-hexanoyl]amino]propanoylamino]methyl]-4-[[(10S,23S)-10-ethyl-18-fluoro-10-hydroxy-19-methyl-5,9-dioxo-8-oxa-4,15-diazahexacyclo[14.7.1.02,14.04,13.06,11.020,24]tetracosa-1,6 (11),12,14,16 (24),17,19-heptaen-23-yl]carbamoyloxymethyl]phenoxy]-3,4,5-trihydroxy-tetrahydropyran-2-carboxylic acid Intermediate J (120 mg, 54.5%). LCMS m/z 641.5 [M+H]+

Linker-Payload LP-1

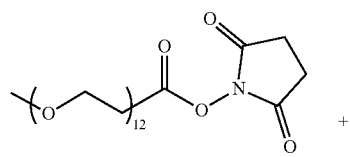

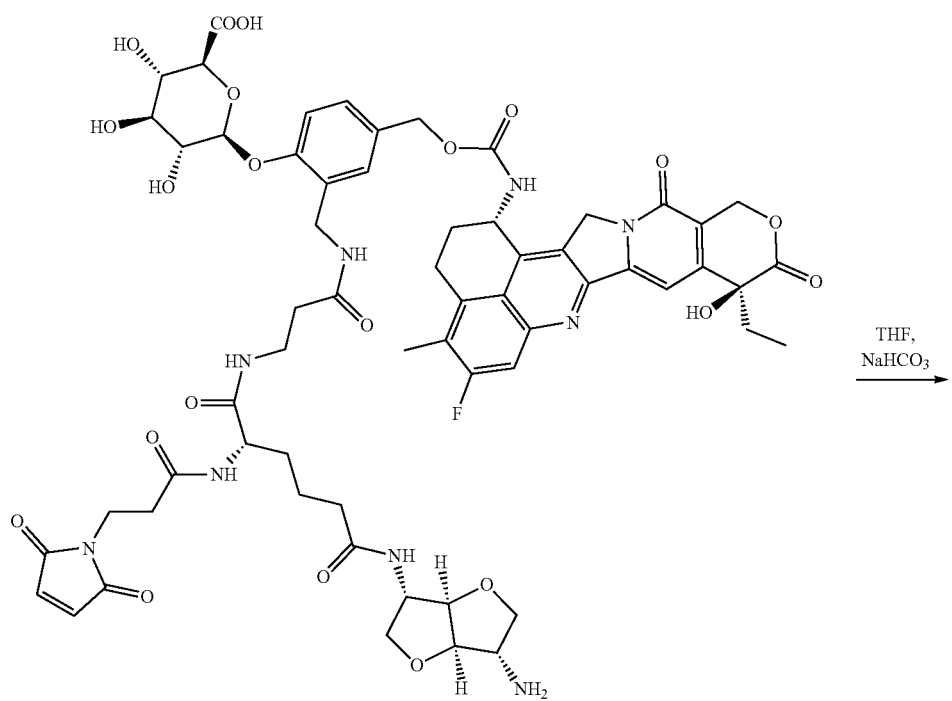

-continued

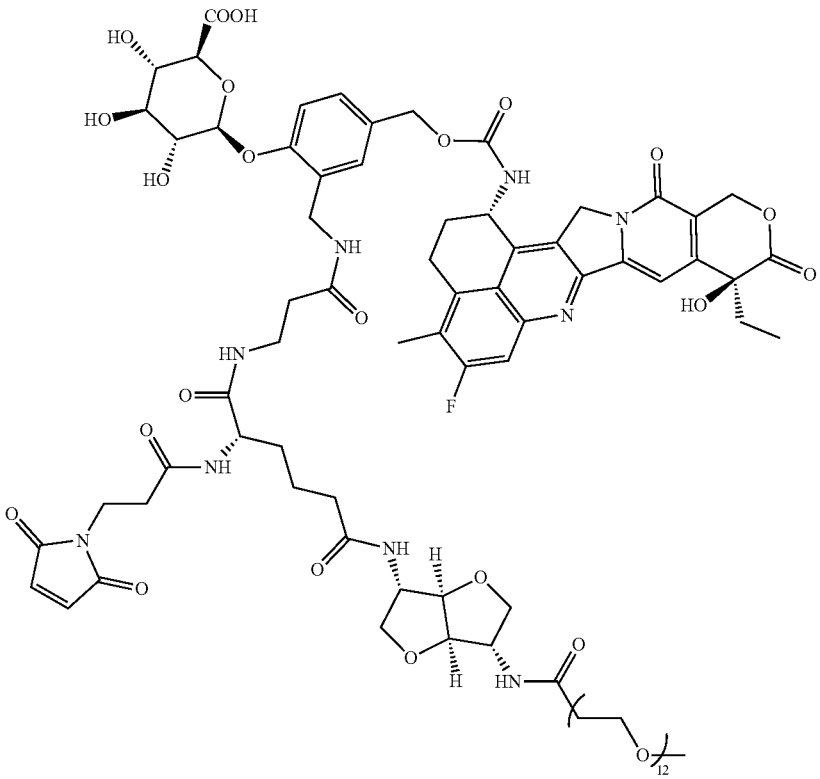

To a solution of Intermediate J (100 mg, 78.0 μmol, 1.0 eq) in THF (1 mL) was added NaHCO$_3$ (13.1 mg, 156 μmol, 2.0 eq) and 2,5-dioxopyrrolidin-1-yl 2,5,8,11,14,17,20,23,26,29,32,35-dodecaoxaoctatriacontan-38-oate Intermediate 10 (64.2 mg, 93.6 μmol, 1.2 eq). The reaction mixture was stirred at 20-25° C. for 16 h. LC-MS analysis showed formation of the desired product and completion of the reaction. Solvent was removed under reduced pressure to get crude product. Solvent was removed under reduced pressure to get crude product. The crude product was purified via silica gel column (5%-50% MeCN in water, 0.1% formic acid) to give give (2S,3S,4S,5R,6S)-6-(2-((3-((S)-6-(((3S,3aR,6S,6aR)-6-(2,5,8,11,14,17,20,23,26,29,32,35-dodecaoxaoctatriacontan-38-amido)hexahydrofuro[3,2-b]furan-3-yl)amino)-2-(3-(2,5-dioxo-2,5-dihydro-1H-pyrrol-1-yl)propanamido)-6-oxohexanamido)propanamido)methyl)-4-(((((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)carbamoyl)oxy)methyl)phenoxy)-3,4,5-trihydroxytetrahydro-2H-pyran-2-carboxylic acid LP-1 (60 mg, 40%). LCMS m/z 927.2 [M+2H]$^{2+}$ Synthesis of LP-T1

Intermediate 34

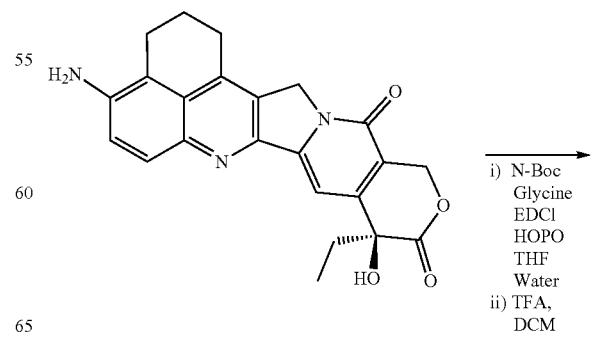

i) N-Boc Glycine
   EDCl
   HOPO
   THF
   Water
ii) TFA, DCM

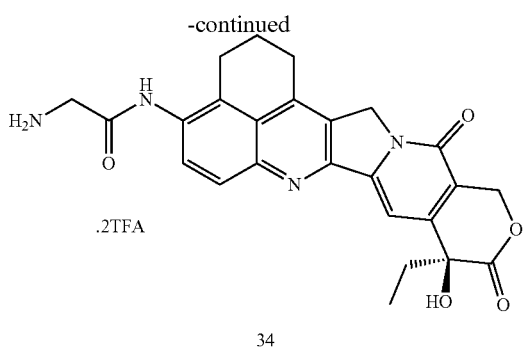

34

3-(((ethylimino)methylene)amino)-N,N-dimethylpropan-1-amine hydrochloride (CAS No. 2495742-21-5, 0.618 g, 3.22 mmol) was added to a solution of (tert-butoxycarbonyl)glycine (0.564 g, 3.22 mmol) in water (10 mL) and stirred at room temperature for 30 min. To this was added to a solution of (S)-4-amino-9-ethyl-9-hydroxy-1,2,3,9,12,15-hexahydro-10H,13H-benzo[de]pyrano[3',4':6,7]indolizino[1,2-b]quinoline-10,13-dione (1 g, 2.48 mmol) and 2-hydroxypyridine 1-oxide (0.303 g, 2.73 mmol) in THF (5 mL) and the reaction stirred at 21° C. for 18 h. Following this time no reaction was observed so another equivalent of acid and EDCl were added and the reaction stirred for a further 60 h at 21° C. Following this time the reaction mixture was concentrated and the residue treated with 2,2,2-trifluoroacetic acid (1.912 mL, 24.79 mmol) in CH2Cl2 (1.9 mL) and the resulting mixture was stirred for 30 minutes at 21° C. Following this time the reaction mixture was concentrated and the residue purified by reverse phase HPLC on a Teledyne ISCO Accq Prep on C18 solid phase (40-60% MeCN/water [0.1% formic acid]). Appropriate fractions were combined and lyophilised to give (S)-2-amino-N-(9-ethyl-9-hydroxy-10,13-dioxo-2,3,9,10,13,15-hexahydro-1H,12H-benzo[de]pyrano[3',4':6,7]indolizino[1,2-b]quinolin-4-yl)acetamide bis(2,2,2-trifluoroacetate) Intermediate 34 (600 mg, 1.303 mmol, 52.6%) as an amorphous yellow solid. $^1$H NMR (400 MHz, DMSO) δ 10.23 (s, 1H), 8.17 (s, 2H), 8.01 (d, J=9.1 Hz, 1H), 7.89 (d, J=9.1 Hz, 1H), 7.32 (s, 1H), 6.51 (s, 1H), 5.44 (s, 2H), 5.28 (s, 2H), 3.93 (s, 2H), 3.19 (t, J=6.1 Hz, 2H), 3.03 (t, J=6.2 Hz, 2H), 2.06 (q, J=6.1 Hz, 2H), 1.98-1.79 (m, J=7.2 Hz, 2H), 0.89 (t, J=7.2 Hz, 3H). LCMS (ESI) m/z [M+H]+ 462.1.

Intermediate 35

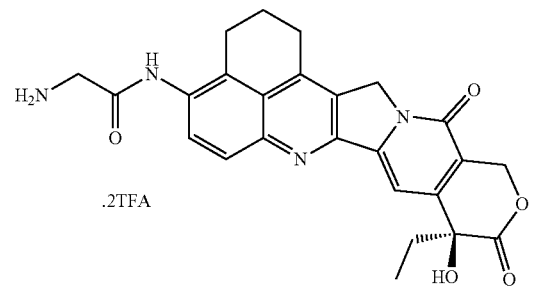

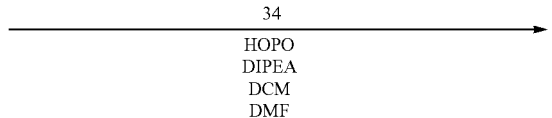

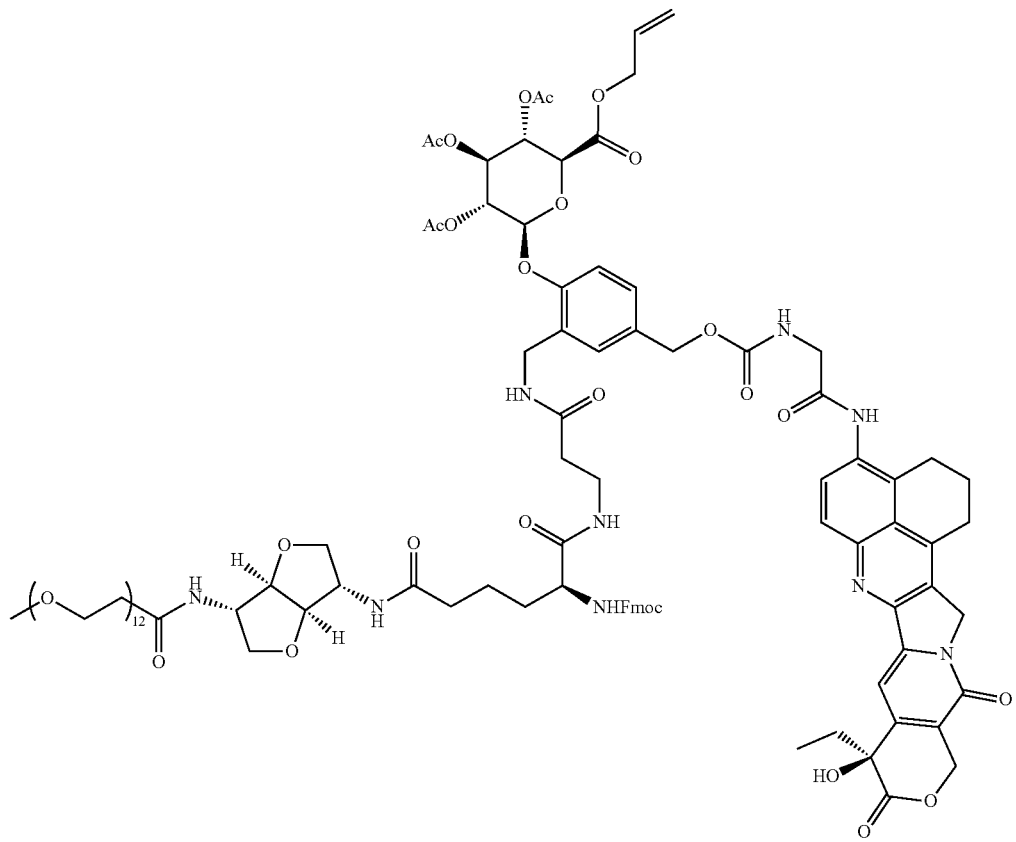

35

To a solution of Intermediate 34 (59.1 mg, 0.09 mmol) and DIPEA (0.060 mL, 0.34 mmol) in DMF (4 mL) and DCM (6 mL) was added Intermediate 18 (154 mg, 0.09 mmol) and HOPO (10.49 mg, 0.09 mmol) and the reaction stirred at 25° C. for 18 h. Following this time the reaction mixture was concentrated and purified by reverse phase flash column chromatography (10-90% MeCN/Water [+0.1% formic acid]) to give (2S,3R,4S,5S,6S)-2-(2-((S)-5-(4-(((3S,3aR,6S,6aR)-6-(2,5,8,11,14,17,20,23,26,29,32,35-dodecaoxaoctatriacontan-38-amido)hexahydrofuro[3,2-b]furan-3-yl)amino)-4-oxobutyl)-1-(9H-fluoren-9-yl)-3,6,10-trioxo-2-oxa-4,7,11-triazadodecan-12-yl)-4-((((2—(((S)-9-ethyl-9-hydroxy-10,13-dioxo-2,3,9,10,13,15-hexahydro-1H,12H-benzo[de]pyrano[3',4':6,7]indolizino[1,2-b]quinolin-4-yl)amino)-2-oxoethyl)carbamoyl)oxy)methyl)phenoxy)-6-((allyloxy)carbonyl)tetrahydro-2H-pyran-3,4,5-triyl triacetate Intermediate 35 (100 mg, 0.047 mmol, 55.1%) as a yellow solid. LCMS (ESI) m/z [M+H]+ 2115.9

Intermediate 36

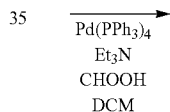

35 → Pd(PPh$_3$)$_4$
Et$_3$N
CHOOH
DCM

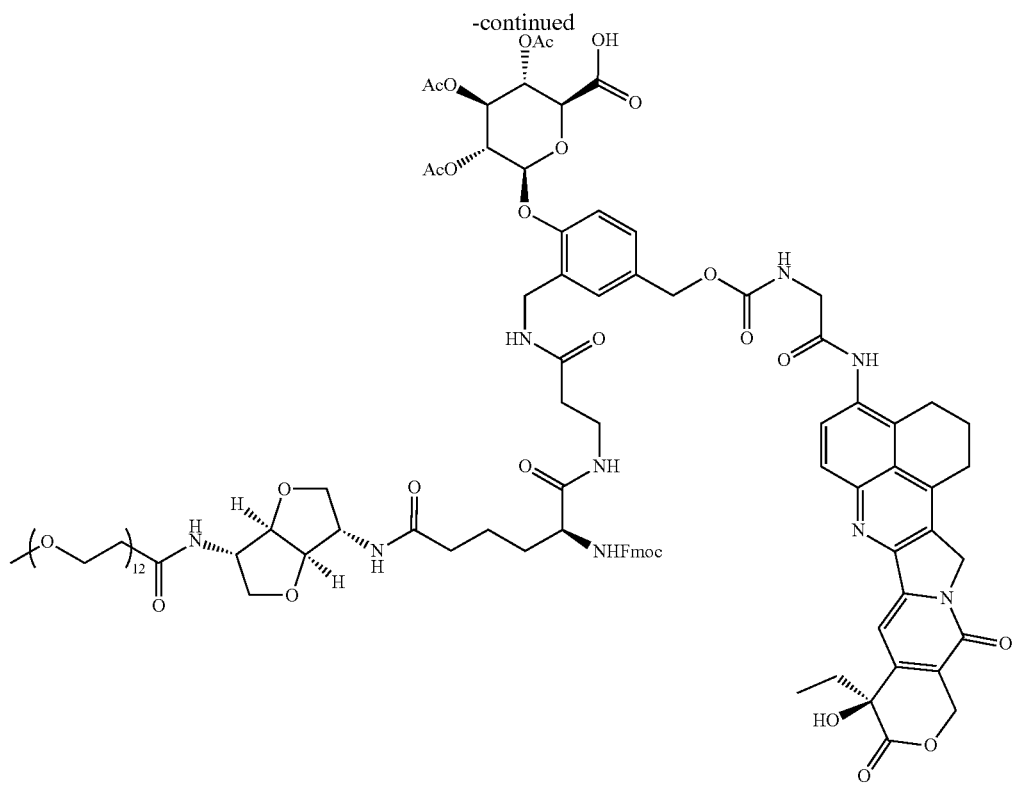

36

To a solution of Intermediate 35 (120 mg, 0.06 mmol), formic acid (4.28 μl, 0.11 mmol), and triethylamine (0.016 mL, 0.11 mmol) in DCM (5 mL) was added Pd(Ph₃P)₄ (6.56 mg, 5.67 μmol). The reaction mixture was stirred for 4 h at 21° C. Following this time the reaction mixture was concentrated to give (2S,3S,4S,5R,6S)-6-(2-((S)-5-(4-(((3S,3aR,6S,6aR)-6-(2,5,8,11,14,17,20,23,26,29,32,35-dodecaoxaoctatriacontan-38-amido)hexahydrofuro[3,2-b]furan-3-yl)amino)-4-oxobutyl)-1-(9H-fluoren-9-yl)-3,6,10-trioxo-2-oxa-4,7,11-triazadodecan-12-yl)-4-(((2-(((S)-9-ethyl-9-hydroxy-10,13-dioxo-2,3,9,10,13,15-hexahydro-1H,12H-benzo[de]pyrano[3',4':6,7]indolizino[1,2-b]quinolin-4-yl)amino)-2-oxoethyl)carbamoyl)oxy)methyl)phenoxy)-3,4,5-triacetoxytetrahydro-2H-pyran-2-carboxylic acid Intermediate 36 (115 mg, 0.055 mmol, 98%) as a yellow gum, which was used without further purification. LCMS (ESI) m/z [M+H]+ 2076.9.

Intermediate 37

36 →  K₂CO₃
MeOH
THF
Water

-continued

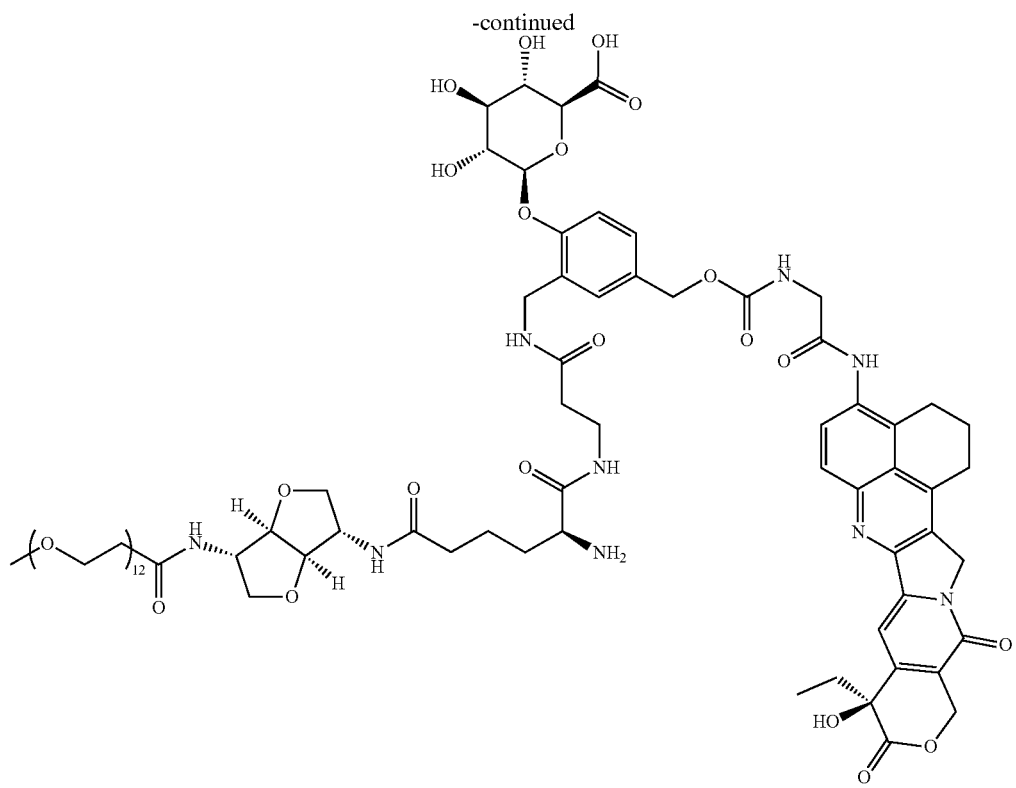

37

To a solution of Intermediate 36 (115 mg, 0.06 mmol) in MeOH (1 mL) and THF (1 mL) was added aqueous potassium carbonate (0.032 mL, 0.55 mmol) and a further addition of water (2 mL). The resulting reaction mixture was stirred for 24 h at 21° C. Following this time aqueous citric acid (1 M) was added until the pH was less than 7.0 and the mixture was stirred for 1 h at 21° C. Following this time the organics were removed in vacuo, and the aqueous was directly purified by reverse phase flash column chromatography (20-30% MeCN/water [0.1% formic acid]) to give (2S,3S,4S,5R,6S)-6-(2-((3-((S)-6-(((3S,3aR,6S,6aR)-6-(2, 5,8,11,14,17,20,23,26,29,32,35-dodecaoxaoctatriacontan-38-amido)hexahydrofuro[3,2-b]furan-3-yl)amino)-2-amino-6-oxohexanamido)propanamido)methyl)-4-((((2-(((S)-9-ethyl-9-hydroxy-10,13-dioxo-2,3,9,10,13,15-hexahydro-1H,12H-benzo[de]pyrano[3',4':6,7]indolizino[1,2-b]quinolin-4-yl)amino)-2-oxoethyl)carbamoyl)oxy) methyl)phenoxy)-3,4,5-trihydroxytetrahydro-2H-pyran-2-carboxylic acid (56 mg, 0.32 mmol, 58.5% yield) Intermediate 37 as a white solid. LCMS (ESI) m/z [M+H]+ 1727.8.

LP-T1

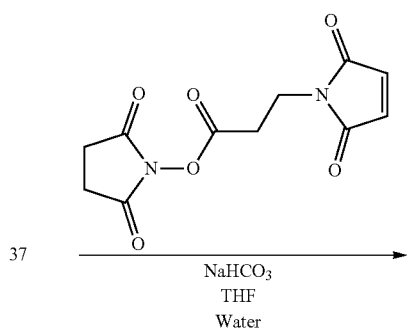

37 $\xrightarrow{\text{NaHCO}_3 \\ \text{THF} \\ \text{Water}}$

-continued

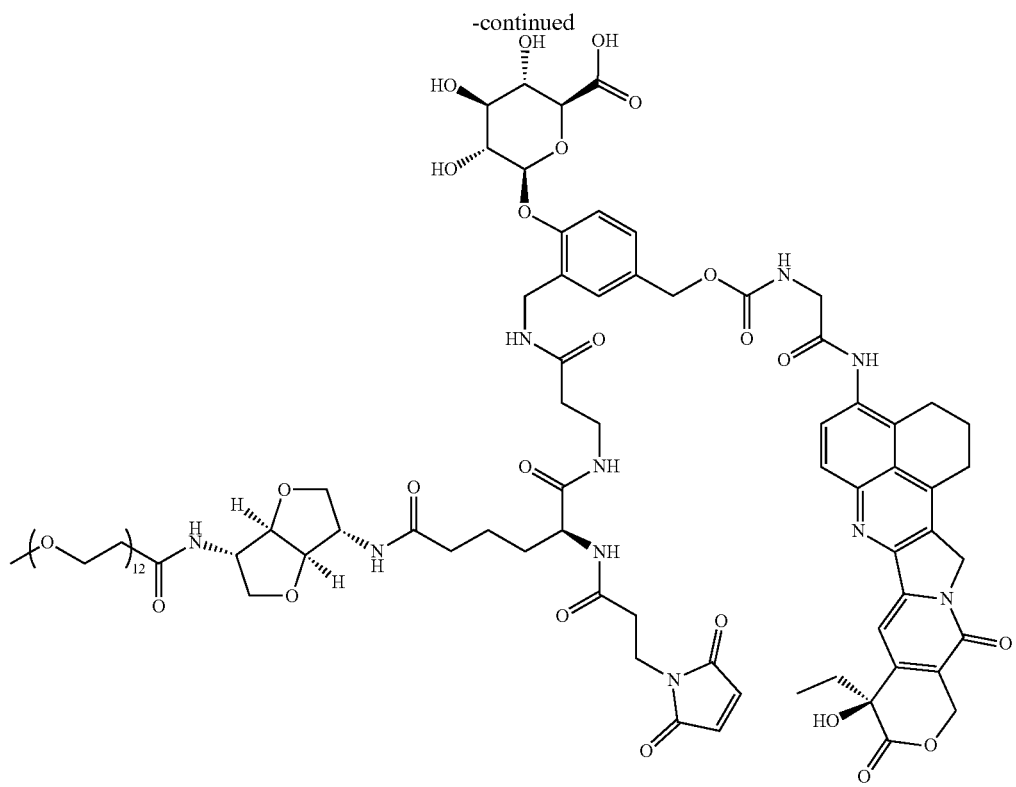

LP-T1

To a solution of Intermediate 37 (56.0 mg, 0.03 mmol) and 2,5-dioxopyrrolidin-1-yl 3-(2,5-dioxo-2,5-dihydro-1H-pyrrol-1-yl)propanoate (9.50 mg, 0.04 mmol) in THF (1 mL) was added sodium hydrogen carbonate (3.27 mg, 0.04 mmol) in water (1 mL). The resulting reaction mixture was then stirred for 2 h at 21° C. Following this time the reaction mixture was concentrated in vacuo to remove the THF. The remaining aqueous solution was then purified directly by reverse phase flash column chromatography (20-40% MeCN/water [0.1% formic acid]) to give (2S,3S,4S,5R,6S)-6-(2-((3-((S)-6-(((3S,3aR,6S,6aR)-6-(2,5,8,11,14,17,20,23,26,29,32,35-dodecaoxaoctatriacontan-38-amido)hexahydrofuro[3,2-b]furan-3-yl)amino)-2-(3-(2,5-dioxo-2,5-dihydro-1H-pyrrol-1-yl)propanamido)-6-oxohexanamido)propanamido)methyl)-4-((((2-(((S)-9-ethyl-9-hydroxy-10,13-dioxo-2,3,9,10,13,15-hexahydro-1H,12H-benzo[de]pyrano[3',4':6,7]indolizino[1,2-b]quinolin-4-yl)amino)-2-oxoethyl)carbamoyl)oxy)methyl)phenoxy)-3,4,5-trihydroxytetrahydro-2H-pyran-2-carboxylic acid LP-T1 (45 mg, 0.024 mmol, 73.9%) as a white solid. LCMS (ESI) m/z [M+H]+ 1878.8.

Synthesis of LP-2

Intermediate 38

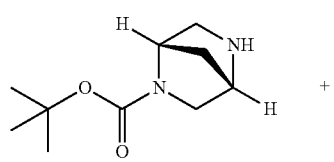

+

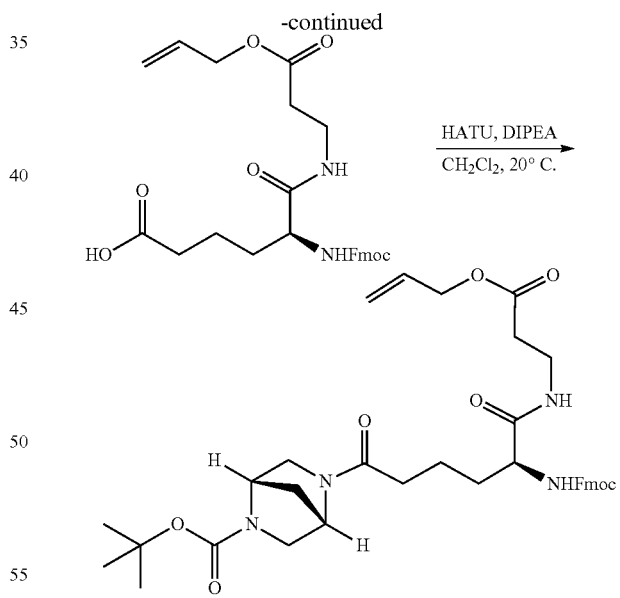

38

To a solution of (S)-5-((((9H-fluoren-9-yl)methoxy)carbonyl)amino)-6-((3-(allyloxy)-3-oxopropyl)amino)-6-oxohexanoic acid (1.0 g, 2.02 mmol) in DCM (20 mL) was added HATU (1.0 g, 2.63 mmol) and DIPEA (1.06 mL, 6.07 mmol). The reaction mixture was stirred at 20° C. for 15 min then tert-butyl (1S,4S)-2,5-diazabicyclo[2.2.1]heptane-2-carboxylate (0.481 g, 2.43 mmol) was added and reaction mixture was stirred for an additional 2 h. The reaction mixture was diluted with EtOAc (2×300 mL) and the organic layer was washed with water (1×300 mL) followed by brine (1×200 mL). Dried over magnesium sulfate then solvent was removed under reduced pressure. Purified by flash column chromatography (80-100% EtOAc/hexanes) to provide tert-butyl (1S,4S)-5-((S)-5-((((9H-fluoren-9-yl)methoxy)carbonyl)amino)-6-((3-(allyloxy)-3-oxopropyl)amino)-6-oxohexanoyl)-2,5-diazabicyclo[2.2.1]heptane-2-carboxylate Intermediate 38 (1.250 g, 1.85 mmol, 92% yield) as a white solid. $^1$H NMR (500 MHz, CDCl$_3$) δ 7.76 (d, J=7.6 Hz, 2H), 7.62 (d, J=7.5 Hz, 2H), 7.40 (t, J=7.5 Hz, 2H), 7.31 (t, J=7.5 Hz, 2H), 6.00 (d, J=7.8 Hz, 1H), 5.89 (m, 1H), 5.30-5.18 (m, 2H), 4.91 (d, J=10.9 Hz, 1H), 4.65-4.47 (m, 3H), 4.46-4.31 (m, 3H), 4.22 (t, J=7.2 Hz, 1H), 4.10 (d, J=9.9 Hz, 1H), 3.58-3.32 (m, 6H), 2.60 (t, J=6.9 Hz, 2H), 2.38-2.16 (m, 2H), 1.94-1.56 (m, 6H), 1.46 (q, J=6.2 Hz, 9H); LCMS (ESI) m/z [M+H]+ 675.4.

Intermediate 39

7.83 (d, J=7.5 Hz, 2H), 7.70 (t, J=9.1 Hz, 2H), 7.42 (t, J=7.5 Hz, 2H), 7.40-7.27 (m, 3H), 5.32-5.14 (m, 1H), 4.73-4.63 (m, 1H), 4.55 (d, J=26.8 Hz, 1H), 4.42 (d, J=8.4 Hz, 2H), 4.26 (t, J=6.9 Hz, 1H), 4.09 (d, J=8.7 Hz, 1H), 3.60 (d, J=9.7 Hz, 1H), 3.54-3.40 (m, 5H), 3.33-3.18 (m, 2H), 2.53 (m, 3H), 2.38 (dt, J=15.5, 7.2 Hz, 1H), 2.29 (d, J=7.4 Hz, 1H), 2.01-1.55 (m, 6H), 1.55-1.42 (m, 9H). LCMS (ESI) m/z [M+H]+ 635.3

Intermediate 40

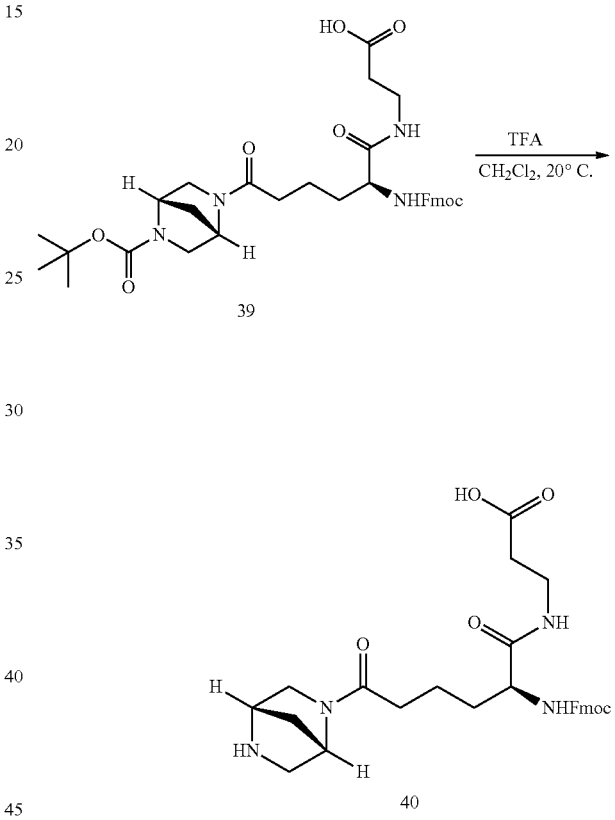

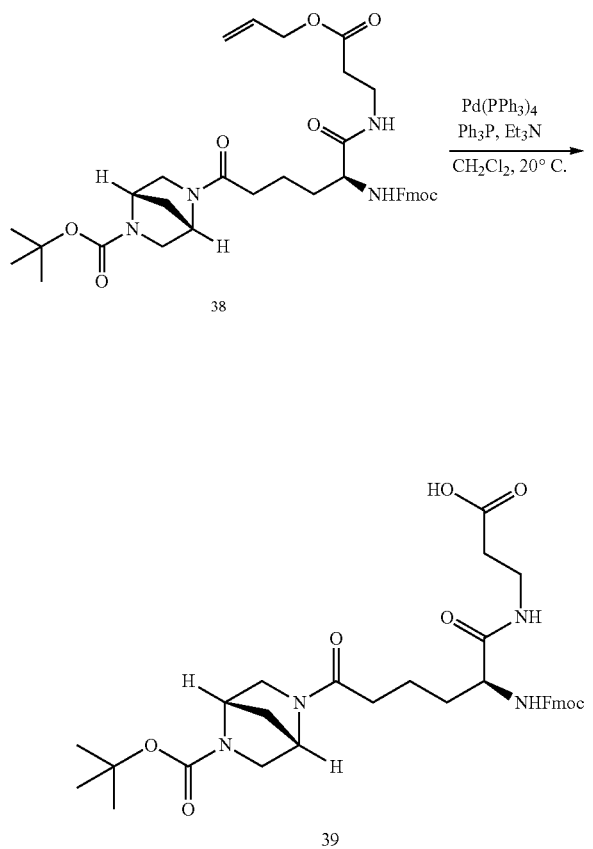

To a solution of Intermediate 38 (1.0 g, 1.48 mmol) in DCM (20 mL) was added triphenylphosphine (0.039 g, 0.15 mmol) followed by triethylamine (0.310 mL, 2.22 mmol) then tetrakis(triphenylphosphine)palladium(0) (0.171 g, 0.15 mmol). The reaction mixture was stirred at 20° C. for 5 h. Purified by flash column chromatography (0-15% MeOH:DCM) to provide 3-((S)-2-((((9H-fluoren-9-yl)methoxy)carbonyl)amino)-6-((1S,4S)-5-(tert-butoxycarbonyl)-2,5-diazabicyclo[2.2.1]heptan-2-yl)-6-oxohexanamido)propanoic acid Intermediate 39 (0.8 g, 1.26 mmol, 85% yield) as a white solid. 1H NMR (500 MHz, CDCl$_3$) δ

To a solution of Intermediate 39 (1.0 g, 1.58 mmol) in DCM (20 mL) was added trifluoroacetic acid (0.12 mL, 1.58 mmol). The reaction mixture was stirred at 20° C. for 5 h. Purified by flash column chromatography (0-15% MeOH:DCM) to provide 3-((S)-2-((((9H-fluoren-9-yl)methoxy)carbonyl)amino)-6-((1S,4S)-2,5-diazabicyclo[2.2.1]heptan-2-yl)-6-oxohexanamido)propanoic acid Intermediate 40 (0.76 g, 1.42 mmol, 90% yield) as a colorless gum. $^1$H NMR (500 MHz, MeOD) δ 7.82 (d, J=7.5 Hz, 2H), 7.69 (dd, J=10.0, 7.4 Hz, 2H), 7.41 (t, J=7.5 Hz, 2H), 7.33 (tt, J=7.5, 1.6 Hz, 2H), 5.70-5.61 (m, 1H), 4.82 (s, 1H), 4.50 (d, J=16.9 Hz, 1H), 4.46-4.35 (m, 2H), 4.24 (t, J=6.8 Hz, 1H), 4.06 (ddd, J=13.0, 8.2, 5.2 Hz, 1H), 3.89 (d, J=6.7 Hz, 1H), 3.78-3.65 (m, 1H), 3.61-3.52 (m, 2H), 3.53-3.36 (m, 4H), 3.34 (s, 1H), 2.64-2.47 (m, 3H), 2.46-2.33 (m, 1H), 2.22-2.11 (m, 1H), 2.01 (dt, J=13.3, 9.5 Hz, 2H), 1.84-1.70 (m, 2H), 1.66 (h, J=6.3 Hz, 2H). LCMS (ESI) m/z [M+H]+ 535.8.

Intermediate 41

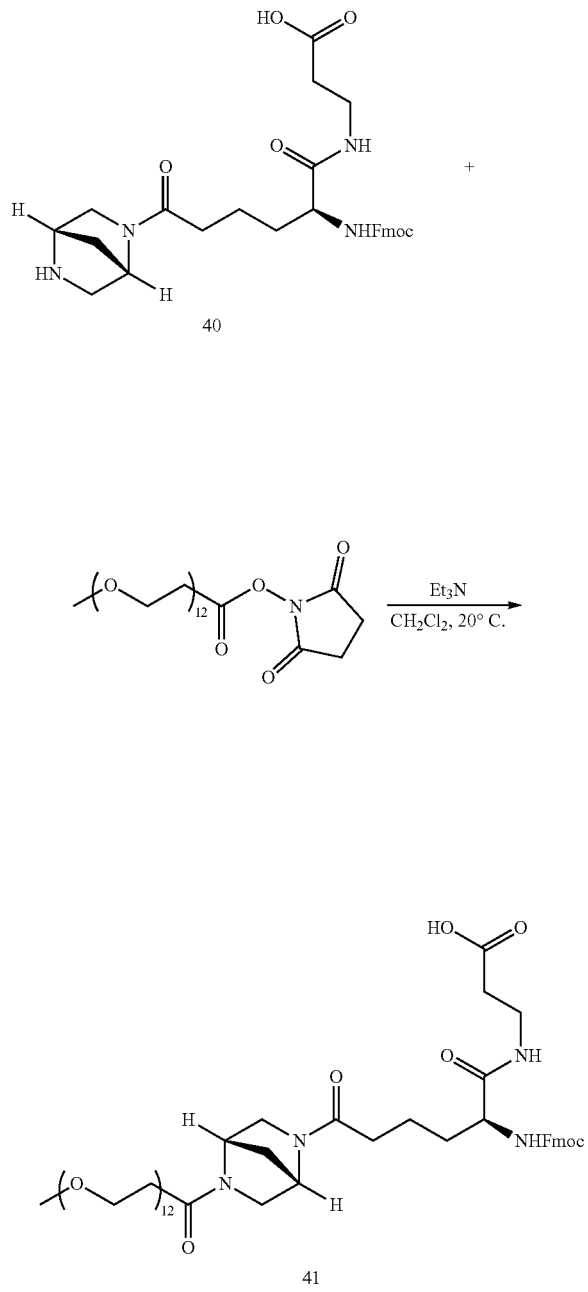

To a solution of Intermediate 40 (1.0 g, 1.54 mmol) in DCM (20 mL) was added triethylamine (0.645 mL, 4.63 mmol) followed by 2,5-dioxopyrrolidin-1-yl 2,5,8,11,14,17,20,23,26,29,32,35-dodecaoxaoctatriacontan-38-oate (1.269 g, 1.85 mmol). The reaction mixture was stirred at 20° C. for 4 h. Purified by flash column chromatography (0-15% MeOH:DCM) to provide 3-((S)-6-((1S,4S)-5-(2,5,8,11,14, 17,20,23,26,29,32,35-dodecaoxaoctatriacontan-38-oyl)-2,5-diazabicyclo[2.2.1]heptan-2-yl)-2-((((9H-fluoren-9-yl) methoxy)carbonyl)amino)-6-oxohexanamido)propanoic acid Intermediate 41 (1.12 g, 1.01 mmol, 95% yield) as a colorless gum. LCMS (ESI) m/z (M+NH$_4$)$^+$1122.7.

Intermediate 42

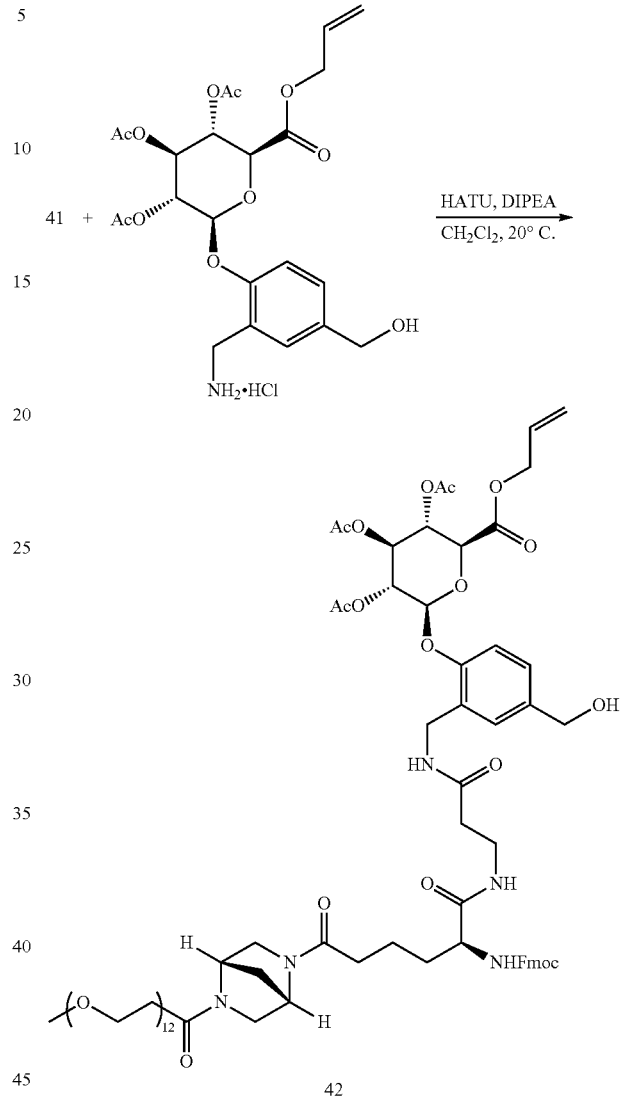

To a solution of Intermediate 41 (0.4 g, 0.36 mmol) in DCM (10 mL) was added HATU (0.186 g, 0.49 mmol) and DIPEA (0.2 mL, 1.15 mmol). Stirred at 20° C. for 15 minutes, then (2S,3S,4S,5R,6S)-2-((allyloxy)carbonyl)-6-(2-(aminomethyl)-4-(hydroxymethyl)phenoxy)tetrahydro-2H-pyran-3,4,5-triyl triacetate hydrochloride (Intermediate 4.HCl) (0.198 g, 0.37 mmol) was added in one portion. Stirred for an additional 30 min. Water (20 mL) was added and stirred for an additional 30 min. Layers were separated and the aqueous layer was extracted with DCM (3×20 mL). Combined organic layers were washed with brine (1×50 mL). Dried over Na$_2$SO$_4$ then solvent was evaporated in vacuo. Purified by flash column chromatography (5-40% MeOH:DCM) to provide (2S,3R,4S,5S,6S)-2-(2-((S)-5-(4-((1S,4S)-5-(2,5,8,11,14,17,20,23,26,29,32,35-dodecaoxaoctatriacontan-38-oyl)-2,5-diazabicyclo[2.2.1]heptan-2-yl)-4-oxobutyl)-1-(9H-fluoren-9-yl)-3,6,10-trioxo-2-oxa-4,7,11-triazadodecan-12-yl)-4-(hydroxymethyl)phenoxy)-6-((allyloxy)carbonyl)tetrahydro-2H-pyran-3,4,5-triyl triacetate Intermediate 42 (300.9 mg, 0.19 mmol, 52.5% yield) as a colourless gum. $^1$H NMR (DMSO-d$_6$) δ: 8.19 (br s, 1H), 7.96 (br d, J=5.5 Hz, 1H), 7.88 (d, J=7.5 Hz, 2H), 7.72 (t, J=6.4 Hz, 2H), 7.47 (br d, J=10.1 Hz, 1H), 7.41 (t, J=7.5 Hz, 2H), 7.32 (t, J=7.5 Hz, 2H), 7.16 (br d, J=8.3 Hz, 1H), 7.12 (s, 1H), 7.00 (d, J=8.3 Hz, 1H), 5.83-5.93 (m, 1H), 5.45-5.56 (m, 2H), 5.22-5.35 (m, 2H), 5.07-5.17 (m, 3H), 4.65-4.77 (m, 3H), 4.50-4.65 (m, 3H), 4.41 (d, J=5.6 Hz, 2H), 4.16-4.29 (m, 4H), 4.03-4.13 (m, 1H), 3.93 (br d, J=8.3 Hz, 1H), 3.56-3.65 (m, 2H), 3.46-3.53 (m, 43H), 3.39-3.44 (m, 3H), 3.33-3.34 (m, 1H), 3.21-3.25 (m, 5H), 3.11-3.20 (m, 2H), 2.65-2.68 (m, 1H), 2.52-2.55 (m, 2H), 2.29-2.46 (m, 6H), 2.22 (br d, J=14.9 Hz, 1H), 2.06-2.15 (m, 2H), 1.94-2.05 (m, 9H), 1.85 (br s, 1H), 1.77 (br s, 1H), 1.71 (br s, 2H), 1.52 (br d, J=7.6 Hz, 4H), 1.23 (s, 1H), 1.14 (s, 1H). LCMS (ESI) m/z [M+H]+ 1581.7.
Intermediate 43
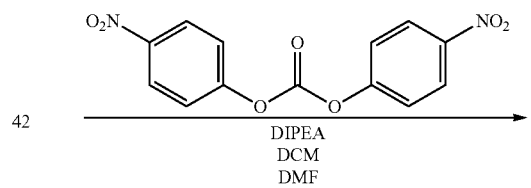
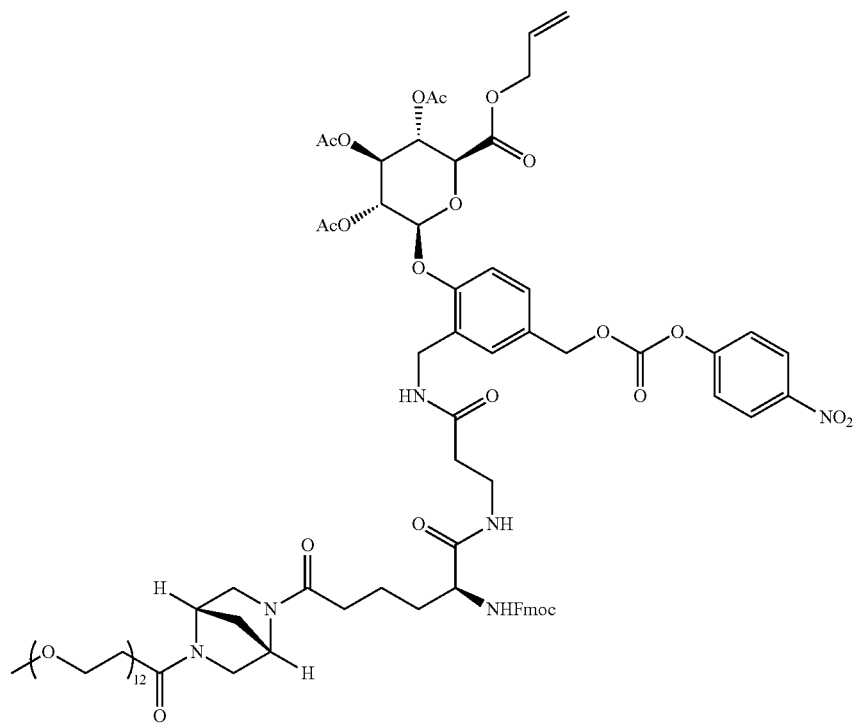
43

To a solution of Intermediate 42 (100 mg, 0.06 mmol) in DMF (1.0 mL) and DCM (1.0 mL) at 25° C. was added bis(4-nitrophenyl) carbonate (115 mg, 0.38 mmol), followed by DIPEA (0.055 mL, 0.32 mmol). The reaction mixture was then stirred at 21° C. for 1 h. Following this time the reaction mixture was concentrated in vacuo and the residue triturated in ether (5 mL). The resulting solid was dissolved then in DCM (2 mL) and to the resulting solution was added ether (10 mL), the mixture was sonicated and centrifugated and the supernatant removed. This process was repeated twice, recovering resulting solid after each cycle, until no further precipitate was formed. This resulted in (2S,3R,4S,5S,6S)-2-(2-((S)-5-(4-((1S,4S)-5-(2,5,8,11,14,17,20,23,26,29,32,35-dodecaoxaoctatriacontan-38-oyl)-2,5-diazabicyclo[2.2.1]heptan-2-yl)-4-oxobutyl)-1-(9H-fluoren-9-yl)-3,6,10-trioxo-2-oxa-4,7,11-triazadodecan-12-yl)-4-((((4-nitrophenoxy)carbonyl)oxy)methyl)phenoxy)-6-((allyloxy)carbonyl)tetrahydro-2H-pyran-3,4,5-triyl triacetate Intermediate 43 (100 mg, 0.06 mmol, 91% yield) as a white solid that was taken through to the next step without further purification. LCMS (ESI) m/z [M+H]+ 1748.5.

Intermediate 44

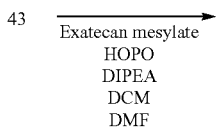

43 Exatecan mesylate
HOPO
DIPEA
DCM
DMF

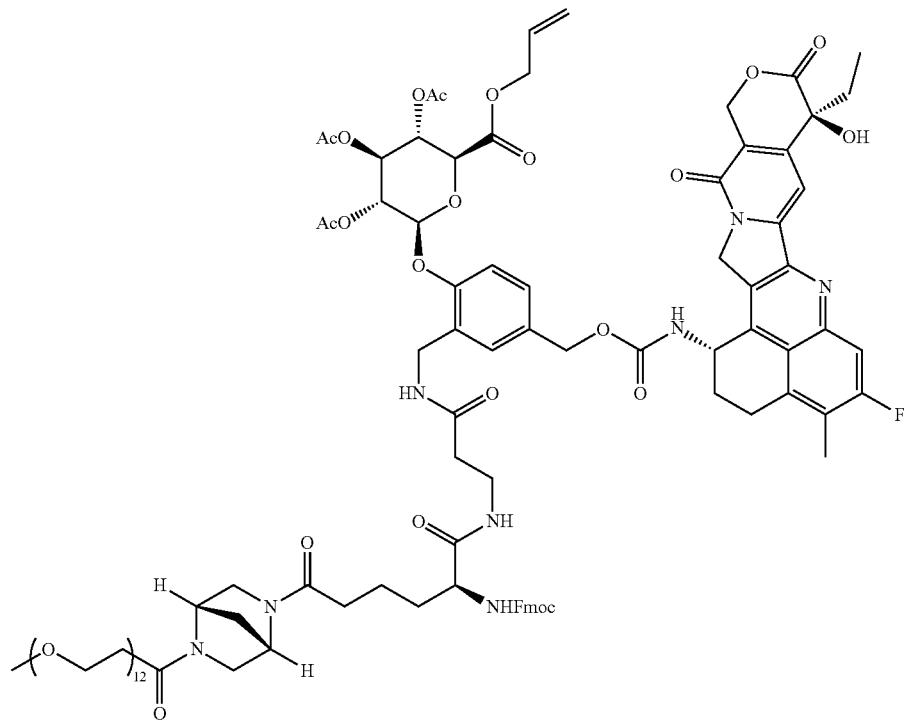

44

To a solution of Intermediate 43 (75 mg, 0.04 mmol) in DCM (1 mL), was added 2-hydroxypyridine 1-oxide (5.24 mg, 0.05 mmol) and exatecan mesylate (23.95 mg, 0.05 mmol) in DMF (1 mL) and DIPEA (0.022 mL, 0.13 mmol). The resulting mixture was stirred at 21° C. for 18 h. Following this time the reaction mixture was concentrated in vacuo and the residue purified by reverse phase flash column chromatography (30-50% MeCN/water [0.1% formic acid]) to give (2S,3R,4S,5S,6S)-2-(2-((S)-5-(4-((1S,4S)-5-(2,5,8,11,14,17,20,23,26,29,32,35-dodecaoxaoctatriacontan-38-oyl)-2,5-diazabicyclo[2.2.1]heptan-2-yl)-4-oxobutyl)-1-(9H-fluoren-9-yl)-3,6,10-trioxo-2-oxa-4,7,11-triazadodecan-12-yl)-4-(((((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)carbamoyl)oxy)methyl)phenoxy)-6-((allyloxy)carbonyl)tetrahydro-2H-pyran-3,4,5-triyl triacetate Intermediate 44 (43.0 mg, 0.021 mmol, 49%) as white solid. LCMS (ESI) m/z [M+H]+ 2044.2.

Intermediate 45

44 $\xrightarrow{\text{Pd(PPh}_3)_4\\ \text{Et}_3\text{N}\\ \text{CHOOH}\\ \text{DCM}}$

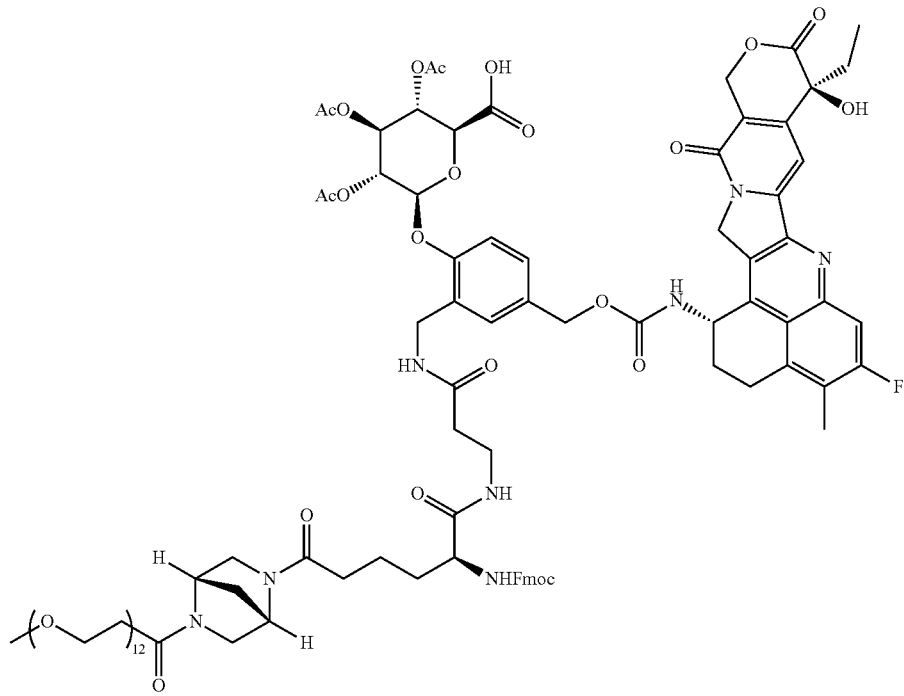

To a solution of Intermediate 44 (43.0 mg, 0.02 mmol) in DCM (2 mL) was added formic acid (1.587 µl, 0.04 mmol), triethylamine (5.86 µl, 0.04 mmol), and Pd(Ph₃P)₄ (2.431 mg, 2.10 µmol). The reaction mixture was then stirred for 18 h at 21° C., following this time the reaction mixture was concentrated in vacuo to give (2S,3S,4S,5R,6S)-6-(2-((S)-5-(4-((1S,4S)-5-(2,5,8,11,14,17,20,23,26,29,32,35-dodecaoxaoctatriacontan-38-oyl)-2,5-diazabicyclo[2.2.1]heptan-2-yl)-4-oxobutyl)-1-(9H-fluoren-9-yl)-3,6,10-trioxo-2-oxa-4,7,11-triazadodecan-12-yl)-4-(((((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)carbamoyl)oxy)methyl)phenoxy)-3,4,5-triacetoxytetrahydro-2H-pyran-2-carboxylic acid Intermediate 45 (37.0 mg, 0.02 mmol, 88%) and used in the next step without further purification. LCMS (ESI) m/z [M+H]+ 2005.8.

Intermediate 46

45 →
K₂CO₃
MeOH
THF
Water

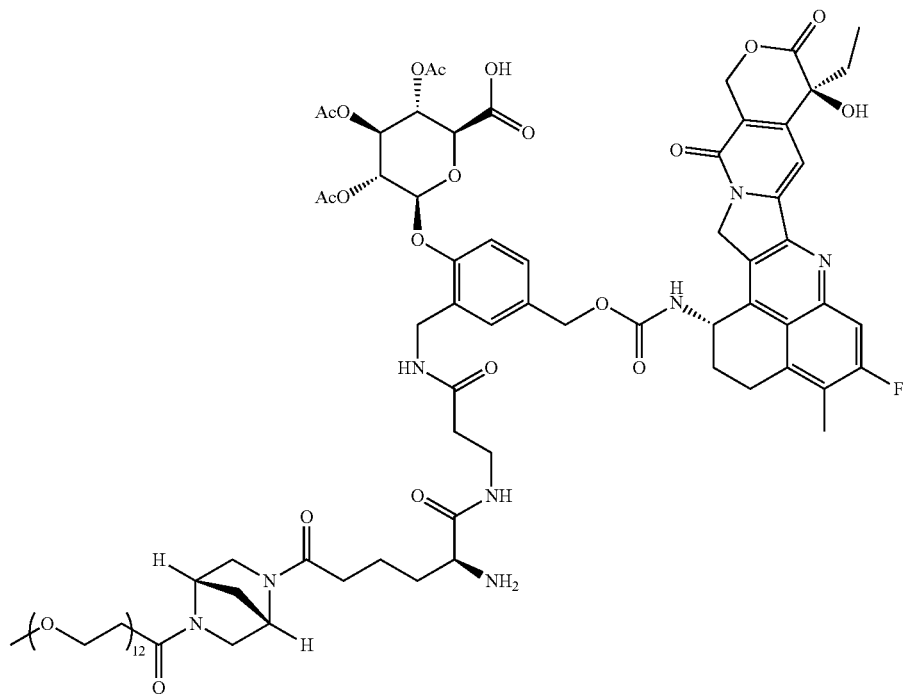

To a solution of Intermediate 45 (37.0 mg, 0.02 mmol) in THF (0.5 mL), was added aqueous potassium carbonate (10.51 μl, 0.18 mmol) and water (0.5 mL). The resulting reaction mixture was stirred 36 h at 21° C. Following this time aqueous citric acid (1 M) was added until the pH was less than 7.0. The reaction mixture was directly purified by reverse phase flash column (20-40% MeCN/water [0.1% formic acid]) to give (2S,3S,4S,5R,6S)-6-(2-((3-((S)-6-((1S,4S)-5-(2,5,8,11,14,17,20,23,26,29,32,35-dodecaoxaocta-triacontan-38-oyl)-2,5-diazabicyclo[2.2.1]heptan-2-yl)-2-amino-6-oxohexanamido)propanamido)methyl)-4-(((((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)carbamoyl)oxy)methyl)phenoxy)-3,4,5-trihydroxytetrahydro-2H-pyran-2-carboxylic acid Intermediate 46 (10 mg, 6.04 μmol, 32.7% yield) as a colourless gum. LCMS (ESI) m/z [M+H]+ 1656.7.

LP-2

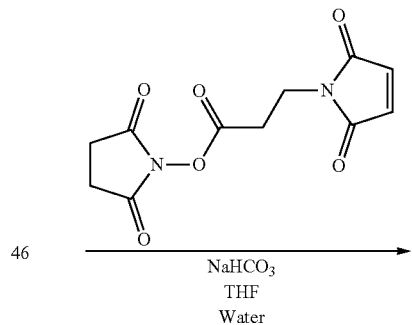

46 ——NaHCO₃, THF, Water——>

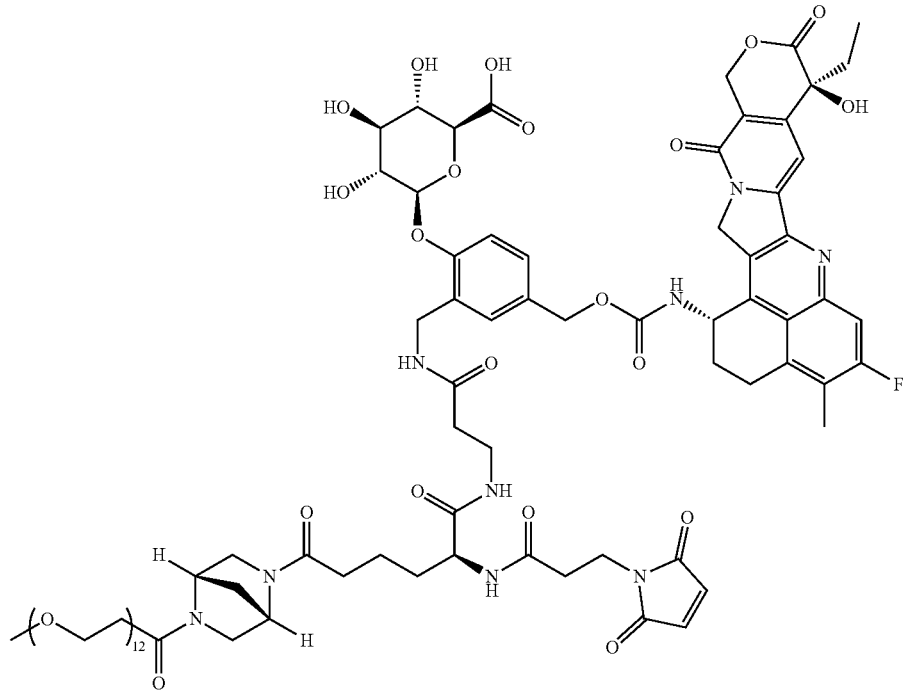

LP-2

To a solution of Intermediate 46 (10 mg, 6.04 µmol) and 2,5-dioxopyrrolidin-1-yl 3-(2,5-dioxo-2,5-dihydro-1H-pyrrol-1-yl)propanoate (1.929 mg, 7.25 µmol) in THF (1 mL) was added a solution of sodium hydrogen carbonate (0.761 mg, 9.06 µmol) in water (1 mL) and the reaction mixture stirred for 3 h at 21° C. Following this time the reaction mixture was concentrated in vacuo to remove THF and the remaining aqueous was directly purified by reverse phase flash column chromatography (30-40% MeCN/water [0.1% formic acid]) to give (2S,3S,4S,5R,6S)-6-(2-((3-((S)-6-((1S,4S)-5-(2,5,8,11,14,17,20,23,26,29,32,35-dodecaoxaoctatriacontan-38-oyl)-2,5-diazabicyclo[2.2.1]heptan-2-yl)-2-(3-(2,5-dioxo-2,5-dihydro-1H-pyrrol-1-yl)propanamido)-6-oxohexanamido)propanamido)methyl)-4-(((((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)carbamoyl)oxy)methyl)phenoxy)-3,4,5-trihydroxytetrahydro-2H-pyran-2-carboxylic acid LP-2 (7.5 mg, 4.15 µmol, 68.7%) as a white solid. LCMS (ESI) m/z [M–H]– 1806.6.

Synthesis of LP-3

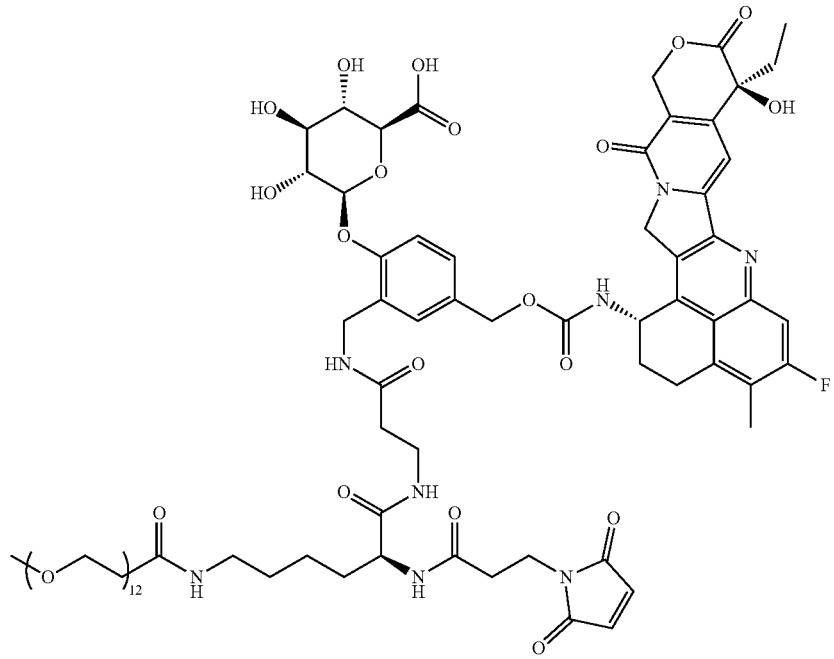

Reference linker-payload LP-3 was prepared by an analogous synthetic procedure to that disclosed above.

Synthesis of LP-4

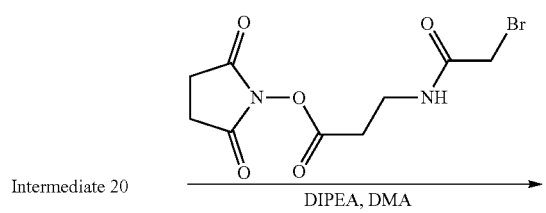

Intermediate 20    DIPEA, DMA

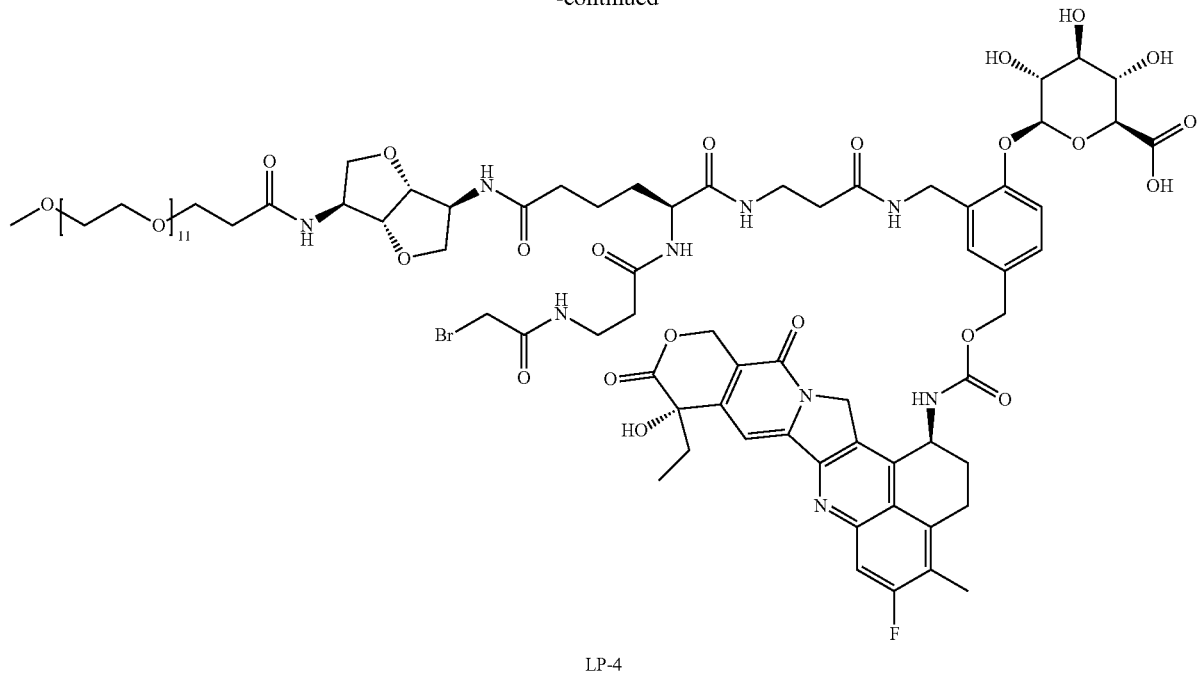

LP-4

2,5-dioxopyrrolidin-1-yl 3-(2-bromoacetamido)propanoate (65.0 mg, 0.21 mmol) was added to Intermediate 20 (300 mg, 0.18 mmol) and DIEA (0.031 mL, 0.18 mmol) in DMA (5 mL) at 25° C. under nitrogen. The resulting mixture was stirred at 25° C. for 2 hours.

The crude mixture was set onto C18-flash chromatography directly for $1^{st}$ purification; elution gradient 0 to 100% MeCN in water (0.1% FA). Pure fractions were evaporated to dryness to afford crude product. The crude product was purified by preparative HPLC (Column: Sunfire Prep C18 OBD column, 19*250 mm, 5 um; Mobile Phase A: Water (0.1% FA), Mobile Phase B: ACN; Flow rate: 25 mL/min; Gradient: 32% B to 36% B in 15 min; Wave Length: 254 nm/220 nm; RT1 (min): 13.72) and MeCN as eluents. Fractions containing the desired compound were freeze dried directly to dryness to afford (2S,3S,4S,5R,6S)-6-(2-((S)-8-(4-(((3S,3aR,6S,6aR)-6-(2,5,8,11,14,17,20,23,26,29,32,35-dodecaoxaoctatriacontan-38-amido)hexahydrofuro[3,2-b]furan-3-yl)amino)-4-oxobutyl)-15-bromo-3,7,10,14-tetraoxo-2,6,9,13-tetraazapentadecyl)-4-((((((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino-[1,2-b]quinolin-1-yl)carbamoyl)oxy)methyl)phenoxy)-3,4,5-trihydroxytetrahydro-2H-pyran-2-carboxylic acid (LP-4) (47.0 mg, 14.08%) as a yellow solid. $^1$H NMR (400 MHz, DMSO) δ 0.88 (t, J=7.2 Hz, 3H), 1.38-1.60 (m, 4H), 1.79-1.95 (m, 2H), 2.03 (d, J=7.2 Hz, 2H), 2.18 (s, 2H), 2.31 (d, J=8.0 Hz, 6H), 2.38 (d, J=2.0 Hz, 3H), 3.14 (s, 1H), 3.25-3.32 (br, 7H), 3.31 (s, 3H), 3.40-3.44 (m, 3H), 3.46-3.48 (m, 3H), 3.50-3.53 (m, 37H), 3.55-3.62 (m, 5H), 3.82 (d, J=6.0 Hz, 5H), 4.01-4.11 (m, 3H), 4.17 (d, J=6.8 Hz, 1H), 4.30 (s, 2H), 4.36 (s, 3H), 4.94-5.15 (m, 3H), 5.29 (s, 4H), 5.46 (s, 3H), 5.56 (d, J=4.0 Hz, 1H), 6.55 (s, 1H), 7.09 (d, J=8.0 Hz, 1H), 7.18-7.26 (m, 1H), 7.26-7.35 (m, 2H), 7.75-7.81 (m, 1H), 7.92-7.96 (br, 1H), 8.06 (s, 1H), 8.12 (s, 1H), 8.17 (s, 1H), 8.25-8.31 (br, 2H) (One proton was exchanged) ES$^+$ (M+1=1894)

Antibody-Drug Conjugation

ADC-1: Herceptin-WT-LP-1 (DAR 8)

LP-1 was added as a DMSO solution (16 molar equivalent/antibody, 0.64 μmole, in 0.128 mL DMSO) to 1.82 mL of the Herceptin-wt antibody solution in PBS, 1 mM EDTA, pH 7.4 (6.0 mg, 40.0 nanomoles) for a 10% (v/v) final DMSO concentration. The solution left to react at room temperature for 1 hours with gentle shaking. Then the conjugation was quenched by addition of N-acetyl cysteine (3.2 micromoles, 32.03 μL at 100 mM), then purified in and formulated in PBS pH 7.4 by spin filtration using a 15 mL AMICON ULTRACELL 30 kDa MWCO spin filter, sterile-filtered and analysed.

UHPLC analysis on a SHIMADZU PROMINENCE system using a THERMO SCIENTIFIC MAbPac 50 mm×2.1 mm column eluting with a gradient of water and acetonitrile on a reduced sample of ADC at 214 nm and 330 nm shows a mixture of light chain conjugated to 1 molecule of LP-1, and heavy chain conjugated to 3.0 molecules of LP-1, consistent with a drug-per-antibody ratio (DAR) of 7.9 molecules of LP-1 per antibody.

UHPLC analysis on a SHIMADZU PROMINENCE system using A TOSOH BIOSCIENCE TSKgel SuperSW mAb HTP 4 μm 4.6×150 mm column (with a 4 μm 3.0×20 mm guard column) eluting with 0.3 mL/minute sterile-filtered SEC buffer containing 200 mM potassium phosphate pH 6.95, 250 mM potassium chloride and 10% isopropanol (v/v) on a sample of ADC at 280 nm shows a monomer purity of 97.9%. UHPLC SEC analysis gives a concentration of final ADC at 2.86 mg/mL in 1.6 mL, obtained mass of is 4.5 mg (75% yield).

LC-MS analysis on a EXACTIVE PLUS EMR mass spectrometer connected to DIONEX 3000 HPLC equipment using a THERMO SCIENTIFIC MAbPac 50 mm×2.1 mm column eluting with a gradient of water and acetonitrile on a de-glycosylated and reduced sample of ADC at 214 nm shows a mixture of light chain conjugated to 1 molecule LP-1, and heavy chain conjugated to 3.0 molecules of LP-1, consistent with a drug-per-antibody ratio (DAR) of 7.9 molecules of LP-1 per antibody.

UHPLC analysis on a SHIMADZU PROMINENCE system using A PROTEOMIX HIC Butyl-NP5, 5um, non-porous, 4.6×35 mm (SEPAX) column eluting with a gradient of 1.5M ammonium sulphate, 25 mM sodium acetate, pH 7.4 and 25 mM sodium acetate, pH 7.4 with 20% acetonitrile (v/v) on a neat sample of ADC at 214 nm shows singly conjugated LP-1, consistent with a drug-per-antibody ratio (DAR) of 8 molecules of LP-1 per antibody.

ADC-2: Herceptin-WT-LP-2 (DAR 8)

LP-2 was added as a DMSO solution (13 molar equivalent/antibody, 1.3 μmole, in 0.130 mL DMSO) to 3.0 mL of the Herceptin-wt antibody solution in PBS, 1 mM EDTA, pH 7.4 (15.0 mg, 100.0 nanomoles) for a 10% (v/v) final DMSO concentration. The solution left to react at room temperature for 1 hours with gentle shaking. Then the conjugation was quenched by addition of N-acetyl cysteine (6.5 micromoles, 65.0 μL at 100 mM), then purified in in PBS pH 7.4 by SECprep-AKTA and formulated in 20 mM His\His HCl, 240 mM sucrose pH 6.0 by spin filtration using a 15 mL AMICON ULTRACELL 30 kDa MWCO spin filter, sterile-filtered and analysed.

UHPLC analysis on a SHIMADZU PROMINENCE system using a THERMO SCIENTIFIC MAbPac 50 mm×2.1 mm column eluting with a gradient of water and acetonitrile on a reduced sample of ADC at 214 nm and 330 nm shows a mixture of light chain conjugated to 1 molecule of LP-2, and heavy chain conjugated to 3.0 molecules of LP-2, consistent with a drug-per-antibody ratio (DAR) of 7.98 molecules of LP-2 per antibody.

UHPLC analysis on a SHIMADZU PROMINENCE system using a TOSOH BIOSCIENCE TSKgel SuperSW mAb HTP 4 μm 4.6×150 mm column (with a 4 μm 3.0×20 mm guard column) eluting with 0.3 mL/minute sterile-filtered SEC buffer containing 200 mM potassium phosphate pH 6.95, 250 mM potassium chloride and 10% isopropanol (v/v) on a sample of ADC at 280 nm shows a monomer purity of 99.23%.

LC-MS analysis on a EXACTIVE PLUS EMR mass spectrometer connected to DIONEX 3000 HPLC equipment using a THERMO SCIENTIFIC MAbPac 50 mm×2.1 mm column eluting with a gradient of water and acetonitrile on a de-glycosylated and reduced sample of ADC at 214 nm shows a mixture of light chain conjugated to 1 molecule of LP-2, and heavy chain conjugated to 3.0 molecules of LP-2, consistent with a drug-per-antibody ratio (DAR) of 8.0 molecules of LP-2 per antibody.

UHPLC analysis on a SHIMADZU PROMINENCE system using a PROTEOMIX HIC Butyl-NP5, 5 um, non-porous, 4.6×35 mm (Sepax) column eluting with a gradient of 1.5M ammonium sulphate, 25 mM sodium acetate, pH 7.4 and 25 mM sodium acetate, pH 7.4 with 20% acetonitrile (v/v) on a neat sample of ADC at 214 nm shows singly conjugated to LP-2, consistent with a drug-per-antibody ratio (DAR) of 8 molecules of LP-2 per antibody.

ADC-3: Herceptin-WT-LP-3 (DAR 8) (Reference)

LP-3 was added as a DMSO solution (14 molar equivalent/antibody, 1.4 μmole, in 0.39 mL DMSO) to 6.0 mL of the Herceptin-wt antibody solution in PBS, 1 mM EDTA, pH 7.4 (30.0 mg, 200.0 nanomoles) for a 10% (v/v) final DMSO concentration. The solution left to react at room temperature for 1 hours with gentle shaking. Then the conjugation was quenched by addition of N-acetyl cysteine (14 micromoles, 130.0 μL at 100 mM), then purified in in PBS pH 7.4 by SECprep-AKTA and formulated in 20 mM His\His HCl, 240 mM sucrose pH 6.0 by spin filtration using a 15 mL AMICON ULTRACELL 30 kDa MWCO spin filter, sterile-filtered and analysed.

UHPLC analysis on a SHIMADZU PROMINENCE system using a THERMO SCIENTIFIC MAbPac 50 mm×2.1 mm column eluting with a gradient of water and acetonitrile on a reduced sample of ADC at 214 nm and 330 nm shows a mixture of light chain conjugated to 1 molecule of LP-3, and heavy chain conjugated to 3.0 molecules of LP-3, consistent with a drug-per-antibody ratio (DAR) of 7.89 molecules of LP-3 per antibody.

UHPLC analysis on a SHIMADZU PROMINENCE system using a TOSOH BIOSCIENCE TSKgel SuperSW mAb HTP 4 μm 4.6×150 mm column (with a 4 μm 3.0×20 mm guard column) eluting with 0.3 mL/minute sterile-filtered SEC buffer containing 200 mM potassium phosphate pH 6.95, 250 mM potassium chloride and 10% isopropanol (v/v) on a sample of ADC at 280 nm shows a monomer purity of 98.67%.

LC-MS analysis on a EXACTIVE PLUS EMR mass spectrometer connected to DIONEX 3000 HPLC equipment using a THERMO SCIENTIFIC MAbPac 50 mm×2.1 mm column eluting with a gradient of water and acetonitrile on a de-glycosylated and reduced sample of ADC at 214 nm shows a mixture of light chain conjugated to 1 molecule of LP-3, and heavy chain conjugated to 3.0 molecules of LP-3, consistent with a drug-per-antibody ratio (DAR) of 8.0 molecules of LP-3 per antibody.

UHPLC analysis on a SHIMADZU PROMINENCE system using a PROTEOMIX HIC Butyl-NP5, 5 um, non-porous, 4.6×35 mm (Sepax) column eluting with a gradient of 1.5M ammonium sulphate, 25 mM sodium acetate, pH 7.4 and 25 mM sodium acetate, pH 7.4 with 20% acetonitrile (v/v) on a neat sample of ADC at 214 nm shows singly conjugated to LP-3, consistent with a drug-per-antibody ratio (DAR) of 8 molecules of LP-3 per antibody.

ADC-4: Herceptin-WT-LP-4 (DAR 8)

LP-4 was added as a DMSO solution (25 molar equivalent/antibody, 4.0 μmole, in 0.166 mL DMSO) to 2.0 mL of the Herceptin-wt antibody solution in PBS, 1 mM EDTA, 15% Borate buffer pH 8.3 (20.0 mg, 133.0 nanomoles) for a 10% (v/v) final DMSO concentration. The solution left to react at room temperature for 1 hours with gentle shaking. Purified in PBS pH 7.4 using AKTA-SECPrep and formulated in 20 mM Histidine/Histidine HCl, 240 mM sucrose pH 6.0 by spin filtration using a 15 mL Amicon Ultracell 30 kDa MWCO spin filter, sterile-filtered and analysed.

UHPLC analysis on a Shimadzu Prominence system using a Thermo Scientific MAbPac 50 mm×2.1 mm column eluting with a gradient of water and acetonitrile on a reduced sample of ADC at 214 nm and 330 nm shows a mixture of light chain conjugated to 1 molecule of LP-4, and heavy chain conjugated to 3.0 molecules of LP-4, consistent with a drug-per-antibody ratio (DAR) of 7.87 molecules of LP-4 per antibody.

UHPLC analysis on a Shimadzu Prominence system using a Tosoh Bioscience TSKgel SuperSW mAb HTP 4 μm 4.6×150 mm column (with a 4 μm 3.0×20 mm guard column) eluting with 0.3 mL/minute sterile-filtered SEC buffer containing 200 mM potassium phosphate pH 6.95, 250 mM potassium chloride and 10% isopropanol (v/v) on a sample of ADC at 280 nm shows a monomer purity of 99.68%. UHPLC SEC analysis gives a concentration of final ADC at 4.92 mg/mL in 3.5 mL, obtained mass of is 17.2 mg (86% yield).

LC-MS analysis on a Exactive Plus EMR mass spectrometer connected to Dionex 3000 HPLC equipment using a Thermo Scientific MAbPac 50 mm×2.1 mm column eluting with a gradient of water and acetonitrile on a de-glycosylated and reduced sample of ADC at 214 nm shows a mixture of light chain conjugated to 1 molecule of LP-4, and heavy chain conjugated to 3.0 molecules of LP-4, consistent with a drug-per-antibody ratio (DAR) of 8.0 molecules of LP-4 per antibody.

UHPLC analysis on a Shimadzu Prominence system using a Proteomix HIC Butyl-NP5, 5 um, non-porous, 4.6×35 mm (Sepax) column eluting with a gradient of 1.5M ammonium sulphate, 25 mM sodium acetate, pH 7.4 and 25 mM sodium acetate, pH 7.4 with 20% acetonitrile (v/v) on a neat sample of ADC at 214 nm shows singly conjugated to LP-4, consistent with a drug-per-antibody ratio (DAR) of 7.96 molecules of LP-4 per antibody.

ADC-M1: Herceptin-WT-LP-M1 (DAR 4)

A 100 mM solution of (TCEP) in phosphate-buffered saline pH 7.4 (PBS) was added (3.0 molar equivalent/antibody, 150 nanomoles, 15 mL) to a 7.5 mL solution of antibody (75 mg, 500 nanomoles) in reduction buffer containing PBS and 1 mM ethylenediaminetetraacetic acid (EDTA) and a final antibody concentration of 10.0 mg/mL. The reduction mixture was allowed to react at RT for 2 hours in an orbital shaker with gentle (60 rpm) shaking before dilution to 3.0 mg/mL. LP-M1 was added as a DMA solution (10 molar equivalent/antibody, 100.0 micromoles, in 0.60 mL DMA) to 5.0 mL of this diluted reduced antibody solution (15 mg, 100 nanomoles) for a 10% (v/v) final DMA concentration and a final antibody concentration of ~2.7 mg/mL. The resulting solution was mixed for 1 hour at room temperature, quenched with N-acetyl-L-cysteine (5 molar equivalent/LP, 5 micromoles, 50 mL at 100 mM) and purified on an AKTA™ Start FPLC using a GE HEALTHCARE HILOAD 26/600 column packed with Superdex 200 PG, eluting with 2.6 mL/min PBS. Monomer fractions of ADC-M1 were pooled and formulated into 20 mM Histidine 240 mM Sucrose pH 6.0 by spin filtration using a 15 mL Amicon Ultracell 30 kDa MWCO spin filter, sterile-filtered and analysed.

UHPLC analysis on a Shimadzu Prominence system using a Thermo Scientific MAbPac 50 mm×2.1 mm column eluting with a gradient of water and acetonitrile on a reduced sample of ADC-M1 at 214 nm shows a mixture of unconjugated light chain, light chains attached to a single molecule of LP-M1, unconjugated heavy chains and heavy chains attached to up to three molecules of LP-M1, consistent with a drug-per-antibody ratio (DAR) of 3.61 molecules of LP-M1 per antibody.

UHPLC analysis on a Shimadzu Prominence system using a Tosoh Bioscience TSKgel SuperSW mAb HTP 4 μm 4.6×150 mm column (with a 4 μm 3.0×20 mm guard column) eluting with 0.3 mL/minute sterile-filtered SEC buffer containing 200 mM potassium phosphate pH 6.95, 250 mM potassium chloride and 10% isopropanol (v/v) on a sample of ADC-M1 at 280 nm shows a monomer purity of 100%. Reduced SDS-PAGE analysis gives a concentration of final ADC-M1 at 2.09 mg/mL in 5.0 mL, obtained mass of ADC-M1 is 10.45 mg (70% yield).

ADC-T1: Herceptin-WT-LP-T1 (DAR 8)

LP-T1 was added as a DMSO solution (15 molar equivalent/antibody, 1.46 μmole, in 0.145 mL DMSO) to 2.84 mL of the Herceptin-wt antibody solution in PBS, 1 mM EDTA, pH 7.4 (15.0 mg, 97.5 nanomoles) for a 10% (v/v) final DMSO concentration. The solution left to react at room temperature for 1 hours with gentle shaking. Then the conjugation was quenched by addition of N-acetyl cysteine (7.3 micromoles, 73.13 μL at 100 mM), then purified in in PBS pH 7.4 by SECprep-AKTA and formulated in 20 mM His\His HCl, 240 mM sucrose pH 6.0 by spin filtration using a 15 mL Amicon Ultracell 30 kDa MWCO spin filter, sterile-filtered and analysed.

UHPLC analysis on a Shimadzu Prominence system using a Thermo Scientific MAbPac 50 mm×2.1 mm column eluting with a gradient of water and acetonitrile on a reduced sample of ADC at 214 nm and 330 nm shows a mixture of light chain conjugated to 1 molecule of LP-T1/, and heavy chain conjugated to 3.0 molecules of LP-T1, consistent with a drug-per-antibody ratio (DAR) of 7.98 molecules of LP-T1 per antibody.

UHPLC analysis on a Shimadzu Prominence system using a Tosoh Bioscience TSKgel SuperSW mAb HTP 4 μm 4.6×150 mm column (with a 4 μm 3.0×20 mm guard column) eluting with 0.3 mL/minute sterile-filtered SEC buffer containing 200 mM potassium phosphate pH 6.95, 250 mM potassium chloride and 10% isopropanol (v/v) on a sample of ADC at 280 nm shows a monomer purity of 99.23%.

LC-MS analysis on a Exactive Plus EMR mass spectrometer connected to Dionex 3000 HPLC equipment using a Thermo Scientific MAbPac 50 mm×2.1 mm column eluting with a gradient of water and acetonitrile on a de-glycosylated and reduced sample of ADC at 214 nm shows a mixture of light chain conjugated to 1 molecule of LP-T1, and heavy chain conjugated to 3.0 molecules of LP-T1, consistent with a drug-per-antibody ratio (DAR) of 8.0 molecules of LP-T1 per antibody.

UHPLC analysis on a Shimadzu Prominence system using a Proteomix HIC Butyl-NP5, Sum, non-porous, 4.6× 35 mm (Sepax) column eluting with a gradient of 1.5M ammonium sulphate, 25 mM sodium acetate, pH 7.4 and 25 mM sodium acetate, pH 7.4 with 20% acetonitrile (v/v) on a neat sample of ADC at 214 nm shows singly conjugated to LP-T1, consistent with a drug-per-antibody ratio (DAR) of 8 molecules of LP-T1 per antibody.

Control ADC-1

A DAR 8 negative control ADC (Control ADC-1) was prepared by conjugating a negative control antibody NIP228 (as disclosed in WO2015127273A1, the contents of which are incorporated by reference) and LP-1 by a conjugation process analogous to that described by ADC-1. NIP228 is an IgG1 that has complementary binding to transferrin, a transmembrane protein whose expression is low on the tested cell lines, therefore making it a suitable negative control.

ADC toxicity evaluated on 3D NCI-N87, JIMT1 and MDAMB468 Media from NCI-N87, JIMT1 and MDAMB468 cells at 80-90% confluency in a T175 flask was aspirated and the flask rinsed with PBS (about 10 ml) and emptied. TrypLE (5 ml) Express Enzyme (1×) was added, the flask returned to the 37° C. incubator with 5% $CO_2$ for about 5 minutes, then the flask was shaken to detach the cells from the bottom. 10 mL cell media (RPMI 1640 for NCI-N87 and MDAMB468, DMEM for JIMT1, both supplement with 50% Fetal Bovine Serum) was added to the flask and the cell suspension was transferred to a sterile 50 ml falcon tube, then centrifuged (400 g for 5 min). The supernatant was aspirated, and the pellet re-suspended in 10 mL culture medium. The cell suspension was well pipetted to break possible aggregates and 10 μL solution were mixed with 10 μL trypan blue cell-stained cells. 20 μL mix were then transferred on a cell counting slide and the cell concentration and viability measured using the LUNA II. According to previous experiments that allowed us to determine the best seeding density, NCI-N87, JIMT1 and MDAMB468 cell lines were respectively seeded at 10000, 3000 and 3000 cells/well in a CORNING SPHEROID 96-well microplate.

A stock solution (650 µL) of antibody drug conjugate (ADC) was made by dilution of filter-sterilised ADC into cell culture medium. A set of 9×5-fold dilutions of the previous ADC solution were made in a 2 mL deep 96 well plate by serial transfer of 65 µl onto 585 µl of cell culture medium. ADC dilution was dispensed (50 µl/well) into 2 replicate wells of the 96-well plate, containing 50 µl cell suspension seeded 48 h before. Control wells received 50 µl cell culture medium. The 96-well plate containing cells and ADCs was incubated at 37° C. in a $CO_2$-gassed incubator for 6 days. At the end of the incubation period, plates were equilibrated to room temperature for 10 min before CELL-TITER-GLO 3D Cell Viability Assay was dispensed (100 µl per well) into each well. Plates were pipette mixed for 5 minutes after which the plates were incubated for 25 minutes at room temperature. Well luminescence was measured, and percentage cell survival was calculated from the mean luminescence in the 2 ADC-treated wells compared to the mean luminescence in the 6 control untreated wells (100%). $IC_{50}$ was determined from the dose-response data using GRAPHPAD PRISM using the non-linear regression (curve fit) algorithm: Sigmoidal,4PL, X is log(concentration).

TABLE 1

| ADC | Linker Payload | $IC_{50}$ NCI-N87 (µg/mL) | $IC_{50}$ JIMT1 (µg/mL) | $IC_{50}$ MDAMB468 (µg/mL) |
| --- | --- | --- | --- | --- |
| ADC-1 | LP-1 | 0.70 | 10.64 | 17.24 |
| Control ADC-1 | LP-1 | ND | 209.26 | 25.25 |

ADC Toxicity Evaluated on 3D SKOV3 and SKOV3 GUSB KO

Media from SKOV3 WT and SKOV3 GUSB KO (β-Glucuronidase knockout cell line, generated using CRISPR targeting) cells at 80-90% confluency in a T175 flask was aspirated and the flask rinsed with PBS (about 10 ml) and emptied. TrypLE (5 ml) Express Enzyme (1×) was added, the flask returned to the 37° C. incubator with 5% $CO_2$ for about 5 minutes, then the flask was shaken to detach the cells from the bottom. 10 mL cell media (McCoy's 5 A supplemented with 50% Fetal Bovine Serum) was added to the flask and the cell suspension was transferred to a sterile 50 ml falcon tube, then centrifuged (400 g for 5 min). The supernatant was aspirated, and the pellet re-suspended in 10 mL culture medium. The cell suspension was well pipetted to break possible aggregates and 10 uL solution were mixed with 10 uL trypan blue cell-stained cells. 20 uL mix were then transferred on a cell counting slide and the cell concentration and viability measured using the LUNA II. According to previous experiments that allowed us to determine the best seeding density, SKOV3 and SKOV3 GUSB KO were seeded at 3000 cells/well in a CORNING SPHEROID 96-well microplate.

A stock solution (650 µL) of antibody drug conjugate (ADC) was made by dilution of filter-sterilised ADC into cell culture medium. A set of 9×5-fold dilutions of the previous ADC solution were made in a 2 mL deep 96 well plate by serial transfer of 65 µl onto 585 µl of cell culture medium. ADC dilution was dispensed (50 µl/well) into 2 replicate wells of the 96-well plate, containing 50 µl cell suspension seeded 48 h before. Control wells received 50 µl cell culture medium. The 96-well plate containing cells and ADCs was incubated at 37° C. in a $CO_2$-gassed incubator for 6 days. At the end of the incubation period, plates were equilibrated to room temperature for 10 min before CELL-TITER-GLO 3D Cell Viability Assay was dispensed (100 µl per well) into each well. Plates were pipette mixed for 5 minutes after which the plates were incubated for 25 minutes at room temperature. Well luminescence was measured, and percentage cell survival was calculated from the mean luminescence in the 2 ADC-treated wells compared to the mean luminescence in the 6 control untreated wells (100%). $IC_{50}$ was determined from the dose-response data using GraphPad Prism using the non-linear regression (curve fit) algorithm: Sigmoidal,4PL, X is log(concentration).

TABLE 2

| ADC | Linker Payload | $IC_{50}$ SKOV3 (µg/mL) | $IC_{50}$ SKOV3 GUSB KO (µg/mL) |
| --- | --- | --- | --- |
| ADC-1 | LP-1 | 0.30 | 42.57 |
| Control ADC-1 | LP-1 | ND | ND |

ADC Toxicity Evaluated on NCI-N87, MDAMB468, SKOV3 WT and SKOV3 GUSB KO

Media from NCI-N87, MDAMB468, SKOV3 WT and SKOV3 GUSB KO cells at 80-90% confluency in a T175 flask was aspirated and the flask rinsed with PBS (about 10 mL) and emptied. TrypLE (5 ml) Express Enzyme (1×) was added, the flask returned to the 37° C. incubator with 5% $CO_2$ for about 5 minutes. The flask was then shaken to detach the cells from the bottom. 10 mL RPMI 1640 and McCoy 5 A cell media, both supplemented with 50% Fetal Bovine Serum, were added to the flasks and the cell suspensions were transferred to sterile 50 ml falcon tubes, then centrifuged (400 g for 5 min). The supernatant was aspirated, and the pellet re-suspended in 10 mL culture medium. The cell suspension was well pipetted to break possible aggregates and 10 µL solution were mixed with 10 µL trypan blue cell-stained cells. 20 µL mix were then transferred on a cell counting slide and the cell concentration and viability measured using the LUNA II. According to previous experiments that allowed us to determine the best seeding density, MDAMB468, SKOV3 WT and SKOV3 GUSB KO cell lines were seeded at 3000 cells/wells while the NCI-N87 were seeded at 10000 cells/wells.

A stock solution (550 µL) of Antibody Drug Conjugate (ADC) was made by dilution of filter-sterilised ADC into cell culture medium. A set of 9×5-fold dilutions of the previous ADC solution were made in a 2 mL deep 96 well plate by serial transfer of 110 µl onto 440 µl of cell culture medium. ADC dilution was dispensed (50 µl/well) into 2 replicate wells of the 96-well plate, containing 50 µl cell suspension seeded the previous day. Control wells received 50 µl cell culture medium. The 96-well plate containing cells and ADCs was incubated at 37° C. in a $CO_2$-gassed incubator for 6 days. At the end of the incubation period, plates were equilibrated to room temperature for 10 min before CellTiter-Glo (Promega) was dispensed (100 µl per well) into each well. Plates were placed on an orbital shaker for 10 min before stabilisation at room temperature for 1 min. Well luminescence was measured, and percentage cell survival was calculated from the mean luminescence in the 2 ADC-treated wells compared to the mean luminescence in the 6 control untreated wells (100%). $IC_{50}$ was determined from the dose-response data using GRAPHPAD PRISM using the non-linear regression (curve fit) algorithm: Sigmoidal,4PL, X is log(concentration).

TABLE 3

| ADC | Linker Payload | IC$_{50}$ NCI-N87 (µg/mL) | IC$_{50}$ MDAMB468 (µg/mL) |
|---|---|---|---|
| ADC-M1 | LP-M1 | 0.005 | ND (>1000) |

TABLE 4

| ADC | Linker Payload | IC$_{50}$ NCI-N87 (µg/mL) | IC$_{50}$ MDAMB468 (µg/mL) | IC$_{50}$ SKOV3 WT 3D (µg/mL) | IC$_{50}$ SKOV3 GUSB KO 3D (µg/mL) |
|---|---|---|---|---|---|
| ADC-T1 | LP-T1 | 0.03876 | 49.9 | 0.008412 | 0.02956 |
| ADC-1 | LP-1 | 0.0674 | 12.89 | 0.0002876 | 12.89 |

TABLE 5

| Asset Number | Linker Payload | IC$_{50}$ NCI-N87 (µg/mL) | IC$_{50}$ MDAMB468 (µg/mL) | IC$_{50}$ SKOV3 WT 3D (µg/mL) | IC$_{50}$ SKOV3 GUSB KO 3D (µg/mL) |
|---|---|---|---|---|---|
| ADC-2 | LP-2 | 0.04284 | 8.295 | 0.005861 | 16.46 |
| ADC-3 | LP-3 | 0.05484 | 5.299 | 0.005232 | 8.862 |
| ADC-1 | LP-1 | 0.0674 | 12.89 | 0.0002876 | 12.89 | kD Colloidal Stability Data for ADC-2, ADC-3, ADC-1

Figure 7:
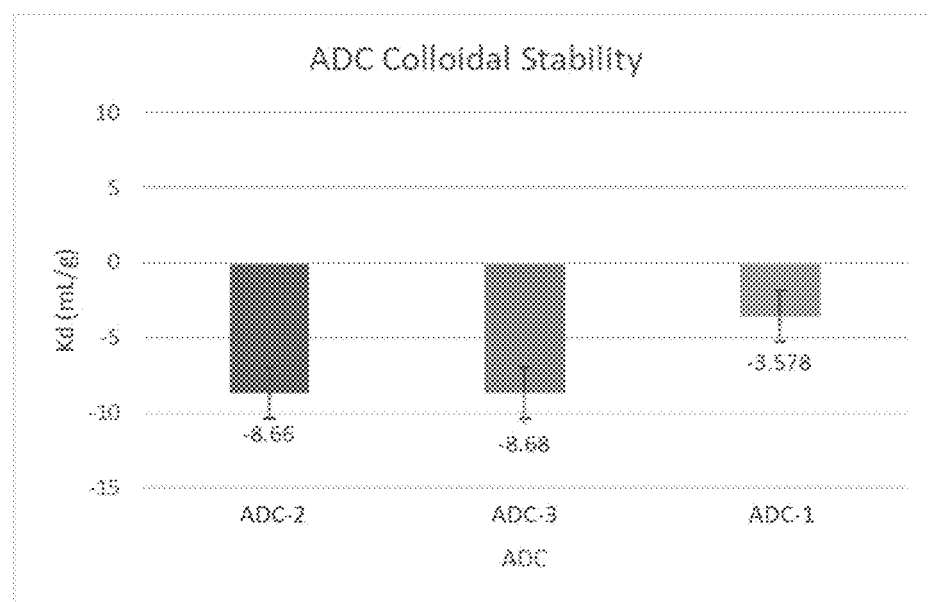
FIG. 7 illustrates colloidal stability data for ADC-3, ADC-2 and ADC-1.

Colloidal stability describes a protein's propensity to form aggregates and precipitate out of solution. The kD values below represent the rate constant for this precipitation process, the lower (more negative) the value, the higher the conjugate's propensity for precipitation. All the ADCs as well as the native mAb were concentrated to ~10 mg/mL in 20 mM His/His HCL, 240 mM sucrose pH 6.0. Serial dilutions in the formulation buffer were performed. Each sample was tested 3 times in triplicates. The Kd values are the average of each triplicate. Outlier results (marked "*") were omitted from average calculations. Results are shown in Table 6 and FIG. 7, which demonstrate a statistically significant reduced propensity for precipitation for ADC-1 compared to ADC-2 and ADC-3.

TABLE 6

| | kD (mL/g) | | | |
|---|---|---|---|---|
| ADC | Run1 | Run2 | Run3 | Average, N = 3 |
| ADC-2 | −11.23 | −7.36 | −7.39 | −8.66 |
| ADC-3 | −10.95 | −8.67 | −6.42 | −8.68 |
| ADC-1 | −3.99 | −3.166 | 618* | −3.58 |

The above description of illustrative embodiments is intended only to acquaint others skilled in the art with the Applicant's specification, its principles, and its practical application so that others skilled in the art may readily adapt and apply the specification in its numerous forms, as they may be best suited to the requirements of a particular use. This description and its specific examples, while indicating embodiments of this specification, are intended for purposes of illustration only. This specification, therefore, is not limited to the illustrative embodiments described in this specification, and may be variously modified. In addition, it is to be appreciated that various features of the specification that are, for clarity reasons, described in the context of separate embodiments, also may be combined to form a single embodiment. Conversely, various features of the specification that are, for brevity reasons, described in the context of a single embodiment, also may be combined to form sub-combinations thereof.

Statements of Disclosure M

1M. A conjugate of Formula (IM)

$$Ab-(G^A-J^A-D^M)_k \quad (IM)$$

or a pharmaceutically acceptable salt thereof, wherein
Ab is an antibody or antigen-binding fragment thereof,
k is an integer from 1 to 10,
each $G^A$ is independently a conjugation group conjugated to the antibody or antigen-binding fragment thereof,
each $D^M$ is

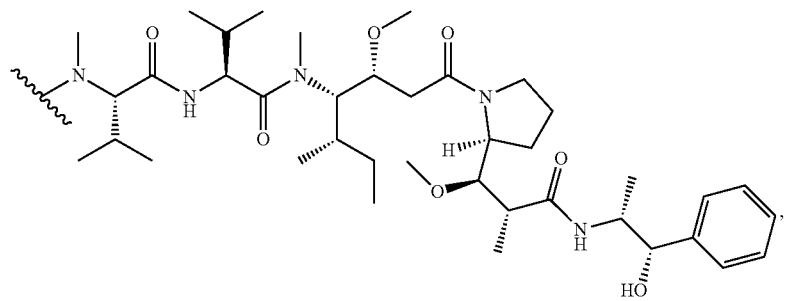 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@H](C)[C@@H](O)c1ccccc1)OC)C(C)C)C(C)C]

each $J^A$ is independently a group of Formula (IMA)

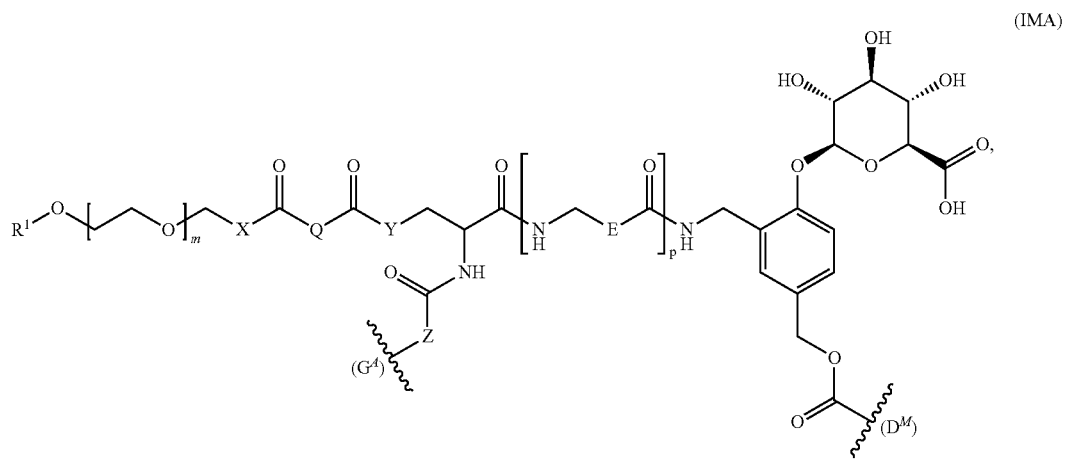

E is $(CH_2)_{n1}$, wherein n1 is 0, 1, 2 or 3,
Q is

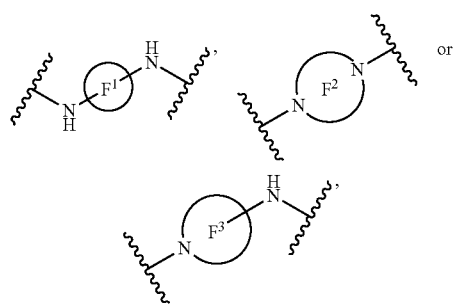

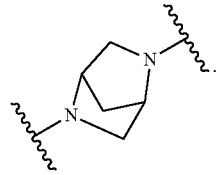

wherein Ring $F^1$ is a saturated bicyclic ring having 6, 7, or 8 carbon atoms and optionally 1 or 2 oxygen atoms, Ring $F^2$ is a saturated bicyclic ring having the 2 nitrogen atoms shown, 4, 5, 6, 7 or 8 carbon atoms and optionally 1 oxygen atom, and Ring $F^3$ is a saturated bicyclic ring having the 1 nitrogen atom shown, 5, 6, 7 or 8 carbon atoms and optionally 1 oxygen atom, $R^1$ is $C_{1-4}$ alkyl,
X is $(CH_2)_{n2}$, wherein n2 is 0, 1, 2 or 3,
Y is $(CH_2)_{n3}$, wherein n3 is 0, 1, 2, 3 or 4,
Z is $(CH_2)_{n4}$, wherein n4 is 1, 2, 3, 4 or 5,
m is an integer from 5 to 17,
p is 1 or 0,
($G^A$) indicates the point of attachment to $G^A$, and
($D^M$) indicates the point of attachment to $D^M$.

2M. A conjugate of Formula (IM) or a pharmaceutically acceptable salt thereof, as disclosed in statement 1M, wherein Q is

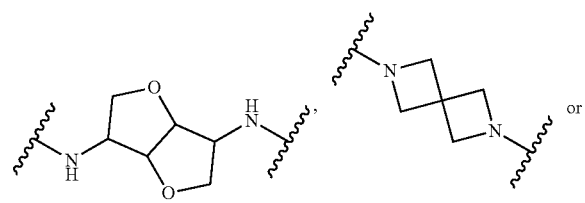

-continued

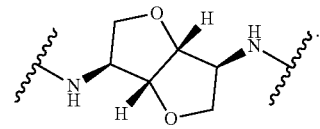 [SMILES: *N[C@H]1CO[C@H]2[C@@H]1OC[C@@H]2N*]

3M. A conjugate of Formula (IM) or a pharmaceutically acceptable salt thereof, as disclosed in statement 1M, wherein Q is 4M. A conjugate of Formula (IM) or a pharmaceutically acceptable salt thereof, as disclosed in any one of statements 1M to 3M, wherein m is 9, 10, 11, 12 or 13.

5M. A conjugate of Formula (IM) or a pharmaceutically acceptable salt thereof, as disclosed in any one of statements 1M to 4M, wherein $R^1$ is $CH_3$.

6M. A conjugate of Formula (IM) or a pharmaceutically acceptable salt thereof, as disclosed any one of statements 1M to 5M, wherein E is $CH_2$.

7M. A conjugate of Formula (IM) or a pharmaceutically acceptable salt thereof, as disclosed in any one of statements 1M to 6M, wherein X is $CH_2$.

8M. A conjugate of Formula (IM) or a pharmaceutically acceptable salt thereof, as disclosed in any one of statements 1M to 7M, wherein Y is $(CH_2)_2$.

9M. A conjugate of Formula (IM) or a pharmaceutically acceptable salt thereof, as disclosed in any one of statements 1M to 8M, wherein Z is $(CH_2)_2$.

10M. A conjugate of Formula (IM) or a pharmaceutically acceptable salt thereof, as disclosed in any one of statements 1M to 9M, wherein p is 1.

11M. A conjugate of Formula (IM) or a pharmaceutically acceptable salt thereof, as disclosed in statement 1M, wherein each $J^A$ is a group of Formula (IMB)

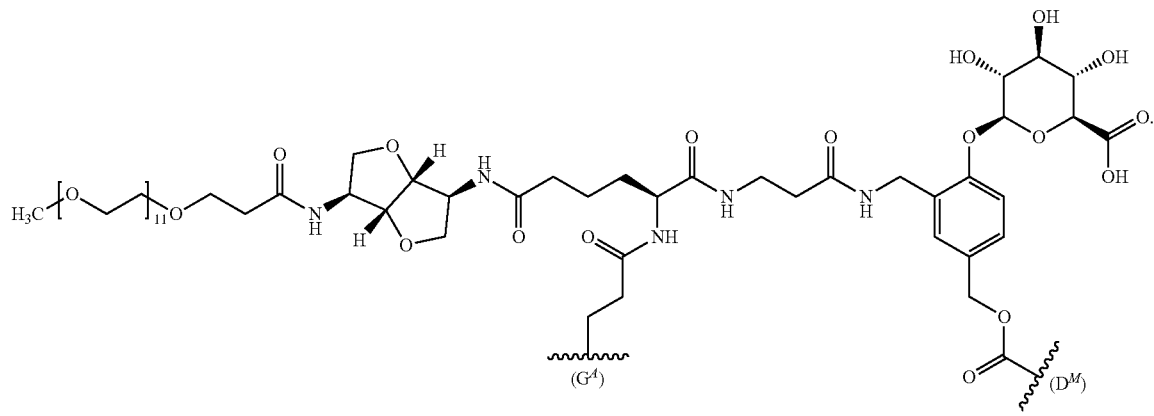

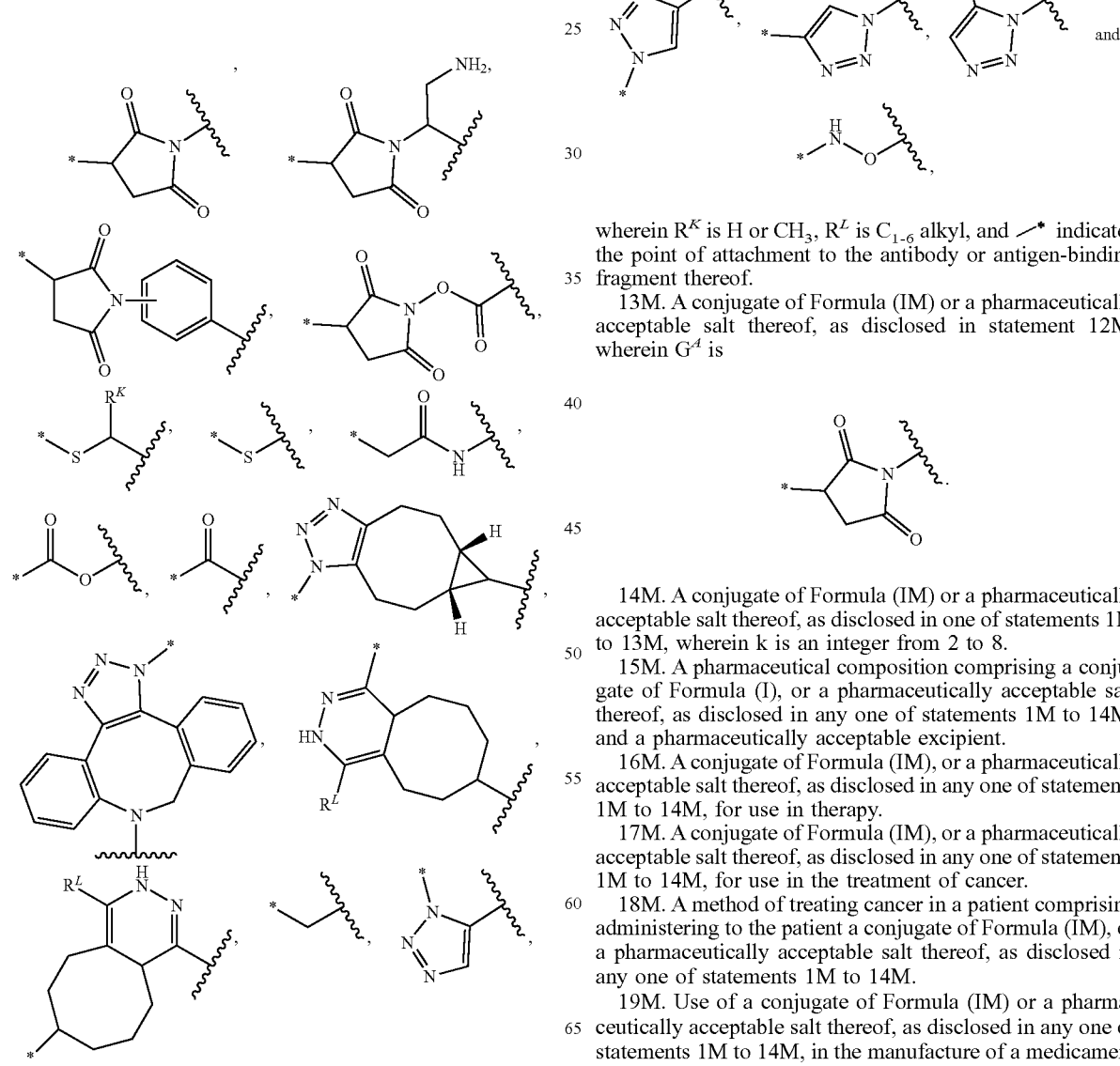

12M. A conjugate of Formula (IM) or a pharmaceutically acceptable salt thereof, as disclosed in any one of statements 1M to 11M, wherein $G^A$ is selected from wherein $R^K$ is H or $CH_3$, $R^L$ is $C_{1-6}$ alkyl, and ⟶* indicates the point of attachment to the antibody or antigen-binding fragment thereof.

13M. A conjugate of Formula (IM) or a pharmaceutically acceptable salt thereof, as disclosed in statement 12M, wherein $G^A$ is 14M. A conjugate of Formula (IM) or a pharmaceutically acceptable salt thereof, as disclosed in one of statements 1M to 13M, wherein k is an integer from 2 to 8.

15M. A pharmaceutical composition comprising a conjugate of Formula (I), or a pharmaceutically acceptable salt thereof, as disclosed in any one of statements 1M to 14M, and a pharmaceutically acceptable excipient.

16M. A conjugate of Formula (IM), or a pharmaceutically acceptable salt thereof, as disclosed in any one of statements 1M to 14M, for use in therapy.

17M. A conjugate of Formula (IM), or a pharmaceutically acceptable salt thereof, as disclosed in any one of statements 1M to 14M, for use in the treatment of cancer.

18M. A method of treating cancer in a patient comprising administering to the patient a conjugate of Formula (IM), or a pharmaceutically acceptable salt thereof, as disclosed in any one of statements 1M to 14M.

19M. Use of a conjugate of Formula (IM) or a pharmaceutically acceptable salt thereof, as disclosed in any one of statements 1M to 14M, in the manufacture of a medicament for the treatment of cancer.

20M. A compound of Formula (IIM)

$$G^B\text{-}J^B\text{-}D^M \quad (IIM)$$

or a salt thereof, wherein $G^B$ is a conjugation group for conjugation to an antibody or antigen-binding fragment thereof, $J^B$ is a group of Formula (IIMA)

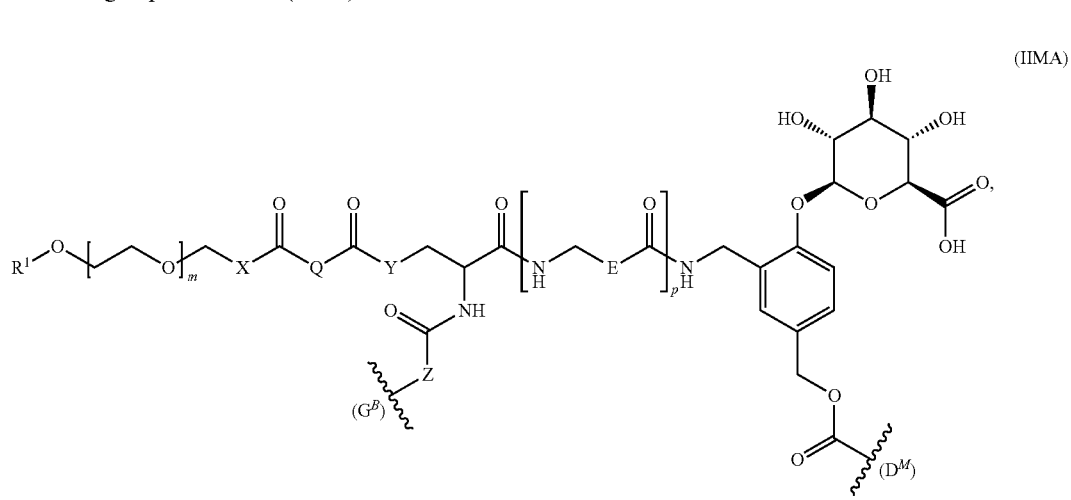

wherein $D^M$, E, Q, $R^1$, X, Y, Z, m and p are as defined for a conjugate of Formula (IM) in any one of statements 1M to 10M, ($G^B$) indicates the point of attachment to $G^B$, and ($D^M$) indicates the point of attachment to $D^M$.

21M. A compound of Formula (IIM) or a salt thereof, as disclosed in statement 20M, wherein $G^B$ is selected from

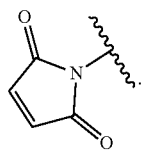

wherein $X^1$ is CH or N,
h is 0 or 1,
Hal is Cl, Br or I,
$R^K$ is H or $CH_3$, and
$R^L$ is $C_{1-6}$ alkyl.

22M. A compound of Formula (IIM) or a salt thereof, as disclosed in statement 21M, wherein $G^B$ is

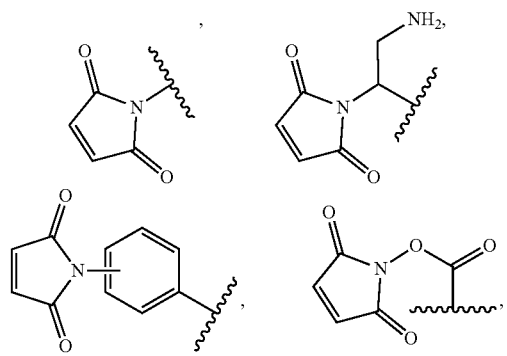

-continued

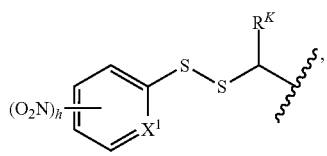

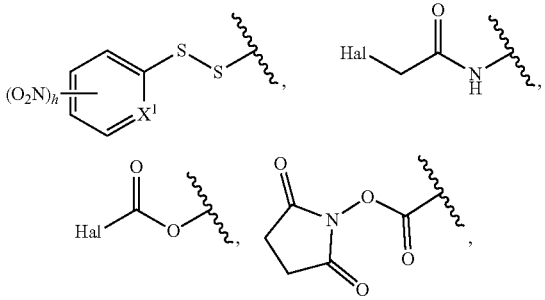

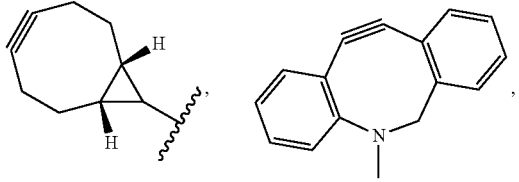

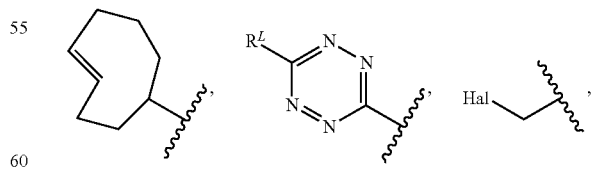

and

23M. A compound of Formula (IIM) or a salt thereof, as disclosed in statement 20M, that is that is
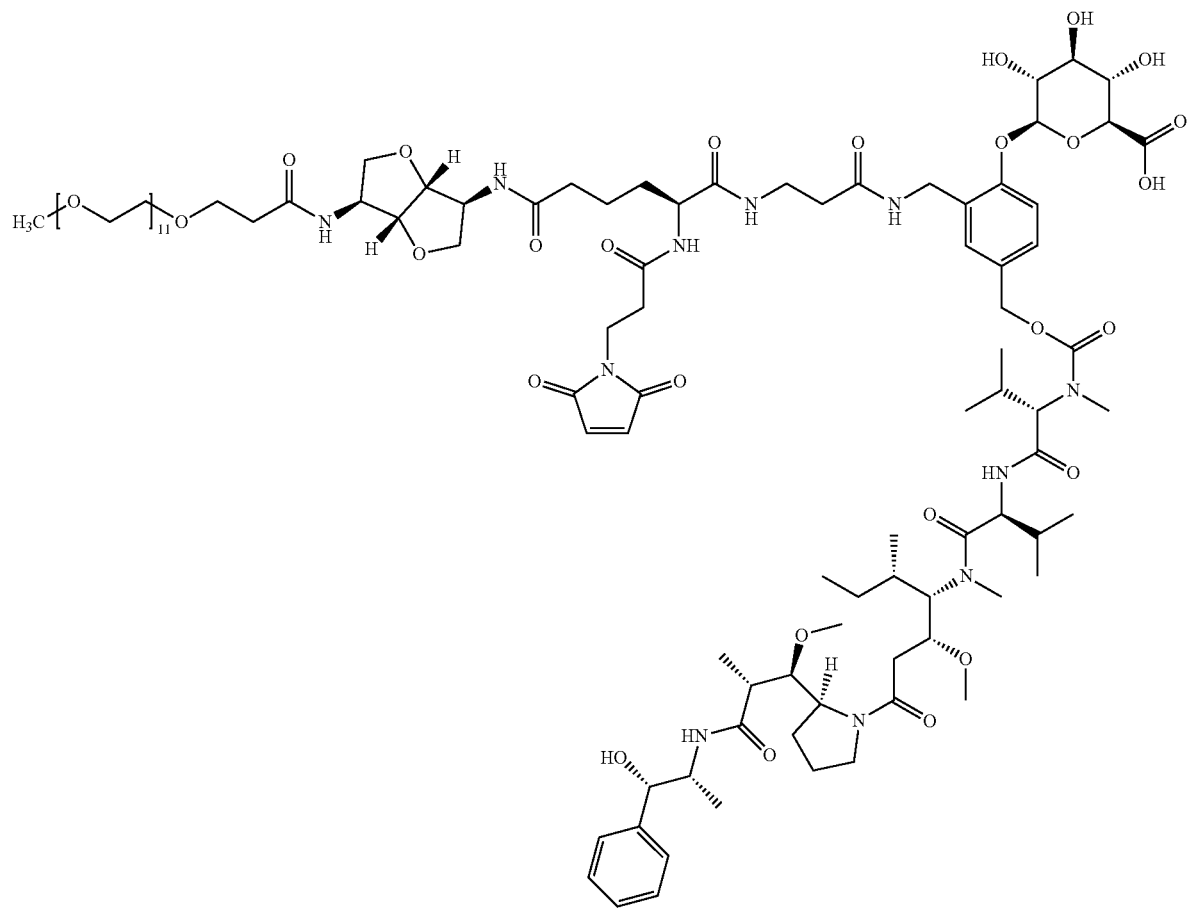

(2S,3S,4S,5R,6S)-6-(2-((3-((S)-6-(((3S,3aR,6S,6aR)-6-(2,5,8,11,14,17,20,23,26,29,32,35-dodecaoxaoctatriacontan-38-amido)hexahydrofuro[3,2-b]furan-3-yl)amino)-2-(3-(2,5-dioxo-2,5-dihydro-1H-pyrrol-1-yl)propanamido)-6-oxohexanamido)propanamido)methyl)-4-((5S,8S,11S,12R)-11-((S)-sec-butyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenoxy)-3,4,5-trihydroxytetrahydro-2H-pyran-2-carboxylic acid, or a salt thereof.

Statements of Disclosure P

1P. A conjugate of Formula (I)

$$Ab\text{-}(G^A\text{-}J^A\text{-}D^R)_k \quad (I)$$

or a pharmaceutically acceptable salt thereof, wherein
Ab is an antibody or antigen-binding fragment thereof,
k is an integer from 1 to 10,
each $G^A$ is independently a conjugation group conjugated to the antibody or antigen-binding fragment thereof,
each $D^R$ is independently a drug comprising a nitrogen atom $N^R$,
each $J^A$ is independently a group of Formula (IA)

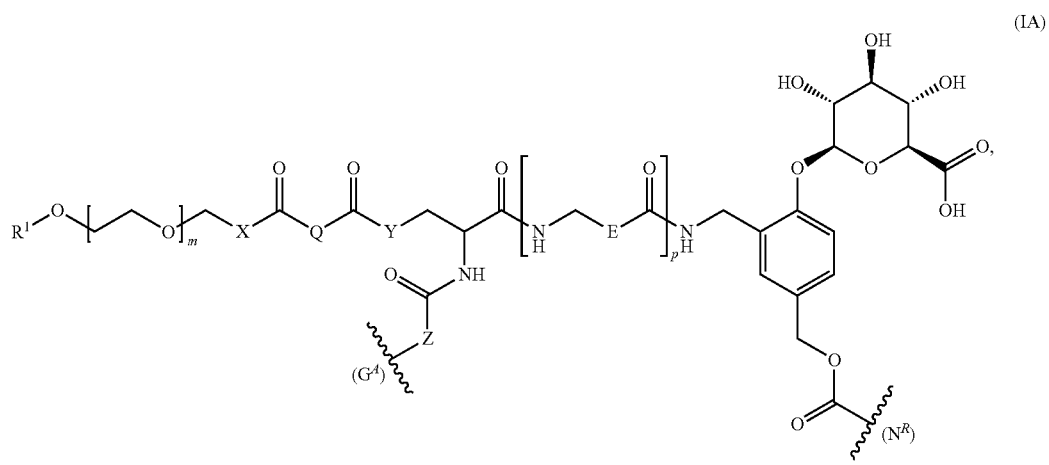

E is $(CH_2)_{n1}$, wherein n1 is 0, 1, 2 or 3,
Q is

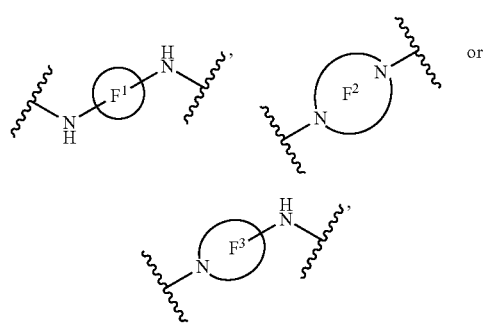

wherein Ring $F^1$ is a saturated bicyclic ring having 6, 7, or 8 carbon atoms and optionally 1 or 2 oxygen atoms, Ring $F^2$ is a saturated bicyclic ring having the 2 nitrogen atoms shown, 4, 5, 6, 7 or 8 carbon atoms and optionally 1 oxygen atom, and Ring $F^3$ is a saturated bicyclic ring having the 1 nitrogen atom shown, 5, 6, 7 or 8 carbon atoms and optionally 1 oxygen atom,
$R^1$ is $C_{1-4}$ alkyl,
X is $(CH_2)_{n2}$, wherein n2 is 0, 1, 2 or 3,
Y is $(CH_2)_{n3}$, wherein n3 is 0, 1, 2, 3 or 4,
Z is $(CH_2)_{n4}$, wherein n4 is 1, 2, 3, 4 or 5,
m is an integer from 5 to 17,
p is 1 or 0,
$(G^A)$ indicates the point of attachment to $G^A$, and
$(N^R)$ indicates the point of attachment to the nitrogen atom $N^R$.

2P. A conjugate of Formula (I) or a pharmaceutically acceptable salt thereof, as disclosed in statement 1P, wherein Q is

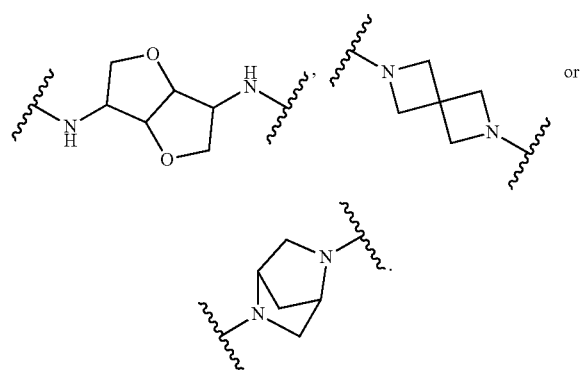

3P. A conjugate of Formula (I) or a pharmaceutically acceptable salt thereof, as disclosed in statement 1P, wherein Q is

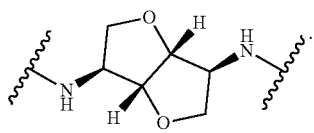 [SMILES: *N[C@H]1CO[C@H]2[C@@H]1OC[C@@H]2N*]

4P. A conjugate of Formula (I) or a pharmaceutically acceptable salt thereof, as disclosed in any one of statements 1P to 3P, wherein m is 9, 10, 11, 12 or 13.

5P. A conjugate of Formula (I) or a pharmaceutically acceptable salt thereof, as disclosed in any one of statements 1P to 4P, wherein $R^1$ is $CH_3$.

6P. A conjugate of Formula (I) or a pharmaceutically acceptable salt thereof, as disclosed in any one of statements 1P to 5P, wherein E is $CH_2$.

7P. A conjugate of Formula (I) or a pharmaceutically acceptable salt thereof, as disclosed in any one of statements 1P to 6P, wherein X is $CH_2$.

8P. A conjugate of Formula (I) or a pharmaceutically acceptable salt thereof, as disclosed in any one of statements 1P to 7P, wherein Y is $(CH_2)_2$.

9P. A conjugate of Formula (I) or a pharmaceutically acceptable salt thereof, as disclosed in any one of statements 1P to 8P, wherein Z is $(CH_2)_2$.

10P. A conjugate of Formula (I) or a pharmaceutically acceptable salt thereof, disclosed in any one of statements 1P to 9P, wherein p is 1.

11P. A conjugate of Formula (I) or a pharmaceutically acceptable salt thereof, as disclosed in statement 1P, wherein each $J^4$ is a group of Formula (IB)

12P. A conjugate of Formula (I) or a pharmaceutically acceptable salt thereof, as disclosed in any one of statements 1P to 11P, wherein $G^A$ is selected from

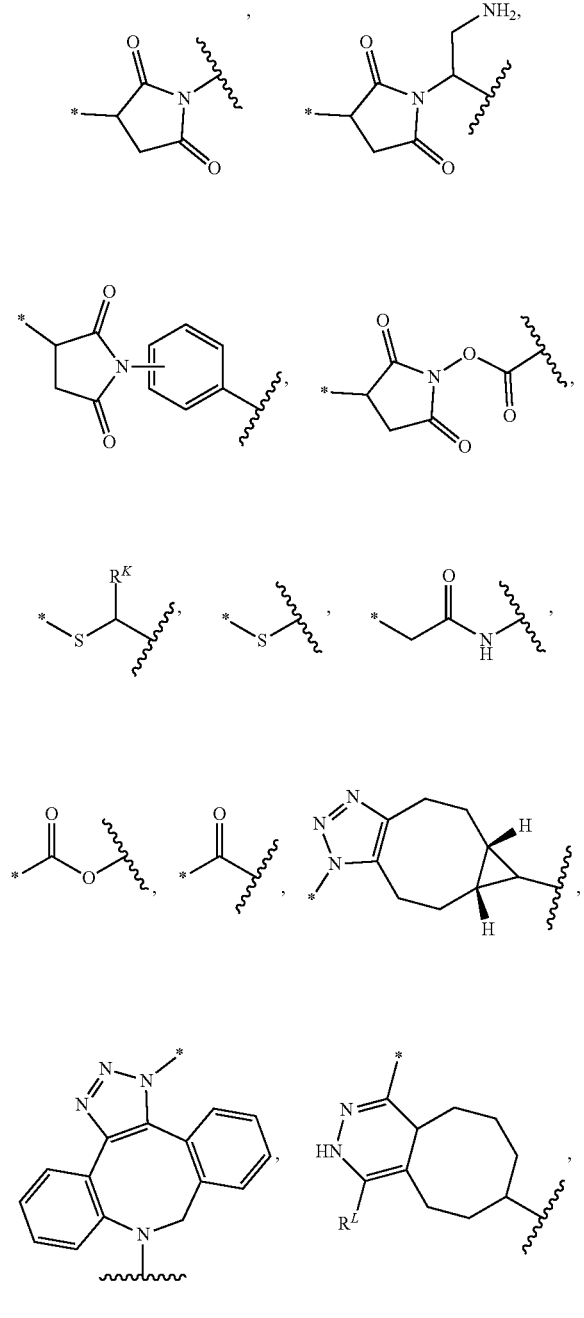

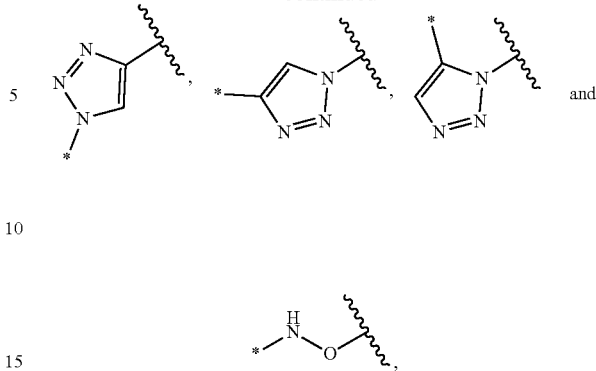

wherein $R^K$ is H or $CH_3$, $R^L$ is $C_{1-6}$ alkyl, and —* indicates the point of attachment to the antibody or antigen-binding fragment thereof.

13P. A conjugate of Formula (I) or a pharmaceutically acceptable salt thereof, as disclosed in statement 12P, wherein $G^A$ is

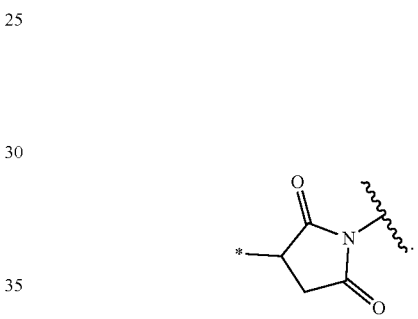

14P. A conjugate of Formula (I) or a pharmaceutically acceptable salt thereof, as disclosed in any one of statements 1P to 13P, wherein k is an integer from 2 to 8.

15P. A pharmaceutical composition comprising a conjugate of Formula (I) or a pharmaceutically acceptable salt thereof, as disclosed in any one of statements 1P to 14P, and a pharmaceutically acceptable excipient.

16P. A conjugate of Formula (I) or a pharmaceutically acceptable salt thereof, as disclosed in any one of statements 1P to 14P, for use in therapy.

17P. A conjugate of Formula (I) or a pharmaceutically acceptable salt thereof, as disclosed in any one of statements 1P to 14P, for use in the treatment of cancer.

18P. A method of treating cancer in a patient comprising administering to the patient a conjugate of Formula (I) or a pharmaceutically acceptable salt thereof, as disclosed in any one of statements 1P to 14P.

19P. Use of a conjugate of Formula (I) or a pharmaceutically acceptable salt thereof, as disclosed in any one of statements 1P to 14P, in the manufacture of a medicament for the treatment of cancer.

20P. A compound of Formula (II)

$$G^B\text{-}J^B\text{-}D^R \qquad (II)$$

or a salt thereof, wherein $G^B$ is a conjugation group for conjugation to an antibody or antigen-binding fragment thereof, $D^R$ is a drug comprising a nitrogen atom $N^R$,
$J^B$ is a group of Formula (IIA)

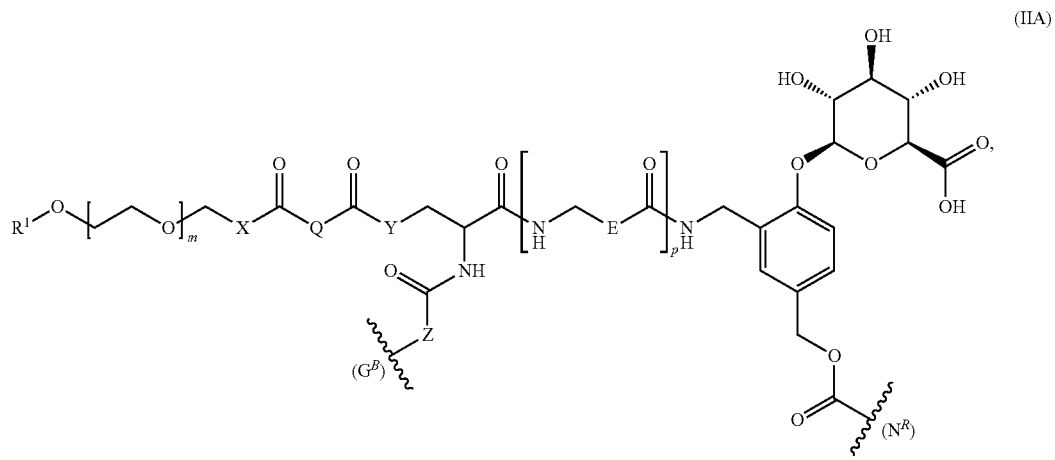

wherein E, Q, $R^1$, X, Y, Z, m and p are as defined for a conjugate of Formula (I) in any one of statements 1P to 10P, ($G^B$) indicates the point of attachment to $G^B$, and ($N^R$) indicates the point of attachment to the nitrogen atom $N^R$.

21P. A compound of Formula (II) or a salt thereof, as disclosed in statement 20P, wherein $G^B$ is selected from

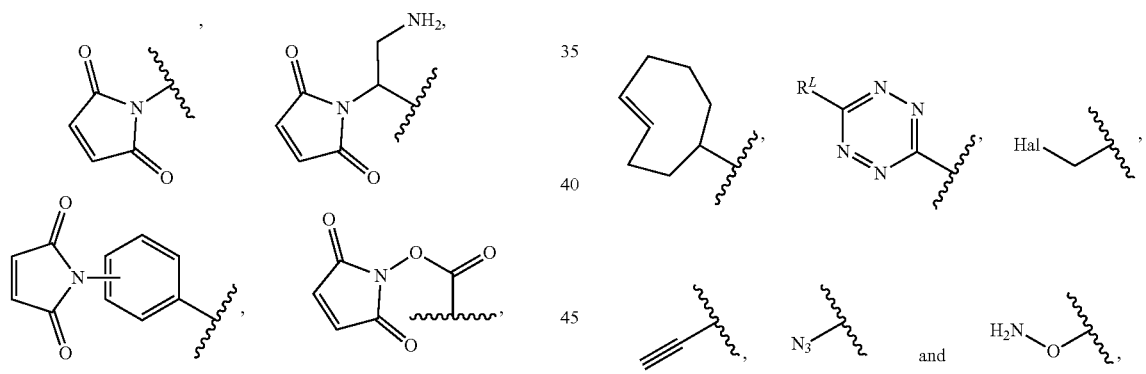

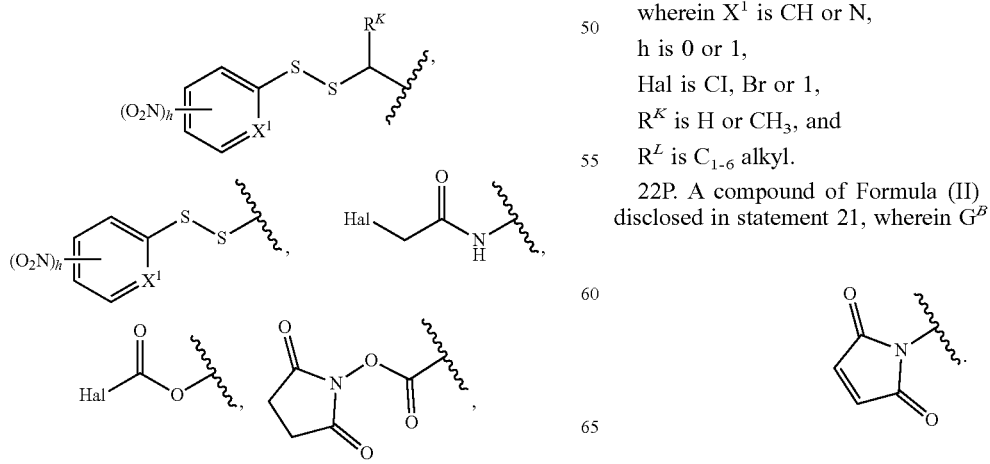

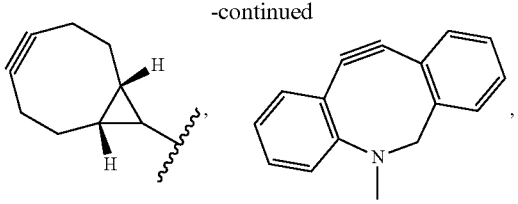

wherein $X^1$ is CH or N,
h is 0 or 1,
Hal is Cl, Br or I,
$R^K$ is H or $CH_3$, and
$R^L$ is $C_{1-6}$ alkyl.

22P. A compound of Formula (II) or a salt thereof, as disclosed in statement 21, wherein $G^B$ is 23P. A compound of Formula (III)

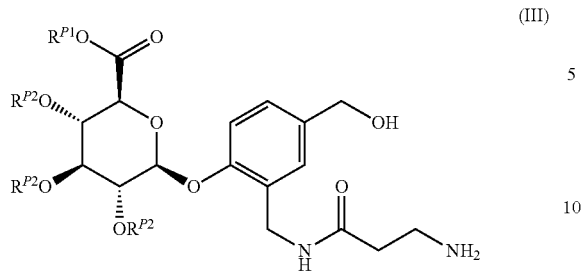

or a salt thereof, wherein $R^{P1}$ is a carboxylic acid protecting group, and each $R^{P2}$ is independently an alcohol protecting group.

24P. A compound of Formula (V)

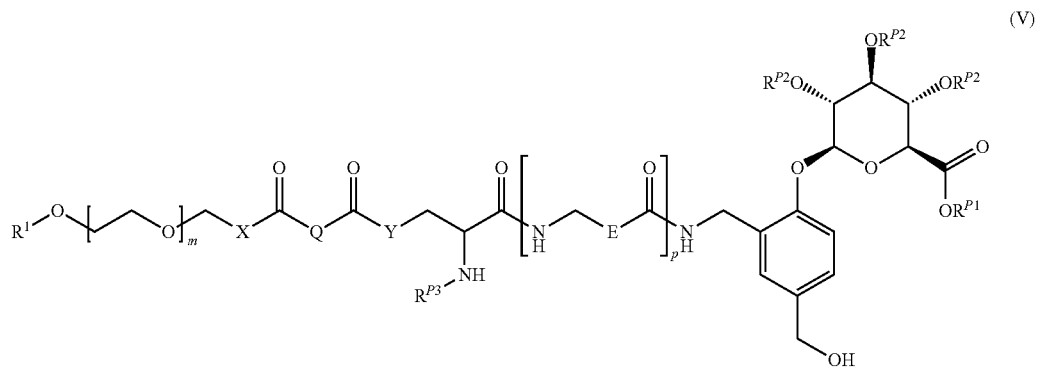

or a salt thereof, wherein E, Q, $R^1$, X, Y, m and p are as defined for a conjugate of Formula (I) in any one of statements 1P to 10P, $R^{P1}$ is a carboxylic acid protecting group, each $R^{P2}$ is independently an alcohol protecting group and $R^{P3}$ is an amine protecting group.

25P. A compound of Formula (VII)

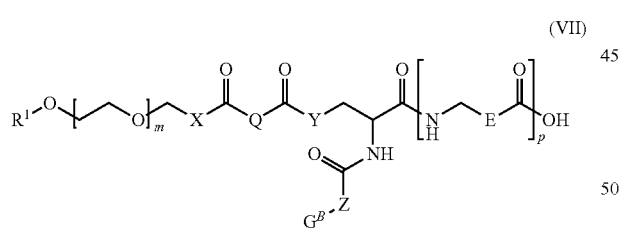

or a salt thereof, wherein $G^B$ is a conjugation group for conjugation to an antibody or antigen-binding fragment thereof, and E, Q, $R^1$, X, Y, Z, m and p are as defined for a conjugate of Formula (I) in any one of statements 1P to 10P.

The invention claimed is:
1. A conjugate of Formula (I)

or a pharmaceutically acceptable salt thereof, wherein
Ab is an antibody or antigen-binding fragment thereof,
k is an integer from 1 to 10,
each $G^A$ is independently a conjugation group conjugated to the antibody or antigen-binding fragment thereof, each $D^R$ is independently a drug comprising a nitrogen atom $N^R$,
each $J^A$ is independently a group of Formula (IA)

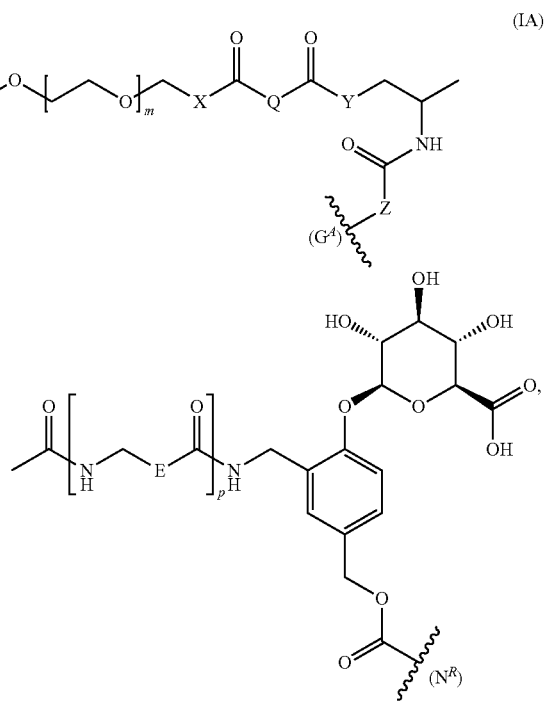

E is $(CH_2)_{n1}$, wherein n1 is 0, 1, 2 or 3,
Q is

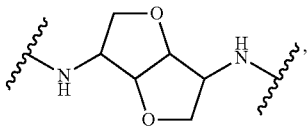 [SMILES: *NC1COC2C(N*)COC12]

$R^1$ is $C_{1-4}$ alkyl,
X is $(CH_2)_{n2}$, wherein n2 is 0, 1, 2 or 3,
Y is $(CH_2)_{n3}$, wherein n3 is 0, 1, 2, 3 or 4,
Z is $(CH_2)_{n4}$, wherein n4 is 1, 2, 3, 4 or 5,
m is an integer from 5 to 17,
p is 1 or 0,
($G^A$) indicates the point of attachment to $G^A$, and
($N^R$) indicates the point of attachment to the nitrogen atom $N^R$.

2. The conjugate of Formula (I), or a pharmaceutically acceptable salt thereof, as claimed in claim 1, wherein Q is

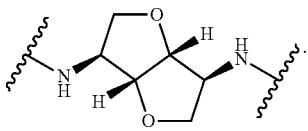 [SMILES: *N[C@H]1CO[C@H]2[C@@H]1OC[C@@H]2N*]

3. The conjugate of Formula (I), or a pharmaceutically acceptable salt thereof, as claimed in claim 1, wherein m is 9, 10, 11, 12 or 13.

4. The conjugate of Formula (I), or a pharmaceutically acceptable salt thereof, as claimed in claim 1, wherein $R^1$ is $CH_3$.

5. The conjugate of Formula (I), or a pharmaceutically acceptable salt thereof, as claimed in claim 1, wherein n1 is 1.

6. The conjugate of Formula (I), or a pharmaceutically acceptable salt thereof, as claimed in claim 1, wherein n2 is 1.

7. The conjugate of Formula (I), or a pharmaceutically acceptable salt thereof, as claimed in claim 1, wherein n3 is 2.

8. The conjugate of Formula (I), or a pharmaceutically acceptable salt thereof, as claimed in claim 1, wherein n4 is 2.

9. The conjugate of Formula (I), or a pharmaceutically acceptable salt thereof, as claimed in claim 1, wherein p is 1.

10. The conjugate of Formula (I), or a pharmaceutically acceptable salt thereof, as claimed in claim 1, wherein each $J^A$ is a group of Formula (IB)

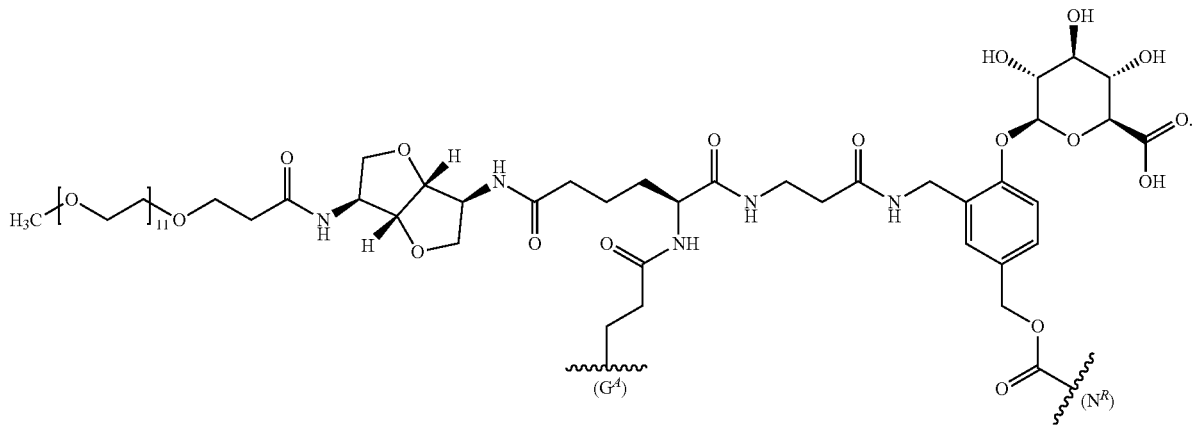

(IB)

11. The conjugate of Formula (I), or a pharmaceutically acceptable salt thereof, as claimed in claim 10, wherein $G^A$ is

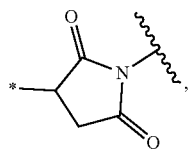 [SMILES: *C1CC(=O)N(*)C1=O]

wherein ⁎ indicates the point of attachment to the antibody or antigen-binding fragment thereof.

12. The conjugate of Formula (I), or a pharmaceutically acceptable salt thereof, as claimed in claim 10, wherein $G^A$ is

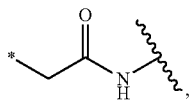 [SMILES: *CC(=O)N*]

wherein ⁎ indicates the point of attachment to the antibody or antigen-binding fragment thereof.

13. The conjugate of Formula (I), or a pharmaceutically acceptable salt thereof, as claimed in claim 1, wherein $G^A$ is selected from

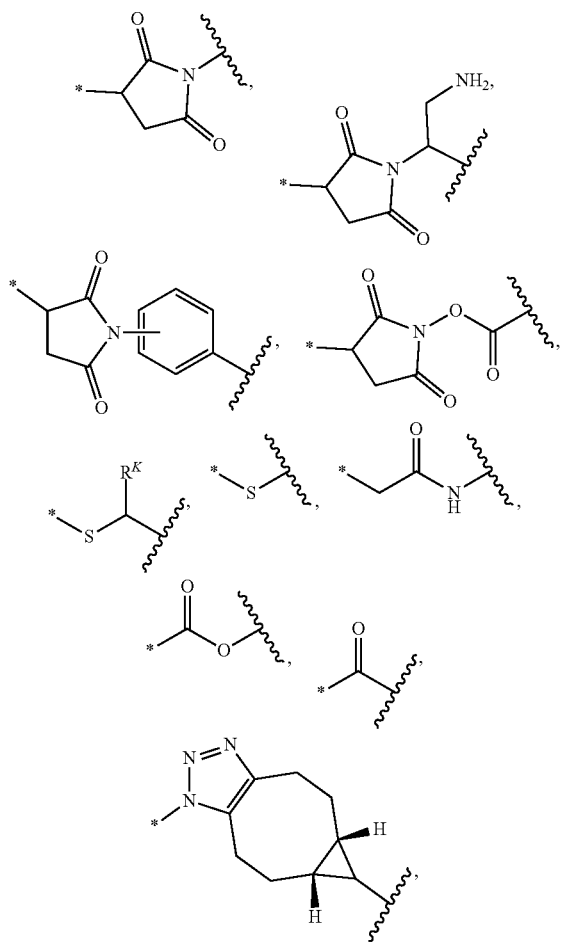

-continued

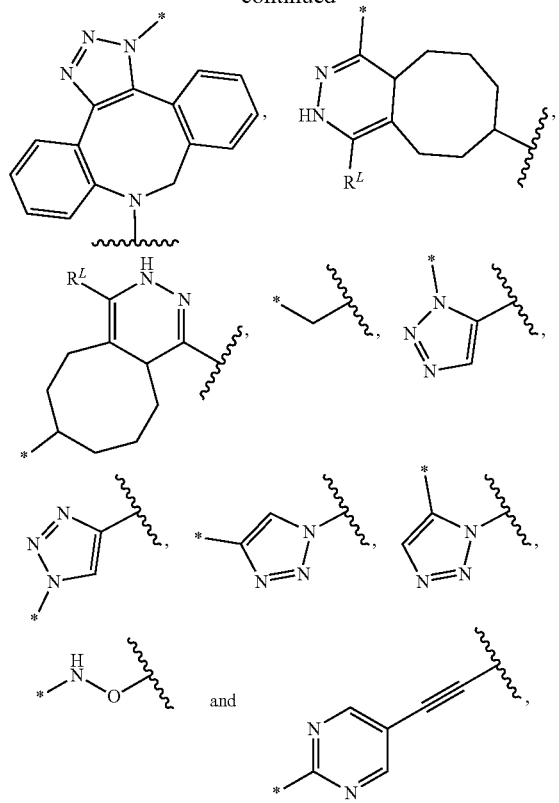

wherein $R^K$ is H or $CH_3$, $R^L$ is $C_{1-6}$ alkyl, and ⁎ indicates the point of attachment to the antibody or antigen-binding fragment thereof.

14. The conjugate of Formula (I), or a pharmaceutically acceptable salt thereof, as claimed in claim 13, wherein $G^A$ is

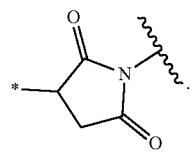 [SMILES: *C1CC(=O)N(*)C1=O]

15. The conjugate of Formula (I), or a pharmaceutically acceptable salt thereof, as claimed in claim 13, wherein $G^A$ is

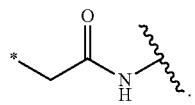

16. The conjugate of Formula (I), or a pharmaceutically acceptable salt thereof, as claimed in claim 1, wherein k is an integer from 2 to 8.

17. A pharmaceutical composition comprising the conjugate of Formula (I), or a pharmaceutically acceptable salt thereof, as claimed in claim 1, and a pharmaceutically acceptable excipient.

18. A method of treating cancer in a patient comprising administering to the patient the conjugate of Formula (I), or a pharmaceutically acceptable salt thereof, as claimed in claim 1.

19. A compound of Formula (II)

$$G^B\text{-}J^B\text{-}D^R \quad (II),$$

or a salt thereof, wherein $G^B$ is a conjugation group for conjugation to an antibody or antigen-binding fragment thereof, $D^R$ is a drug comprising a nitrogen atom $N^R$, $J^B$ is a group of Formula (IIA)

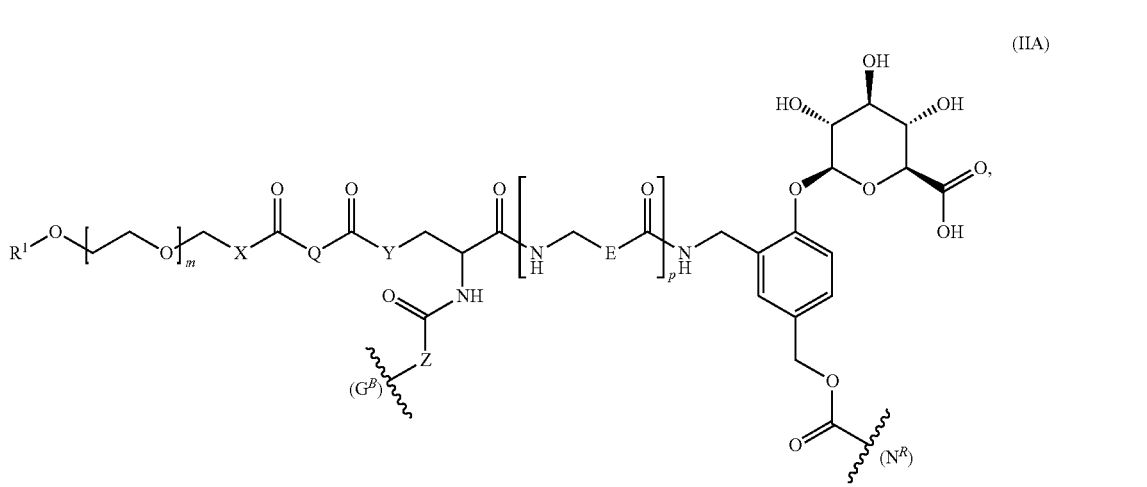

E is $(CH_2)_{n1}$, wherein n1 is 0, 1, 2 or 3,

Q is

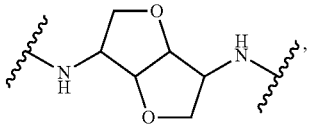

$R^1$ is $C_{1-4}$ alkyl,

X is $(CH_2)_{n2}$, wherein n2 is 0, 1, 2 or 3,

Y is $(CH_2)_{n3}$, wherein n3 is 0, 1, 2, 3 or 4,

Z is $(CH_2)_{n4}$, wherein n4 is 1, 2, 3, 4 or 5, m is an integer from 5 to 17, p is 1 or 0, ($G^B$) indicates the point of attachment to $G^B$, and ($N^R$) indicates the point of attachment to the nitrogen atom $N^R$.

20. The compound of Formula (II), or a salt thereof, as claimed in claim 19, wherein $G^B$ is selected from

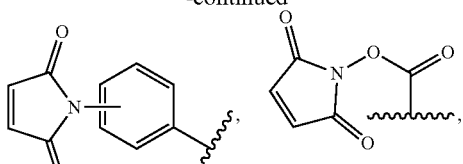

-continued

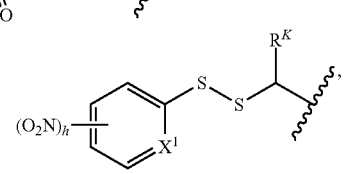

-continued
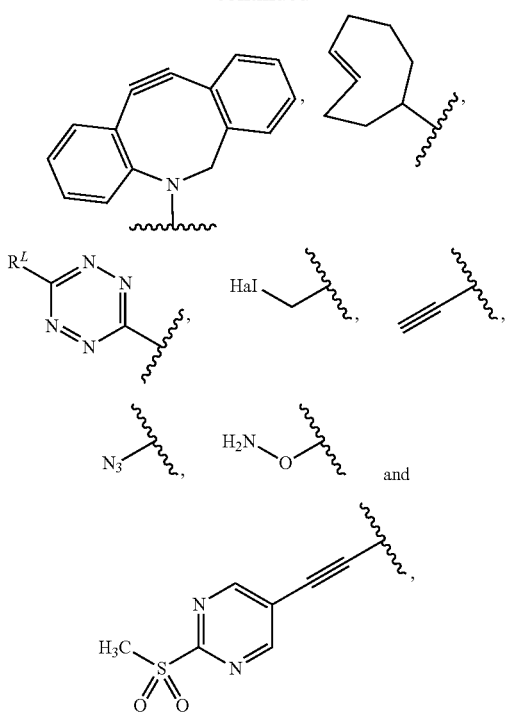
wherein $X^1$ is CH or N,
h is 0 or 1,
Hal is Cl, Br or I,
$R^K$ is H or $CH_3$, and
$R^L$ is $C_{1-6}$ alkyl.
21. The compound of Formula (II), or a salt thereof, as claimed in claim 20, wherein $G^B$ is
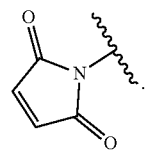
22. The compound of Formula (II), or a salt thereof, as claimed in claim 20, wherein $G^B$ is
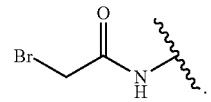
23. A compound of Formula (V)
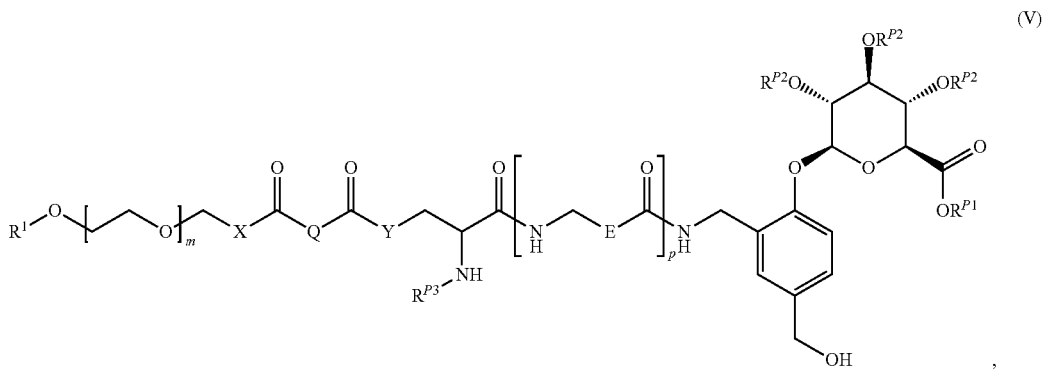

or a salt thereof, wherein

E is $(CH_2)_{n1}$, wherein n1 is 0, 1, 2 or 3,

Q is

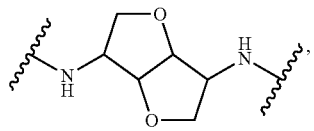

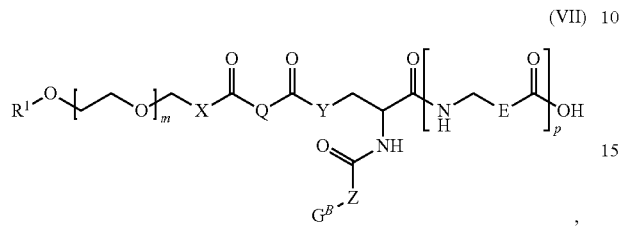
(VII)

$R^1$ is $C_{1-4}$ alkyl,

X is $(CH_2)_{n2}$, wherein n2 is 0, 1, 2 or 3,

Y is $(CH_2)_{n3}$, wherein n3 is 0, 1, 2, 3 or 4, m is an integer from 5 to 17, p is 1 or 0, $R^{P1}$ is a carboxylic acid protecting group, each $R^{P2}$ is independently an alcohol protecting group and $R^{P3}$ is an amine protecting group.

24. A compound of Formula (VII)

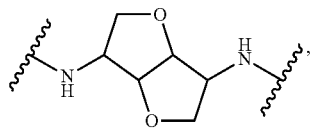 [SMILES: *NC1COC2C(N*)COC12]

or a salt thereof, wherein $G^B$ is a conjugation group for conjugation to an antibody or antigen-binding fragment thereof, E is $(CH_2)_{n1}$, wherein n1 is 0, 1, 2 or 3, Q is $R^1$ is $C_{1-4}$ alkyl, X is $(CH_2)_{n2}$, wherein n2 is 0, 1, 2 or 3, Y is $(CH_2)_{n3}$, wherein n3 is 0, 1, 2, 3 or 4, Z is $(CH_2)_{n4}$, wherein n4 is 1, 2, 3, 4 or 5, m is an integer from 5 to 17, and p is 1 or 0.

25. A compound of Formula (VIII)

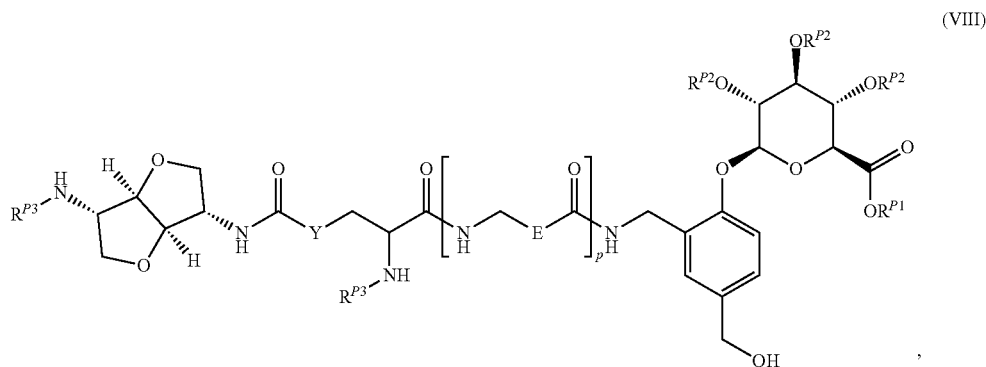

or a salt thereof, wherein

E is $(CH_2)_{n1}$, wherein n1 is 0, 1, 2 or 3,

Y is $(CH_2)_{n3}$, wherein n3 is 0, 1, 2, 3 or 4, p is 1 or 0, $R^{P1}$ is a carboxylic acid protecting group, each $R^{P2}$ is independently an alcohol protecting group and $R^{P3}$ is an amine protecting group.

26. A compound of Formula (IX)

$$G^B\text{-}J^B\text{-}D^R \qquad (IX),$$

or a salt thereof, wherein $G^B$ is a conjugation group for conjugation to an antibody or antigen-binding fragment thereof, $D^R$ is a drug comprising a nitrogen atom $N^R$, $J^B$ is a group of Formula (IXA)

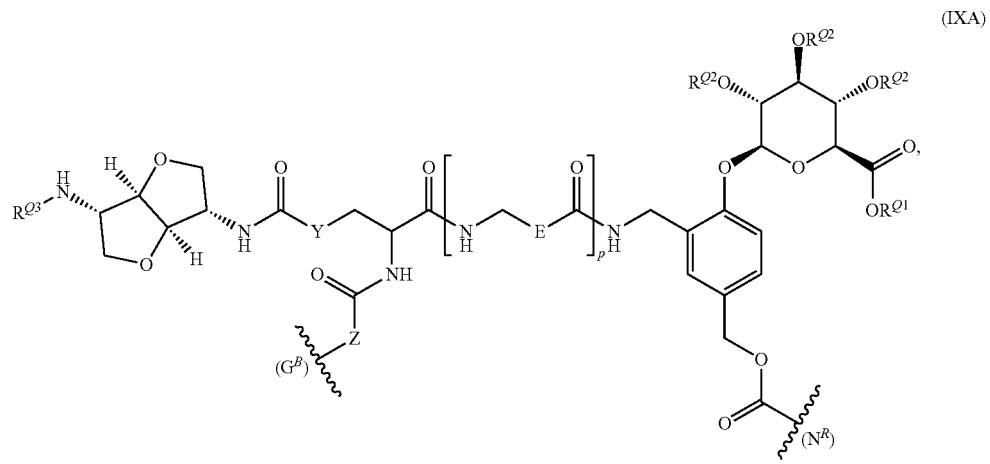

wherein

E is $(CH_2)_{n1}$, wherein n1 is 0, 1, 2 or 3,

Y is $(CH_2)_{n3}$, wherein n3 is 0, 1, 2, 3 or 4,

Z is $(CH_2)_{n4}$, wherein n4 is 1, 2, 3, 4 or 5, p is 1 or 0, $(G^B)$ indicates the point of attachment to $G^B$, and $(N^R)$ indicates the point of attachment to the nitrogen atom $N^R$, $R^{Q1}$ is H or $R^{P1}$, $R^{Q2}$ is H or $R^{P2}$ and $R^{Q3}$ is H or $R^{P3}$, wherein $R^{P1}$ is a carboxylic acid protecting group, each $R^{P2}$ is independently an alcohol protecting group and $R^{P3}$ is an amine protecting group.

* * * * *